US012448363B2

(12) United States Patent
Coburn et al.

(10) Patent No.: US 12,448,363 B2
(45) Date of Patent: Oct. 21, 2025

(54) KINASE INHIBITORS

(71) Applicant: Vidya Therapeutics, Inc., Encinitas, CA (US)

(72) Inventors: Craig Alan Coburn, San Diego, CA (US); Dange Vijay Kumar, San Diego, CA (US); Daniel John Buzard, San Diego, CA (US); Nidhi Arora, San Diego, CA (US)

(73) Assignee: VIDYA THERAPEUTICS, INC., Encinitas, CA (US)

( * ) Notice: Subject to any disclaimer, the term of this patent is extended or adjusted under 35 U.S.C. 154(b) by 367 days.

(21) Appl. No.: 18/007,705

(22) PCT Filed: Jun. 2, 2021

(86) PCT No.: PCT/US2021/035509

§ 371 (c)(1),
(2) Date: Dec. 1, 2022

(87) PCT Pub. No.: WO2021/247748

PCT Pub. Date: Dec. 9, 2021

(65) Prior Publication Data

US 2023/0219923 A1 Jul. 13, 2023

Related U.S. Application Data

(60) Provisional application No. 63/136,593, filed on Jan. 12, 2021, provisional application No. 63/136,577, filed on Jan. 12, 2021, provisional application No. 63/136,587, filed on Jan. 12, 2021, provisional application No. 63/033,728, filed on Jun. 2, 2020, provisional application No. 63/033,724, filed on Jun. 2, 2020, provisional application No. 63/033,729, filed on Jun. 2, 2020.

(51) Int. Cl.

| | |
|---|---|
| ***C07D 401/04*** | (2006.01) |
| ***A61P 35/00*** | (2006.01) |
| ***C07D 403/04*** | (2006.01) |
| ***C07D 471/04*** | (2006.01) |
| ***C07D 471/10*** | (2006.01) |

(52) U.S. Cl.
CPC ............ *C07D 401/04* (2013.01); *A61P 35/00* (2018.01); *C07D 403/04* (2013.01); *C07D 471/04* (2013.01); *C07D 471/10* (2013.01)

(58) Field of Classification Search
CPC ...... C07D 401/04; C07D 471/04; A61P 35/00
See application file for complete search history.

(56) References Cited

U.S. PATENT DOCUMENTS

2015/0005279 A1 1/2015 Bonafoux et al.

FOREIGN PATENT DOCUMENTS

WO 2016/065236 A1 4/2016
WO WO-2016065226 A1 * 4/2016 ........... C07D 401/04

OTHER PUBLICATIONS

Watterson et al., "Discovert of Branebrutinib (BMS-986195): A Strategy for Identifying a Highly Potent and Selective Covalent Inhibitor Providing Rapid in Vivo Inactivation of Bruton's Tyrosine Kinase (BTK)", Journal of Medicinal Chemistry, vol. 62, No. 7, Mar. 20, 2019, pp. 3228-3250.

* cited by examiner

*Primary Examiner* — Andrew S Rosenthal
(74) *Attorney, Agent, or Firm* — WILSON SONSINI GOODRICH & ROSATI

(57) ABSTRACT

Disclosed herein are 1H-indole-7-carboxamide derivatives as protein kinase inhibitors, in particular Bruton's tyrosine kinase (BTK) inhibitors, pharmaceutical compositions comprising them, processes for preparing them and uses of such protein kinase inhibitors to treat or prevent diseases, disorders and conditions associated with kinase function. In particular, the present invention relates to selective BTK inhibitors.

25 Claims, No Drawings

KINASE INHIBITORS

FIELD OF THE INVENTION

The present invention relates generally to protein kinase inhibitors, in particular Bruton tyrosine kinase (BTK) inhibitors, pharmaceutical compositions comprising them, processes for preparing them and uses of such inhibitors to treat or prevent diseases, disorders and conditions associated with kinase function.

BACKGROUND

Protein kinases are a large group of intracellular and transmembrane signaling proteins in eukaryotic cells. These enzymes are responsible for transfer of the terminal (gamma) phosphate from ATP to specific amino acid residues of target proteins. Phosphorylation of specific amino acid residues in target proteins can modulate their activity leading to profound changes in cellular signaling and metabolism. Protein kinases can be found in the cell membrane, cytosol and organelles such as the nucleus and are responsible for mediating multiple cellular functions including metabolism, cellular growth and differentiation, cellular signaling, modulation of immune responses, and cell death. Serine kinases specifically phosphorylate serine or threonine residues in target proteins. Similarly, tyrosine kinases, including tyrosine receptor kinases, phosphorylate tyrosine residues in target proteins. Tyrosine kinase families include: TEC, SRC, ABL, JAK, CSK, FAK, SYK, FER, ACK and the receptor tyrosine kinase subfamilies including ERBB, FGFR, VEGFR, RET and EPH. Subclass I of the receptor tyrosine kinase superfamily includes the ERBB receptors and comprises four members: ErbB1 (also called epidermal growth factor receptor (EGFR)), ErbB2, ErbB3 and ErbB4.

Kinases exert control on key biological processes related to health and disease. Furthermore, aberrant activation or excessive expression of various protein kinases are implicated in the mechanism of multiple diseases and disorders characterized by benign and malignant proliferation, as well as diseases resulting from inappropriate activation of the immune system. Thus, inhibitors of select kinases or kinase families are considered useful in the treatment of cancer, vascular disease, autoimmune diseases, and inflammatory conditions including, but not limited to: solid tumors, hematological malignancies, thrombus, arthritis, graft versus host disease, lupus erythematosus, psoriasis, colitis, illeitis, multiple sclerosis, uveitis, coronary artery vasculopathy, systemic sclerosis, atherosclerosis, asthma, transplant rejection, allergy, ischemia, dermatomyositis, pemphigus, and the like.

Tec kinases are a family of non-receptor tyrosine kinases predominantly, but not exclusively, expressed in cells of hematopoietic origin. The Tec family includes TEC, Bruton's tyrosine kinase (BTK), inducible T-cell kinase (ITK), resting lymphocyte kinase (RLK/TXK for Tyrosine Protein Kinase), and bone marrow-expressed kinase (BMX/ETK).

BTK is important in B-cell receptor signaling and regulation of B-cell development and activation. Mutation of the gene encoding BTK in humans leads to X-linked agammaglobulinemia which is characterized by reduced immune function, including impaired maturation of B-cells, decreased levels of immunoglobulin and peripheral B cells, and diminished T-cell independent immune response. BTK is activated by Src-family kinases and phosphorylates PLC gamma leading to effects on B-cell function and survival. Additionally, BTK is important for cellular function of mast cells, macrophage and neutrophils indicating that BTK inhibition is effective in treatment of diseases mediated by these and related cells including inflammation, bone disorders, and allergic disease. BTK inhibition is also important in survival of lymphoma cells indicating that inhibition of BTK is useful in the treatment of lymphomas and other cancers. As such, inhibitors of BTK and related kinases are of great interest as antiinflammatory, as well as anti-cancer, agents. BTK is also important for platelet function and thrombus formation indicating that BTK-selective inhibitors are also useful as antithrombotic agents. Furthermore, BTK is required for inflammasome activation, and inhibition of BTK may be used in treatment of inflammasome-related disorders, including; stroke, gout, type 2 diabetes, obesity-induced insulin resistance, atherosclerosis and Muckle-Wells syndrome. In addition, BTK is expressed in HIV infected T-cells and treatment with BTK inhibitors sensitizes infected cells to apoptotic death and results in decreased virus production. Accordingly, BTK inhibitors are considered useful in the treatment of HIV-AIDS and other viral infections.

Further, BTK is important in neurological function. Specifically targeting BTK in the brain and CNS has the potential to significantly advance the treatment of neurological diseases such as progressive and relapsing forms of MS and primary CNS lymphoma (PCNSL). PCNSL is a rare brain tumor with an annual incidence in the United States of approximately 1900 new cases each year and constitutes approximately 3% of all newly diagnosed brain tumors.

PCNSL is highly aggressive and unlike other lymphomas outside the CNS, prognosis remains poor despite improvements in treatments in the front-line setting. High dose methotrexate remains the backbone of treatment and is used in combination with other cytotoxic agents, and more recently the addition of rituximab. From initial diagnosis, 5-year survival has improved from 19% to 30% between 1990 and 2000 but has not improved in the elderly population (>70 years), due to 20% or more of these patients being considered unfit for chemotherapy. Tumor regression is observed in ~85% of patients regardless of the treatment modality in the front-line setting, however, approximately half of these patients will experience recurrent disease within 10-18 months after initial treatment and most relapses occur within the first 2 years of diagnosis.

Thus, the prognosis for patients with relapsed/refractory PCNSL (R/R PCNSL) remains poor with a median survival of ~2 months without further treatment. As there is no uniform standard of care for the treatment of R/R PCNSL, participation in clinical trials is encouraged. New safe and effective treatments are urgently needed.

Btk is involved in the signal transduction in the B cell antigen receptor (BCR) signaling pathway and integrates BCR and Toll-like receptor (TLR) signaling. Genes in these pathways frequently harbor mutations in diffuse large B-cell lymphoma (DLBCL), including CD79B and myeloid differentiation primary response 88 (MyD88). Ibrutinib, a first-generation irreversible selective inhibitor of Btk, has been approved for chronic lymphocytic leukemia/small cell lymphocytic lymphoma (CLL/SLL), previously treated Mantle Cell lymphoma (MCL) and Marginal Zone Lymphoma (MZL), Waldenström's macroglobulin, and previously treated chronic Graft Versus Host Disease. In clinical studies the recommended dose of ibrutinib (480 mg/d in CLL or 560 mg/d in MCL) was escalated to 840 mg to achieve adequate brain exposure in primary CNS lymphoma.

Aberrant activation of the NF-κB pathway in PCNSL is emerging as a potential mechanism for more targeted therapy. In particular, activating mutations of CARD11 as well as of MyD88 (Toll-like receptor pathway) have been implicated. The activating exchange of leucine to proline at position 265 of MyD88, noted to occur in between 38% (11/29) and 50% (7/14) of patients, is the most frequent mutation identified thus far in PCNSL. In addition, the coding region of CD79B, a component of the B-cell receptor-signaling pathway, appears to contain mutations in 20% of cases, suggesting that dysregulation of the B-cell receptor and NF-κB pathways contribute to the pathogenesis of PCNSL. These data suggest that BCR pathway mutations and Btk dependence are of particular relevance to PCNSL.

Recently, several clinical studies have reported substantial single-agent clinical activity in the treatment of PCNSL with response rates of 70-77%. The majority of patients, however, discontinued therapy by 9 months. Although ibrutinib therapy has been reported to be generally well tolerated with manageable adverse events, there are reports of sometimes fatal fungal infections. Of note, escalating doses beyond 560 mg to 840 mg/day have been used to achieve higher brain exposure and these higher doses may be associated with off-target effects mediated by ibrutinib's kinase selectivity profile. Finally, the combination of high dose ibrutinib in conjunction with high-dose steroids may contribute to exacerbate the increased fungal infections. Therefore, a second generation of Btk inhibitor with an improved efficacy and safety profile due to greater brain penetration and Btk inactivation rate with greater kinase selectivity may be beneficial for PCNSL patients.

Additionally, there remains a need for compounds that modulate protein kinases generally, as well as compounds that modulate specific protein kinases, such as BTK, as well as compounds that modulate specific protein kinases and selectively cross the blood/brain barrier for related compositions and methods for treating diseases, disorders and conditions that would benefit from such modulation and selectivity.

BRIEF SUMMARY

In one aspect, compounds are provided having the structure of Formula (I):

Formula (I)

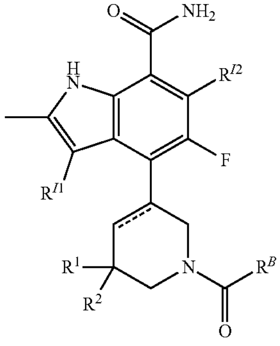

or a pharmaceutically acceptable salt, solvate, hydrate, isomer, tautomer, racemate, or isotope thereof, wherein:

$\overline{- - -}$ represents a single bond or a double bond;

$R^1$ is —H, —$CH_3$ or —F;

$R^2$ is —H, —$CH_3$ or —F;

or $R^1$ and $R^2$ together with the C atom to which they are attached form a $C_{3-6}$-membered carbocyclic ring;

$R^{I1}$ is —Cl, —F, —CN, —$CH_3$, —$CH_2F$, —$CHF_2$ or —$CF_3$;

$R^{I2}$ is —H or —F; and $R^B$ is —CH═$CH_2$, —C≡CH or —C≡C—$CH_3$;

and wherein when $R^{I1}$ is —$CH_3$, at least one of $R^1$ and $R^2$ is —$CH_3$ or —F.

In another aspect, compounds are provided having the structure of Formula (II):

Formula (II)

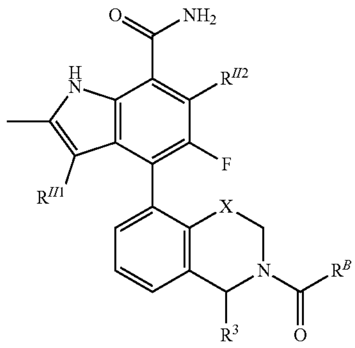

or a pharmaceutically acceptable salt, solvate, hydrate, isomer, tautomer, racemate or isotope thereof, wherein:

$R^3$ is H, Me or cyclopropyl;

X is —$CH_2CH_2$— or —$CR^{x1}R^{x2}$—;

$R^{x1}$ is H, F or Me;

$R^{x2}$ is H, F or Me;

or $R^{x1}$ and $R^{x2}$ together with the C atom to which there are attached form a $C_{3-6}$-membered carbocyclic ring;

or $R^{x1}$ is H and $R^{x2}$ and $R^3$ together form an alkylene bridge;

$R^{II1}$ is Cl, F, —$CH_2F$, —$CHF_2$, —$CF_3$ or —CN;

$R^{II2}$ is H or F; and $R^B$ is —CH═$CH_2$, —C≡CH or —C≡C—$CH_3$.

In yet another aspect, compounds are provided having the structure of Formula (III):

Formula (III)

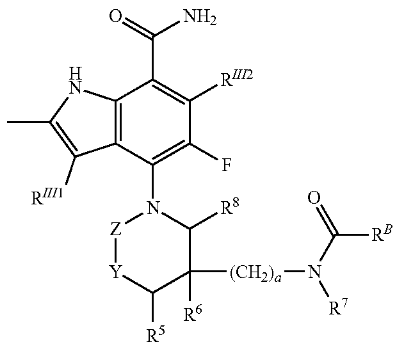

or a pharmaceutically acceptable salt, solvate, hydrate, isomer, tautomer, racemate or isotope thereof, wherein:

Z is —$CH_2$—, —CHMe- or a bond;

Y is —$CHR^4$— or a bond;

$R^4$ is H, F, or OH;

$R^5$ is H, F, or Me;

$R^6$ is H or Me;

$R^7$ is H or Me;

$R^8$ is H;

or $R^5$ and $R^7$, taken together, form a 5- or 6-membered heterocycle;

or $R^6$ and $R^7$, taken together, form a 4-, 5- or 6-membered heterocycle;

or $R^8$ and $R^7$, taken together, form a 5- or 6-membered heterocycle;

a is 0, 1 or 2;

$R^{III1}$ is Cl, F, $—CH_2F$, $—CHF_2$, $—CF_3$ or —CN; or $R^{III1}$ is $—CH_3$ when $R^4$ is F or OH, or when $R^5$ is F, or when $R^5$ and $R^7$ or $R^8$ and $R^7$, taken together, form a 5- or 6-membered heterocycle, or when $R^6$ and $R^7$, taken together, form a 4-, 5- or 6-membered heterocycle;

$R^{III2}$ is H or F; and $R^B$ is $—CH{=}CH_2$, $—C{\equiv}CH$ or $—C{\equiv}C—CH_3$.

In one embodiment, a pharmaceutical composition is provided comprising a compound having the structure of Formula (I), Formula (II) or Formula (III), or a pharmaceutically acceptable salt, solvate, hydrate, isomer, tautomer, racemate, or isotope thereof, and at least one pharmaceutically acceptable excipient.

In one embodiment, a method of modulating a protein kinase is provided comprising contacting the protein kinase with an effective amount of a compound having the structure of Formula (I), Formula (II) or Formula (III), or a pharmaceutically acceptable salt, solvate, hydrate, isomer, tautomer, racemate, isotope, or pharmaceutical composition thereof. In one embodiment, the protein kinase is BTK.

In one embodiment, a method for treating a BTK dependent condition is provided, comprising administering to a subject in need thereof an effective amount of a compound having the structure of Formula (I), Formula (II) or Formula (III), or a pharmaceutically acceptable salt, solvate, hydrate, isomer, tautomer, racemate, isotope, or pharmaceutical composition thereof.

In one embodiment, the use of a compound having the structure of Formula (I), Formula (II) or Formula (III), or a pharmaceutically acceptable salt, solvate, hydrate, isomer, tautomer, racemate, isotope, or pharmaceutical composition thereof is provided, in the manufacture of a medicament.

DETAILED DESCRIPTION

Unless defined otherwise, all technical and scientific terms used herein have the same meaning as is commonly understood by one of skill in the art to which the claimed subject matter belongs. It is to be understood that the detailed description is exemplary and explanatory only and are not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, ranges and amounts can be expressed as "about" a particular value or range. About also includes the exact amount. Hence "about 100 μL" means "about 100 μL" and also "100 μL." In some embodiments, about means within 5% of the value. Hence, "about 100 μL" means 95-105 uL. Generally, the term "about" includes an amount that would be expected to be within experimental error.

As used herein, "alkyl" means a straight chain or branched saturated hydrocarbon group. "Lower alkyl" means a straight chain or branched alkyl group having from 1 to 8 carbon atoms, in some embodiments from 1 to 6 carbon atoms, in some embodiments from 1 to 4 carbon atoms, and in some embodiments from 1 to 2 carbon atoms. Examples of straight chain lower alkyl groups include, but are not limited to, methyl, ethyl, n-propyl, n-butyl, n-pentyl, n-hexyl, n-heptyl, and n-octyl groups. Examples of branched lower alkyl groups include, but are not limited to, isopropyl, iso-butyl, sec-butyl, t-butyl, neopentyl, isopentyl, and 2,2-dimethylpropyl groups.

"Alkenyl" groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to $—CH{=}CH_2$, $—CH{=}CH(CH_3)$, $—CH{=}C(CH_3)_2$, $—C(CH_3){=}CH_2$, $—C(CH_3){=}CH(CH_3)$, $—C(CH_2CH_3){=}CH_2$, $—CH{=}CHCH_2CH_3$, $—CH{=}CH(CH_2)_2CH_3$, $—CH{=}CH(CH_2)_3CH_3$, $—CH{=}CH(CH_2)_4CH_3$, vinyl, cyclohexenyl, cyclopentenyl, cyclohexadienyl, butadienyl, pentadienyl, and hexadienyl among others.

"Alkynyl" groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to $—C{\equiv}CH$, $—C{\equiv}C(CH_3)$, $—C{\equiv}C(CH_2CH_3)$, $—CH_2C{\equiv}CH$, $—CH_2C{\equiv}C(CH_3)$, and $—CH_2C{\equiv}C(CH_2CH_3)$, among others.

As used herein, "alkylene" means a divalent alkyl group. Examples of straight chain lower alkylene groups include, but are not limited to, methylene (i.e., $—CH_2—$), ethylene (i.e., $—CH_2CH_2—$), propylene (i.e., $—CH_2CH_2CH_2—$), and butylene (i.e., $—CH_2CH_2CH_2CH_2—$). As used herein, "heteroalkylene" is an alkylene group of which one or more carbon atoms is replaced with a heteroatom such as, but not limited to, N, O, S, or P.

"Alkoxy" refers to an alkyl as defined above joined by way of an oxygen atom (i.e., —O-alkyl). Examples of lower alkoxy groups include, but are not limited to, methoxy, ethoxy, n-propoxy, n-butoxy, isopropoxy, sec-butoxy, tert-butoxy, and the like.

The terms "carbocyclic" and "carbocycle" denote a ring structure wherein the atoms of the ring are carbon. Carbocycles may be monocyclic or polycyclic. Carbocycle encompasses both saturated and unsaturated rings. Carbocycle encompasses both cycloalkyl and aryl groups. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N substituents wherein N is the size of the carbocyclic ring with for example, alkyl, amino, hydroxy, cyano, carboxy, nitro, thio, alkoxy, and halogen groups.

"Cycloalkyl" groups are alkyl groups forming a ring structure, which can be substituted or unsubstituted. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups.

"Aryl" groups are cyclic aromatic hydrocarbons that do not contain heteroatoms. Thus, aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The terms "aryl" and "aryl groups" include fused rings wherein at least one ring, but not necessarily all rings, are aromatic, such as fused aromatic-aliphatic ring systems (e.g., indanyl, tetrahydronaphthyl, and the like).

"Carbocyclealkyl" refers to an alkyl as defined above with one or more hydrogen atoms replaced with carbocycle. Examples of carbocyclealkyl groups include, but are not limited to, benzyl and the like.

As used herein, "heterocycle" or "heterocyclyl" groups include aromatic and non-aromatic ring compounds (heterocyclic rings) containing 3 or more ring members, of which one or more is a heteroatom such as, but not limited to, N, O, S, or P. A heterocycle group as defined herein can be a heteroaryl group or a partially or completely saturated cyclic group including at least one ring heteroatom. In some embodiments, heterocycle groups include 3 to 20 ring members, whereas other such groups have 3 to 15 ring members. At least one ring contains a heteroatom, but every ring in a polycyclic system need not contain a heteroatom. For example, a dioxolanyl ring and a benzodioxolanyl ring system (methylenedioxyphenyl ring system) are both heterocycle groups within the meaning herein. A heterocycle group designated as a $C_2$-heterocycle can be a 5-membered ring with two carbon atoms and three heteroatoms, a 6-membered ring with two carbon atoms and four heteroatoms and so forth. Likewise, a $C_4$-heterocycle can be a 5-membered ring with one heteroatom, a 6-membered ring with two heteroatoms, and so forth. The number of carbon atoms plus the number of heteroatoms sums up to equal the total number of ring atoms. A saturated heterocyclic ring refers to a heterocyclic ring containing no unsaturated carbon atoms.

"Heteroaryl" groups are aromatic ring compounds containing 5 or more ring members, of which, one or more is a heteroatom such as, but not limited to, N, O, and S. A heteroaryl group designated as a $C_2$-heteroaryl can be a 5-membered ring with two carbon atoms and three heteroatoms, a 6-membered ring with two carbon atoms and four heteroatoms and so forth. Likewise, a $C_4$-heteroaryl can be a 5-membered ring with one heteroatom, a 6-membered ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl.

"Heterocyclealkyl" refers to an alkyl as defined above with one or more hydrogen atoms replaced with heterocycle. Examples of heterocyclealkyl groups include, but are not limited to, morpholinoethyl and the like.

"Halo" or "halogen" refers to fluorine, chlorine, bromine and iodine.

"Haloalkyl" refers to an alkyl as defined above with one or more hydrogen atoms replaced with halogen. Examples of lower haloalkyl groups include, but are not limited to, $-CF_3$, $-CH_2CF_3$, and the like.

"Haloalkoxy" refers to an alkoxy as defined above with one or more hydrogen atoms replaced with halogen. Examples of lower haloalkoxy groups include, but are not limited to $-OCF_3$, $-OCH_2CF_3$, and the like.

"Hydroxyalkyl" refers to an alkyl as defined above with one or more hydrogen atoms replaced with $-OH$. Examples of lower hydroxyalkyl groups include, but are not limited to $-CH_2OH$, $-CH_2CH_2OH$, and the like.

As used herein, the term "optionally substituted" refers to a group (e.g., an alkyl, carbocycle, or heterocycle) having 0, 1, or more substituents, such as 0-25, 0-20, 0-10 or 0-5 substituents. Substituents include, but are not limited to $-OR^a$, $-NR^aR^b$, $-S(O)_2R^a$ or $-S(O)_2OR^a$, halogen, cyano, alkyl, haloalkyl, alkoxy, carbocycle, heterocycle, carbocyclalkyl, or heterocyclealkyl, wherein each $R^a$ and $R^b$ is, independently, H, alkyl, haloalkyl, carbocycle, or heterocycle, or $R^a$ and $R^b$, together with the atom to which they are attached, form a 3-8 membered carbocycle or heterocycle.

"Isomer" is used herein to encompass all chiral, diastereomeric or racemic forms of a structure, unless a particular stereochemistry or isomeric form is specifically indicated. Such compounds can be enriched or resolved optical isomers at any or all asymmetric atoms as are apparent from the depictions, at any degree of enrichment. Both racemic and diastereomeric mixtures, as well as the individual optical isomers can be synthesized to be substantially free of their enantiomeric or diastereomeric partners, and these are all within the scope of certain embodiments of the disclosure. The isomers resulting from the presence of a chiral center comprise a pair of non-superimposable isomers that are called "enantiomers." Single enantiomers of a pure compound are optically active (i.e., they can rotate the plane of plane polarized light and designated R or S).

"Isolated optical isomer" means a compound which has been substantially purified from the corresponding optical isomer(s) of the same formula. For example, the isolated isomer may be at least about 80%, at least 80% or at least 85% pure. In other embodiments, the isolated isomer is at least 90% pure or at least 98% pure, or at least 99% pure by weight.

"Substantially enantiomerically or diastereomerically" pure means a level of enantiomeric or diastereomeric enrichment of one enantiomer with respect to the other enantiomer or diastereomer of at least about 80%, and more specifically in excess of 80%, 85%, 90%, 95%, 98%, 99%, 99.5% or 99.9%.

The terms “racemate” and “racemic mixture” refer to an equal mixture of two enantiomers. A racemate is labeled “(±)” because it is not optically active (i.e., will not rotate plane-polarized light in either direction since its constituent enantiomers cancel each other out).

A “hydrate” is a compound that exists in combination with water molecules. The combination can include water in stoichiometric quantities, such as a monohydrate or a dihydrate, or can include water in random amounts. As the term is used herein a “hydrate” refers to a solid form; that is, a compound in a water solution, while it may be hydrated, is not a hydrate as the term is used herein.

A “solvate” is similar to a hydrate except that a solvent other that water is present. For example, methanol or ethanol can form an “alcoholate”, which can again be stoichiometric or non-stoichiometric. As the term is used herein a “solvate” refers to a solid form; that is, a compound in a solvent solution, while it may be solvated, is not a solvate as the term is used herein.

“Isotope” refers to atoms with the same number of protons but a different number of neutrons, and an isotope of a compound of Formulas (I) includes any such compound wherein one or more atoms are replaced by an isotope of that atom. For example, carbon 12, the most common form of carbon, has six protons and six neutrons, whereas carbon 13 has six protons and seven neutrons, and carbon 14 has six protons and eight neutrons. Hydrogen has two stable isotopes, deuterium (one proton and one neutron) and tritium (one proton and two neutrons). While fluorine has several isotopes, fluorine 19 is longest-lived. Thus, an isotope of a compound having the structure of Formulas (I) includes, but not limited to, compounds of Formulas (I) wherein one or more carbon 12 atoms are replaced by carbon-13 and/or carbon-14 atoms, wherein one or more hydrogen atoms are replaced with deuterium and/or tritium, and/or wherein one or more fluorine atoms are replaced by fluorine-19.

“Salt” generally refers to an organic compound, such as a carboxylic acid or an amine, in ionic form, in combination with a counter ion. For example, salts formed between acids in their anionic form and cations are referred to as “acid addition salts”. Conversely, salts formed between bases in the cationic form and anions are referred to as “base addition salts.”

The term “pharmaceutically acceptable” refers an agent that has been approved for human consumption and is generally non-toxic. For example, the term “pharmaceutically acceptable salt” refers to nontoxic inorganic or organic acid and/or base addition salts (see, e.g., Lit et al., Salt Selection for Basic Drugs, Int. J. Pharm., 33, 201-217, 1986) (incorporated by reference herein).

Pharmaceutically acceptable base addition salts of compounds of the disclosure include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N'dibenzylethylenediamine, chloroprocaine, choline, diethanolamine, ethylenediamine, meglumine (N-methylglucamine), and procaine.

Pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aromatic aliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, hippuric, malonic, oxalic, embonic (pamoic), methanesulfonic, ethanesulfonic, benzenesulfonic, panthothenic, trifluoromethanesulfonic, 2-hydroxyethanesulfonic, p-toluenesulfonic, sulfanilic, cyclohexylaminosulfonic, stearic, alginic, Phydroxybutyric, salicylic, -galactaric, and galacturonic acid.

Although pharmaceutically unacceptable salts are not generally useful as medicaments, such salts may be useful, for example as intermediates in the synthesis of the compounds described herein, for example in their purification by recrystallization.

In certain embodiments, the disclosure provides a pharmaceutical composition comprising a compound as described herein, or a pharmaceutically acceptable isomer, racemate, hydrate, solvate, isotope, or salt thereof, together with at least one pharmaceutically acceptable carrier, diluent, or excipient. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid, or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent can include any sustained release material known in the art, such as glyceryl monostearate or glyceryl distearate, alone or mixed with a wax.

As used herein, the term “pharmaceutical composition” refers to a composition containing one or more of the compounds described herein, or a pharmaceutically acceptable isomer, racemate, hydrate, solvate, homolog or salt thereof, formulated with a pharmaceutically acceptable carrier, which can also include other additives, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein. Conventional procedures and ingredients for the selection and preparation of suitable formulations are described, for example, in Remington: The Science and Practice of Pharmacy, 21st Ed., Gennaro, Ed., Lippencott Williams & Wilkins (2005) and in The United States Pharmacopeia: The National Formulary (USP 36 NF31), published in 2013.

In other embodiments, there are provided methods of making a composition of a compound described herein including formulating a compound of the disclosure with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

As used herein, the term "pharmaceutically acceptable carrier" refers to any ingredient other than the disclosed compounds, or a pharmaceutically acceptable isomer, racemate, hydrate, solvate, homolog or salt thereof (e.g., a carrier capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents, or flavoring agents. The compositions can also be sterilized if desired.

The route of administration can be any route which effectively transports the active compound of the disclosure to the appropriate or desired site of action, such as oral, nasal, pulmonary, buccal, subdermal, intradermal, transdermal, or parenteral, e.g., rectal, depot, subcutaneous, intravenous, intraurethral, intramuscular, intranasal, ophthalmic solution, or an ointment, the oral route being preferred.

Dosage forms can be administered once a day, or more than once a day, such as twice or thrice daily. Alternatively, dosage forms can be administered less frequently than daily, such as every other day, or weekly, if found to be advisable by a prescribing physician. Dosing regimens include, for example, dose titration to the extent necessary or useful for the indication to be treated, thus allowing the patient's body to adapt to the treatment and/or to minimize or avoid unwanted side effects associated with the treatment. Other dosage forms include delayed or controlled-release forms. Suitable dosage regimens and/or forms include those set out, for example, in the latest edition of the Physicians' Desk Reference, incorporated herein by reference.

As used herein, the term "administering" or "administration" refers to providing a compound, a pharmaceutical composition comprising the same, to a subject by any acceptable means or route, including (for example) by oral, parenteral (e.g., intravenous), or topical administration.

As used herein, the term "treatment" refers to an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

As used herein, the term "subject" refers to an animal (e.g., a mammal, such as a human). A subject to be treated according to the methods described herein may be one who has been diagnosed with a neurodegenerative disease involving demyelination, insufficient myelination, or underdevelopment of a myelin sheath, e.g., a subject diagnosed with multiple sclerosis or cerebral palsy, or one at risk of developing the condition. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

As used herein, the term "effective amount" refers to a quantity of a specified agent sufficient to achieve a desired effect in a subject being treated with that agent. Ideally, an effective amount of an agent is an amount sufficient to inhibit or treat the disease without causing substantial toxicity in the subject. The effective amount of an agent will be dependent on the subject being treated, the severity of the affliction, and the manner of administration of the pharmaceutical composition. Methods of determining an effective amount of the disclosed compound sufficient to achieve a desired effect in a subject will be understood by those of skill in the art in light of this disclosure.

As used herein, the terms "modulate" or "modulating" refer to the ability to increase or decrease the activity of one or more protein kinases. Accordingly, compounds of the invention can be used in methods of modulating a protein kinase by contacting the protein kinase with any one or more of the compounds or compositions described herein. In some embodiments, the compounds can act as inhibitors of one or more protein kinases. In some embodiments, the compounds can act to stimulate the activity of one or more protein kinases. In further embodiments, the compounds of the invention can be used to modulate activity of a protein kinase in an individual in need of modulation of the receptor by administering a modulating amount of a compound as described herein.

As used herein, the term "BTK-mediated" or BTK-modulated or "BTK-dependent" diseases or disorders means any disease or other deleterious condition in which BTK, or a mutant thereof, is known to play a role. Accordingly, another embodiment of the present application relates to treating or lessening the severity of one or more diseases in which BTK, or a mutant thereof, is known to play a role. Specifically, the present application relates to a method of treating or lessening the severity of a disease or condition selected from a proliferative disorder or an autoimmune disorder, wherein said method comprises administering to a patient in need thereof a compounds of Formula (I) or a composition according to the present application.

Compounds

Disclosed herein are compounds having the structure of formula (I):

Formula (I)

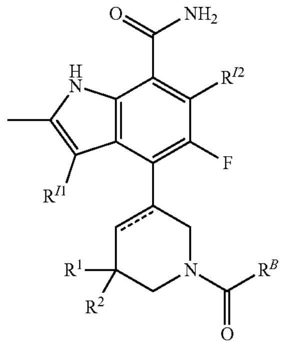

or a pharmaceutically acceptable salt, solvate, hydrate, isomer, tautomer, racemate, or isotope thereof, wherein:

- - - represents a single bond or a double bond;

$R^1$ is —H, —$CH_3$ or —F;

$R^2$ is —H, —$CH_3$ or —F;

or $R^1$ and $R^2$ together with the C atom to which they are attached form a $C_{3-6}$-membered carbocyclic ring;

$R^{I1}$ is —Cl, —F, —CN, —$CH_3$, —$CH_2F$, —$CHF_2$ or —$CF_3$;

$R^{I2}$ is —H or —F; and $R^B$ is —CH═$CH_2$, —C≡CH or —C≡C—$CH_3$;

and wherein when $R^1$ is —$CH_3$, at least one of $R^1$ and $R^2$ is —$CH_3$ or —F.

In some embodiments - - - represents a single bond. In other embodiments - - - represents a double bond.

In some embodiments $R^1$ is —H. In other embodiments $R^1$ is —$CH_3$. In other embodiments $R^1$ is —F. In some embodiments $R^1$ is —H and $R^2$ is —H. In other embodiments $R^1$ is —H and $R^2$ is —$CH_3$. In other embodiments $R^1$ is —H and $R^2$ is —F. In other embodiments $R^1$ is —$CH_3$. and $R^2$ is —$CH_3$. In other embodiments $R^1$ is —$CH_3$. and $R^2$ is —F. In other embodiments $R^1$ is —F. and $R^2$ is —F.

In some embodiments $R^1$ and $R^2$ together with the C atom to which they are attached form a $C_{3-6}$-membered carbocyclic ring. In some embodiments $R^1$ and $R^2$ together with the C atom to which they are attached form a cyclopropyl ring. In some embodiments $R^1$ and $R^2$ together with the C atom to which they are attached form a cyclopropyl ring. In some embodiments $R^1$ and $R^2$ together with the C atom to which they are attached form a cyclobutyl ring. In some embodiments $R^1$ and $R^2$ together with the C atom to which they are attached form a cyclopentyl ring. In some embodiments $R^1$ and $R^2$ together with the C atom to which they are attached form a cyclohexyl ring.

In some embodiments $R^{I1}$ is —Cl, —F, —CN, —$CH_2F$, —$CHF_2$ or —$CF_3$. In other embodiments $R^{I1}$ is —Cl or —F. In other embodiments $R^{I1}$ is —Cl. In other embodiments $R^1$ is —F. In other embodiments $R^{I1}$ is —CN. In other embodiments $R^{I1}$ is F, —$CH_2F$, —$CHF_2$ or —$CF_3$.

In some embodiments $R^{I2}$ is —H. In some embodiments $R^{I2}$ is —F.

In some embodiments $R^B$ is —CH═$CH_2$. In other embodiments $R^B$ is —C≡CH. In still other embodiments $R^B$ is —C≡C—$CH_3$.

In some embodiments - - - represents a single bond, $R^{I2}$ is —H, $R^1$ is —H; and $R^2$ is —H. In other embodiments - - - represents a single bond, $R^{I2}$ is —F, $R^1$ is —H; and $R^2$ is —H. In other embodiments - - - represents a single bond, $R^{I1}$ is —Cl, $R^{I2}$ is —F, $R^1$ is —H; and $R^2$ is —H.

In some embodiments are compounds having the structure of formula (I-S) or (I-R):

(I-S)

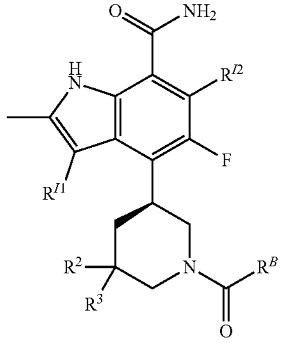

(I-R)

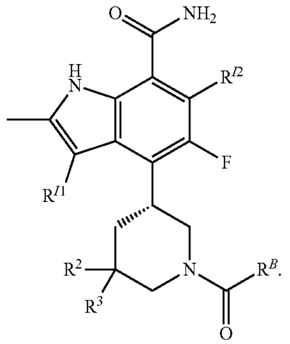

In some embodiments are compounds having the structure as shown below:
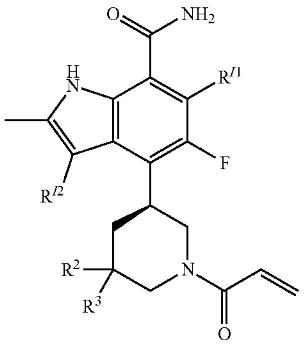
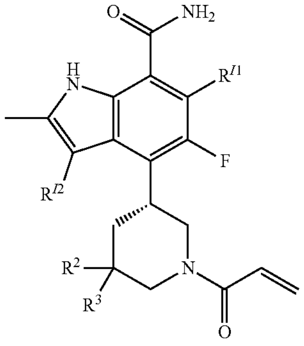
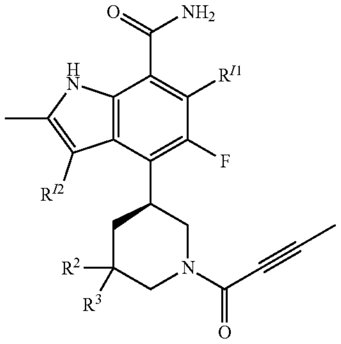
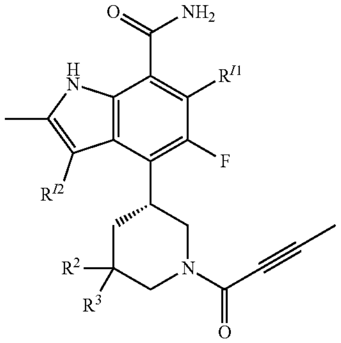
-continued
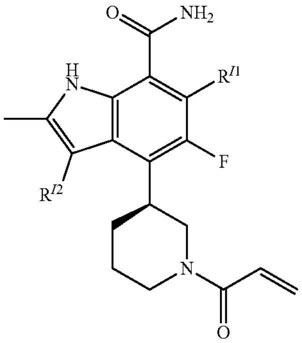
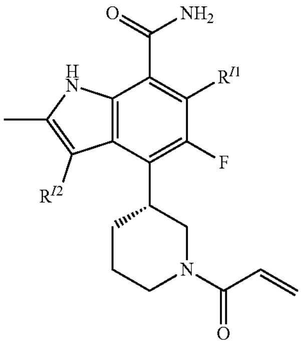
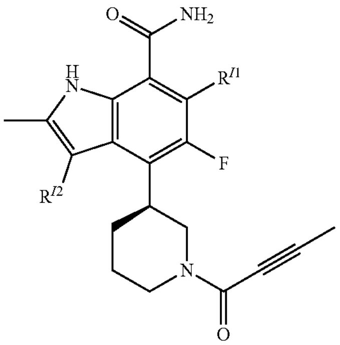
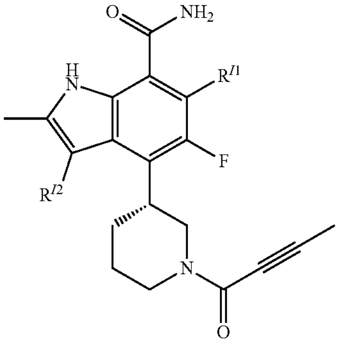
In one embodiment, a compound of Formula (I) is provided, or a pharmaceutically acceptable salt, solvate, hydrate, isomer, tautomer, racemate, or isotope thereof, having the structure of a compound of Table 1, below:

TABLE 1
| REPRESENTATIVE COMPOUNDS OF FORMULA (I) | | |
|---|---|---|
| Cmpd. No. | Structure | Name |
| 1 | 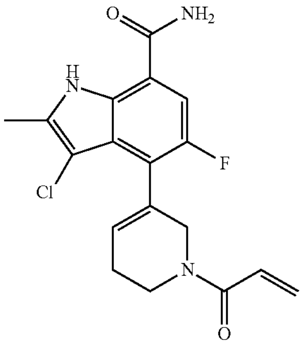 [SMILES: C=CC(=O)N1CCC=C(c2c(F)cc(C(N)=O)c3[nH]c(C)c(Cl)c23)C1] | 4-(1-acryloyl-1,2,5,6-tetrahydropyridin-3-yl)-3-chloro-5-fluoro-2-methyl-1H-indole-7-carboxamide |
| 2 | 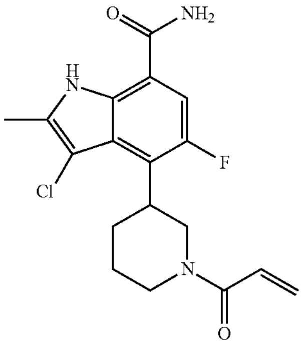 | 4-(1-acryloylpiperidin-3-yl)-3-chloro-5-fluoro-2-methyl-1H-indole-7-carboxamide |
| 2a | 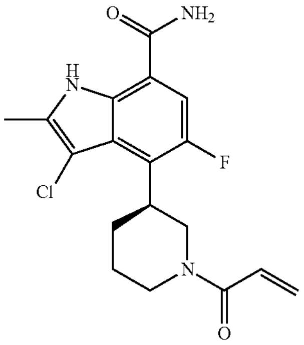 (S)- | (S)-4-(1-acryloylpiperidin-3-yl)-3-chloro-5-fluoro-2-methyl-1H-indole-7-carboxamide |
| and | | |
| 2b | 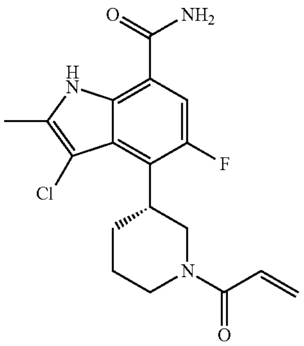 [SMILES: C=CC(=O)N1CCCC(c2c(F)cc(C(N)=O)c3[nH]c(C)c(Cl)c23)C1] (R)- | (R)-4-(1-acryloylpiperidin-3-yl)-3-chloro-5-fluoro-2-methyl-1H-indole-7-carboxamide |

TABLE 1-continued

| REPRESENTATIVE COMPOUNDS OF FORMULA (I) | | |
|---|---|---|
| Cmpd. No. | Structure | Name |
| 3 | 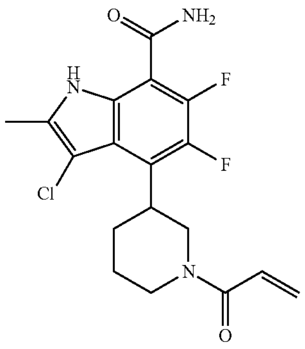 [SMILES: C=CC(=O)N1CCCC(c2c(F)c(F)c(C(N)=O)c3[nH]c(C)c(Cl)c23)C1] | 4-(1-acryloylpiperidin-3-yl)-3-chloro-5,6-difluoro-2-methyl-1H-indole-7-carboxamide |
| 4 | 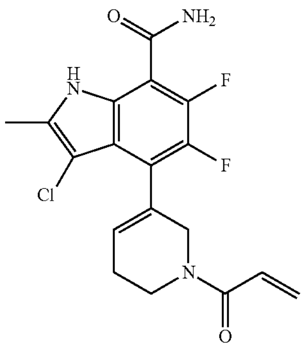 [SMILES: C=CC(=O)N1CCC=C(c2c(F)c(F)c(C(N)=O)c3[nH]c(C)c(Cl)c23)C1] | 4-(1-acryloyl-1,2,5,6-tetrahydropyridin-3-yl)-3-chloro-5,6-difluoro-2-methyl-1H-indole-7-carboxamide |
| 5 | 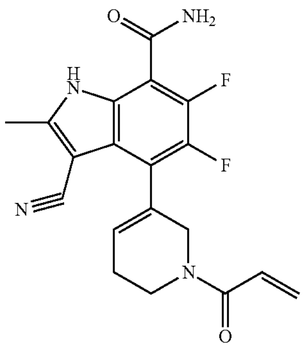 [SMILES: C=CC(=O)N1CCC=C(c2c(F)c(F)c(C(N)=O)c3[nH]c(C)c(C#N)c23)C1] | 4-(1-acryloyl-1,2,5,6-tetrahydropyridin-3-yl)-3-cyano-5,6-difluoro-2-methyl-1H-indole-7-carboxamide |
| 6a | 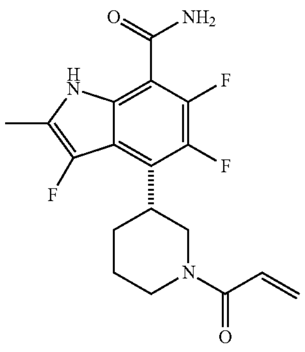 | (R)-4-(1-acryloylpiperidin-3-yl)-3,5,6-trifluoro-2-methyl-1H-indole-7-carboxamide |

TABLE 1-continued

| REPRESENTATIVE COMPOUNDS OF FORMULA (I) | | |
|---|---|---|
| Cmpd. No. | Structure | Name |
| 6b | 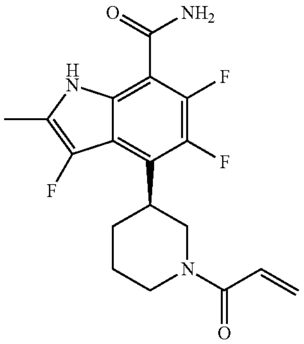 [SMILES: C=CC(=O)N1CCC[C@@H](c2c(F)c(F)c(C(N)=O)c3[nH]c(C)c(F)c23)C1] | (S)-4-(1-acryloylpiperidin-3-yl)-3,5,6-trifluoro-2-methyl-1H-indole-7-carboxamide |
| 7 | 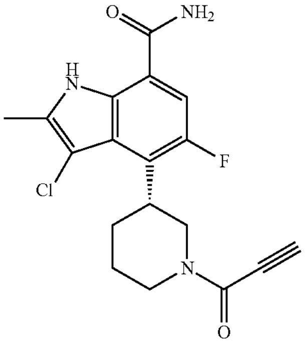<br>Assumed | (R)-3-chloro-5-fluoro-2-methyl-4-(1-propioloylpiperidin-3-yl)-1H-indole-7-carboxamide |
| 8 | 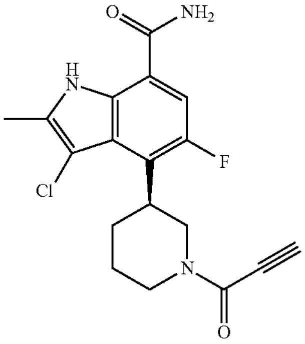<br>Assumed | (S)-3-chloro-5-fluoro-2-methyl-4-(1-propioloylpiperidin-3-yl)-1H-indole-7-carboxamide |
| 9 | 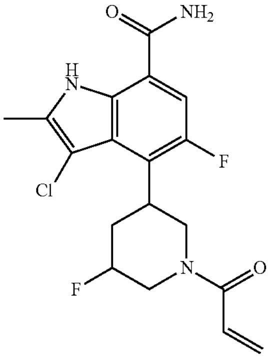 [SMILES: C=CC(=O)N1CC(F)CC(c2c(F)cc(C(N)=O)c3[nH]c(C)c(Cl)c23)C1] | 4-(1-acryloyl-5-fluoropiperidin-3-yl)-3-chloro-5-fluoro-2-methyl-1H-indole-7-carboxamide |

TABLE 1-continued

| REPRESENTATIVE COMPOUNDS OF FORMULA (I) | | |
|---|---|---|
| Cmpd. No. | Structure | Name |
| 10 | 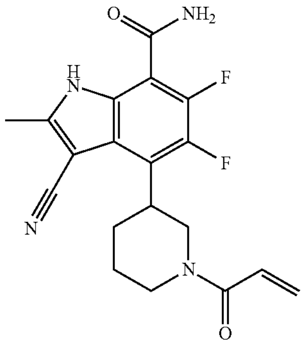 [SMILES: C=CC(=O)N1CCCC(c2c(F)c(F)c(C(N)=O)c3[nH]c(C)c(C#N)c23)C1] | 4-(1-acryloylpiperidin-3-yl)-3-cyano-5,6-difluoro-2-methyl-1H-indole-7-carboxamide |
| 11 | 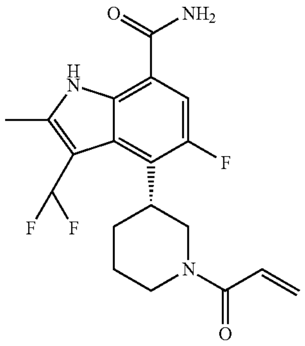 Assumed | (R)-4-(1-acryloylpiperidin-3-yl)-3-(difluoromethyl)-5-fluoro-2-methyl-1H-indole-7-carboxamide |
| 12 | 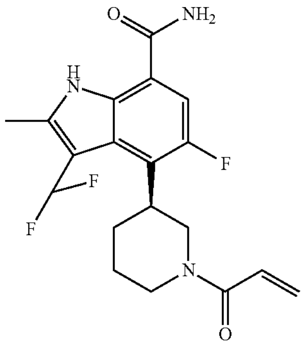 Assumed | (S)-4-(1-acryloylpiperidin-3-yl)-3-(difluoromethyl)-5-fluoro-2-methyl-1H-indole-7-carboxamide |
| 13 | 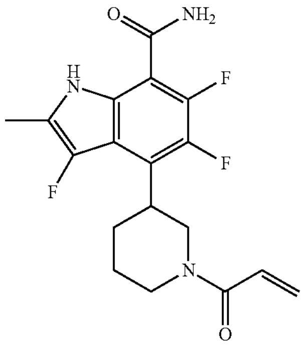 [SMILES: C=CC(=O)N1CCCC(c2c(F)c(F)c(C(N)=O)c3[nH]c(C)c(F)c23)C1] | 4-(1-acryloylpiperidin-3-yl)-3,5,6-trifluoro-2-methyl-1H-indole-7-carboxamide |

TABLE 1-continued

| REPRESENTATIVE COMPOUNDS OF FORMULA (I) | | |
|---|---|---|
| Cmpd. No. | Structure | Name |
| 14 | 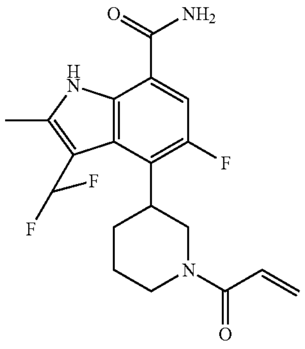 [SMILES: C=CC(=O)N1CCCC(c2c(F)cc(C(N)=O)c3[nH]c(C)c(C(F)F)c23)C1] | 4-(1-acryloylpiperidin-3-yl)-3-(difluoromethyl)-5-fluoro-2-methyl-1H-indole-7-carboxamide |
| 15 | 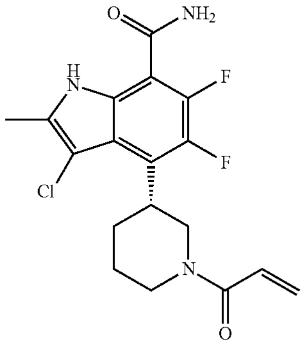 assumed | (R)-4-(1-acryloylpiperidin-3-yl)-3-chloro-5,6-difluoro-2-methyl-1H-indole-7-carboxamide |
| 16 | 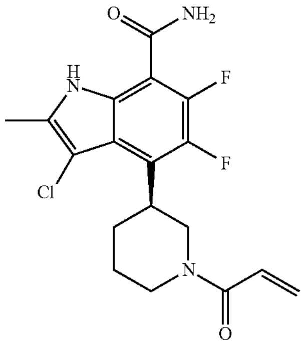 assumed | (S)-4-(1-acryloylpiperidin-3-yl)-3-chloro-5,6-difluoro-2-methyl-1H-indole-7-carboxamide |
| 17 | 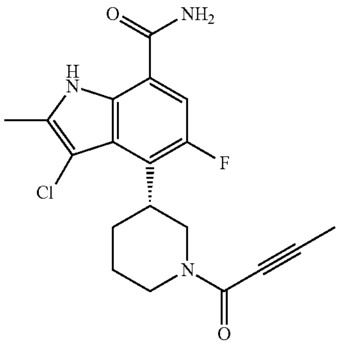 Assumed | (R)-4-(1-(but-2-ynoyl)piperidin-3-yl)-3-chloro-5-fluoro-2-methyl-1H-indole-7-carboxamide |

TABLE 1-continued

| REPRESENTATIVE COMPOUNDS OF FORMULA (I) | | |
|---|---|---|
| Cmpd. No. | Structure | Name |
| 18 | 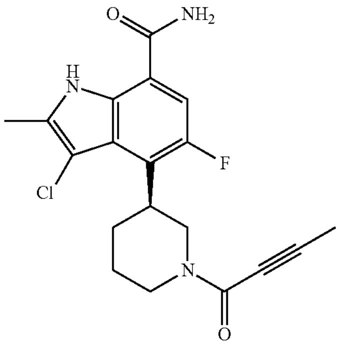 Assumed | (S)-4-(1-(but-2-ynoyl)piperidin-3-yl)-3-chloro-5-fluoro-2-methyl-1H-indole-7-carboxamide |
| 19 | 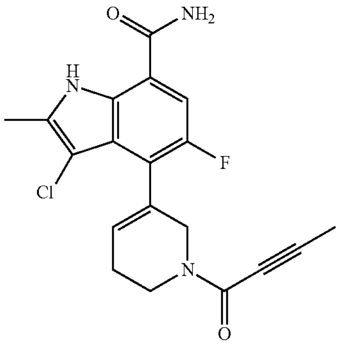 [SMILES: CC#CC(=O)N1CCC=C(c2c(F)cc(C(N)=O)c3[nH]c(C)c(Cl)c23)C1] | 4-(1-(but-2-ynoyl)-1,2,5,6-tetrahydropyridin-3-yl)-3-chloro-5-fluoro-2-methyl-1H-indole-7-carboxamide |

In another embodiment, a compound of Formula (I) is provided, or a pharmaceutically acceptable salt, solvate, hydrate, isomer, tautomer, racemate, or isotope thereof, having the structure of a compound of Table 2, below.

TABLE 2

| FURTHER REPRESENTATIVE COMPOUNDS OF FORMULA (I) |
|---|
| 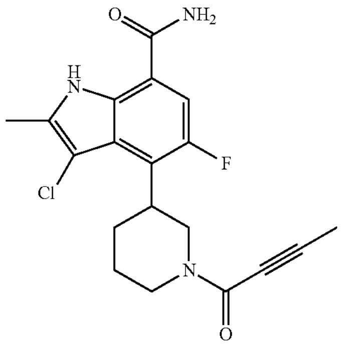 [SMILES: CC#CC(=O)N1CCCC(c2c(F)cc(C(N)=O)c3[nH]c(C)c(Cl)c23)C1] |

TABLE 2-continued

| FURTHER REPRESENTATIVE COMPOUNDS OF FORMULA (I) |
|---|
| 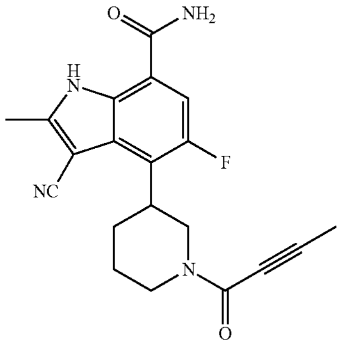 [SMILES: CC#CC(=O)N1CCCC(c2c(F)cc(C(N)=O)c3[nH]c(C)c(C#N)c23)C1] |
| 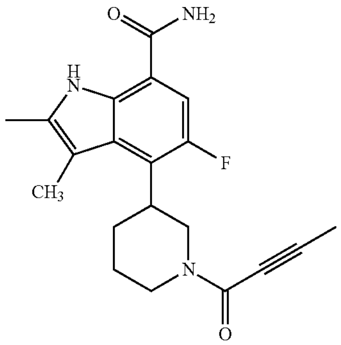 |

TABLE 2-continued
| FURTHER REPRESENTATIVE COMPOUNDS OF FORMULA (I) |
| --- |
| 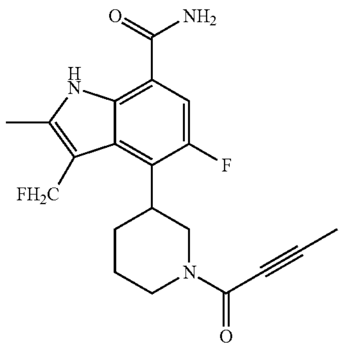 |
| 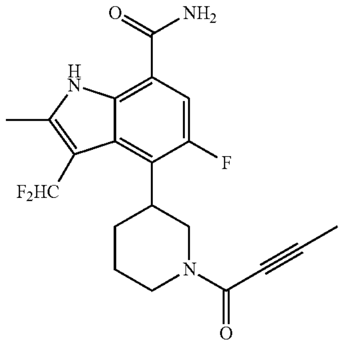 [SMILES: CC#CC(=O)N1CCCC(c2c(F)cc(C(N)=O)c3[nH]c(C)c(C(F)F)c23)C1] |
| 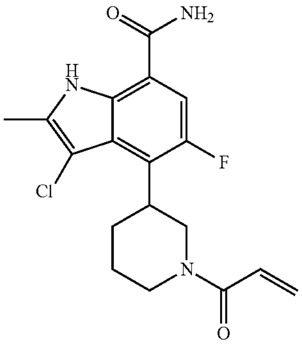 [SMILES: C=CC(=O)N1CCCC(c2c(F)cc(C(N)=O)c3[nH]c(C)c(Cl)c23)C1] |
| 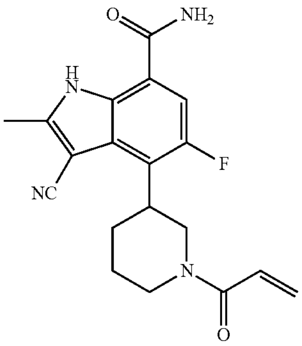 |
TABLE 2-continued
| FURTHER REPRESENTATIVE COMPOUNDS OF FORMULA (I) |
| --- |
| 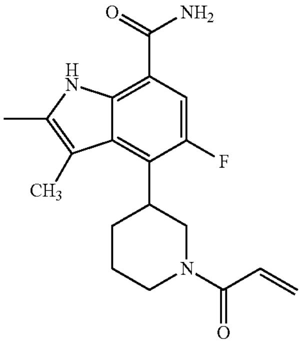 [SMILES: C=CC(=O)N1CCCC(c2c(F)cc(C(N)=O)c3[nH]c(C)c(C)c23)C1] |
| 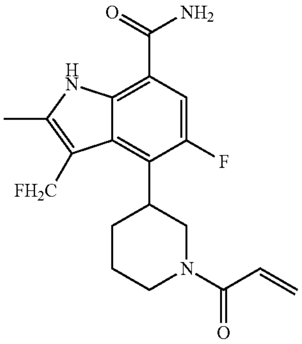 |
| 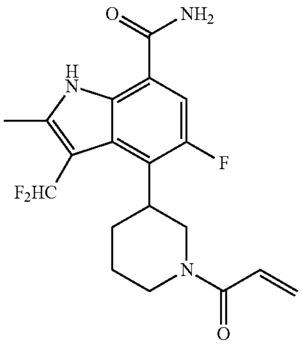 [SMILES: C=CC(=O)N1CCCC(c2c(F)cc(C(N)=O)c3[nH]c(C)c(C(F)F)c23)C1] |
| 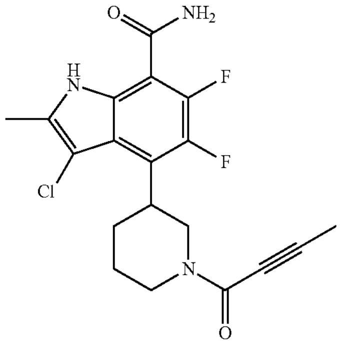 [SMILES: CC#CC(=O)N1CCCC(c2c(F)c(F)c(C(N)=O)c3[nH]c(C)c(Cl)c23)C1] |

TABLE 2-continued
| FURTHER REPRESENTATIVE COMPOUNDS OF FORMULA (I) |
|---|
| 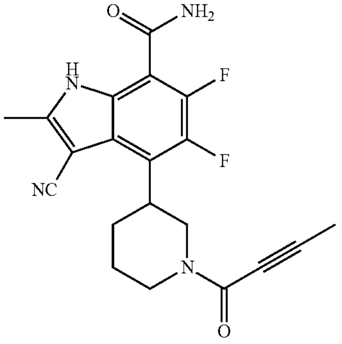 [SMILES: CC#CC(=O)N1CCCC(c2c(F)c(F)c(C(N)=O)c3[nH]c(C)c(C#N)c23)C1] |
| 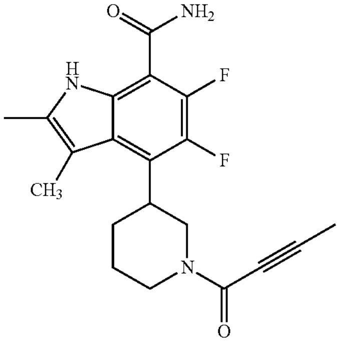 |
| 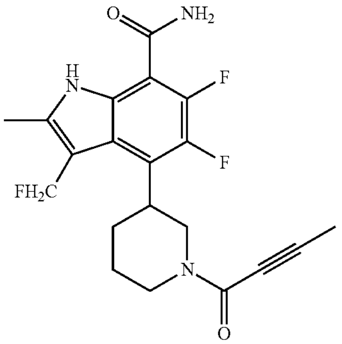 |
| 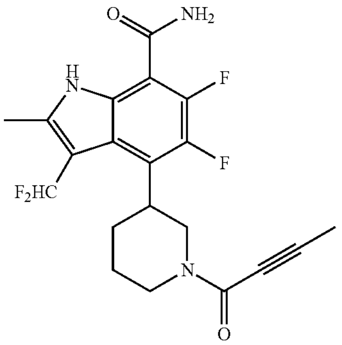 |
TABLE 2-continued
| FURTHER REPRESENTATIVE COMPOUNDS OF FORMULA (I) |
|---|
| 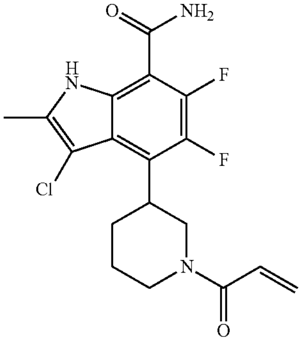 [SMILES: C=CC(=O)N1CCCC(c2c(F)c(F)c(C(N)=O)c3[nH]c(C)c(Cl)c23)C1] |
| 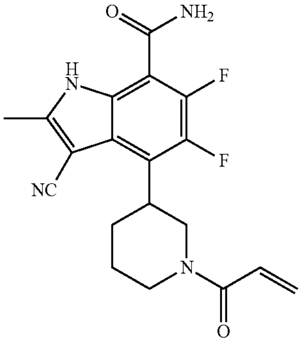 |
| 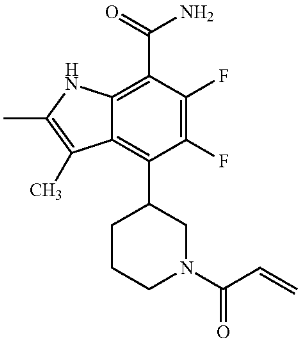 [SMILES: C=CC(=O)N1CCCC(c2c(F)c(F)c(C(N)=O)c3[nH]c(C)c(C)c23)C1] |
| 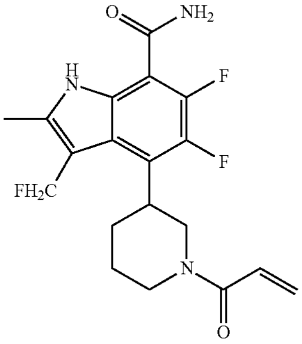 |

TABLE 2-continued
| FURTHER REPRESENTATIVE COMPOUNDS OF FORMULA (I) |
|---|
| 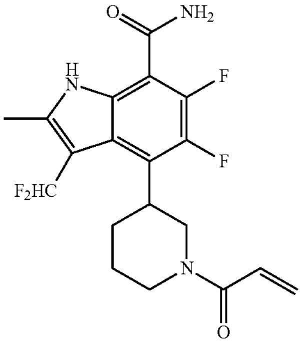 |
| 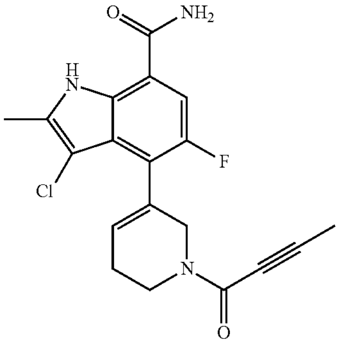 [SMILES: CC#CC(=O)N1CCC=C(c2c(F)cc(C(N)=O)c3[nH]c(C)c(Cl)c23)C1] |
| 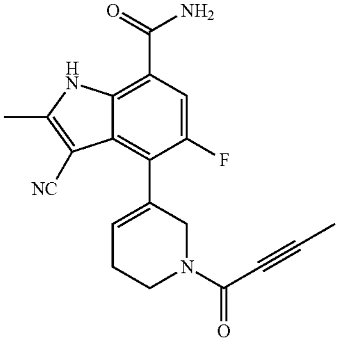 |
| 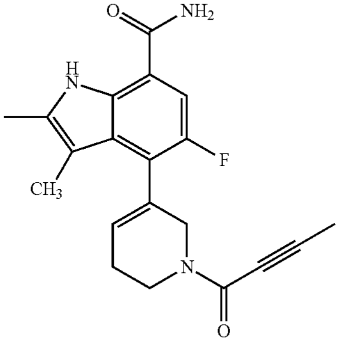 [SMILES: CC#CC(=O)N1CCC=C(c2c(F)cc(C(N)=O)c3[nH]c(C)c(C)c23)C1] |
TABLE 2-continued
| FURTHER REPRESENTATIVE COMPOUNDS OF FORMULA (I) |
|---|
| 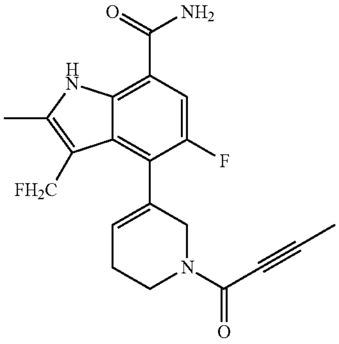 |
| 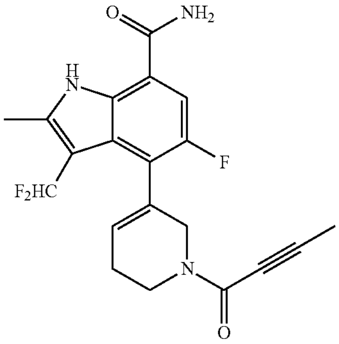 [SMILES: CC#CC(=O)N1CCC=C(c2c(F)cc(C(N)=O)c3[nH]c(C)c(C(F)F)c23)C1] |
| 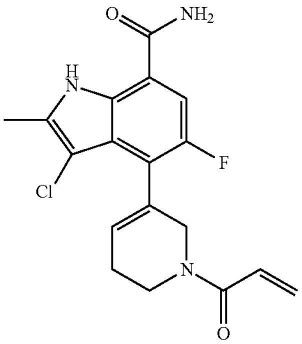 [SMILES: C=CC(=O)N1CCC=C(c2c(F)cc(C(N)=O)c3[nH]c(C)c(Cl)c23)C1] |
| 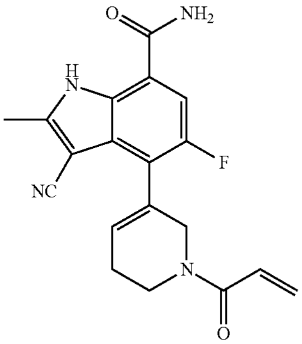 |

TABLE 2-continued
| FURTHER REPRESENTATIVE COMPOUNDS OF FORMULA (I) |
| --- |
| 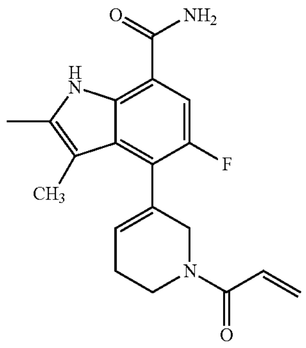 |
| 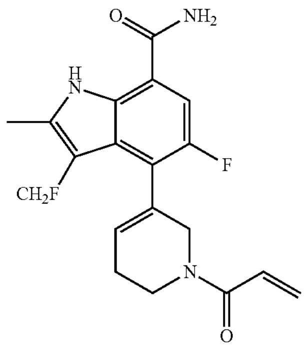 |
| 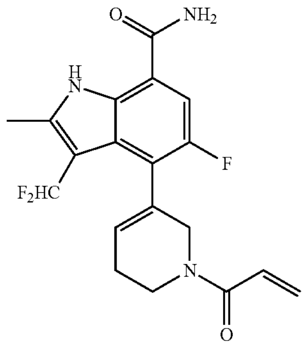 [SMILES: C=CC(=O)N1CCC=C(c2c(F)cc(C(N)=O)c3[nH]c(C)c(C(F)F)c23)C1] |
| 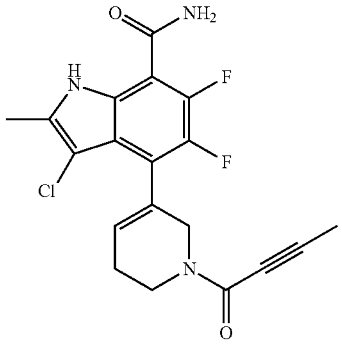 [SMILES: CC#CC(=O)N1CCC=C(c2c(F)c(F)c(C(N)=O)c3[nH]c(C)c(Cl)c23)C1] |
TABLE 2-continued
| FURTHER REPRESENTATIVE COMPOUNDS OF FORMULA (I) |
| --- |
| 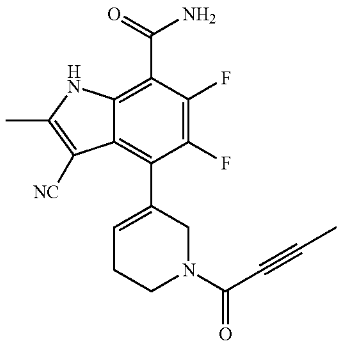 [SMILES: CC#CC(=O)N1CCC=C(c2c(F)c(F)c(C(N)=O)c3[nH]c(C)c(C#N)c23)C1] |
| 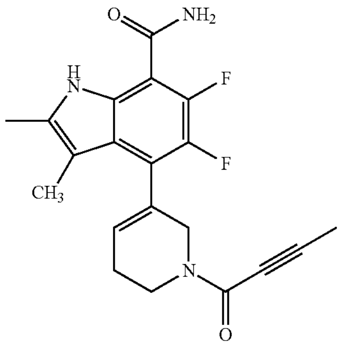 |
| 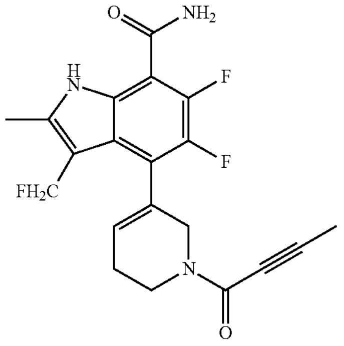 |
| 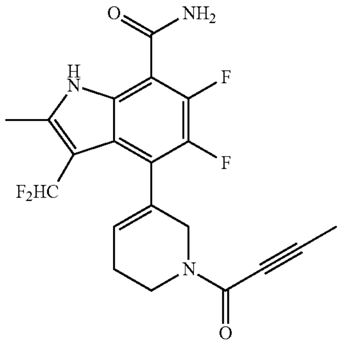 [SMILES: CC#CC(=O)N1CCC=C(c2c(F)c(F)c(C(N)=O)c3[nH]c(C)c(C(F)F)c23)C1] |

TABLE 2-continued
| FURTHER REPRESENTATIVE COMPOUNDS OF FORMULA (I) |
| --- |
| 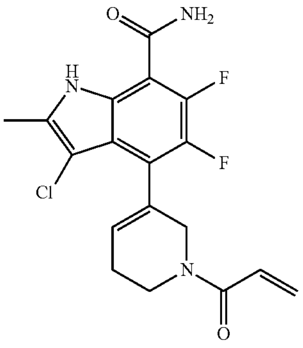 [SMILES: C=CC(=O)N1CCC=C(c2c(F)c(F)c(C(N)=O)c3[nH]c(C)c(Cl)c23)C1] |
| 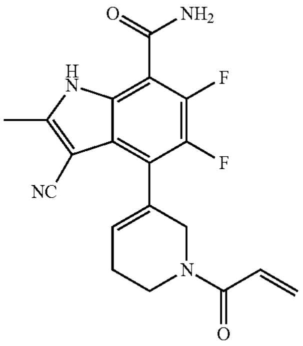 |
| 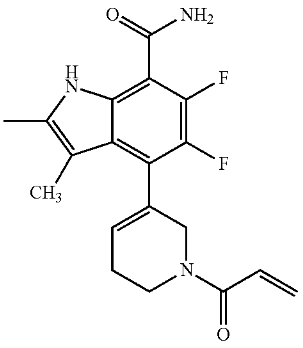 [SMILES: C=CC(=O)N1CCC=C(c2c(F)c(F)c(C(N)=O)c3[nH]c(C)c(C)c23)C1] |
| 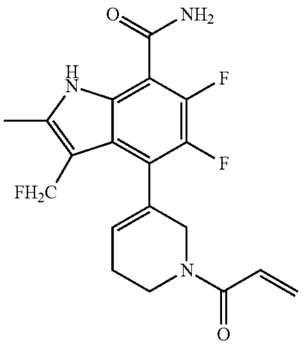 |
TABLE 2-continued
| FURTHER REPRESENTATIVE COMPOUNDS OF FORMULA (I) |
| --- |
| 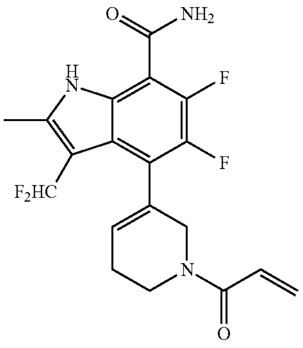 [SMILES: C=CC(=O)N1CCC=C(c2c(F)c(F)c(C(N)=O)c3[nH]c(C)c(C(F)F)c23)C1] |
| 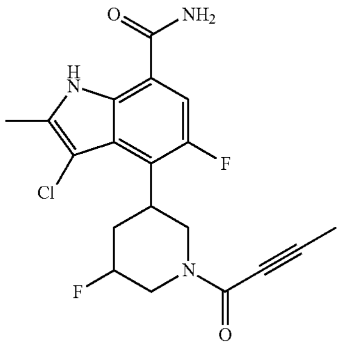 [SMILES: CC#CC(=O)N1CC(F)CC(c2c(F)cc(C(N)=O)c3[nH]c(C)c(Cl)c23)C1] |
| 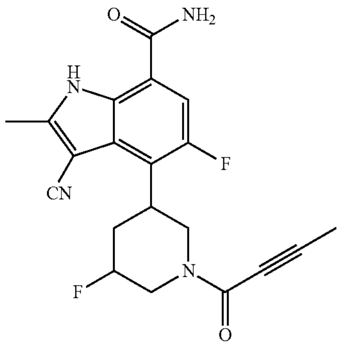 [SMILES: CC#CC(=O)N1CC(F)CC(c2c(F)cc(C(N)=O)c3[nH]c(C)c(C#N)c23)C1] |
| 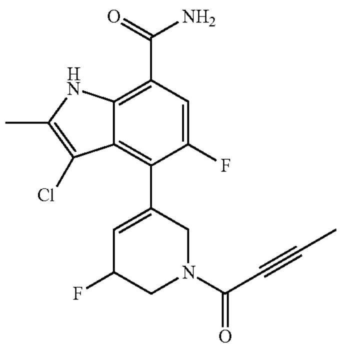 [SMILES: CC#CC(=O)N1CC(c2c(F)cc(C(N)=O)c3[nH]c(C)c(Cl)c23)=CC(F)C1] |

TABLE 2-continued
FURTHER REPRESENTATIVE COMPOUNDS OF FORMULA (I)
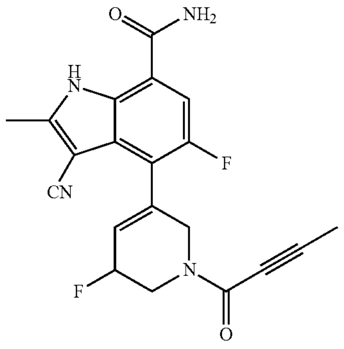 [SMILES: CC#CC(=O)N1CC(c2c(F)cc(C(N)=O)c3[nH]c(C)c(C#N)c23)=CC(F)C1]
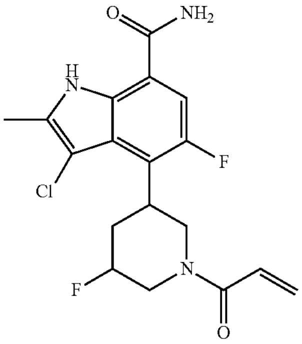 [SMILES: C=CC(=O)N1CC(F)CC(c2c(F)cc(C(N)=O)c3[nH]c(C)c(Cl)c23)C1]
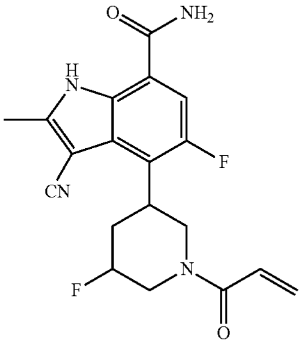 [SMILES: C=CC(=O)N1CC(F)CC(c2c(F)cc(C(N)=O)c3[nH]c(C)c(C#N)c23)C1]
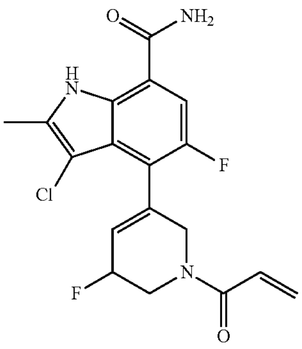 [SMILES: C=CC(=O)N1CC(c2c(F)cc(C(N)=O)c3[nH]c(C)c(Cl)c23)=CC(F)C1]
TABLE 2-continued
FURTHER REPRESENTATIVE COMPOUNDS OF FORMULA (I)
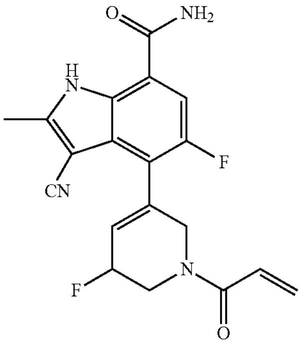 [SMILES: C=CC(=O)N1CC(c2c(F)cc(C(N)=O)c3[nH]c(C)c(C#N)c23)=CC(F)C1]
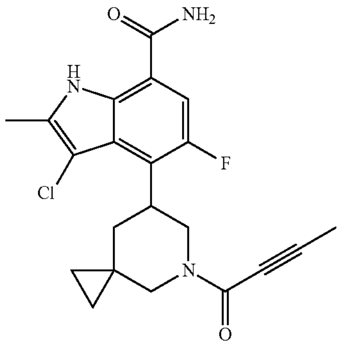 [SMILES: CC#CC(=O)N1CC(c2c(F)cc(C(N)=O)c3[nH]c(C)c(Cl)c23)CC2(CC2)C1]
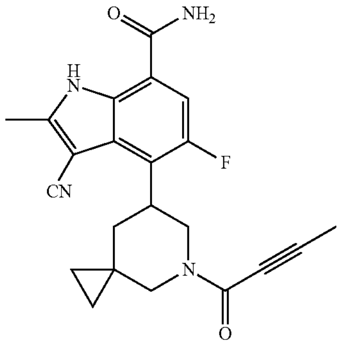 [SMILES: CC#CC(=O)N1CC(c2c(F)cc(C(N)=O)c3[nH]c(C)c(C#N)c23)CC2(CC2)C1]
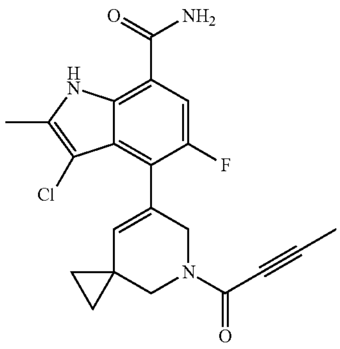 [SMILES: CC#CC(=O)N1CC(c2c(F)cc(C(N)=O)c3[nH]c(C)c(Cl)c23)=CC2(CC2)C1]

TABLE 2-continued

| FURTHER REPRESENTATIVE COMPOUNDS OF FORMULA (I) |
|---|
| 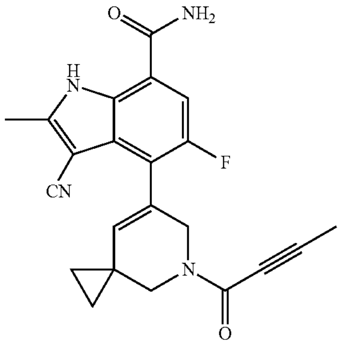 [SMILES: CC#CC(=O)N1CC(c2c(F)cc(C(N)=O)c3[nH]c(C)c(C#N)c23)=CC2(CC2)C1] |
| 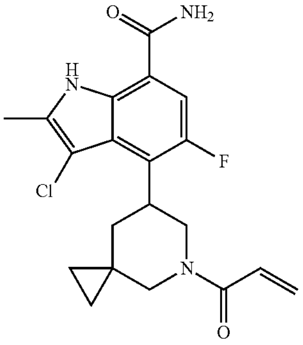 [SMILES: C=CC(=O)N1CC(c2c(F)cc(C(N)=O)c3[nH]c(C)c(Cl)c23)CC2(CC2)C1] |
| 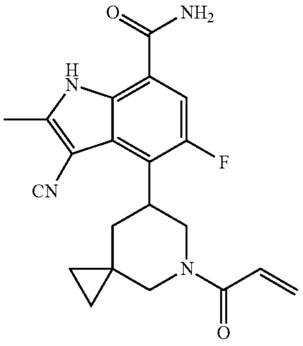 |
| 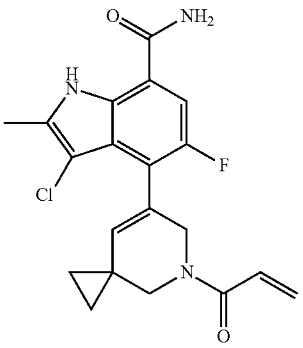 |

TABLE 2-continued

| FURTHER REPRESENTATIVE COMPOUNDS OF FORMULA (I) |
|---|
| 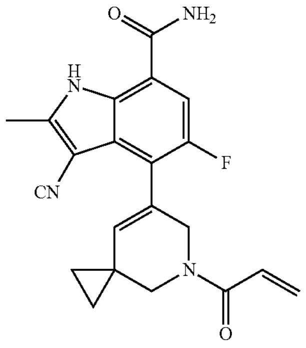 [SMILES: C=CC(=O)N1CC(c2c(F)cc(C(N)=O)c3[nH]c(C)c(Cl)c23)=CC2(CC2)C1] |

Also disclosed herein are compounds having the structure of formula (II):

(II)

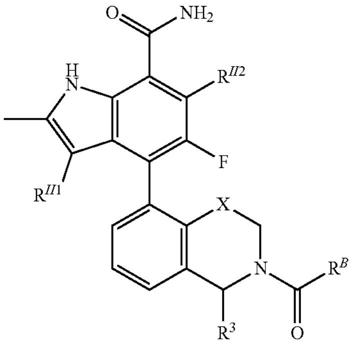

or a pharmaceutically acceptable salt, solvate, hydrate, isomer, tautomer, racemate or isotope thereof, wherein:

$R^3$ is H, Me or cyclopropyl;

X is $—CH_2CH_2—$ or $—CR^{x1}R^{x2}—$;

$R^{x1}$ is H, F or Me;

$R^{x2}$ is H, F or Me;

or $R^{x1}$ and $R^{x2}$ together with the C atom to which there are attached form a $C_{3-6}$-membered carbocyclic ring;

or $R^{x1}$ is H and $R^{x2}$ and $R^3$ together form an alkylene bridge; and $R^{II1}$ is Cl, F, $—CH_2F$, $—CHF_2$, $—CF_3$ or —CN;

$R^{II2}$ is H or F;

$R^B$ is $—CH{=}CH_2$, $—C{\equiv}CH$ or $—C{\equiv}C—CH_3$.

In one embodiment, $R^3$ is H. In another embodiment, $R^3$ is Me. In yet another embodiment, $R^3$ is cyclopropyl. In other embodiments, $R^3$ is H or Me.

In one embodiment X is —$CH_2CH_2$—:
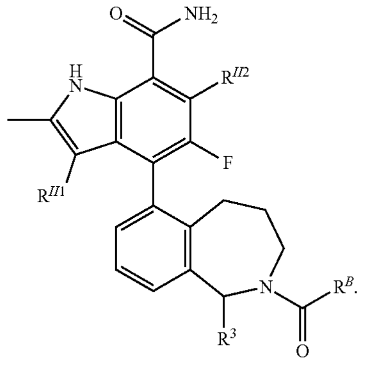
In one embodiment X is —$CR^{x1}R^{x2}$—:
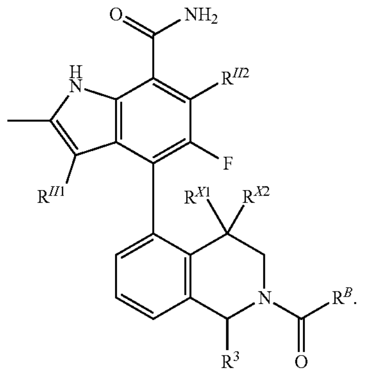
In one embodiment X is —$CR^{x1}R^{x2}$—, $R^{x1}$ is H, and $R^{x2}$ is H:
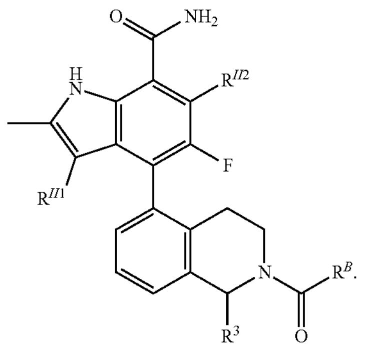
In one embodiment X is —$CR^{x1}R^{x2}$, $R^{x1}$ is H, and $R^{x2}$ is F:
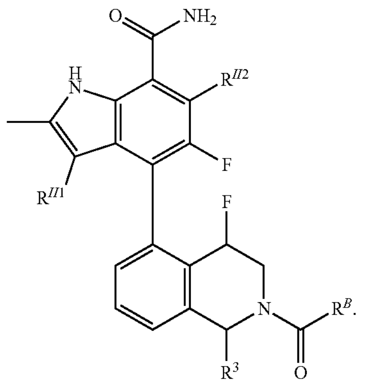
In one embodiment X is —$CR^{x1}R^{x2}$, $R^{x1}$ is F, and $R^{x2}$ is F:
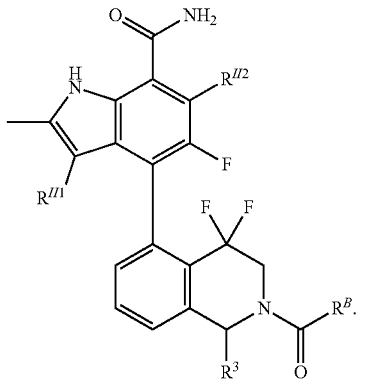
In one embodiment X is —$CR^{x1}R^{x2}$, $R^{x1}$ is Me, and $R^{x2}$ is F:
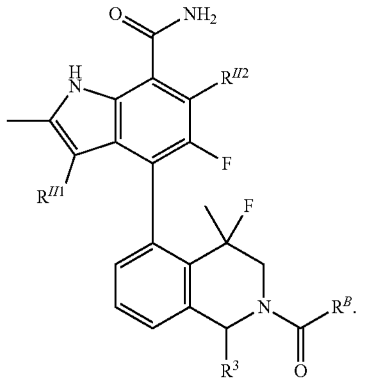

In one embodiment X is —$CR^{x1}R^{x2}$, $R^{x1}$ is Me, and $R^{x2}$ is Me:

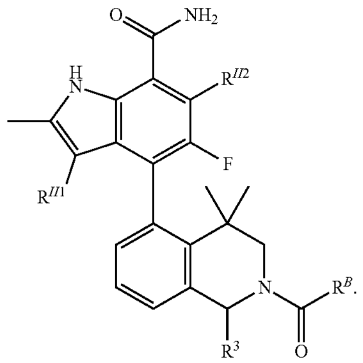

In one embodiment, X is —$CR^{x1}R^{x2}$— and $R^{x1}$ and $R^{x2}$, together with the C atom to which there are attached, form a $C_{3-6}$-membered carbocyclic ring. In some embodiments, $R^{x1}$ and $R^{x2}$, together with the C atom to which there are attached, form a cyclopropyl, a cyclobutyl, a cyclopentyl, or a cyclohexyl ring:

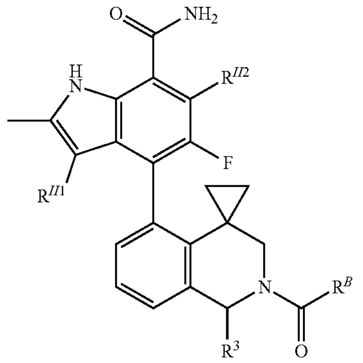

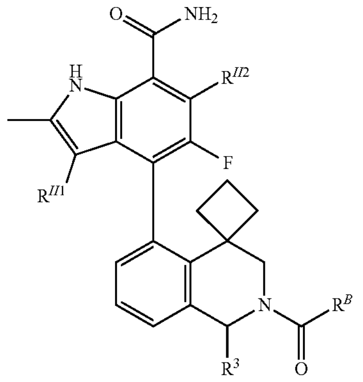

-continued

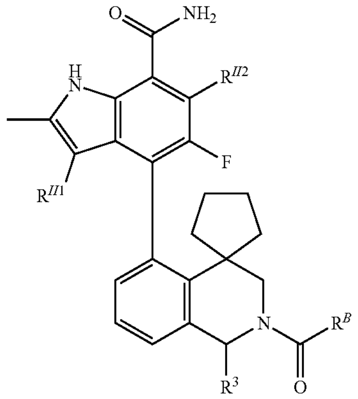

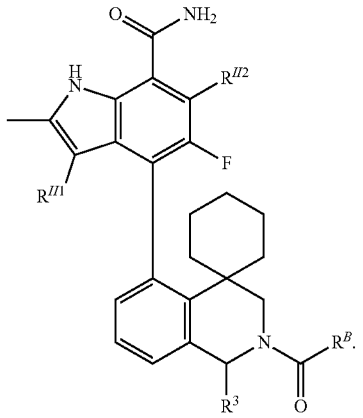

In one embodiment, X is —$CR^{x1}R^{x2}$—, $R^{x1}$ is H, and $R^{x2}$ and $R^3$, together, form an alkylene bridge. In one embodiment, $R^{x2}$ and $R^3$, together, form a methylene bridge:

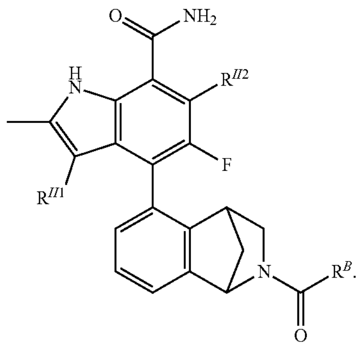

In one embodiment, $R^B$ is $—CH{=}CH_2$:

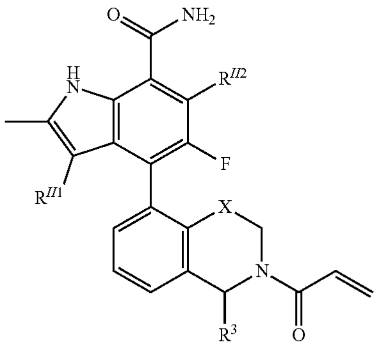
.

In one embodiment, $R^B$ is $—C{\equiv}CH$:

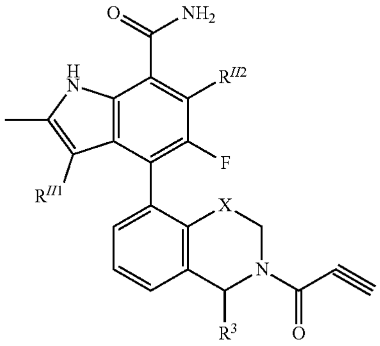
.

In one embodiment, $R^B$ is $—C{\equiv}C—CH_3$:

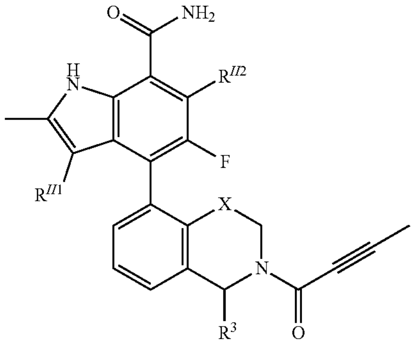
.

In one embodiment, $R^{II1}$ is Cl, F, or —CN. In one embodiment, $R^{II1}$ is Cl. In another embodiment, $R^{II1}$ is F. In another embodiment, $R^{II1}$ is CN.

In one embodiment, $R^{II1}$ is $—CH_2F$, $—CHF_2$, or $—CF_3$. In one embodiment, $R^{II1}$ is $—CH_2F$. In another embodiment, $R^{II1}$ is $—CHF_2$. In another embodiment, $R^{II1}$ is $—CF_3$.

In one embodiment, $R^{II2}$ is H. In another embodiment, $R^{II2}$ is F.

In one embodiment, a compound of Formula (II) is provided, or a pharmaceutically acceptable salt, solvate, hydrate, isomer, tautomer, racemate, or isotope thereof, having the structure of a compound below:

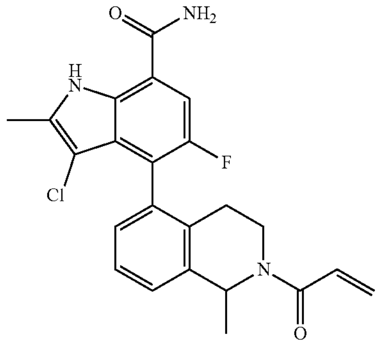
,

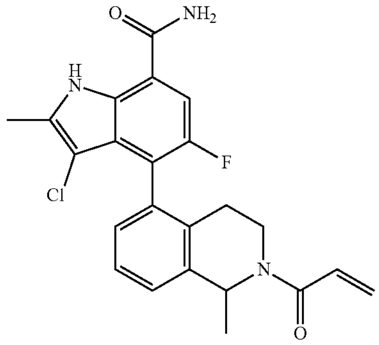
,

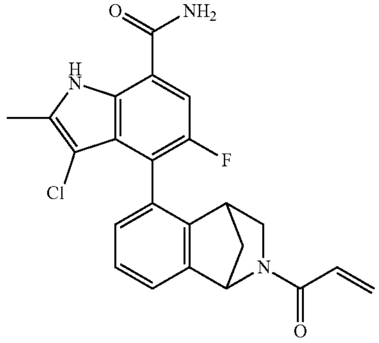
,

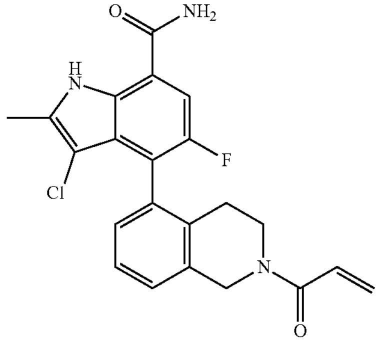
,

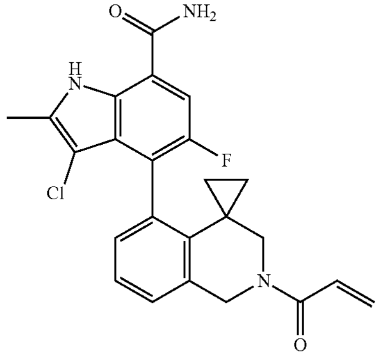
,

-continued

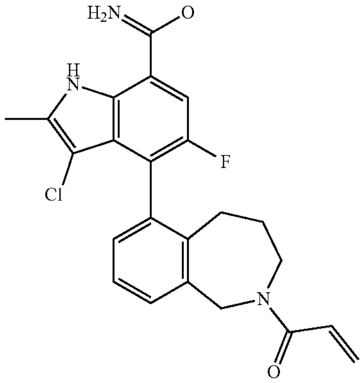

, or

-continued

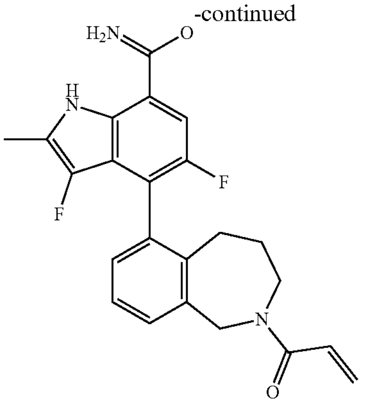

.

In one embodiment, a compound of Formula (II) is provided, or a pharmaceutically acceptable salt, solvate, hydrate, isomer, tautomer, racemate, or isotope thereof, having the structure of a compound of Table 3.

TABLE 3

REPRESENTATIVE COMPOUNDS OF FORMULA (II)

| Compound No. | Structure | Name |
|---|---|---|
| 20a | 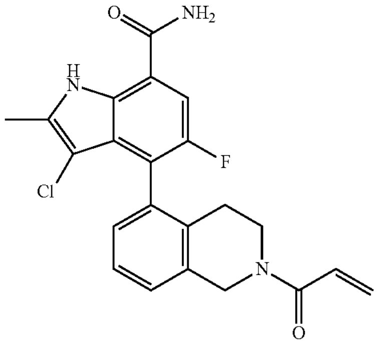 [SMILES: C=CC(=O)N1CCc2c(cccc2-c2c(F)cc(C(N)=O)c3[nH]c(C)c(Cl)c23)C1] | 4-(2-acryloyl-1,2,3,4-tetrahydroisoquinolin-5-yl)-3-chloro-5-fluoro-2-methyl-1H-indole-7-carboxamide |
| 20b | 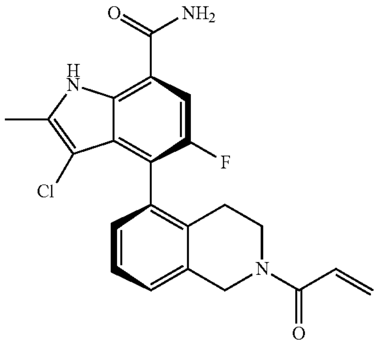 (R)- | (R)-4-(2-acryloyl-1,2,3,4-tetrahydroisoquinolin-5-yl)-3-chloro-5-fluoro-2-methyl-1H-indole-7-carboxamide |

TABLE 3-continued

REPRESENTATIVE COMPOUNDS OF FORMULA (II)

| Compound No. | Structure | Name |
|---|---|---|
| 20c | 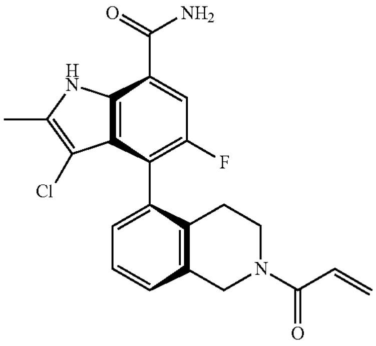 | (5)-4-(2-acryloyl-1,2,3,4-tetrahydroisoquinolin-5-yl)-3-chloro-5-fluoro-2-methyl-1H-indole-7-carboxamide |
| 20d | 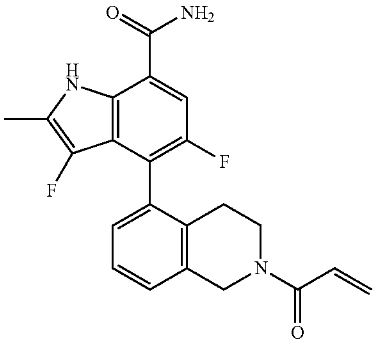 [SMILES: C=CC(=O)N1CCc2c(cccc2-c2c(F)cc(C(N)=O)c3[nH]c(C)c(F)c23)C1] | 4-(2-acryloyl-1,2,3,4-tetrahydroisoquinolin-5-yl)-3,5-difluoro-2-methyl-1H-indole-7-carboxamide |
| 20e | 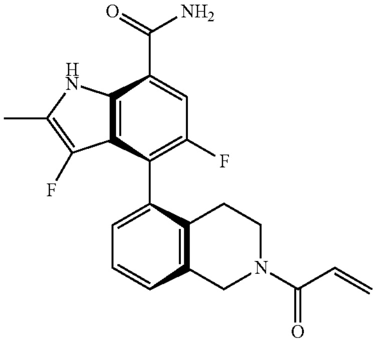 | (S)-4-(2-acryloyl-1,2,3,4-tetrahydroisoquinolin-5-yl)-3,5-difluoro-2-methyl-1H-indole-7-carboxamide |
| 20f | 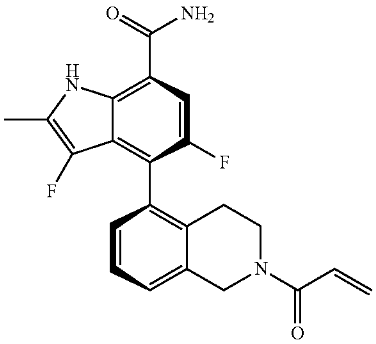 | (R)-4-(2-acryloyl-1,2,3,4-tetrahydroisoquinolin-5-yl)-3,5-difluoro-2-methyl-1H-indole-7-carboxamide |

TABLE 3-continued

REPRESENTATIVE COMPOUNDS OF FORMULA (II)

| Compound No. | Structure | Name |
| --- | --- | --- |
| 20g | 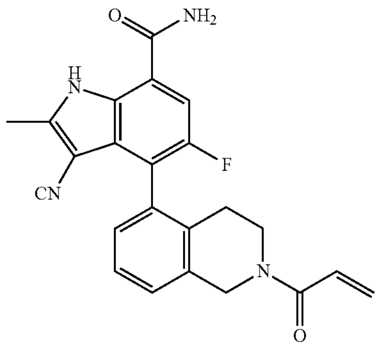 | 4-(2-acryloyl-1,2,3,4-tetrahydroisoquinolin-5-yl)-3-cyano-5-fluoro-2-methyl-1H-indole-7-carboxamide |
| 20h | 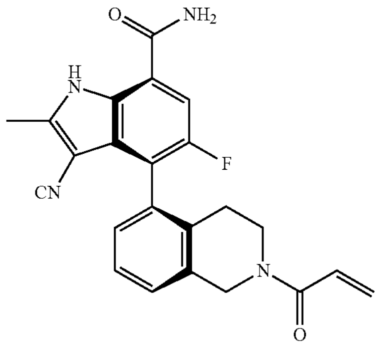 | (S)-4-(2-acryloyl-1,2,3,4-tetrahydroisoquinolin-5-yl)-3-cyano-5-fluoro-2-methyl-1H-indole-7-carboxamide |
| 20i | 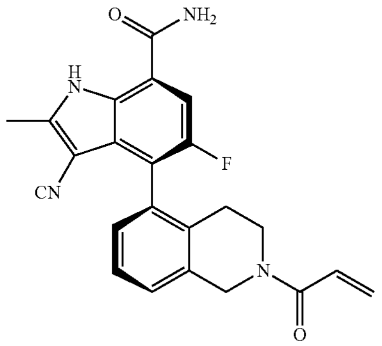 | (R)-4-(2-acryloyl-1,2,3,4-tetrahydroisoquinolin-5-yl)-3-cyano-5-fluoro-2-methyl-1H-indole-7-carboxamide |
| 20j | 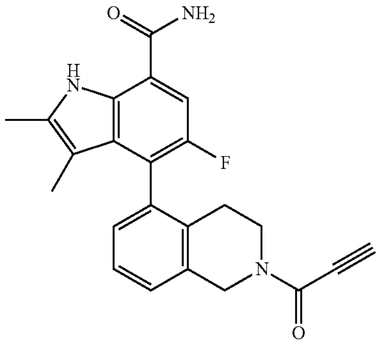 [SMILES: C#CC(=O)N1CCc2c(cccc2-c2c(F)cc(C(N)=O)c3[nH]c(C)c(C)c23)C1] | 5-fluoro-2,3-dimethyl-4-(2-propioloyl-1,2,3,4-tetrahydroisoquinolin-5-yl)-1H-indole-7-carboxamide |

TABLE 3-continued

REPRESENTATIVE COMPOUNDS OF FORMULA (II)

| Compound No. | Structure | Name |
|---|---|---|
| 21a | 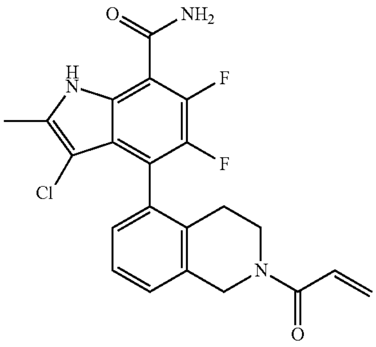 [SMILES: C=CC(=O)N1CCc2c(cccc2-c2c(F)c(F)c(C(N)=O)c3[nH]c(C)c(Cl)c23)C1] | 4-(2-acryloyl-1,2,3,4-tetrahydroisoquinolin-5-yl)-3-chloro-5,6-difluoro-2-methyl-1H-indole-7-carboxamide |
| 21b | 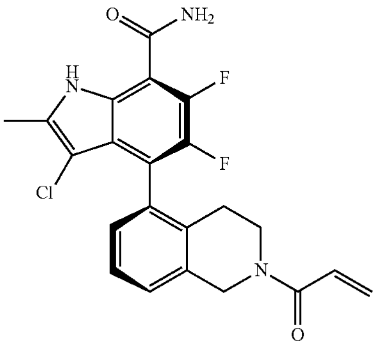 | (R)-4-(2-acryloyl-1,2,3,4-tetrahydroisoquinolin-5-yl)-3-chloro-5,6-difluoro-2-methyl-1H-indole-7-carboxamide |
| 21c | 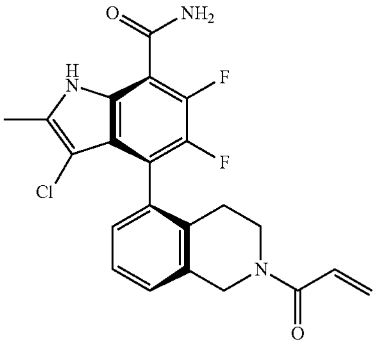 | (5)-4-(2-acryloyl-1,2,3,4-tetrahydroisoquinolin-5-yl)-3-chloro-5,6-difluoro-2-methyl-1H-indole-7-carboxamide |
| 21d | 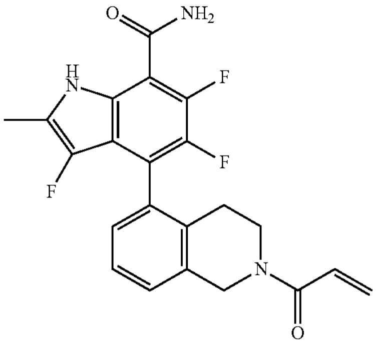 [SMILES: C=CC(=O)N1CCc2c(cccc2-c2c(F)c(F)c(C(N)=O)c3[nH]c(C)c(F)c23)C1] | 4-(2-acryloyl-1,2,3,4-tetrahydroisoquinolin-5-yl)-3,5,6-trifluoro-2-methyl-1H-indole-7-carboxamide |

TABLE 3-continued

REPRESENTATIVE COMPOUNDS OF FORMULA (II)

| Compound No. | Structure | Name |
|---|---|---|
| 21e | 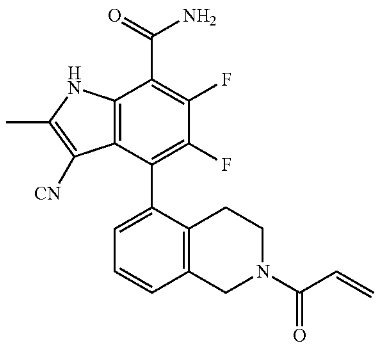 | 4-(2-acryloyl-1,2,3,4-tetrahydroisoquinolin-5-yl)-3-cyano-5,6-difluoro-2-methyl-1H-indole-7-carboxamide |
| 22a | 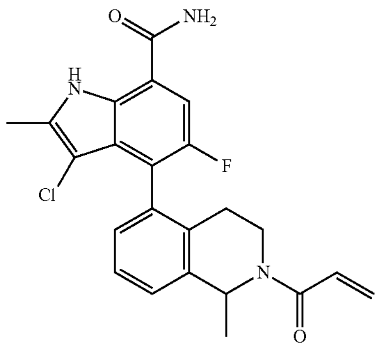 [SMILES: C=CC(=O)N1CCc2c(-c3c(F)cc(C(N)=O)c4[nH]c(C)c(Cl)c34)cccc2C1C] | 4-(2-acryloyl-1-methyl-1,2,3,4-tetrahydroisoquinolin-5-yl)-3-chloro-5-fluoro-2-methyl-1H-indole-7-carboxamide |
| 22b | 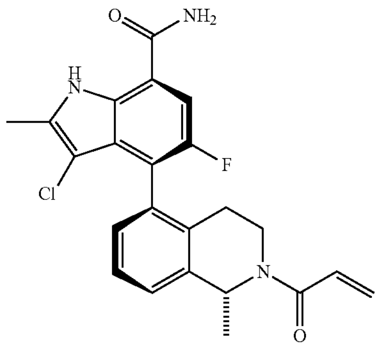 | (R)-4-((R)-2-acryloyl-1-methyl-1,2,3,4-tetrahydroisoquinolin-5-yl)-3-chloro-5-fluoro-2-methyl-1H-indole-7-carboxamide |
| 22c | 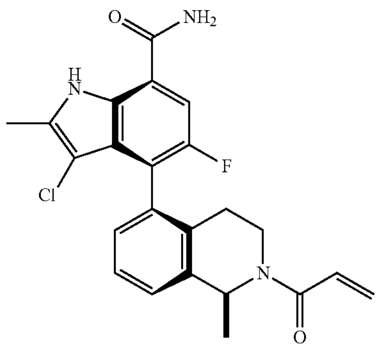 | (S)-4-((S)-2-acryloyl-1-methyl-1,2,3,4-tetrahydroisoquinolin-5-yl)-3-chloro-5-fluoro-2-methyl-1H-indole-7-carboxamide |

TABLE 3-continued

| REPRESENTATIVE COMPOUNDS OF FORMULA (II) | | |
|---|---|---|
| Compound No. | Structure | Name |
| 22d | 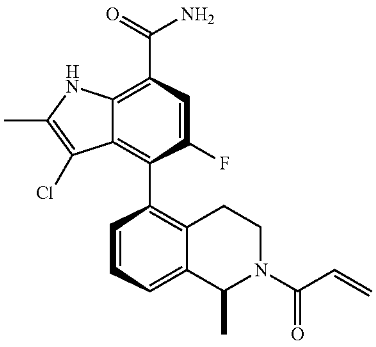 | (R)-4-((S)-2-acryloyl-1-methyl-1,2,3,4-tetrahydroisoquinolin-5-yl)-3-chloro-5-fluoro-2-methyl-1H-indole-7-carboxamide |
| 22e | 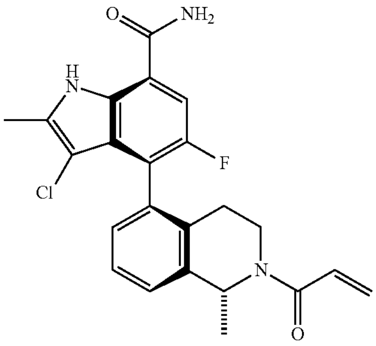 | (S)-4-((R)-2-acryloyl-1-methyl-1,2,3,4-tetrahydroisoquinolin-5-yl)-3-chloro-5-fluoro-2-methyl-1H-indole-7-carboxamide |
| 22f | 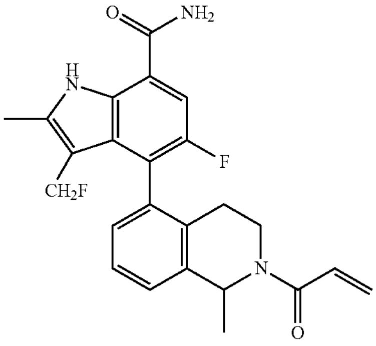 | 4-(2-acryloyl-1-methyl-1,2,3,4-tetrahydroisoquinolin-5-yl)-5-fluoro-3-(fluoromethyl)-2-methyl-1H-indole-7-carboxamide |
| 22g | 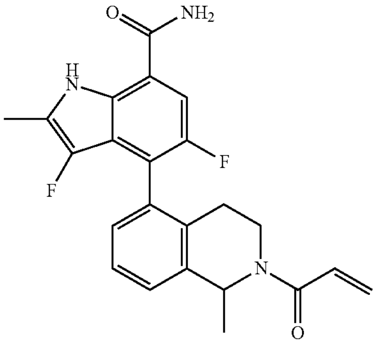 | 4-(2-acryloyl-1-methyl-1,2,3,4-tetrahydroisoquinolin-5-yl)-3,5-difluoro-2-methyl-1H-indole-7-carboxamide |

TABLE 3-continued

| REPRESENTATIVE COMPOUNDS OF FORMULA (II) | | |
|---|---|---|
| Compound No. | Structure | Name |
| 22h | 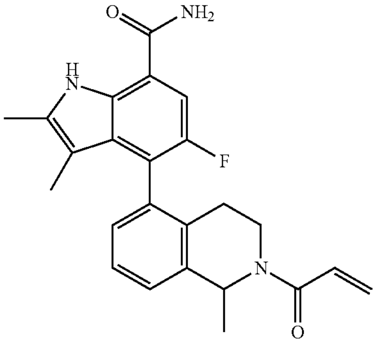 | 4-(2-acryloyl-1-methyl-1,2,3,4-tetrahydroisoquinolin-5-yl)-5-fluoro-2,3-dimethyl-1H-indole-7-carboxamide |
| 22i | 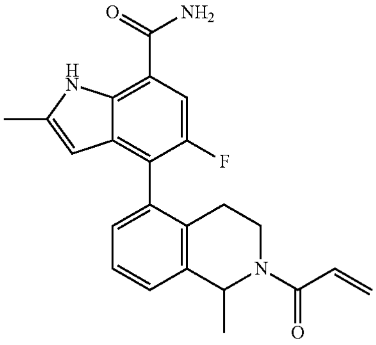 [SMILES: C=CC(=O)N1CCc2c(-c3c(F)cc(C(N)=O)c4[nH]c(C)cc34)cccc2C1C] | 4-(2-acryloyl-1-methyl-1,2,3,4-tetrahydroisoquinolin-5-yl)-5-fluoro-2-methyl-1H-indole-7-carboxamide |
| 23 | 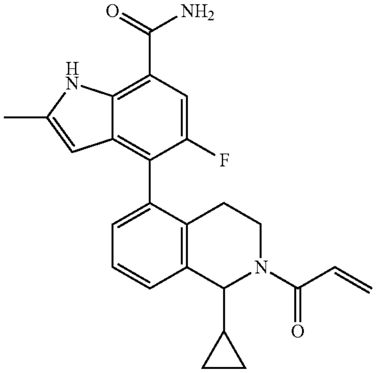 [SMILES: C=CC(=O)N1CCc2c(-c3c(F)cc(C(N)=O)c4[nH]c(C)cc34)cccc2C1C1CC1] | 4-(2-acryloyl-1-cyclopropyl-1,2,3,4-tetrahydroisoquinolin-5-yl)-5-fluoro-2-methyl-1H-indole-7-carboxamide |
| 24a | 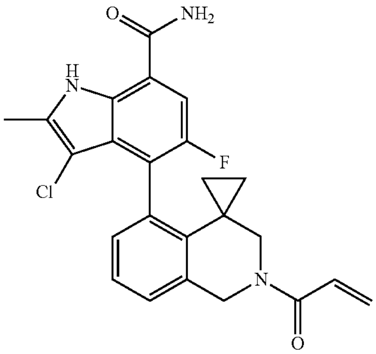 [SMILES: C=CC(=O)N1Cc2cccc(-c3c(F)cc(C(N)=O)c4[nH]c(C)c(Cl)c34)c2C2(CC2)C1] | 4-(2'-Acryloyl-2',3'-dihydro-1'H-spiro[cyclopropane-1,4'-isoquinolin]-5'-yl)-3-chloro-5-fluoro-2-methyl-1H-indole-7-carboxamide |

TABLE 3-continued

| REPRESENTATIVE COMPOUNDS OF FORMULA (II) | | |
|---|---|---|
| Compound No. | Structure | Name |
| 24b | 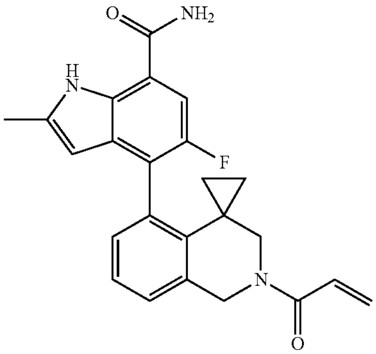 [SMILES: C=CC(=O)N1Cc2cccc(-c3c(F)cc(C(N)=O)c4[nH]c(C)cc34)c2C2(CC2)C1] | 4-(2'-acryloyl-2',3'-dihydro-1'H-spiro[cyclopropane-1,4'-isoquinolin]-5'-yl)-5-fluoro-2-methyl-1H-indole-7-carboxamide |
| 24c | 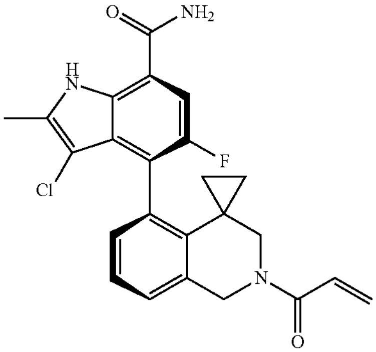 | (R)-4-(2'-acryloyl-2',3'-dihydro-1'H-spiro[cyclopropane-1,4'-isoquinolin]-5'-yl)-3-chloro-5-fluoro-2-methyl-1H-indole-7-carboxamide |
| 24d | 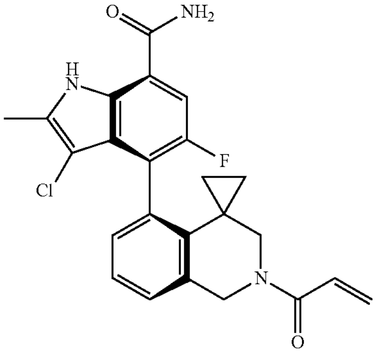 | (S)-4-(2'-acryloyl-2',3'-dihydro-1'H-spiro[cyclopropane-1,4'-isoquinolin]-5'-yl)-3-chloro-5-fluoro-2-methyl-1H-indole-7-carboxamide |
| 25a | 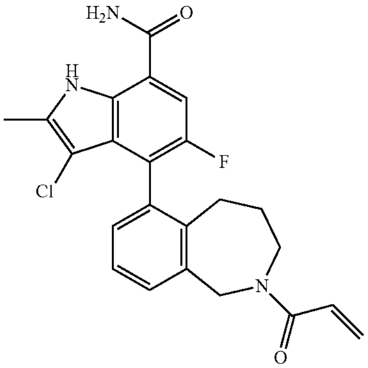 [SMILES: C=CC(=O)N1CCCc2c(cccc2-c2c(F)cc(C(N)=O)c3[nH]c(C)c(Cl)c23)C1] | 4-(2-Acryloyl-2,3,4,5-tetrahydro-1H-benzo[c]azepin-6-yl)-3-chloro-5-fluoro-2-methyl-1H-indole-7-carboxamide |

TABLE 3-continued

| REPRESENTATIVE COMPOUNDS OF FORMULA (II) | | |
|---|---|---|
| Compound No. | Structure | Name |
| 25b | 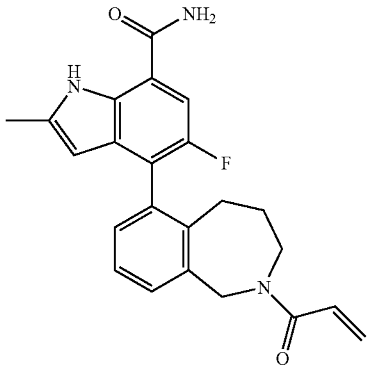 [SMILES: C=CC(=O)N1CCCc2c(cccc2-c2c(F)cc(C(N)=O)c3[nH]c(C)cc23)C1] | 4-(2-acryloyl-2,3,4,5-tetrahydro-1H-benzo[c]azepin-6-yl)-5-fluoro-2-methyl-1H-indole-7-carboxamide |
| 25c | 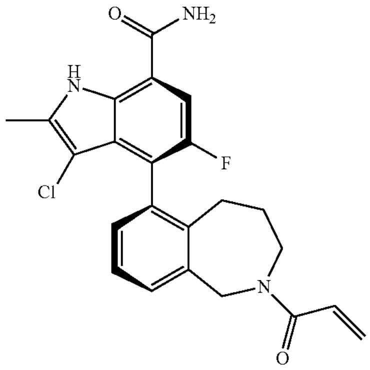 | (R)-3-chloro-5-fluoro-2-methyl-4-(2-prop-2-enoyl-1,3,4,5-tetrahydro-2-benzazepin-6-yl)-1H-indole-7-carboxamide |
| 25d | 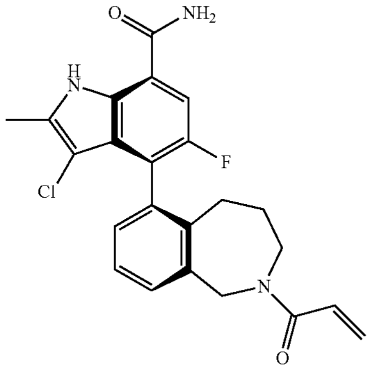 | (S)-3-chloro-5-fluoro-2-methyl-4-(2-prop-2-enoyl-1,3,4,5-tetrahydro-2-benzazepin-6-yl)-1H-indole-7-carboxamide |
| 25e | 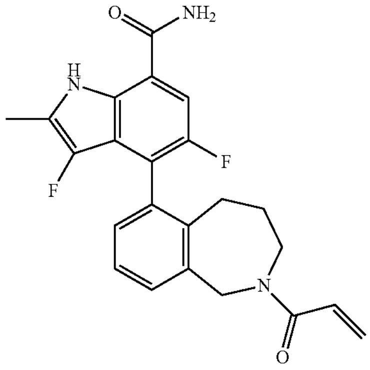 [SMILES: C=CC(=O)N1CCCc2c(cccc2-c2c(F)cc(C(N)=O)c3[nH]c(C)c(F)c23)C1] | 4-(2-acryloyl-2,3,4,5-tetrahydro-1H-benzo[c]azepin-6-yl)-3,5-difluoro-2-methyl-1H-indole-7-carboxamide |

TABLE 3-continued

REPRESENTATIVE COMPOUNDS OF FORMULA (II)

| Compound No. | Structure | Name |
|---|---|---|
| 26 | 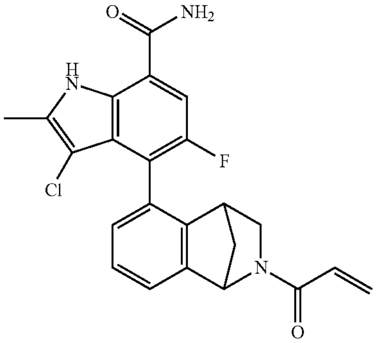 [SMILES: C=CC(=O)N1CC2CC1c1cccc(-c3c(F)cc(C(N)=O)c4[nH]c(C)c(Cl)c34)c12] | 4-(2-acryloyl-1,2,3,4-tetrahydro-1,4-methanoisoquinolin-5-yl)-3-chloro-5-fluoro-2-methyl-1H-indole-7-carboxamide |

In some embodiments, the compounds of formula (II) comprise a mixture of two isomers. In other embodiments, the compounds of formula (II) comprise a mixture of two atropisomers. In other embodiments, the compounds of formula (II) comprise a racemic mixture of two atropisomers. In other embodiments, the compounds of formula (II) comprise a single atropisomer. In other embodiments, the compounds of formula (II) comprise a single (R)-atropisomer. In other embodiments, the compounds of formula (II) comprise a single (S)-atropisomer. In some embodiments, compounds of formula (II-a) or (II-b) are provided:

(II-a)

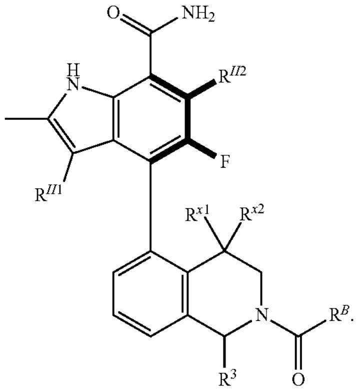

(II-b)

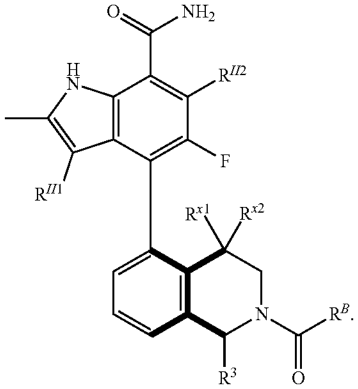

Also disclosed herein are compounds having the structure of Formula (III):

Formula (III)

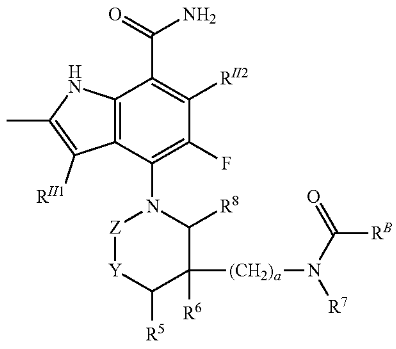

or a pharmaceutically acceptable salt, solvate, hydrate, isomer, tautomer, racemate or isotope thereof, wherein:

Z is $-CH_2-$, $-CHMe-$ or a bond;

Y is $-CHR^4-$ or a bond;

$R^4$ is H, F, or OH;

$R^5$ is H, F, or Me;

$R^6$ is H or Me;

$R^7$ is H or Me;

$R^8$ is H;

or $R^5$ and $R^7$, taken together, form a 5- or 6-membered heterocycle;

or $R^6$ and $R^7$, taken together, form a 4-, 5- or 6-membered heterocycle;

or $R^8$ and $R^7$, taken together, form a 5- or 6-membered heterocycle;

a is 0, 1 or 2;

$R^{III1}$ is Cl, F, $-CH_2F$, $-CHF_2$, $-CF_3$ or $-CN$; or $R^{III1}$ is $-CH_3$ when $R^4$ is F or OH, or when $R^5$ is F, or when $R^5$ and $R^7$ or $R^8$ and $R^7$, taken together, form a 5- or 6-membered heterocycle, or when $R^6$ and $R^7$, taken together, form a 4-, 5- or 6-membered heterocycle;

$R^{III2}$ is H or F; and $R^B$ is $-CH{=}CH_2$, $-C{\equiv}CH$ or $-C{\equiv}C-CH_3$.

In one embodiment of Formula (III), Z is a bond, Y is a bond and a compound is provided having the structure of Formula (IV):

(IV)

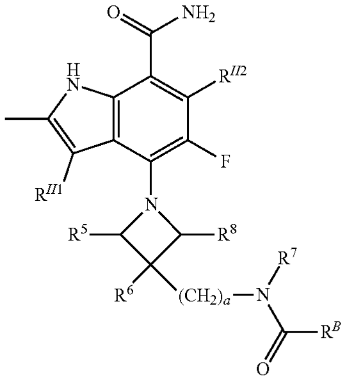

or a pharmaceutically acceptable salt, solvate, hydrate, isomer, tautomer, racemate or isotope thereof, wherein $R^{III1}$, $R^{III2}$, $R^B$, a, $R^5$, $R^6$, $R^7$ and $R^8$ are as defined above in the context of Formula (III).

In one embodiment of Formula (III), Z is —$CH_2$—, Y is a bond and a compound is provided having the structure of Formula (V-a):

(V-a)

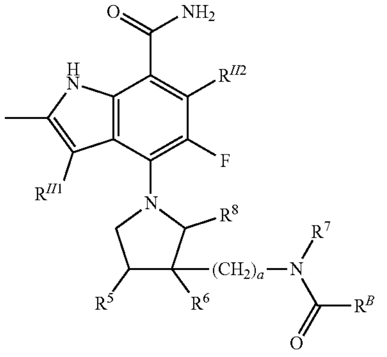

or a pharmaceutically acceptable salt, solvate, hydrate, isomer, tautomer, racemate or isotope thereof, wherein $R^{III1}$, $R^{III2}$, $R^B$, a, $R^5$, $R^6$, $R^7$ and $R^8$ are as defined above in the context of Formula (III).

In one embodiment of Formula (III), Z is a bond, Y is —$CHR^4$— and a compound is provided having the structure of Formula (V-b):

(V-b)

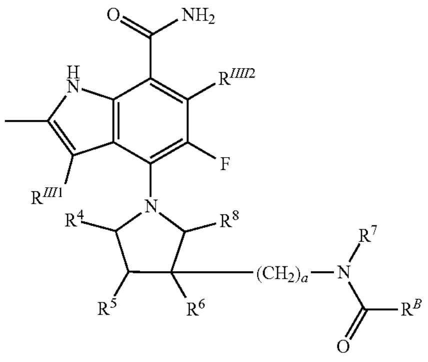

or a pharmaceutically acceptable salt, solvate, hydrate, isomer, tautomer, racemate or isotope thereof, wherein $R^{III1}$, $R^{III2}$, $R^B$, a, $R^4$, $R^5$, $R^6$, $R^7$ and $R^8$ are as defined above in the context of Formula (III). In one embodiment of Formula (III-b), $R^4$ is H. In another embodiment of Formula (III-b), $R^4$ is F. In another embodiment of Formula (III-b), $R^4$ is —OH.

In one embodiment of Formula (III), Z is —$CH_2$—, Y is —$CHR^4$— and a compound is provided having the structure of Formula (VI-a):

(VI-a)

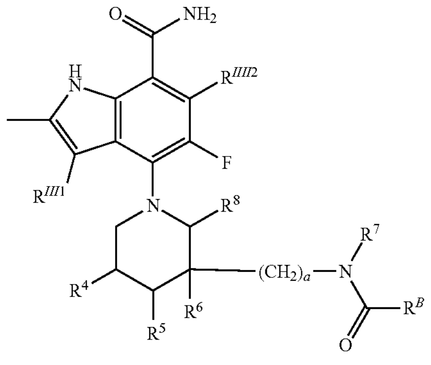

or a pharmaceutically acceptable salt, solvate, hydrate, isomer, tautomer, racemate or isotope thereof, wherein $R^{III1}$, $R^{III2}$, $R^B$, a, $R^4$, $R^5$, $R^6$, $R^7$ and $R^8$ are as defined above in the context of Formula (III). In one embodiment of Formula (VI-a), $R^4$ is F. In another embodiment of Formula (VI-a), $R^4$ is —OH.

In one embodiment of Formula (VI-a), $R^4$ is H and a compound is provided having the structure of Formula (VI-a-1):

(VI-a-1)

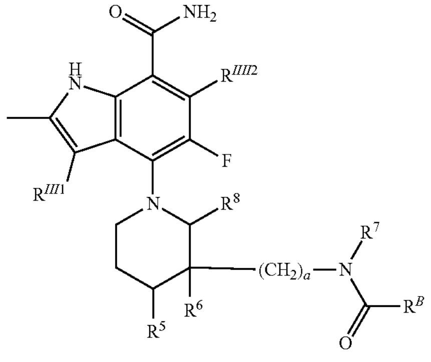

or a pharmaceutically acceptable salt, solvate, hydrate, isomer, tautomer, racemate or isotope thereof, wherein $R^{III1}$, $R^{III2}$, $R^B$, a, $R^5$, $R^6$, $R^7$ and $R^8$ are as defined above in the context of Formula (III).

In one embodiment of Formula (III), Z is —CHMe-, Y is —$CHR^4$— and a compound is provided having the structure of Formula (VI-b):

(VI-b)

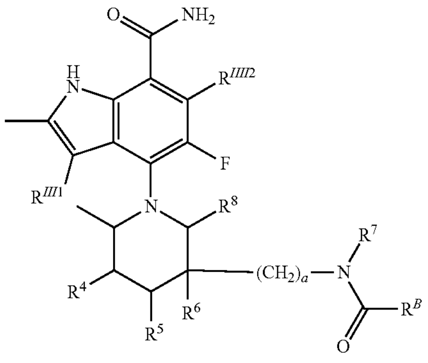

or a pharmaceutically acceptable salt, solvate, hydrate, isomer, tautomer, racemate or isotope thereof, wherein $R^{III1}$, $R^{III2}$, $R^B$, a, $R^4$, $R^5$, $R^6$, $R^7$ and $R^8$ are as defined above in the context of Formula (III). In one embodiment of Formula (VI-b), $R^4$ is H. In another embodiment of Formula (VI-b), $R^4$ is F. In another embodiment of Formula (VI-b), $R^4$ is —OH.

In one embodiment of Formula (III), $R^7$ and $R^8$ taken together form a 5-membered heterocycle, a is 0, $R^5$ is H, $R^6$ is H and a compound is provided having the structure of Formula (VII-a):

(VII-a)

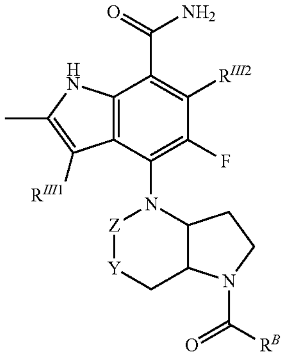

or a pharmaceutically acceptable salt, solvate, hydrate, isomer, tautomer, racemate or isotope thereof, wherein $R^{III1}$, $R^{III2}$, $R^B$, Z and Y are as defined above in the context of Formula (III). In some embodiments of Formula (VII-a), Z is $CH_2$. In some embodiments of Formula (VII-a), Y is $CH_2$. In some embodiments of Formula (VII-a), Z is $CH_2$ and Y is $CH_2$. In some embodiments of Formula (VII-a), Z is CHMe and Y is $CH_2$. In some embodiments of Formula (VII-a), Z is $CH_2$ and Y is $CHR^4$.

In one embodiment of Formula (III), $R^7$ and $R^8$ taken together form a 5-membered heterocycle, a is 1, $R^5$ is H, $R^6$ is H and a compound is provided having the structure of Formula (VII-b):

(VII-b)

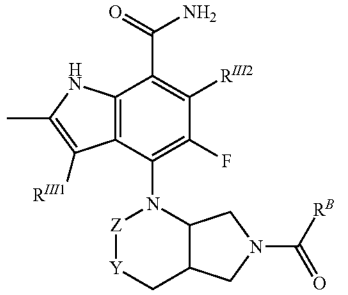

or a pharmaceutically acceptable salt, solvate, hydrate, isomer, tautomer, racemate or isotope thereof, wherein $R^{III1}$, $R^{III2}$, $R^B$, Z and Y are as defined above in the context of Formula (III). In some embodiments of Formula (VII-b), Z is $CH_2$. In some embodiments of Formula (VII-b), Y is $CH_2$. In some embodiments of Formula (VII-b), Z is $CH_2$ and Y is $CH_2$. In some embodiments of Formula (VII-b), Z is CHMe and Y is $CH_2$. In some embodiments of Formula (VII-b), Z is $CH_2$ and Y is $CHR^4$.

In one embodiment of Formula (III), $R^7$ and $R^8$ taken together form a 5-membered heterocycle, a is 2, $R^5$ is H, $R^6$ is H and a compound is provided having the structure of Formula (VII-c):

(VII-c)

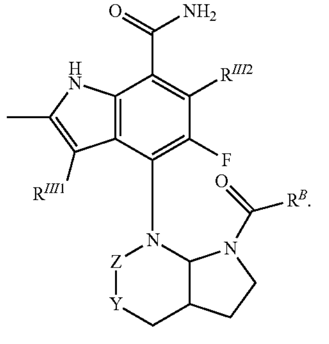

or a pharmaceutically acceptable salt, solvate, hydrate, isomer, tautomer, racemate or isotope thereof, wherein $R^{III1}$, $R^{III2}$, $R^B$, Z and Y are as defined above in the context of Formula (III). In some embodiments of Formula (VII-c), Z is $CH_2$. In some embodiments of Formula (VII-c), Y is $CH_2$. In some embodiments of Formula (VII-c), Z is $CH_2$ and Y is $CH_2$. In some embodiments of Formula (VII-c), Z is CHMe and Y is $CH_2$. In some embodiments of Formula (VII-c), Z is $CH_2$ and Y is $CHR^4$.

In one embodiment of Formula (III), $R^7$ and $R^8$ taken together form a 6-membered heterocycle, a is 0, $R^5$ is H, $R^6$ is H and a compound is provided having the structure of Formula (VIII-a):

(VIII-a)

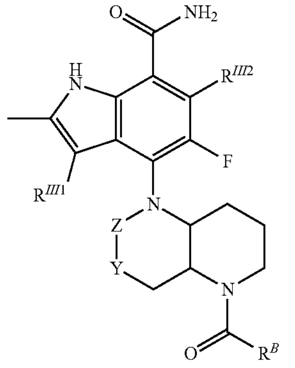

or a pharmaceutically acceptable salt, solvate, hydrate, isomer, tautomer, racemate or isotope thereof, wherein $R^{III1}$, $R^{III2}$, $R^B$, Z and Y are as defined above in the context of Formula (III). In some embodiments of Formula (VIII-a), Z is $CH_2$. In some embodiments of Formula (VIII-a), Y is $CH_2$. In some embodiments of Formula (VIII-a), Z is $CH_2$ and Y is $CH_2$. In some embodiments of Formula (VIII-a), Z is CHMe and Y is $CH_2$. In some embodiments of Formula (VIII-a), Z is $CH_2$ and Y is $CHR^4$.

In one embodiment of Formula (III), $R^7$ and $R^8$ taken together form a 6-membered heterocycle, a is 1, $R^5$ is H, $R^6$ is H and a compound is provided having the structure of Formula (VIII-b):

(VIII-b)

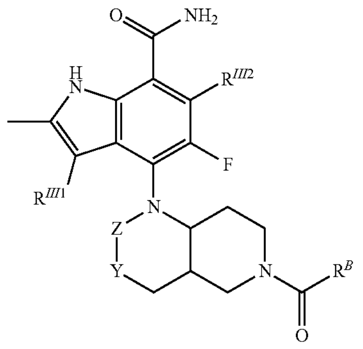

or a pharmaceutically acceptable salt, solvate, hydrate, isomer, tautomer, racemate or isotope thereof, wherein $R^{III1}$, $R^{III2}$, $R^B$, Z and Y are as defined above in the context of Formula (III). In some embodiments of Formula (VIII-b), Z is $CH_2$. In some embodiments of Formula (VIII-b), Y is $CH_2$. In some embodiments of Formula (VIII-b), Z is $CH_2$ and Y is $CH_2$. In some embodiments of Formula (VIII-b), Z is CHMe and Y is $CH_2$. In some embodiments of Formula (VIII-b), Z is $CH_2$ and Y is $CHR^4$.

In one embodiment Formula (III), $R^7$ and $R^8$ together form a 6-membered heterocycle, a is 2, $R^5$ is H, $R^6$ is H and a compound is provided having the structure of Formula (VIII-c):

(VIII-c)

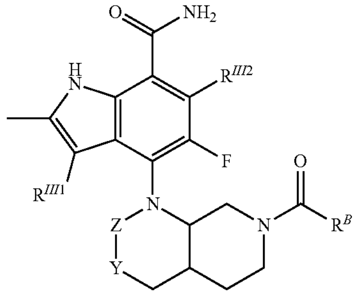

or a pharmaceutically acceptable salt, solvate, hydrate, isomer, tautomer, racemate or isotope thereof, wherein $R^{III1}$, $R^{III2}$, $R^B$, Z and Y are as defined above in the context of Formula (III). In some embodiments of Formula (VIII-c), Z is $CH_2$. In some embodiments of Formula (VIII-c), Y is $CH_2$. In some embodiments of Formula (VIII-c), Z is $CH_2$ and Y is $CH_2$. In some embodiments of Formula (VIII-c), Z is CHMe and Y is $CH_2$. In some embodiments of Formula (VIII-c), Z is $CH_2$ and Y is $CHR^4$.

In one embodiment of Formula (III), $R^6$ and $R^7$ taken together form a 4-membered heterocycle, a is 0, $R^5$ is H, $R^8$ is H and a compound is provided having the structure of Formula (IX-a):

(IX-a)

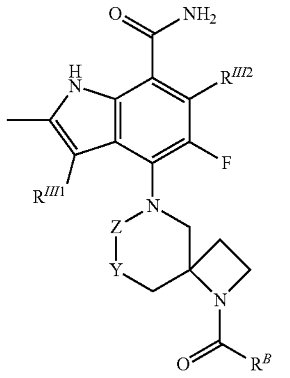

or a pharmaceutically acceptable salt, solvate, hydrate, isomer, tautomer, racemate or isotope thereof, wherein $R^{III1}$, $R^{III2}$, $R^B$, Z and Y are as defined above in the context of Formula (III). In some embodiments of Formula (IX-a), Z is $CH_2$. In some embodiments of Formula (IX-a), Y is $CH_2$. In some embodiments of Formula (IX-a), Z is $CH_2$ and Y is $CH_2$. In some embodiments of Formula (IX-a), Z is CHMe and Y is $CH_2$. In some embodiments of Formula (IX-a), Z is $CH_2$ and Y is $CHR^4$.

In one embodiment of Formula (III), $R^6$ and $R^7$ taken together form a 4-membered heterocycle, a is 1, $R^5$ is H, $R^8$ is H and a compound is provided having the structure of Formula (IX-b):

(IX-b)

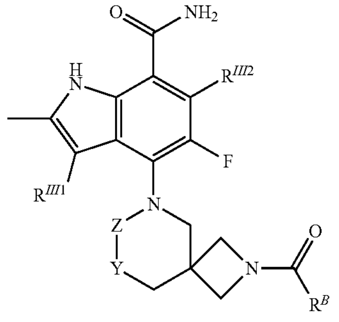

or a pharmaceutically acceptable salt, solvate, hydrate, isomer, tautomer, racemate or isotope thereof, wherein $R^{III1}$, $R^{III2}$, $R^B$, Z and Y are as defined above in the context of Formula (III). In some embodiments of Formula (IX-b), Z is $CH_2$. In some embodiments of Formula (IX-b), Y is $CH_2$. In some embodiments of Formula (IX-b), Z is $CH_2$ and Y is $CH_2$. In some embodiments of Formula (IX-b), Z is CHMe and Y is $CH_2$. In some embodiments of Formula (IX-b), Z is $CH_2$ and Y is $CHR^4$.

In one embodiment of Formula (III), $R^5$ and $R^7$ taken together form a 5-membered heterocycle, a is 2, $R^6$ is H, $R^8$ is H and a compound is provided having the structure of Formula (X-a):

(X-a)

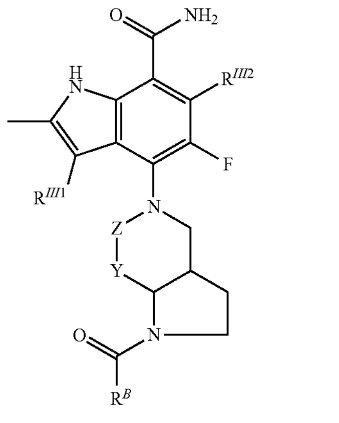

or a pharmaceutically acceptable salt, solvate, hydrate, isomer, tautomer, racemate or isotope thereof, wherein $R^{III1}$, $R^{III2}$, $R^B$, Z and Y are as defined above in the context of Formula (III). In some embodiments of Formula (X-a), Z is $CH_2$. In some embodiments of Formula (X-a), Y is $CH_2$. In some embodiments of Formula (X-a), Z is $CH_2$ and Y is $CH_2$. In some embodiments of Formula (X-a), Z is CHMe and Y is $CH_2$. In some embodiments of Formula (X-a), Z is $CH_2$ and Y is $CHR^4$.

In one embodiment of Formula (III), $R^5$ and $R^7$ taken together form a 5-membered heterocycle, a is 1, $R^6$ is H, $R^8$ is H and a compound is provided having the structure of Formula (X-b):

(X-b)

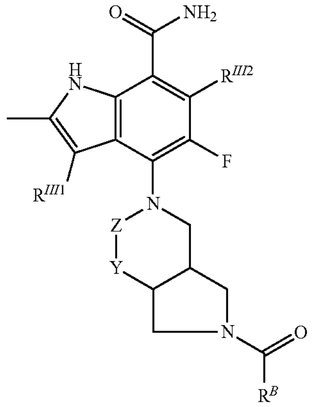

or a pharmaceutically acceptable salt, solvate, hydrate, isomer, tautomer, racemate or isotope thereof, wherein $R^{III1}$, $R^{III2}$, $R^B$, Z and Y are as defined above in the context of Formula (III). In some embodiments of Formula (X-b), Z is $CH_2$. In some embodiments of Formula (X-b), Y is $CH_2$. In some embodiments of Formula (X-b), Z is $CH_2$ and Y is $CH_2$. In some embodiments of Formula (X-b), Z is CHMe and Y is $CH_2$. In some embodiments of Formula (X-b), Z is $CH_2$ and Y is $CHR^4$.

In one embodiment of Formula (III), $R^5$ and $R^7$ taken together form a 5-membered heterocycle, a is 0, $R^6$ is H, $R^8$ is H and a compound is provided having the structure of Formula (X-c):

(X-c)

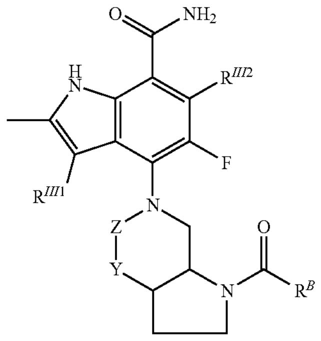

or a pharmaceutically acceptable salt, solvate, hydrate, isomer, tautomer, racemate or isotope thereof, wherein $R^{III1}$, $R^{III2}$, $R^B$, Z and Y are as defined above in the context of Formula (III). In some embodiments of Formula (X-c), Z is $CH_2$. In some embodiments of Formula (X-c), Y is $CH_2$. In some embodiments of Formula (X-c), Z is $CH_2$ and Y is $CH_2$. In some embodiments of Formula (X-c), Z is CHMe and Y is $CH_2$. In some embodiments of Formula (X-c), Z is $CH_2$ and Y is $CHR^4$.

In one embodiment of Formula (III), $R^5$ and $R^7$ taken together form a 6-membered heterocycle, a is 2, $R^6$ is H and a compound is provided having the structure of Formula (XI-a):

(XI-a)

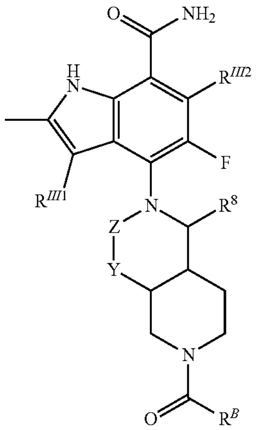

or a pharmaceutically acceptable salt, solvate, hydrate, isomer, tautomer, racemate or isotope thereof, wherein $R^{III1}$, $R^{III2}$, $R^B$, $R^8$, Z and Y are as defined above in the context of Formula (III). In some embodiments of Formula (XI-a), Z is $CH_2$. In some embodiments of Formula (XI-a), Y is $CH_2$. In some embodiments of Formula (XI-a), Z is $CH_2$ and Y is $CH_2$. In some embodiments of Formula (XI-a), Z is CHMe and Y is $CH_2$. In some embodiments of Formula (XI-a), Z is $CH_2$ and Y is $CHR^4$.

In one embodiment of Formula (III), $R^5$ and $R^7$ taken together form a 6-membered heterocycle, a is 1, $R^6$ is H and a compound is provided having the structure of Formula (XI-b):

(XI-b)

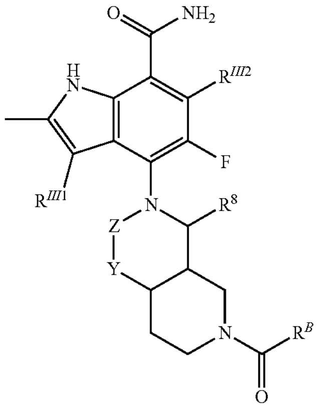

or a pharmaceutically acceptable salt, solvate, hydrate, isomer, tautomer, racemate or isotope thereof, wherein $R^{III1}$, $R^{III2}$, $R^B$, $R^8$, Z and Y are as defined above in the context of Formula (III). In some embodiments of Formula (XI-b), Z is $CH_2$. In some embodiments of Formula (XI-b), Y is $CH_2$. In some embodiments of Formula (XI-b), Z is $CH_2$ and Y is $CH_2$. In some embodiments of Formula (XI-b), Z is CHMe and Y is $CH_2$. In some embodiments of Formula (XI-b), Z is $CH_2$ and Y is $CHR^4$.

In one embodiment of Formula (III), $R^5$ and $R^7$ taken together form a 6-membered heterocycle, a is 0, $R^5$ is H, $R^6$ is H and a compound is provided having the structure of Formula (XI-c):

(XI-c)

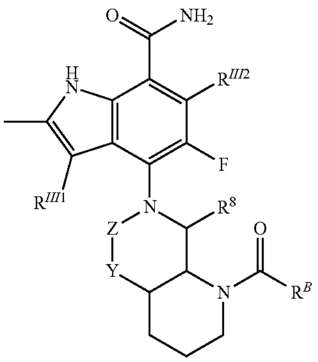

or a pharmaceutically acceptable salt, solvate, hydrate, isomer, tautomer, racemate or isotope thereof, wherein $R^{III1}$, $R^{III2}$, $R^B$, $R^8$, Z and Y are as defined above in the context of Formula (III). In some embodiments of Formula (XI-c), Z is $CH_2$. In some embodiments of Formula (XI-c), Y is $CH_2$. In some embodiments of Formula (XI-c), Z is $CH_2$ and Y is $CH_2$. In some embodiments of Formula (XI-c), Z is CHMe and Y is $CH_2$. In some embodiments of Formula (XI-c), Z is $CH_2$ and Y is $CHR^4$.

In some embodiments of Formula (III), $R^5$ and $R^7$ taken together form a 6-membered heterocycle, $R^6$ is H, Z is $CH_2$ and a compound is provided having the structure of one of Formulas (XII-a), (XII-b) or (XII-c):

(XII-a)

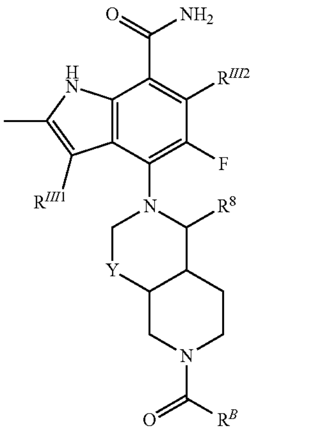

(XII-b)

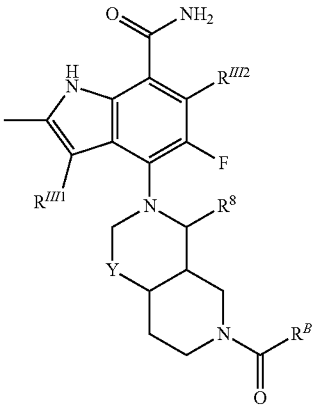

-continued (XII-c)

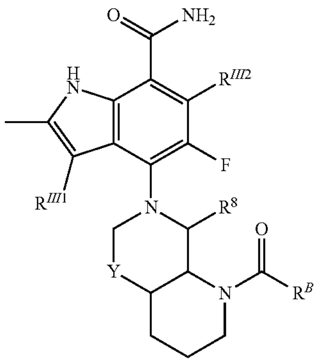

or a pharmaceutically acceptable salt, solvate, hydrate, isomer, tautomer, racemate or isotope thereof, wherein $R^{III1}$, $R^{III2}$, $R^B$, $R^8$ and Y are as defined above in the context of Formula (III).

In some embodiments of Formula (III), $R^5$ and $R^7$ taken together form a 6-membered heterocycle, $R^6$ is H, Z is a bond and a compound is provided having the structure of one of Formulas (XIII-a), (XIII-b) or (XIII-c):

(XIII-a)

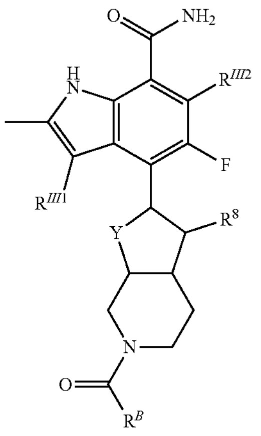

(XIII-b)

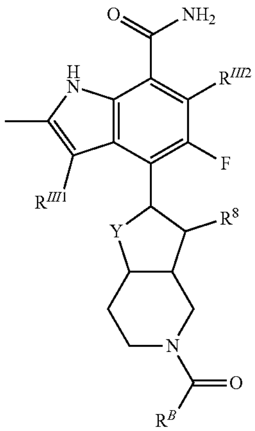

-continued (XIII-c)

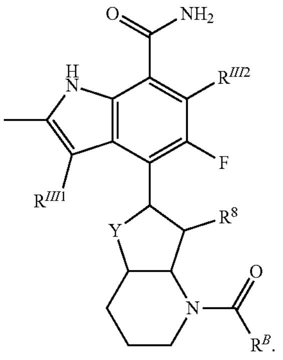

or a pharmaceutically acceptable salt, solvate, hydrate, isomer, tautomer, racemate or isotope thereof, wherein $R^{III1}$, $R^{III2}$, $R^B$, $R^8$ and Y are as defined above in the context of Formula (III).

In some embodiments of Formula (III), $R^5$ is H, $R^6$ is H, $R^7$ is H, $R^8$ is H and a compound is provided having the structure of Formula (XIV):

(XIV)

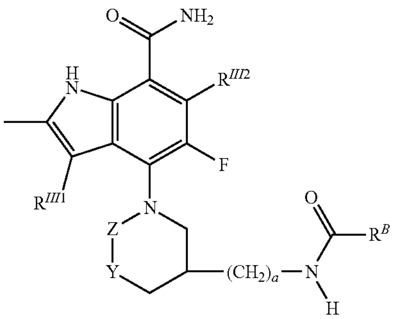

or a pharmaceutically acceptable salt, solvate, hydrate, isomer, tautomer, racemate or isotope thereof, wherein $R^{III1}$, $R^{III2}$, a, $R^B$, Z and Y are as defined above in the context of Formula (III). In some embodiments of Formula (XIV), Z is $CH_2$. In some embodiments of Formula (XIV), Y is $CH_2$. In some embodiments of Formula (XIV), Z is $CH_2$ and Y is $CH_2$. In some embodiments of Formula (XIV), Z is CHMe and Y is $CH_2$. In some embodiments of Formula (XIV), Z is $CH_2$ and Y is $CHR^4$. In some embodiments of Formula (XIV), a is 0. In other embodiments of Formula (XIV), a is 1. In other embodiments of Formula (XIV), a is 2.

In some embodiments of Formula (III), $R^5$ is H, $R^6$ is H, $R^7$ is H, $R^8$ is H, Z is $CH_2$, Y is $CHR^4$ and a compound is provided having the structure of Formula (XV):

(XV)

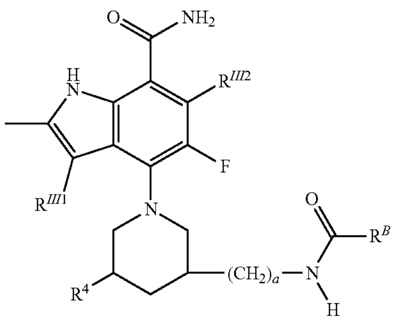

or a pharmaceutically acceptable salt, solvate, hydrate, isomer, tautomer, racemate or isotope thereof, wherein $R^{III1}$, $R^{III2}$, a, $R^4$ and $R^B$ are as defined above in the context of Formula (III).

In some embodiments of Formula (XV), a is 0, 1 or 2, and a compound is provided having the structure of one of Formulas (XV-a), (XV-b) or (XV-c):

(XV-a)

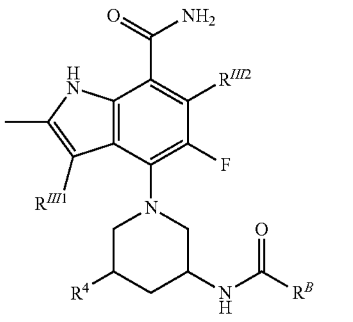

(XV-b)

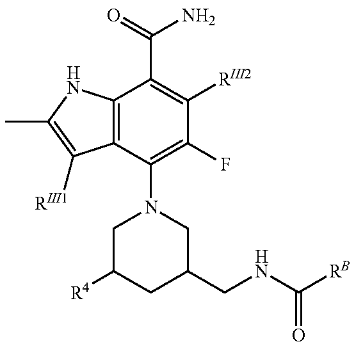

(XV-c)

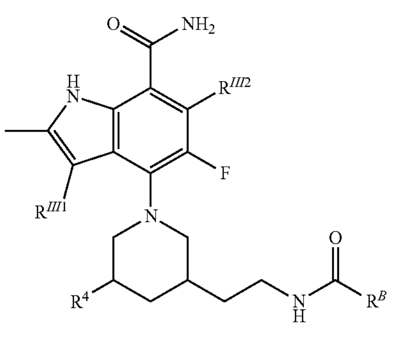

or a pharmaceutically acceptable salt, solvate, hydrate, isomer, tautomer, racemate or isotope thereof, wherein $R^{III1}$, $R^{III2}$, $R^4$ and $R^B$ are as defined above in the context of Formula (III).

In some embodiments of Formula (III), as well as each of the more specific embodiments of any one of Formulas (IV), (V-a), (V-b), (VI-a), (VI-a-1), (VI-b), (VII-a), (VII-b), (VII-c), (VIII-a), (VIII-b), (VIII-c), (IX-a), (IX-b), (X-a), (X-b), (X-c), (XI-a), (XI-b), (XI-c), (XII-a), (XII-b), (XII-c), (XIII-a), (XIII-b), (XIII-c), (XIV), (XV-a), (XV-b) and (XV-c) (hereinafter referred to as "Formulas (III)-(XV)"), $R^{III1}$ is Cl, F, —CN, —$CH_2F$, —$CHF_2$ or —$CF_3$. In other embodiments of any one of Formulas (III)-(XV), $R^{III1}$ is Cl or F. In other embodiments of any one of Formulas (III)-(XV), $R^{III1}$ is Cl. In other embodiments of any one of Formulas (III)-(XV), $R^{III1}$ is F. In other embodiments of any one of Formulas (III)-(XV), $R^{III1}$ is —CN. In other embodiments of any one of Formulas (III)-(XV), $R^{III1}$ is F, —$CH_2F$, —$CHF_2$ or —$CF_3$.

In some embodiments of any one of one of Formulas (III)-(XV), $R^{III1}$ is —$CH_3$ when $R^4$ is F or OH. In other embodiments of any one of one of Formulas (III)-(XV), $R^{III1}$ is —$CH_3$ when $R^5$ is F. In other embodiments of any one of one of Formulas (III)-(XV), $R^{III1}$ is —$CH_3$ when $R^5$ and $R^7$, taken together, form a 5- or 6-membered heterocycle, or when $R^6$ and $R^7$, taken together, form a 4-, 5- or 6-membered heterocycle, or when $R^8$ and $R^7$, taken together, form a 5- or 6-membered heterocycle.

In some embodiments of any one of Formulas (III)-(XV), $R^{III2}$ is H. In some embodiments of any one of Formulas (III)-(XV), $R^{III2}$ is F.

In an embodiment of any one of Formulas (III)-(XV), $R^B$ is —CH═$CH_2$.

In one embodiment of Formula (III), $R^B$ is —CH═$CH_2$ and a compound is provided having the structure of Formula (XVI):

(XVI)

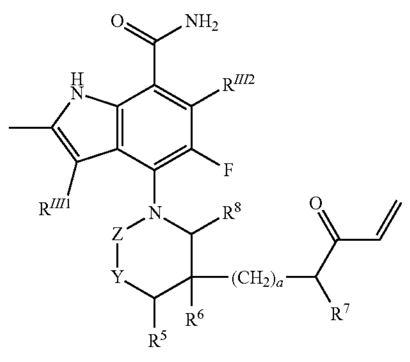

or a pharmaceutically acceptable salt, solvate, hydrate, isomer, tautomer, racemate or isotope thereof, wherein $R^{III1}$, $R^{III2}$, a, Z, Y, $R^5$, $R^6$, $R^7$ and $R^8$ are as defined above in the context of Formula (III).

In an embodiment of any one of Formulas (III)-(XIII), $R^B$ is —C≡CH, and a compound is provided having the structure of Formulas (XVII):

(XVII)

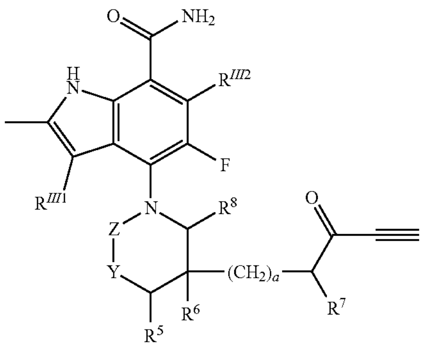

or a pharmaceutically acceptable salt, solvate, hydrate, isomer, tautomer, racemate or isotope thereof, wherein $R^{III1}$, $R^{III2}$, a, Z, Y, $R^5$, $R^6$, $R^7$ and $R^8$ are as defined above in the context of Formula (III).

In an embodiment of any one of Formulas (III)-(XIII), $R^B$ is —C≡C—$CH_3$ and a compound is provided having the structure of Formulas (XVIII):

(XVIII)

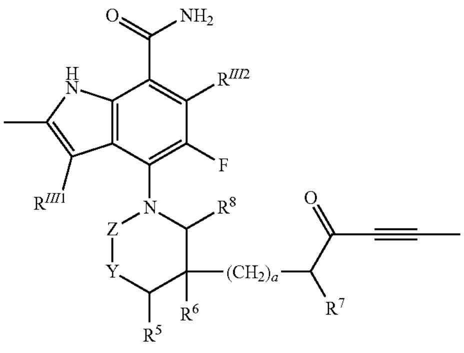

or a pharmaceutically acceptable salt, solvate, hydrate, isomer, tautomer, racemate or isotope thereof, wherein $R^{III1}$, $R^{III2}$, a, Z, Y, $R^5$, $R^6$, $R^7$ and $R^8$ are as defined above in the context of Formula (III).

In one embodiment, a compound of Formula (III) is provided, or a pharmaceutically acceptable salt, solvate, hydrate, isomer, tautomer, racemate, or isotope thereof, having the structure of a compound listed in Table 4.

TABLE 4

REPRESENTATIVE COMPOUNDS OF FORMULA (III)

| Cmpd No. | Structure | Name |
| --- | --- | --- |
| 27 | 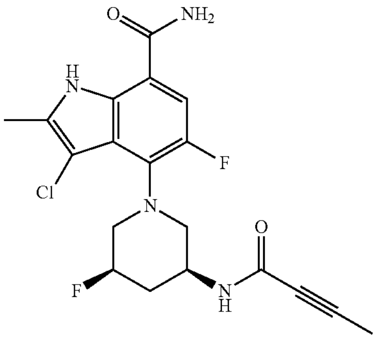 | 4-((3S,5R)-3-(but-2-ynamido)-5-fluoropiperidin-1-yl)-3-chloro-5-fluoro-2-methyl-1H-indole-7-carboxamide |
| 28 | 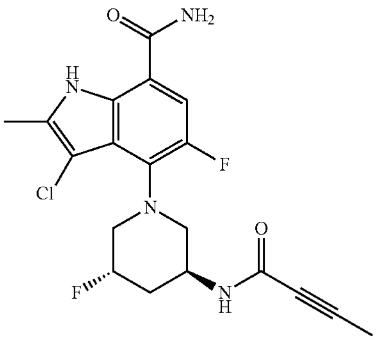 [SMILES: CC#CC(=O)N[C@H]1C[C@H](F)CN(c2c(F)cc(C(N)=O)c3[nH]c(C)c(Cl)c23)C1] | 4-((3S,5S)-3-(but-2-ynamido)-5-fluoropiperidin-1-yl)-3-chloro-5-fluoro-2-methyl-1H-indole-7-carboxamide |

TABLE 4-continued

| REPRESENTATIVE COMPOUNDS OF FORMULA (III) | | |
|---|---|---|
| Cmpd No. | Structure | Name |
| 29 | 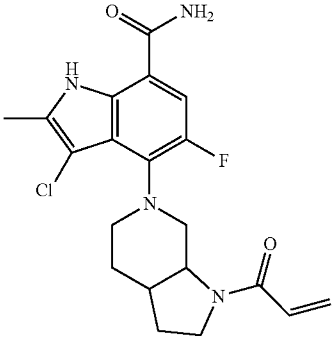 [SMILES: C=CC(=O)N1CCC2CCN(c3c(F)cc(C(N)=O)c4[nH]c(C)c(Cl)c34)CC21] | 4-(1-acryloyloctahydro-6H-pyrrolo[2,3-c]pyridin-6-yl)-3-chloro-5-fluoro-2-methyl-1H-indole-7-carboxamide |
| 29a<br>29b | RT = 8.163 mins<br>RT = 11.102 mins | Two isomers |
| 30 | 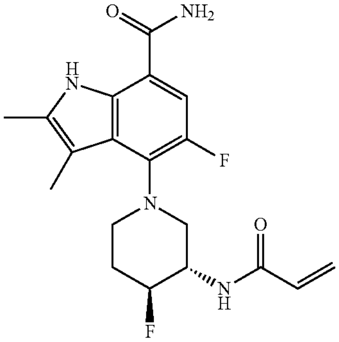 [SMILES: C=CC(=O)N[C@H]1CN(c2c(F)cc(C(N)=O)c3[nH]c(C)c(C)c23)CC[C@@H]1F] | 4-((3S,4S)-3-acrylamido-4-fluoropiperidin-1-yl)-5-fluoro-2,3-dimethyl-1H-indole-7-carboxamide |
| 31 | 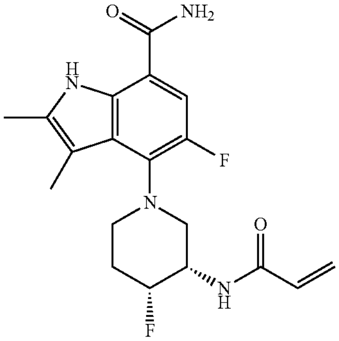 [SMILES: C=CC(=O)N[C@H]1CN(c2c(F)cc(C(N)=O)c3[nH]c(C)c(C)c23)CC[C@H]1F] | 4-((3S,4R)-3-acrylamido-4-fluoropiperidin-1-yl)-5-fluoro-2,3-dimethyl-1H-indole-7-carboxamide |
| 32 | 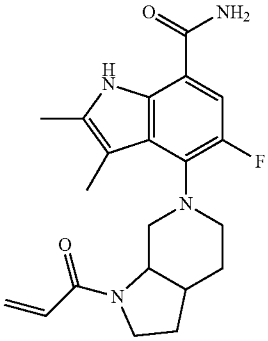 [SMILES: C=CC(=O)N1CCC2CCN(c3c(F)cc(C(N)=O)c4[nH]c(C)c(C)c34)CC21] | 4-(1-acryloyloctahydro-6H-pyrrolo[2,3-c]pyridin-6-yl)-5-fluoro-2,3-dimethyl-1H-indole-7-carboxamide |
| 32a<br>32b | RT = 4.826 mins<br>RT = 6.483 mins | Enantiomeric cis isomers |

TABLE 4-continued

| REPRESENTATIVE COMPOUNDS OF FORMULA (III) | | |
|---|---|---|
| Cmpd No. | Structure | Name |
| 33 | 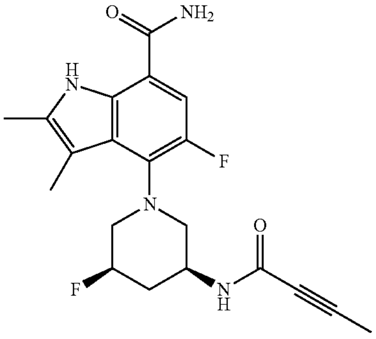 [SMILES: CC#CC(=O)N[C@H]1C[C@@H](F)CN(c2c(F)cc(C(N)=O)c3[nH]c(C)c(C)c23)C1] | 4-((3S,5R)-3-(but-2-ynamido)-5-fluoropiperidin-1-yl)-5-fluoro-2,3-dimethyl-1H-indole-7-carboxamide |
| 34 | 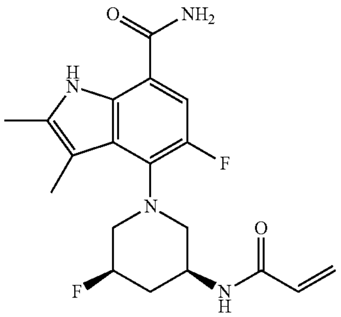 [SMILES: C=CC(=O)N[C@H]1C[C@@H](F)CN(c2c(F)cc(C(N)=O)c3[nH]c(C)c(C)c23)C1] | 4-((3S,5R)-3-acrylamido-5-fluoropiperidin-1-yl)-5-fluoro-2,3-dimethyl-1H-indole-7-carboxamide |
| 35 | 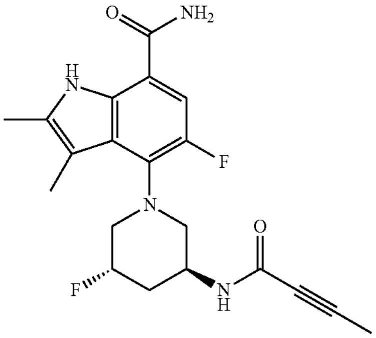 [SMILES: CC#CC(=O)N[C@H]1C[C@H](F)CN(c2c(F)cc(C(N)=O)c3[nH]c(C)c(C)c23)C1] | 4-((3S,5S)-3-(but-2-ynamido)-5-fluoropiperidin-1-yl)-5-fluoro-2,3-dimethyl-1H-indole-7-carboxamide |
| 36 | 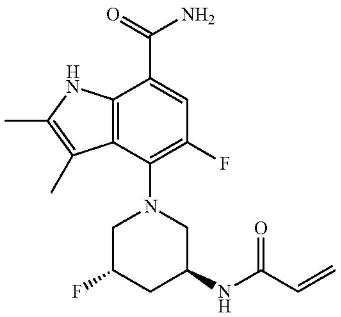 [SMILES: C=CC(=O)N[C@H]1C[C@H](F)CN(c2c(F)cc(C(N)=O)c3[nH]c(C)c(C)c23)C1] | 4-((3S,5R)-3-acrylamido-5-fluoropiperidin-1-yl)-5-fluoro-2,3-dimethyl-1H-indole-7-carboxamide |

TABLE 4-continued

| REPRESENTATIVE COMPOUNDS OF FORMULA (III) | | |
|---|---|---|
| Cmpd No. | Structure | Name |
| 37 | 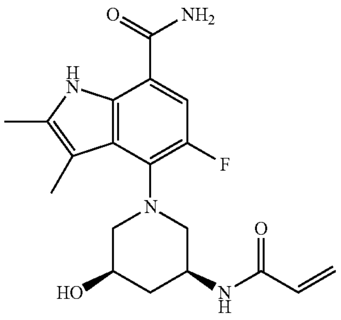 [SMILES: C=CC(=O)N[C@H]1C[C@@H](O)CN(c2c(F)cc(C(N)=O)c3[nH]c(C)c(C)c23)C1] | 4-((3S,5R)-3-acrylamido-5-hydroxypiperidin-1-yl)-5-fluoro-2,3-dimethyl-1H-indole-7-carboxamide |
| 38 | 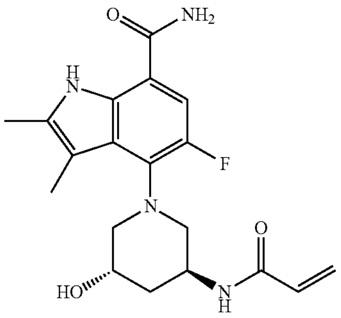 [SMILES: C=CC(=O)N[C@H]1C[C@H](O)CN(c2c(F)cc(C(N)=O)c3[nH]c(C)c(C)c23)C1] | 4-((3S,5S)-3-acrylamido-5-hydroxypiperidin-1-yl)-5-fluoro-2,3-dimethyl-1H-indole-7-carboxamide |
| 39 | 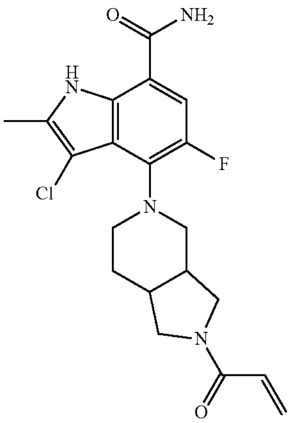 [SMILES: C=CC(=O)N1CC2CCN(c3c(F)cc(C(N)=O)c4[nH]c(C)c(Cl)c34)CC2C1] | 4-(trans-2-acryloyloctahydro-5H-pyrrolo[3,4-c]pyridin-5-yl)-3-chloro-5-fluoro-2-methyl-1H-indole-7-carboxamide |
| 40 | 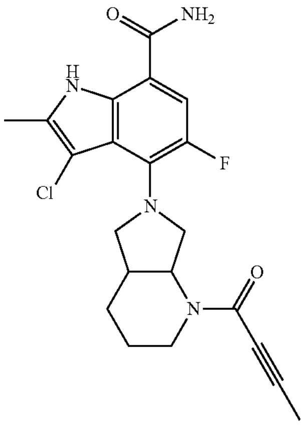 [SMILES: CC#CC(=O)N1CCCC2CN(c3c(F)cc(C(N)=O)c4[nH]c(C)c(Cl)c34)CC21] | 4-(1-(but-2-ynoyl)octahydro-6H-pyrrolo[3,4-b]pyridin-6-yl)-3-chloro-5-fluoro-2-methyl-1H-indole-7-carboxamide |

TABLE 4-continued

| REPRESENTATIVE COMPOUNDS OF FORMULA (III) | | |
|---|---|---|
| Cmpd No. | Structure | Name |
| 41a | 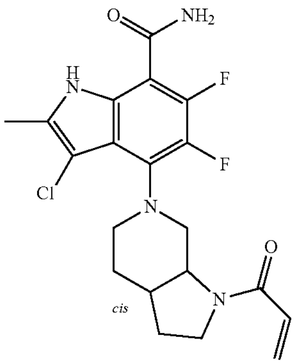 [SMILES: C=CC(=O)N1CCC2CCN(c3c(F)c(F)c(C(N)=O)c4[nH]c(C)c(Cl)c34)CC21] | 4-(1-acryloyloctahydro-6H-pyrrolo[2,3-c]pyridin-6-yl)-3-chloro-5,6-difluoro-2-methyl-1H-indole-7-carboxamide |
| 41b | 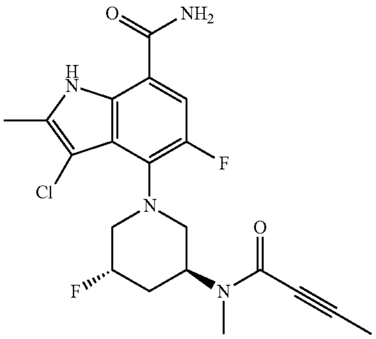 [SMILES: CC#CC(=O)N(C)[C@H]1C[C@H](F)CN(c2c(F)cc(C(N)=O)c3[nH]c(C)c(Cl)c23)C1] | 3-chloro-5-fluoro-4-((3S,5S)-3-fluoro-5-(N-methylbut-2-ynamido)piperidin-1-yl)-2-methyl-1H-indole-7-carboxamide |
| 41c | 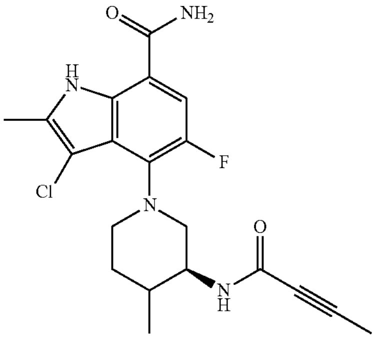 [SMILES: CC#CC(=O)N[C@@H]1CN(c2c(F)cc(C(N)=O)c3[nH]c(C)c(Cl)c23)CCC1C] | 4-((3S)-3-(but-2-ynamido)-4-methylpiperidin-1-yl)-3-chloro-5-fluoro-2-methyl-1H-indole-7-carboxamide |
| 41d | 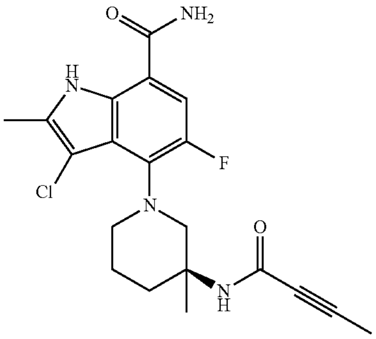 [SMILES: CC#CC(=O)N[C@@]1(C)CCCN(c2c(F)cc(C(N)=O)c3[nH]c(C)c(Cl)c23)C1] | (S)-4-(3-(but-2-ynamido)-3-methylpiperidin-1-yl)-3-chloro-5-fluoro-2-methyl-1H-indole-7-carboxamide |

TABLE 4-continued

| REPRESENTATIVE COMPOUNDS OF FORMULA (III) | | |
|---|---|---|
| Cmpd No. | Structure | Name |
| 41e | 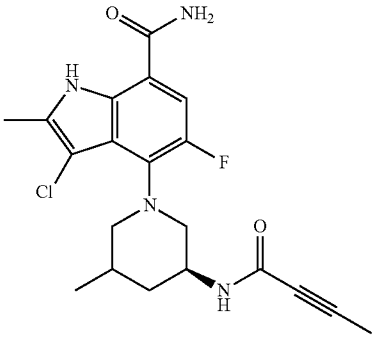 [SMILES: CC#CC(=O)N[C@H]1CC(C)CN(c2c(F)cc(C(N)=O)c3[nH]c(C)c(Cl)c23)C1] | 4-((3S)-3-(but-2-ynamido)-5-methylpiperidin-1-yl)-3-chloro-5-fluoro-2-methyl-1H-indole-7-carboxamide |
| 41f | 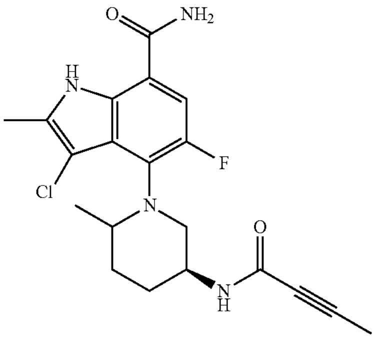 [SMILES: CC#CC(=O)N[C@H]1CCC(C)N(c2c(F)cc(C(N)=O)c3[nH]c(C)c(Cl)c23)C1] | 4-((5S)-5-(but-2-ynamido)-2-methylpiperidin-1-yl)-3-chloro-5-fluoro-2-methyl-1H-indole-7-carboxamide |
| 41g | 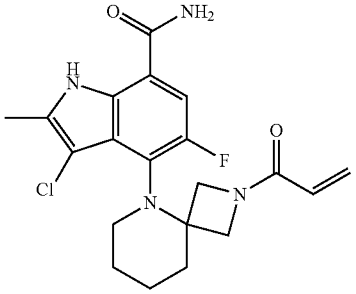 [SMILES: C=CC(=O)N1CC2(CCCCN2c2c(F)cc(C(N)=O)c3[nH]c(C)c(Cl)c23)C1] | 4-(2-acryloyl-2,5-diazaspiro[3.5]nonan-5-yl)-3-chloro-5-fluoro-2-methyl-1H-indole-7-carboxamide |
| 41h | 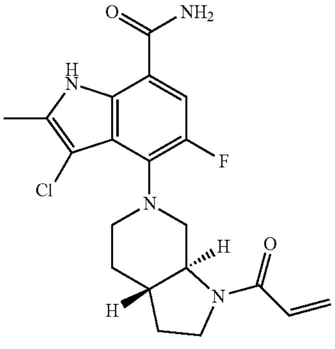 [SMILES: C=CC(=O)N1CC[C@@H]2CCN(c3c(F)cc(C(N)=O)c4[nH]c(C)c(Cl)c34)C[C@H]21] | 4-((3aS,7aS)-1-acryloyloctahydro-6H-pyrrolo[2,3-c]pyridin-6-yl)-3-chloro-5-fluoro-2-methyl-1H-indole-7-carboxamide |

TABLE 4-continued

| REPRESENTATIVE COMPOUNDS OF FORMULA (III) | | |
|---|---|---|
| Cmpd No. | Structure | Name |
| 41i | 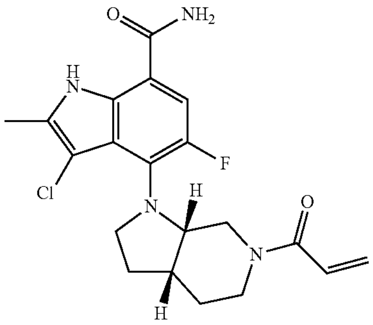 [SMILES: C=CC(=O)N1CC[C@@H]2CCN(c3c(F)cc(C(N)=O)c4[nH]c(C)c(Cl)c34)[C@@H]2C1] | 4-((3aS,7aS)-6-acryloyloctahydro-1H-pyrrolo[2,3-c]pyridin-1-yl)-3-chloro-5-fluoro-2-methyl-1H-indole-7-carboxamide |
| 41j | 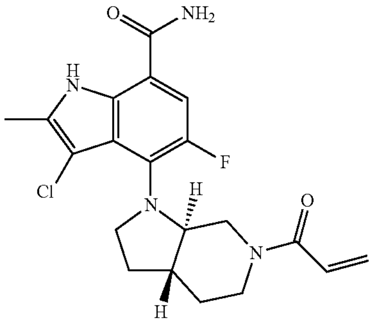 [SMILES: C=CC(=O)N1CC[C@@H]2CCN(c3c(F)cc(C(N)=O)c4[nH]c(C)c(Cl)c34)[C@H]2C1] | 4-((3aS,7aR)-6-acryloyloctahydro-1H-pyrrolo[2,3-c]pyridin-1-yl)-3-chloro-5-fluoro-2-methyl-1H-indole-7-carboxamide |
| 41k | 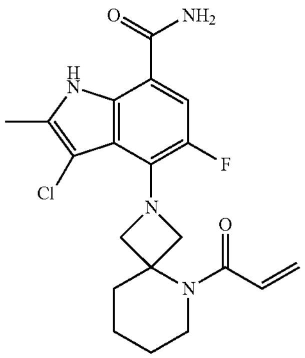 [SMILES: C=CC(=O)N1CCCCC12CN(c1c(F)cc(C(N)=O)c3[nH]c(C)c(Cl)c13)C2] | 4-(5-acryloyl-2,5-diazaspiro[3.5]nonan-2-yl)-3-chloro-5-fluoro-2-methyl-1H-indole-7-carboxamide |
| 41l | 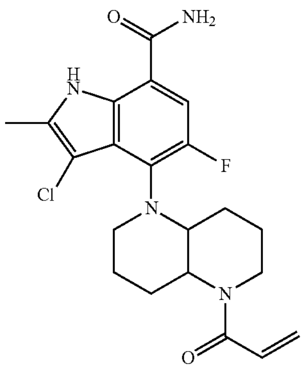 [SMILES: C=CC(=O)N1CCCC2C1CCCN2c1c(F)cc(C(N)=O)c2[nH]c(C)c(Cl)c12] | 4-(5-acryloyloctahydro-1,5-naphthyridin-1(2H)-yl)-3-chloro-5-fluoro-2-methyl-1H-indole-7-carboxamide |

TABLE 4-continued
| REPRESENTATIVE COMPOUNDS OF FORMULA (III) | | |
|---|---|---|
| Cmpd No. | Structure | Name |
| 41m | 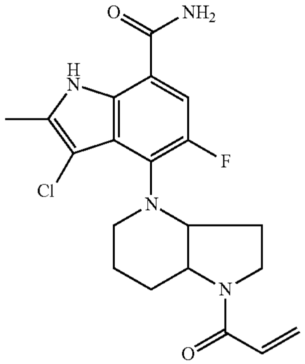 [SMILES: C=CC(=O)N1CCC2C1CCCN2c1c(F)cc(C(N)=O)c2[nH]c(C)c(Cl)c12] | 4-(1-acryloyloctahydro-4H-pyrrolo[3,2-b]pyridin-4-yl)-3-chloro-5-fluoro-2-methyl-1H-indole-7-carboxamide |
| 41n | 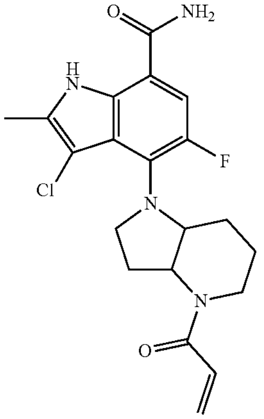 [SMILES: C=CC(=O)N1CCCC2C1CCN2c1c(F)cc(C(N)=O)c2[nH]c(C)c(Cl)c12] | 4-(4-acryloyloctahydro-1H-pyrrolo[3,2-b]pyridin-1-yl)-3-chloro-5-fluoro-2-methyl-1H-indole-7-carboxamide |
| 41o | 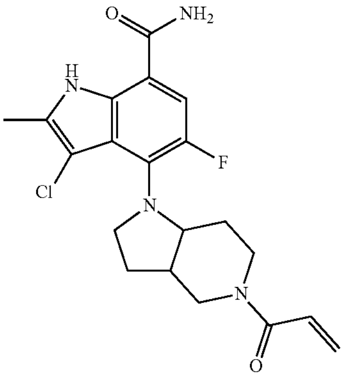 [SMILES: C=CC(=O)N1CCC2C(CCN2c2c(F)cc(C(N)=O)c3[nH]c(C)c(Cl)c23)C1] | 4-(5-acryloyloctahydro-1H-pyrrolo[3,2-c]pyridin-1-yl)-3-chloro-5-fluoro-2-methyl-1H-indole-7-carboxamide |

TABLE 4-continued

REPRESENTATIVE COMPOUNDS OF FORMULA (III)

| Cmpd No. | Structure | Name |
|---|---|---|
| 41p | 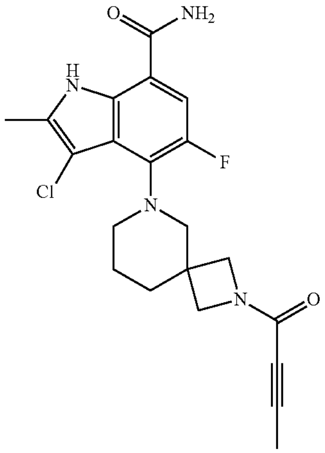 [SMILES: CC#CC(=O)N1CC2(CCCN(c3c(F)cc(C(N)=O)c4[nH]c(C)c(Cl)c34)C2)C1] | 4-(2-(but-2-ynoyl)-2,6-diazaspiro[3.5]nonan-6-yl)-3-chloro-5-fluoro-2-methyl-1H-indole-7-carboxamide |
| 41q | 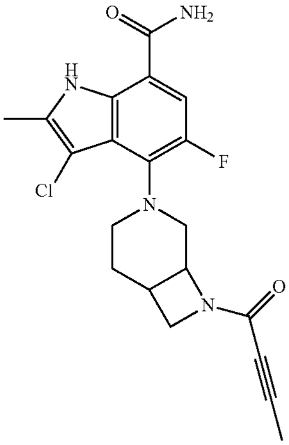 [SMILES: CC#CC(=O)N1CC2CCN(c3c(F)cc(C(N)=O)c4[nH]c(C)c(Cl)c34)CC21] | 4-(8-(but-2-ynoyl)-3,8-diazabicyclo[4.2.0]octan-3-yl)-3-chloro-5-fluoro-2-methyl-1H-indole-7-carboxamide |
| 41r | 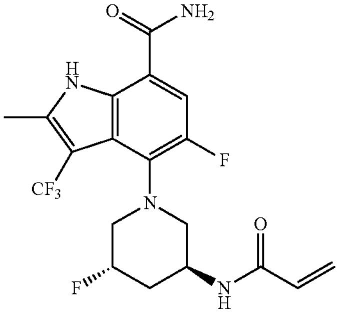 [SMILES: C=CC(=O)N[C@H]1C[C@H](F)CN(c2c(F)cc(C(N)=O)c3[nH]c(C)c(C(F)(F)F)c23)C1] | 4-((3S,5S)-3-acrylamido-5-fluoropiperidin-1-yl)-5-fluoro-2-methyl-3-(trifluoromethyl)-1H-indole-7-carboxamide |
| 41s | 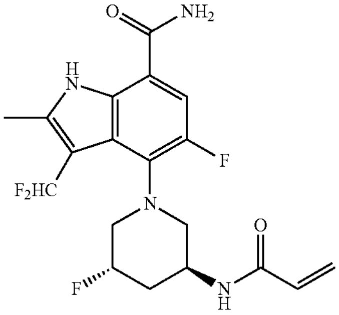 [SMILES: C=CC(=O)N[C@H]1C[C@H](F)CN(c2c(F)cc(C(N)=O)c3[nH]c(C)c(C(F)F)c23)C1] | 4-((3S,5S)-3-acrylamido-5-fluoropiperidin-1-yl)-3-(difluoromethyl)-5-fluoro-2-methyl-1H-indole-7-carboxamide |

TABLE 4-continued

| REPRESENTATIVE COMPOUNDS OF FORMULA (III) | | |
|---|---|---|
| Cmpd No. | Structure | Name |
| 41t | 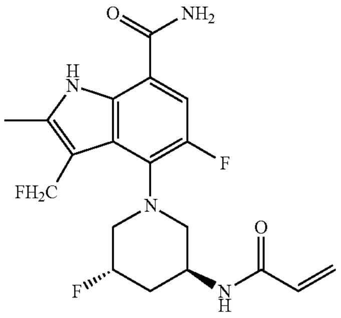 | 4-((3S,5S)-3-acrylamido-5-fluoropiperidin-1-yl)-5-fluoro-3-(fluoromethyl)-2-methyl-1H-indole-7-carboxamide |
| 42a | 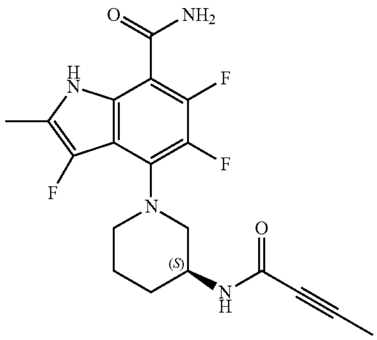 | (S)-4-(3-(but-2-ynamido)piperidin-1-yl)-3,5,6-trifluoro-2-methyl-1H-indole-7-carboxamide |
| 42b | 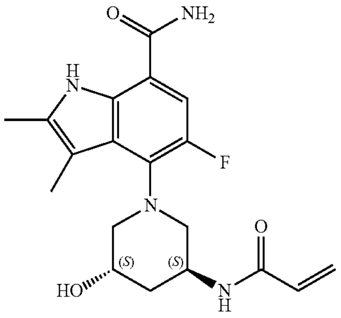 | 4-((3S,5S)-3-acrylamido-5-hydroxypiperidin-1-yl)-5-fluoro-2,3-dimethyl-1H-indole-7-carboxamide |
| 42c | 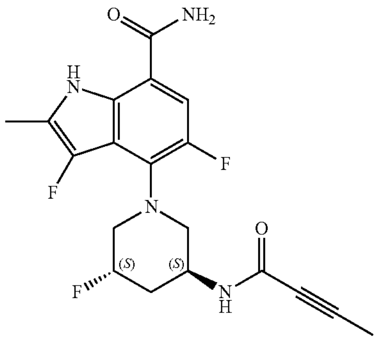 | 4-((3S,5S)-3-(but-2-ynamido)-5-fluoropiperidin-1-yl)-3,5-difluoro-2-methyl-1H-indole-7-carboxamide |

TABLE 4-continued

| REPRESENTATIVE COMPOUNDS OF FORMULA (III) | | |
|---|---|---|
| Cmpd No. | Structure | Name |
| 42d | 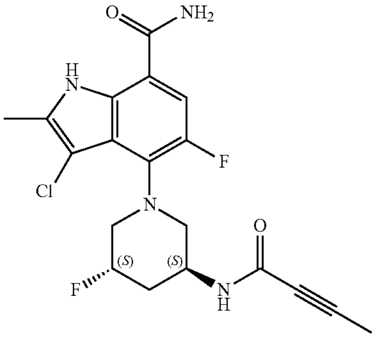 | 4-((3S,5S)-3-(but-2-ynamido)-5-fluoropiperidin-1-yl)-3-chloro-5-fluoro-2-methyl-1H-indole-7-carboxamide |
| 42e | 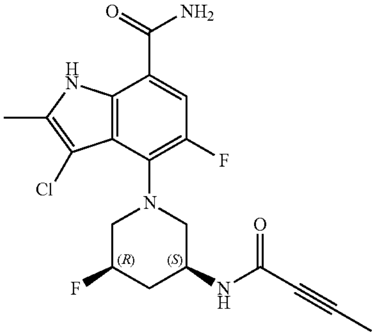 | 4-((3S,5R)-3-(but-2-ynamido)-5-fluoropiperidin-1-yl)-3-chloro-5-fluoro-2-methyl-1H-indole-7-carboxamide |
| 42f | 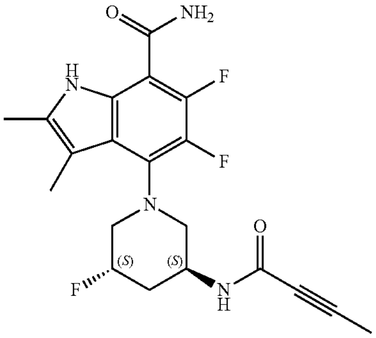 | 4-((3S,5S)-3-(but-2-ynamido)-5-fluoropiperidin-1-yl)-5,6-difluoro-2,3-dimethyl-1H-indole-7-carboxamide |
| 42g | 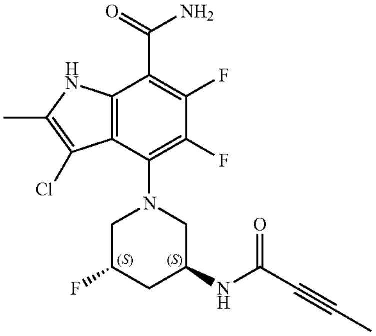 | 4-((3S,5S)-3-(but-2-ynamido)-5-fluoropiperidin-1-yl)-3-chloro-5,6-difluoro-2-methyl-1H-indole-7-carboxamide |

TABLE 4-continued

| REPRESENTATIVE COMPOUNDS OF FORMULA (III) | | |
|---|---|---|
| Cmpd No. | Structure | Name |
| 42h | 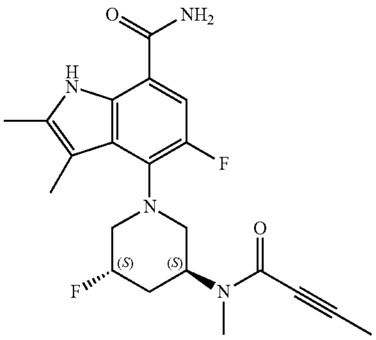 | 5-fluoro-4-((3S,5S)-3-fluoro-5-(N-methylbut-2-ynamido)piperidin-1-yl)-2,3-dimethyl-1H-indole-7-carboxamide |
| 42i | 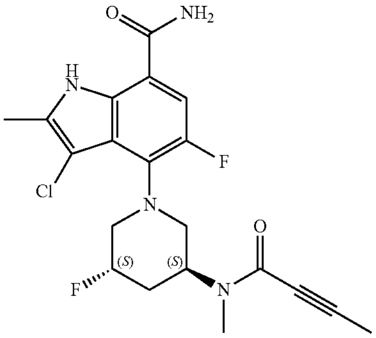 | 3-chloro-5-fluoro-4-((3S,5S)-3-fluoro-5-(N-methylbut-2-ynamido)piperidin-1-yl)-2-methyl-1H-indole-7-carboxamide |
| 42j | 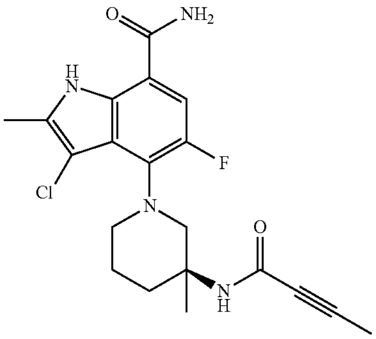 [SMILES: CC#CC(=O)N[C@@]1(C)CCCN(c2c(F)cc(C(N)=O)c3[nH]c(C)c(Cl)c23)C1] | (S)-4-(3-(but-2-ynamido)-3-methylpiperidin-1-yl)-3-chloro-5-fluoro-2-methyl-1H-indole-7-carboxamide |
| 42k | 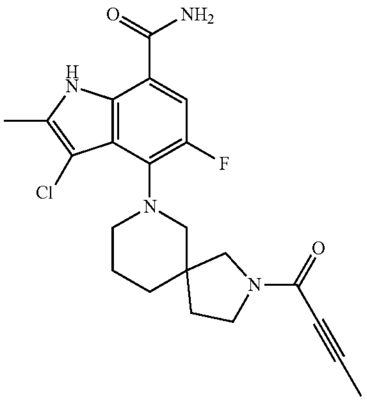 [SMILES: CC#CC(=O)N1CCC2(CCCN(c3c(F)cc(C(N)=O)c4[nH]c(C)c(Cl)c34)C2)C1] | 4-(2-(but-2-ynoyl)-2,7-diazaspiro[4.5]decan-7-yl)-3-chloro-5-fluoro-2-methyl-1H-indole-7-carboxamide |

TABLE 4-continued
| REPRESENTATIVE COMPOUNDS OF FORMULA (III) | | |
|---|---|---|
| Cmpd No. | Structure | Name |
| 42l | 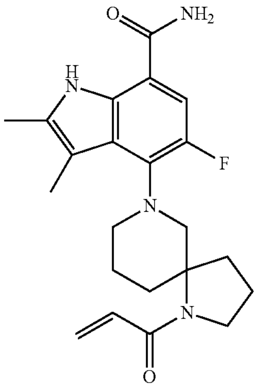 [SMILES: C=CC(=O)N1CCCC12CCCN(c1c(F)cc(C(N)=O)c3[nH]c(C)c(C)c13)C2] | 4-(1-acryloyl-1,7-diazaspiro[4.5]decan-7-yl)-5-fluoro-2,3-dimethyl-1H-indole-7-carboxamide |
| 42m1 | 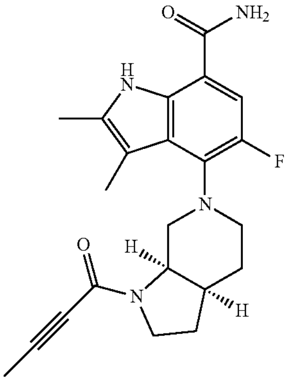 | 4-(1-(but-2-ynoyl)octahydro-6H-pyrrolo[2,3-c]pyridin-6-yl)-5-fluoro-2,3-dimethyl-1H-indole-7-carboxamide Mixture of cis isomers |
| 42m2 | 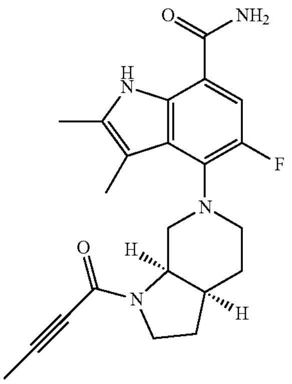 [SMILES: CC#CC(=O)N1CC[C@@H]2CCN(c3c(F)cc(C(N)=O)c4[nH]c(C)c(C)c34)C[C@@H]21] Assumed | 4-((3aS,7aR)-1-(but-2-ynoyl)octahydro-6H-pyrrolo[2,3-c]pyridin-6-yl)-5-fluoro-2,3-dimethyl-1H-indole-7-carboxamide |

TABLE 4-continued

| REPRESENTATIVE COMPOUNDS OF FORMULA (III) | | |
|---|---|---|
| Cmpd No. | Structure | Name |
| 42n | 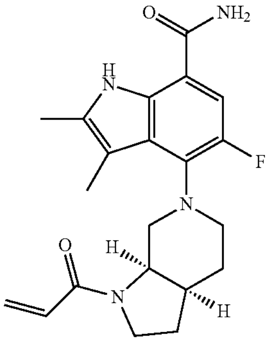 asssumed | 4-((3aS,7aR)-1-acryloyloctahydro-6H-pyrrolo[2,3-c]pyridin-6-yl)-5-fluoro-2,3-dimethyl-1H-indole-7-carboxamide |
| 42o | 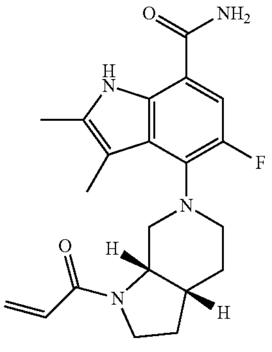 assumed | 4-((3aR,7aS)-1-acryloyloctahydro-6H-pyrrolo[2,3-c]pyridin-6-yl)-5-fluoro-2,3-dimethyl-1H-indole-7-carboxamide |
| 42p | 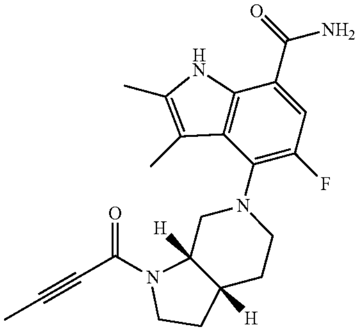 Assumed | 4-((3aR,7aS)-1-(but-2-ynoyl)octahydro-6H-pyrrolo[2,3-c]pyridin-6-yl)-5-fluoro-2,3-dimethyl-1H-indole-7-carboxamide |
| 42q | 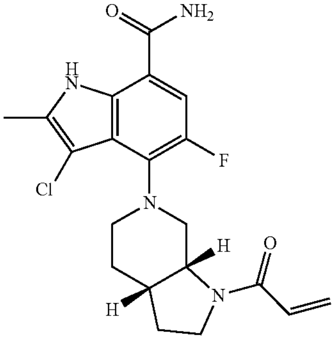 assumed | 4-((3aS,7aR)-1-acryloyloctahydro-6H-pyrrolo[2,3-c]pyridin-6-yl)-3-chloro-5-fluoro-2-methyl-1H-indole-7-carboxamide |

TABLE 4-continued

| REPRESENTATIVE COMPOUNDS OF FORMULA (III) | | |
|---|---|---|
| Cmpd No. | Structure | Name |
| 42r | 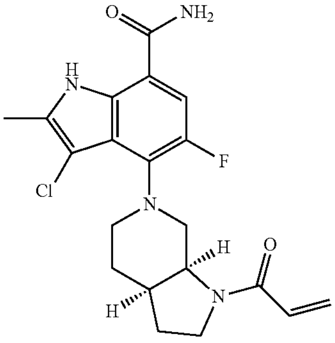 assumed | 4-((3aR,7aS)-1-acryloyloctahydro-6H-pyrrolo[2,3-c]pyridin-6-yl)-3-chloro-5-fluoro-2-methyl-1H-indole-7-carboxamide |
| 42s | 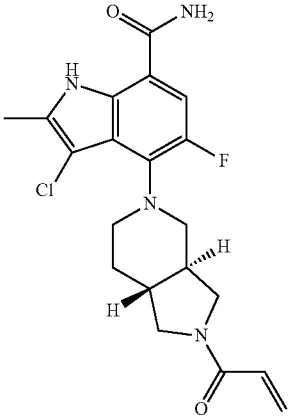 [SMILES: C=CC(=O)N1C[C@@H]2CN(c3c(F)cc(C(N)=O)c4[nH]c(C)c(Cl)c34)CC[C@H]2C1] | 4-((3aS,7aR)-2-acryloyloctahydro-5H-pyrrolo[3,4-c]pyridin-5-yl)-3-chloro-5-fluoro-2-methyl-1H-indole-7-carboxamide |
| 42t | 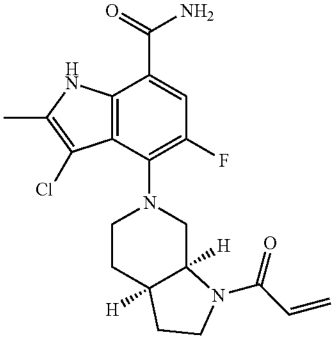 [SMILES: C=CC(=O)N1CC[C@H]2CCN(c3c(F)cc(C(N)=O)c4[nH]c(C)c(Cl)c34)C[C@H]21] | 4-((3aR,7aS)-1-acryloyloctahydro-6H-pyrrolo[2,3-c]pyridin-6-yl)-3-chloro-5-fluoro-2-methyl-1H-indole-7-carboxamide |
| 42u | 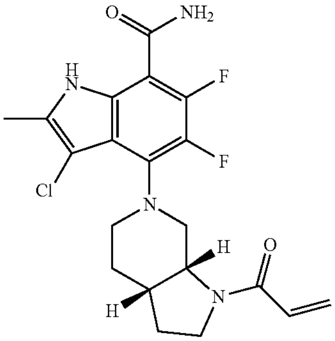 Assumed | 4-((3aS,7aR)-1-acryloyloctahydro-6H-pyrrolo[2,3-c]pyridin-6-yl)-3-chloro-5,6-difluoro-2-methyl-1H-indole-7-carboxamide |

TABLE 4-continued

| REPRESENTATIVE COMPOUNDS OF FORMULA (III) | | |
|---|---|---|
| Cmpd No. | Structure | Name |
| 42v1 | 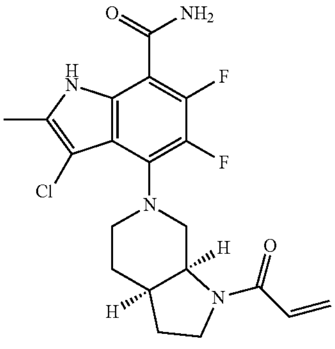 [SMILES: C=CC(=O)N1CC[C@H]2CCN(c3c(F)c(F)c(C(N)=O)c4[nH]c(C)c(Cl)c34)C[C@H]21] Assumed | 4-((3aR,7aS)-1-acryloyloctahydro-6H-pyrrolo[2,3-c]pyridin-6-yl)-3-chloro-5,6-difluoro-2-methyl-1H-indole-7-carboxamide |
| 42v2 | 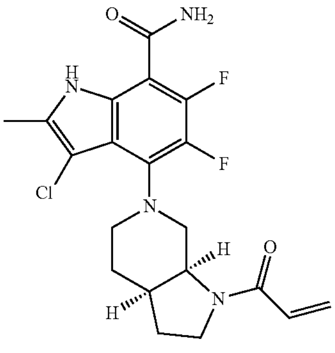 | 4-(1-acryloyloctahydro-6H-pyrrolo[2,3-c]pyridin-6-yl)-3-chloro-5,6-difluoro-2-methyl-1H-indole-7-carboxamide Mixture of cis isomers |
| 42w | 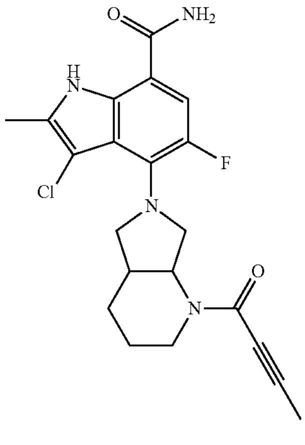 [SMILES: CC#CC(=O)N1CCCC2CN(c3c(F)cc(C(N)=O)c4[nH]c(C)c(Cl)c34)CC21] | 4-(1-(but-2-ynoyl)octahydro-6H-pyrrolo[3,4-b]pyridin-6-yl)-3-chloro-5-fluoro-2-methyl-1H-indole-7-carboxamide |

TABLE 4-continued

REPRESENTATIVE COMPOUNDS OF FORMULA (III)

| Cmpd No. | Structure | Name |
| --- | --- | --- |
| 42x | 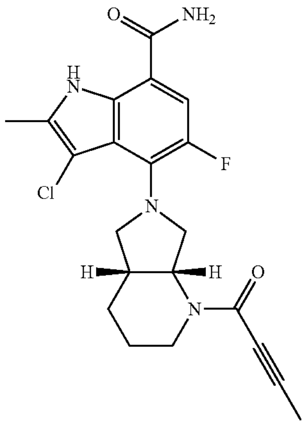 Assumed | 4-((4aR,7aR)-1-(but-2-ynoyl)octahydro-6H-pyrrolo[3,4-b]pyridin-6-yl)-3-chloro-5-fluoro-2-methyl-1H-indole-7-carboxamide |
| 42y | 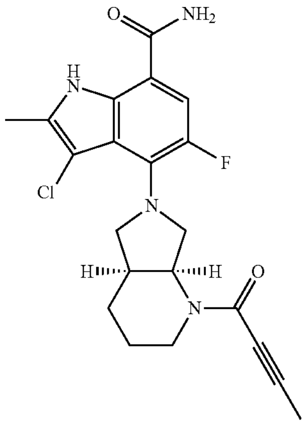 Assumed | 4-((4aS,7aS)-1-(but-2-ynoyl)octahydro-6H-pyrrolo[3,4-b]pyridin-6-yl)-3-chloro-5-fluoro-2-methyl-1H-indole-7-carboxamide |

In further embodiments are pharmaceutically acceptable salts of compounds of formula (I), formula (II), formula (II-a), formula (II-b), formula (IV), formula (V-a), formula (V-b), formula (VI-a), formula (VI-a-1), formula (VI-b), formula (VII-a), formula (VII-b), formula (VII-c), formula (VIII-a), formula (VIII-b), formula (VIII-c), formula (IX-a), formula (IX-b), formula (X-a), formula (X-b), formula (X-c), formula (XI-a), formula (XI-b), formula (XI-c), formula (XII-a), formula (XII-b), formula (XII-c), formula (XIII-a), formula (XIII-b), formula (XIII-c), formula (XIII), formula (XIV), formula (XV-a), formula (XV-b), formula (XV-c), formula (XVI), formula (XVII or formula (XVIII).

In other embodiments are solvates of compounds of formula (I), formula (II), formula (II-a), formula (II-b), formula (IV), formula (V-a), formula (V-b), formula (VI-a), formula (VI-a-1), formula (VI-b), formula (VII-a), formula (VII-b), formula (VII-c), formula (VIII-a), formula (VIII-b), formula (VIII-c), formula (IX-a), formula (IX-b), formula (X-a), formula (X-b), formula (X-c), formula (XI-a), formula (XI-b), formula (XI-c), formula (XII-a), formula (XII-b), formula (XII-c), formula (XIII-a), formula (XIII-b), formula (XIII-c), formula (XIII), formula (XIV), formula (XV-a), formula (XV-b), formula (XV-c), formula (XVI), formula (XVII or formula (XVIII).

In other embodiments are hydrates of compounds of formula (I), formula (II), formula (II-a), formula (II-b), formula (IV), formula (V-a), formula (V-b), formula (VI-a), formula (VI-a-1), formula (VI-b), formula (VII-a), formula (VII-b), formula (VII-c), formula (VIII-a), formula (VIII-b), formula (VIII-c), formula (IX-a), formula (IX-b), formula (X-a), formula (X-b), formula (X-c), formula (XI-a), formula (XI-b), formula (XI-c), formula (XII-a), formula (XII-b), formula (XII-c), formula (XIII-a), formula (XIII-b), formula (XIII-c), formula (XIII), formula (XIV), formula (XV-a), formula (XV-b), formula (XV-c), formula (XVI), formula (XVII or formula (XVIII).

In other embodiments are isomers of compounds of formula (I), formula (II), formula (II-a), formula (II-b), formula (IV), formula (V-a), formula (V-b), formula (VI-a), formula (VI-a-1), formula (VI-b), formula (VII-a), formula (VII-b), formula (VII-c), formula (VIII-a), formula (VIII-b), formula (VIII-c), formula (IX-a), formula (IX-b), formula (X-a), formula (X-b), formula (X-c), formula (XI-a), formula (XI-b), formula (XI-c), formula (XII-a), formula (XII-b), formula (XII-c), formula (XIII-a), formula (XIII-b), formula (XIII-c), formula (XIII), formula (XIV), formula (XV-a), formula (XV-b), formula (XV-c), formula (XVI), formula (XVII or formula (XVIII).

In other embodiments are tautomers of compounds of formula (I), formula (II), formula (II-a), formula (II-b), formula (IV), formula (V-a), formula (V-b), formula (VI-a), formula (VI-a-1), formula (VI-b), formula (VII-a), formula (VII-b), formula (VII-c), formula (VIII-a), formula (VIII-b), formula (VIII-c), formula (IX-a), formula (IX-b), formula (X-a), formula (X-b), formula (X-c), formula (XI-a), formula (XI-b), formula (XI-c), formula (XII-a), formula (XII-b), formula (XII-c), formula (XIII-a), formula (XIII-b), formula (XIII-c), formula (XIII), formula (XIV), formula (XV-a), formula (XV-b), formula (XV-c), formula (XVI), formula (XVII or formula (XVIII).

In other embodiments are racemates of compounds of formula (I), formula (II), formula (II-a), formula (II-b), formula (IV), formula (V-a), formula (V-b), formula (VI-a), formula (VI-a-1), formula (VI-b), formula (VII-a), formula (VII-b), formula (VII-c), formula (VIII-a), formula (VIII-b), formula (VIII-c), formula (IX-a), formula (IX-b), formula (X-a), formula (X-b), formula (X-c), formula (XI-a), formula (XI-b), formula (XI-c), formula (XII-a), formula (XII-b), formula (XII-c), formula (XIII-a), formula (XIII-b), formula (XIII-c), formula (XIII), formula (XIV), formula (XV-a), formula (XV-b), formula (XV-c), formula (XVI), formula (XVII or formula (XVIII).

In other embodiments are isotopic forms of compounds of formula (I), formula (II), formula (II-a), formula (II-b), formula (IV), formula (V-a), formula (V-b), formula (VI-a), formula (VI-a-1), formula (VI-b), formula (VII-a), formula (VII-b), formula (VII-c), formula (VIII-a), formula (VIII-b), formula (VIII-c), formula (IX-a), formula (IX-b), formula (X-a), formula (X-b), formula (X-c), formula (XI-a), formula (XI-b), formula (XI-c), formula (XII-a), formula (XII-b), formula (XII-c), formula (XIII-a), formula (XIII-b), formula (XIII-c), formula (XIII), formula (XIV), formula (XV-a), formula (XV-b), formula (XV-c), formula (XVI), formula (XVII or formula (XVIII).

In further embodiments, are pharmaceutical compositions comprising compounds of formula (I), formula (II), formula (II-a), formula (II-b), formula (IV), formula (V-a), formula (V-b), formula (VI-a), formula (VI-a-1), formula (VI-b), formula (VII-a), formula (VII-b), formula (VII-c), formula (VIII-a), formula (VIII-b), formula (VIII-c), formula (IX-a), formula (IX-b), formula (X-a), formula (X-b), formula (X-c), formula (XI-a), formula (XI-b), formula (XI-c), formula (XII-a), formula (XII-b), formula (XII-c), formula (XIII-a), formula (XIII-b), formula (XIII-c), formula (XIII), formula (XIV), formula (XV-a), formula (XV-b), formula (XV-c), formula (XVI), formula (XVII or formula (XVIII), or a pharmaceutically acceptable salt, solvate, hydrate, isomer, tautomer, racemate or isotope thereof.

In further embodiments, are pharmaceutical compositions comprising compounds of formula (I), formula (II), formula (II-a), formula (II-b), formula (IV), formula (V-a), formula (V-b), formula (VI-a), formula (VI-a-1), formula (VI-b), formula (VII-a), formula (VII-b), formula (VII-c), formula (VIII-a), formula (VIII-b), formula (VIII-c), formula (IX-a), formula (IX-b), formula (X-a), formula (X-b), formula (X-c), formula (XI-a), formula (XI-b), formula (XI-c), formula (XII-a), formula (XII-b), formula (XII-c), formula (XIII-a), formula (XIII-b), formula (XIII-c), formula (XIII), formula (XIV), formula (XV-a), formula (XV-b), formula (XV-c), formula (XVI), formula (XVII or formula (XVIII), or a pharmaceutically acceptable salt, solvate, hydrate, isomer, tautomer, racemate or isotope thereof and at least one pharmaceutically acceptable excipient.

In another embodiment, are pharmaceutical compositions comprising compounds of formula (I), formula (II), formula (II-a), formula (II-b), formula (IV), formula (V-a), formula (V-b), formula (VI-a), formula (VI-a-1), formula (VI-b), formula (VII-a), formula (VII-b), formula (VII-c), formula (VIII-a), formula (VIII-b), formula (VIII-c), formula (IX-a), formula (IX-b), formula (X-a), formula (X-b), formula (X-c), formula (XI-a), formula (XI-b), formula (XI-c), formula (XII-a), formula (XII-b), formula (XII-c), formula (XIII-a), formula (XIII-b), formula (XIII-c), formula (XIII), formula (XIV), formula (XV-a), formula (XV-b), formula (XV-c), formula (XVI), formula (XVII or formula (XVIII), or a pharmaceutically acceptable salt, solvate, hydrate, isomer, tautomer, racemate or isotope thereof and a pharmaceutically acceptable carrier, adjuvant or vehicle.

Diseases

Described herein is a method of inhibiting a protein kinase comprising contacting the protein kinase with an effective amount of a compound of Formula (I), Formula (II) or Formula (III), or a pharmaceutically acceptable salt, solvate, hydrate, isomer, tautomer, racemate, isotope, or pharmaceutical composition thereof. In some embodiments, the protein kinase is BTK.

Described herein are methods for treating a BTK dependent condition, comprising administering to a subject in need thereof, an effective amount of a compound of Formula (I), Formula (II) or Formula (III), or a pharmaceutically acceptable salt, solvate, hydrate, isomer, tautomer, racemate, isotope, or pharmaceutical composition thereof.

In some embodiments the BTK dependent condition is cancer, an autoimmune disease, an inflammatory disease, or a theromboembolic disease. In some embodiments the autoimmune disease is multiple sclerosis, rheumatoid arthritis, psoriasis, Sjogren's syndrome, or systemic lupus erythematosus. In some embodiments the inflammatory disease is urticaria. In some embodiments the BTK dependent condition is cancer. In some embodiments the BTK dependent condition is an autoimmune disease. In some embodiments the BTK dependent condition is an inflammatory disease. In some embodiments the BTK dependent condition is a theromboembolic disease. In some embodiments the BTK dependent condition is multiple sclerosis. In some embodiments the BTK dependent condition is rheumatoid arthritis. In some embodiments the BTK dependent condition is psoriasis. In some embodiments the BTK dependent condition is Sjogren's syndrome. In some embodiments the BTK dependent condition is systemic lupus erythematosus. In some embodiments the BTK dependent condition is urticaria.

In some embodiments are uses of a compound of Formula (I), Formula (II) or Formula (III), or a pharmaceutically acceptable salt, solvate, hydrate, isomer, tautomer, racemate, isotope, or pharmaceutical composition thereof in the manufacture of a medicament. In some embodiments the medicament is for the treatment of cancer. In some embodiments the medicament is for the treatment of an autoimmune disease. In some embodiments the medicament is for the treatment of an inflammatory disease. In some embodiments the medicament is for the treatment of a theromboembolic disease. In some embodiments the medicament is for the treatment of multiple sclerosis. In some embodiments the medicament is for the treatment of rheumatoid arthritis. In some embodiments the medicament is for the treatment of psoriasis. In some embodiments the medicament is for the treatment of Sjogren's syndrome. In some embodiments the medicament is for the treatment of systemic lupus erythematosus. In some embodiments the medicament is for the treatment of urticaria.

Thus, inhibition of BTK activity can be useful for the treatment of allergic disorders and/or autoimmune and/or inflammatory diseases including, but not limited to: SLE, rheumatoid arthritis, multiple vasculitides, idiopathic thrombocytopenic purpura (ITP), myasthenia gravis, alleigic rhinitis, multiple sclerosis (MS), transplant rejection, type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura, sarcoidosis, Sjogren's syndrome, peripheral neuropathies (e.g., Guillain-Barre syndrome), pemphigus vulgaris, and asthma.

In addition, BTK has been reported to play a role in controlling B-cell survival in certain B-cell cancers. For example, BTK has been shown to be important for the survival of BCR-Abl-positive B-cell acute lymphoblastic leukemia cells. Thus, inhibition of BTK activity can be useful for the treatment of B-cell lymphoma and leukemia.

The compounds described herein or pharmaceutically acceptable salts, solvates, hydrates or tautomers thereof may be useful for the treatment of the above listed diseases optionally in combination with a corticosteroid, noncorticosteroidal, immunosupressive, and/or antiinflammatory agents. In one embodiment, the immunosuppressive agent is selected from interferon alpha, interferon gamma, cyclophosphamide, tacrolimus, mycophenolate mofetil, methotrexate, dapsone, sulfasalazine, azathioprine, an anti-CD20 agent (such as rituximab, ofatumumab, obinutuzumab, or veltuzumab, or a biosimilar version thereof), anti-TNFalpha agent (such as entanercept, infliximab, golilumab, adalimumab, or certolizumab pegol or a biosimilar version thereof), anti-IL6 agent toward ligand or its receptors (such as tocilizumab, sarilumab, olokizumab, elsililumab, or siltuximab), anti-IL17 agent to ligand or its receptors (such as secukinumab, ustekinumab, brodalumab, or ixekizumab), anti-IL1 agent to ligand or its receptors (such as with rilonacept, canakinumab, or anakinra), anti-IL2 agent to ligand or its receptors (such as basiliximab or daclizumab), anti-CD2 agent such as alefacept, anti-CD3 agent such as muromonab-cd3, anti-CD80/86 agent such as abatacept or belatacept, anti-sphingosine-1-phosphate receptor agent such as fingolimod, anti-C5 agent such as eculizumab, anti-integrin alpha4 agent such as natalizumab, anti-$\alpha 4\beta 7$ agent such as vedolizumab, anti-mTOR agent such as sirolimus or everolimus, anti-calcineurin agent such as tacrolimus, and anti-BAFF/BlyS agent (such as belimumab, VAY736, or blisibimod), leflunomide and teriflunomide. Preferably, the immunosuppressive agent is rituximab, ofatumumab, obinutuzumab, or veltuzumab, or a biosimilar version thereof.

Synthesis of Compounds

The reactions, processes and synthetic methods described herein are not limited to the specific conditions described in the following experimental section, but rather are intended as a guide to one with suitable skill in this field. For example, reactions may be carried out in any suitable solvent, or other reagents to perform the transformation[s] necessary. Generally, suitable solvents are protic or aprotic solvents which are substantially non-reactive with the reactants, the intermediates or products at the temperatures at which the reactions are carried out (i.e., temperatures which may range from the freezing to boiling temperatures). A given reaction may be carried out in one solvent or a mixture of more than one solvent. Depending on the particular reaction, suitable solvents for a particular work-up following the reaction may be employed.

Unless otherwise indicated, conventional methods of mass spectroscopy (MS), liquid chromatography-mass spectroscopy (LCMS), NMR, HPLC, protein chemistry, biochemistry, recombinant DNA techniques, and pharmacology are employed. Compounds are prepared using standard organic chemistry techniques such as those described in, for example, March's Advanced Organic Chemistry, 7th Edition, John Wiley and Sons, Inc (2013). Alternate reaction conditions for the synthetic transformations described herein may be employed such as variation of solvent, reaction temperature, reaction time, as well as different chemical reagents and other reaction conditions. As necessary, the use of appropriate protecting groups may be required. The incorporation and cleavage of such groups may be carried out using standard methods described in Peter G. M. Wuts and Theodora W. Green, Protecting Groups in Organic Synthesis, 4th Edition, Wiley-Interscience. (2006). All starting materials and reagents are commercially available or readily prepared.

Compounds having the structure of Formula (I), Formula (II) or Formula (III) can be synthesized using standard synthetic techniques known to those of skill in the art. For example, compounds of the present disclosure can be synthesized using the general synthetic procedures set forth in Schemes 1-21.

Preparation of 4-bromo-1H-indole Starting Materials

Scheme 1: 4-bromo-5-fluoro-2-methyl-1H-indole-7-carboxamide

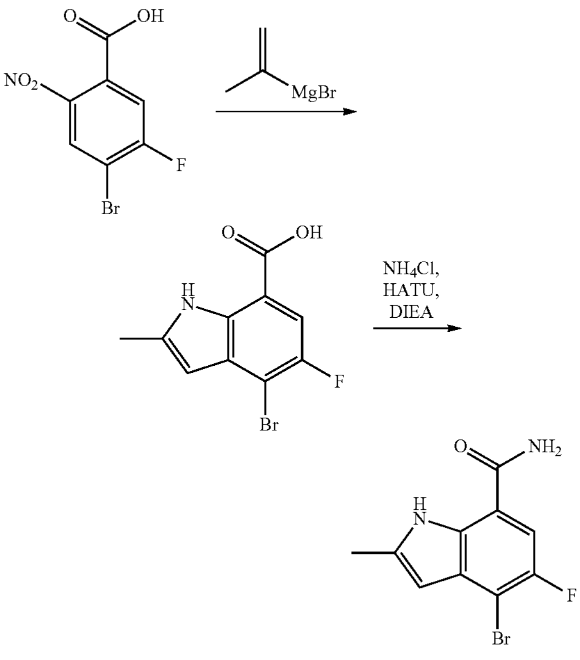

4-bromo-5-fluoro-2-nitrobenzoic acid is reacted with prop-1-en-2-ylmagnesium bromide to obtain 4-bromo-5-fluoro-2-methyl-1H-indole-7-carboxylic acid, which is amidated by treatment with ammonium chloride in the presence of HATU and DIEA to provide 4-bromo-5-fluoro-2-methyl-1H-indole-7-carboxamide ($R^{I2}$, $R^{II2}$, $R^{III2}$=H).

Scheme 2: 4-bromo-5,6-difluoro-2-methyl-1H-indole-7-carboxamide

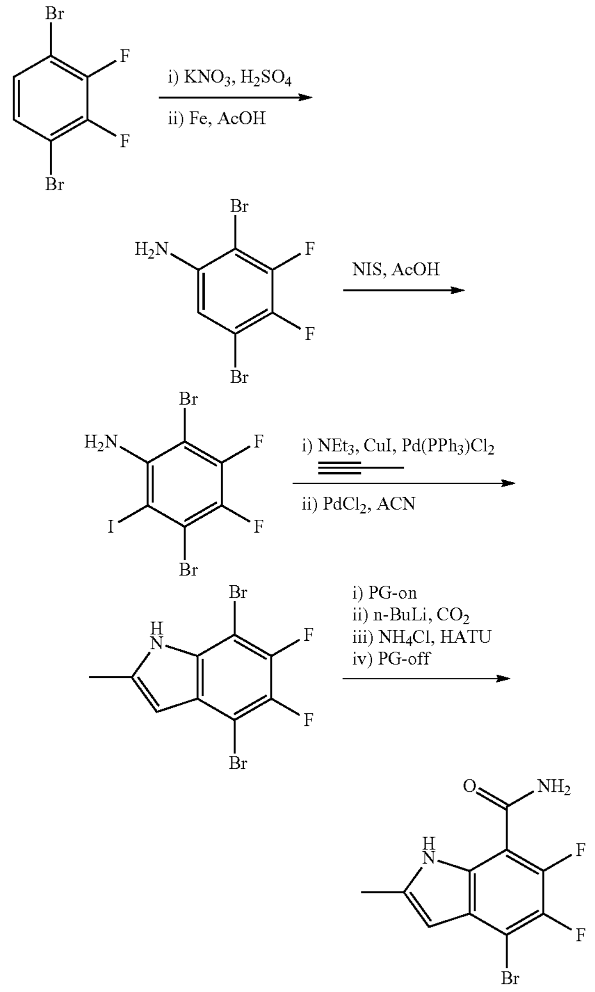

1,4-dibromo-2,3-difluorobenzene is nitrated by treatment with potassium nitrate in sulfuric acid, and the resulting nitro group reduced to form 2,5-dibromo-3,4-difluoroaniline. Iodination followed by reaction with prop-1-yne produces 4,7-dibromo-5,6-difluoro-2-methyl-1H-indole. The indole is then protected (e.g. Boc) and carboxylated at the 7-position by reaction with n-butyl lithium and carbon dioxide to obtain 4-bromo-5,6-difluoro-2-methyl-1H-indole-7-carboxylic acid. The acid is amidated by treatment with ammonium chloride and the indole deprotected, to provide 4-bromo-5,6-difluoro-2-methyl-1H-indole-7-carboxamide ($R^{I2}$, $R^{II2}$, $R^{III2}$ =F).

Synthesis of Compounds Having the Structure of Formula (I)

Coupling with 3-$R^1$-3-$R^2$-1,2,3,6-tetrahydropyridine 4-bromo-5-fluoro-6-$R^{I2}$-2-methyl-1H-indole-7-carboxamide is coupled with N-protected (e.g. Boc) 5-(4,4,5,5-tetramethyl-1,3,2-dioxaborolan-2-yl)-1,2,3,6-tetrahydropyridine. The tetrahydropyridine may be substituted at the 3 position with $R^1$/$R^2$.

Scheme 3: N-protected 4-(5-$R^1$-5-$R^2$--1,2,5,6-tetrahydropyridin-3-yl)-5-fluoro-6-$R^{I2}$-2-methyl-1H-indole-7-carboxamide (- - - = double bond)

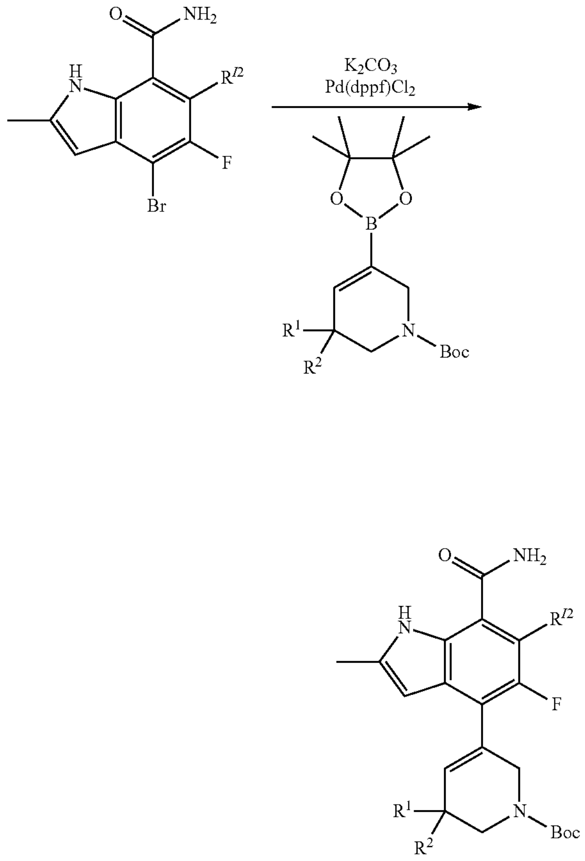

4-bromo-5-fluoro-6-$R^{I2}$-2-methyl-1H-indole-7-carboxamide is coupled with N-protected (e.g. Boc) 5-(4,4,5,5-tetramethyl-1,3,2-dioxaborolan-2-yl)-1,2,3,6-tetrahydro pyridine. The tetrahydropyridine may be substituted at the 3 position with $R^1$/$R^2$.

Reduction to Piperidine (Optional)

Scheme 4: N-protected 4-(5-$R^1$-5-$R^2$-piperidin-3-yl)-5-fluoro-6-$R^{I2}$-2-methyl-1H-indole-7-carboxamide( - - - = single bond)

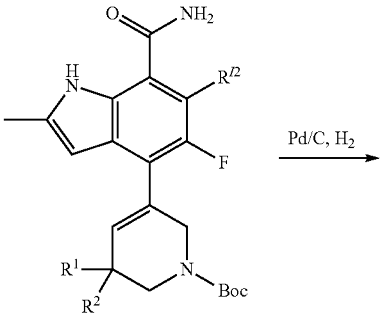

-continued

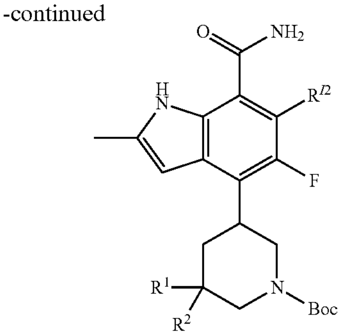

N-protected-5-fluoro-6-$R^{I2}$-2-methyl-4-(1,2,5,6-tetrahydropyridin-3-yl)-1H-indole-7-carboxamide ( $\overline{---}$ =double bond) may be optionally reduced by treatment with a suitable reducing agent (e.g. Pd/C, $H_2$) to obtain N-protected-5-fluoro-6-$R^{I2}$-2-methyl-4-(piperidin-3-yl)-1H-indole-7-carboxamide, wherein the piperidine may be substituted at the 5 position with $R^1$/$R^2$.

Scheme 5: Introduction of $R^{I1}$ and $R^B$

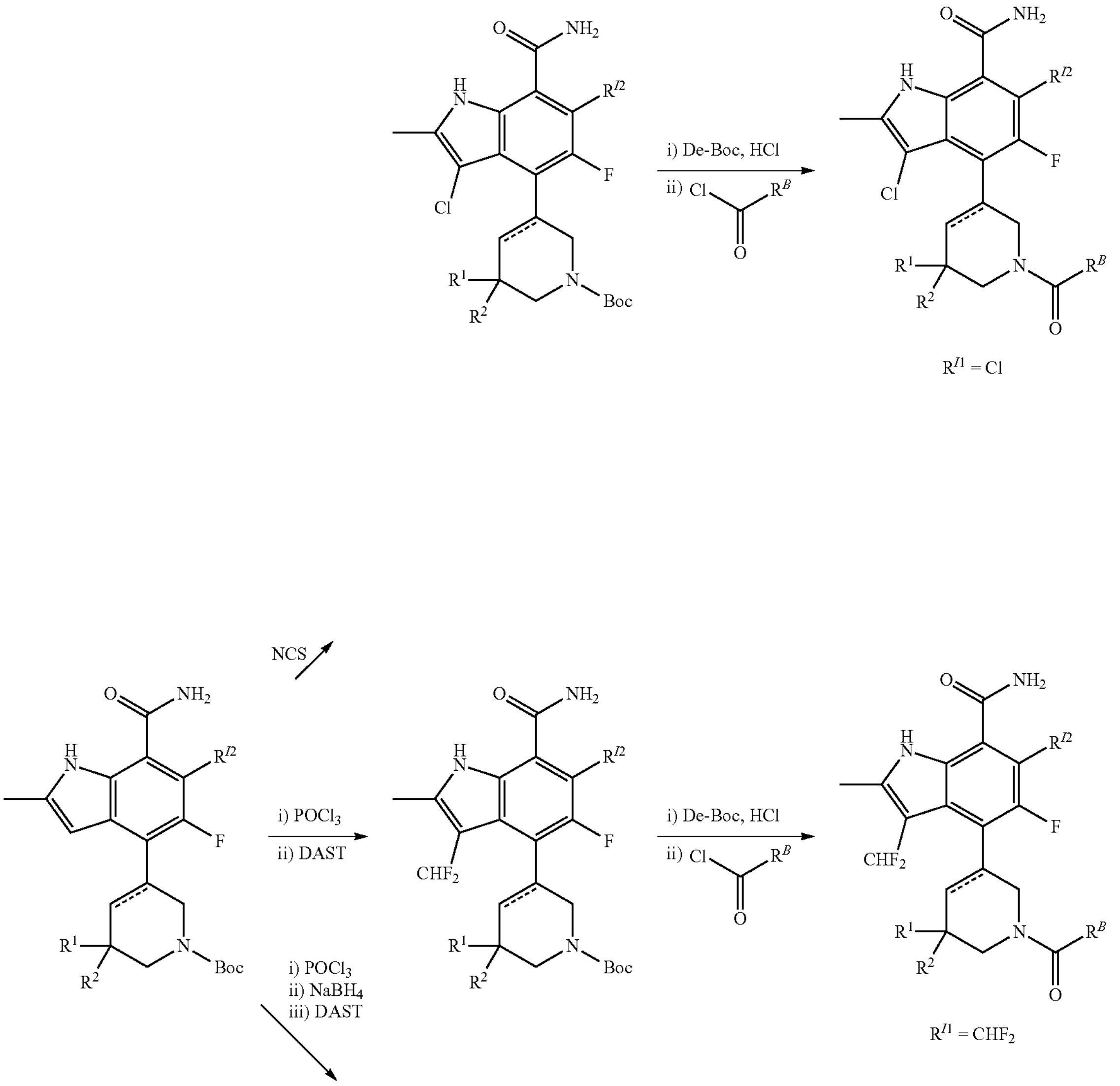

-continued
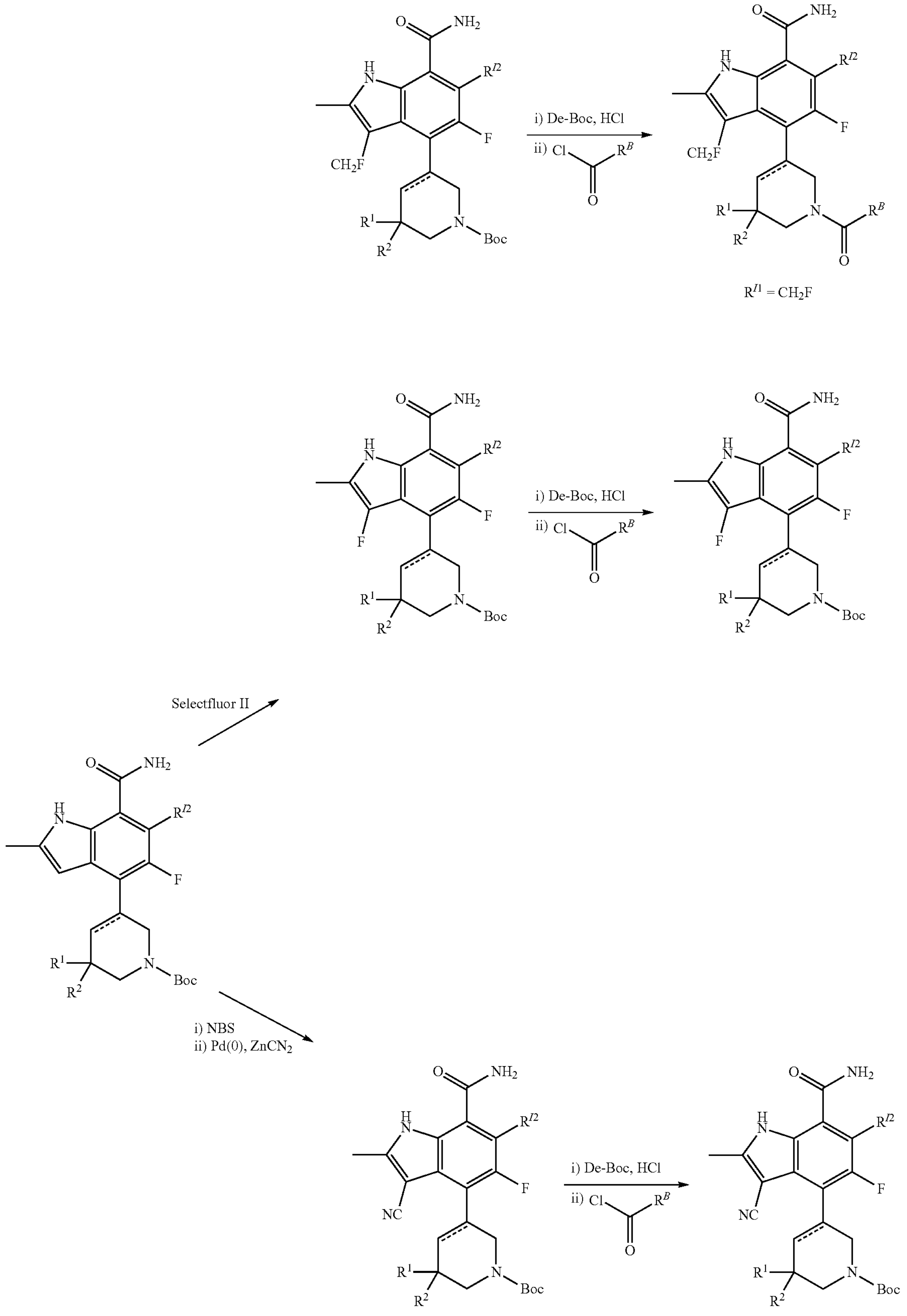

N-protected-5-fluoro-6-$R^{I2}$-2-methyl-4-(1,2,5,6-tetrahydropyridin-3-yl)-1H-indole-7-carboxamide, or N-protected-5-fluoro-6-$R^{I2}$-2-methyl-4-(piperidin-3-yl)-1H-indole-7-carboxamide, (wherein the tetrahydropyridine or piperidine may be substituted with $R^1$/$R^2$), are reacted as shown in scheme 5, namely with:

N-chloro succinimide to provide $R^{I1}$ as Cl; or phosphorus oxychloride to provide the 3-formyl compound which is then treated with diethylaminosulfur trifluoride, ($Et_2NSF_3$; DAST) to provide $R^{I1}$ as $CHF_2$; or phosphorus oxychloride to provide the 3-formyl compound, which is reduced to the hydroxy methyl and then treated with diethylaminosulfur trifluoride, ($Et_2NSF_3$; DAST) to provide $R^{I1}$ as $CH_2F$.

Removal of the protecting group (e.g. removal of Boc protecting group by treatment with HCl) from the piperidine or tetrahydropyridine nitrogen of 3-$R^{I1}$-4-(5-$R^1$-5-$R^2$-piperidin-3-yl)-5-fluoro-6-$R^1$-2-methyl-1H-indole-7-carboxamide or 3-$R^{I1}$-4-(5-$R^1$-5-$R^2$-1,2,5,6-tetrahydropyridin-3-yl)-5-fluoro-6-$R^{I2}$-2-methyl-1H-indole-7-carboxamide, reveals the free amine, which is then treated with an $R^B$ acid chloride, to provide the final compounds of formula (I):

3-$R^{I1}$-4-(5-$R^1$-5-$R^2$-1-$R^B$ carbonyl-piperidin-3-yl)-5-fluoro-6-$R^{I2}$-2-methyl-1H-indole-7-carboxamide; or 3-$R^{I1}$-4-(5-$R^1$-5-$R^2$-1-$R^B$ carbonyl-1,2,5,6-tetrahydropyridin-3-yl)-5-fluoro-6-$R^{I2}$-2-methyl-1H-indole-7-carboxamide.

It should be noted, compounds of formula (I), wherein $\overset{---}{---}$ is a single bond, exist as a pair of isomers:

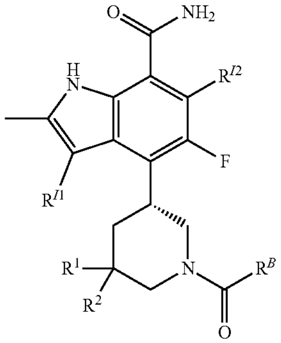

(R)-

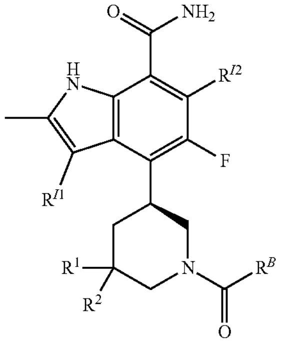

(S)-

Synthesis of Compounds Having the Structure of Formula (II)

Preparation of II-INT-B Intermediates

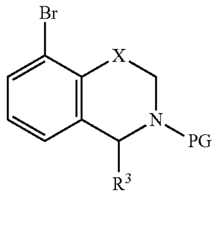

or

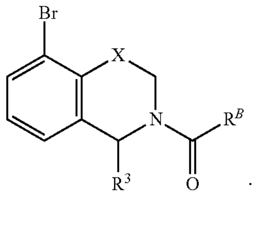

Scheme 6: Preparation of II-INT-B intermediate; X is $CH_2$

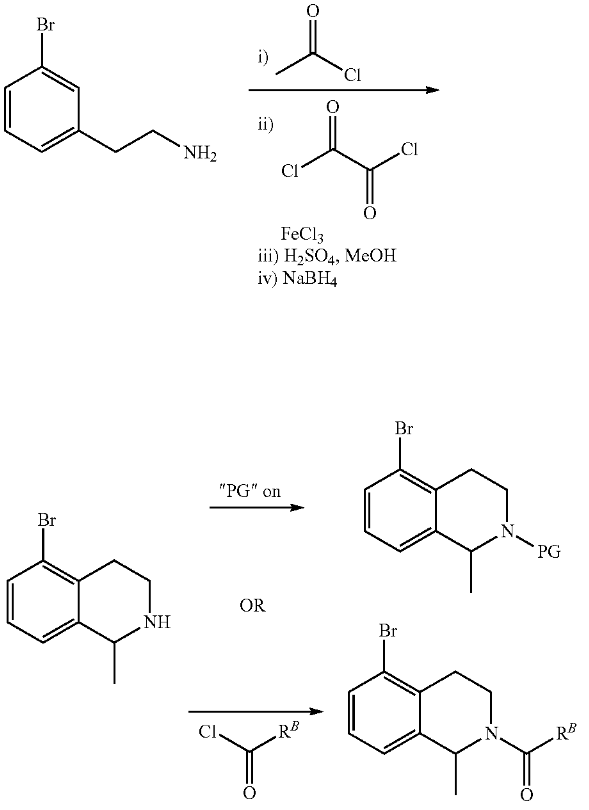

Intermediate II-INT-B, wherein X is $CH_2$ and $R^3$ is Me is prepared by conversion of 2-(3-bromophenyl)ethan-1-amine to the amide by reaction with acetyl chloride. Reaction with oxalyl dichloride and iron chloride, followed by acid treatment provides 5-bromo-1-methyl-3,4-dihydroisoquinoline. Reduction with a suitable reducing agent (e.g. sodium borohydride) provides 5-bromo-1-methyl-1,2,3,4-tetrahydroisoquinoline. The tetrahydroisoquinoline may then be protected with a suitable protecting group (e.g. Boc) or converted to the desired final amide by reaction with the appropriate $R^B$ acid chloride.

Scheme 7: Preparation of II-INT-B intermediate; X is $CH_2CH_2$

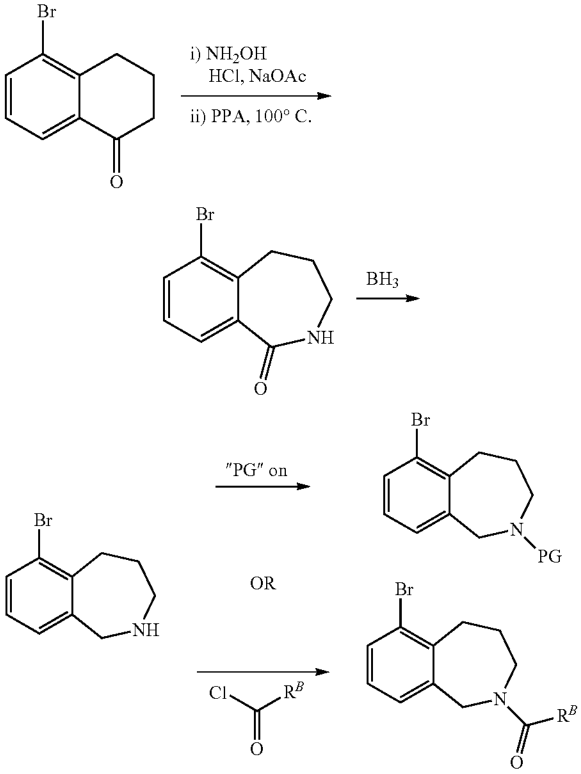

Intermediate II-INT-B, wherein X is $CH_2CH_2$ and R is H is prepared by conversion of 5-bromo-3,4-dihydronaphthalen-1(2H)-one to 6-bromo-2,3,4,5-tetrahydro-1H-benzo[c]azepin-1-one. Reduction with a suitable reducing agent (e.g. $BH_3$) provides 6-bromo-2,3,4,5-tetrahydro-1H-benzo[c]azepine. The azepane may then be protected with a suitable protecting group (e.g. Boc) or converted to the desired final amide by reaction with the appropriate $R^B$ acid chloride.

Scheme 8: Preparation of II-INT-B intermediate; X is cyclopropyl

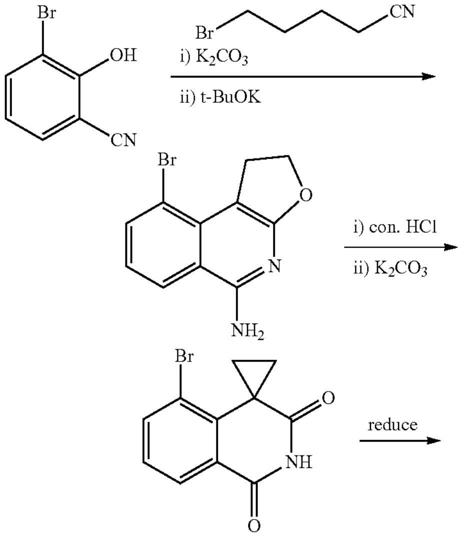

-continued

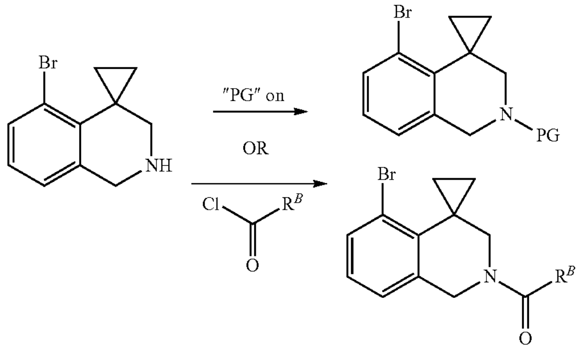

Intermediate II-INT-B, wherein $R^3$ is H and X is $CR^{x1}R^{x2}$ and $R^{x1}$ and $R^{x2}$ together with the C atom to which there are attached form a cyclopropyl ring, is prepared starting from 3-bromo-2-hydroxybenzonitrile. Reaction with 5-bromopentanenitrile followed by treatment with a strong base (e.g. KOtBu) provides 9-bromo-1,2-dihydrofuro[2,3-c]isoquinolin-5-amine. Treatment with acid (e.g. HCl), base (e.g. potassium carbonate) and then heat, followed by reduction provides 5'-bromo-2',3'-dihydro-1'H-spiro[cyclopropane-1,4'-isoquinoline]. The isoquinoline may then be protected with a suitable protecting group (e.g. Boc) or converted to the desired final amide by reaction with the appropriate $R^B$ acid chloride.

Scheme 9: Preparation of II-INT-B-intermediate; $R^{x2}$ and $R^3$ form a methylene bridge

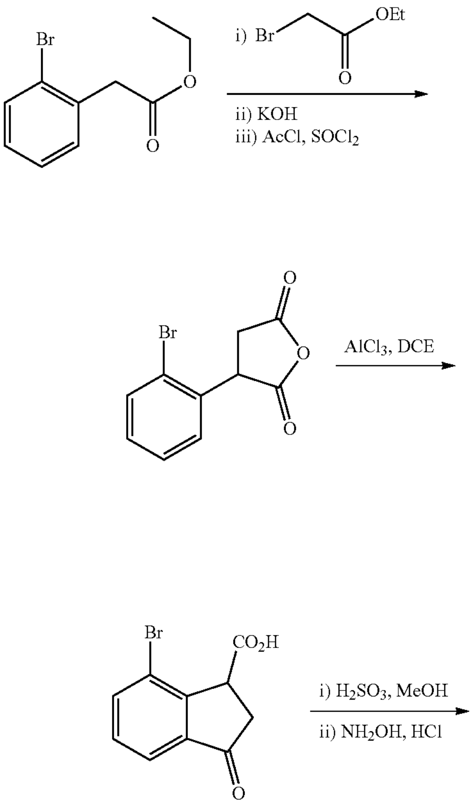

-continued

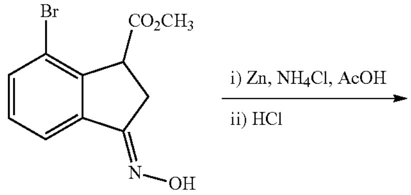

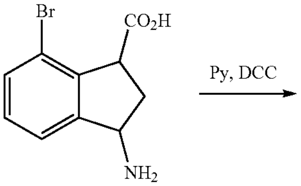

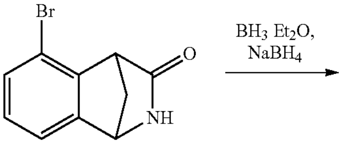

-continued

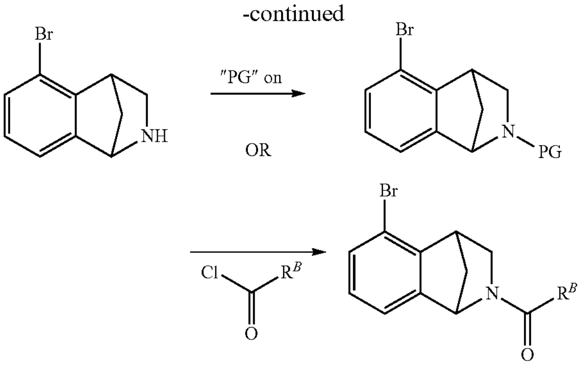

Intermediate II-INT-B, wherein X is $CR^{x1}R^{x2}$ and $R^{x1}$ is H and $R^{x2}$ and $R^3$ together form a methylene bridge, is prepared starting from ethyl 2-(2-bromophenyl)acetate. Reaction with ethyl 2-bromoacetate, followed by treatment with base and then reaction with acyl chloride/thionyl chloride provides 3-(2-bromophenyl)dihydrofuran-2,5-dione. Treatment with aluminum chloride forms 7-bromo-3-oxo-2,3-dihydro-1H-indene-1-carboxylic acid. The acid group may be protected (e.g. as an ester such as the methyl ester), and then the oxo group converted to an amine by reaction with ammonium hydroxide to form the hydroxy imine, which is then reduced to the amine. Treatment with base forms the bridged bicyclic compound which is reduced with a suitable reducing agent (e.g. $BH_3$) to provide 5-bromo-1,2,3,4-tetrahydro-1,4-methanoisoquinoline. The methanoisoquinoline may then be protected with a suitable protecting group (e.g. Boc) or converted to the desired final amide by reaction with the appropriate $R^B$ acid chloride.

Coupling of II-INT-B with 4-bromo-5-fluoro-2-methyl-3-$R^{II1}$-1H-indole-7-carboxamide ($R^{II2}$=H) or 4-bromo-5,6-difluoro-2-methyl-3-$R^{II1}$-1H-indole-7-carboxamide ($R^{II2}$=F)

Scheme 10: Suzuki coupling to form Compounds of formula (II)

ROUTE A

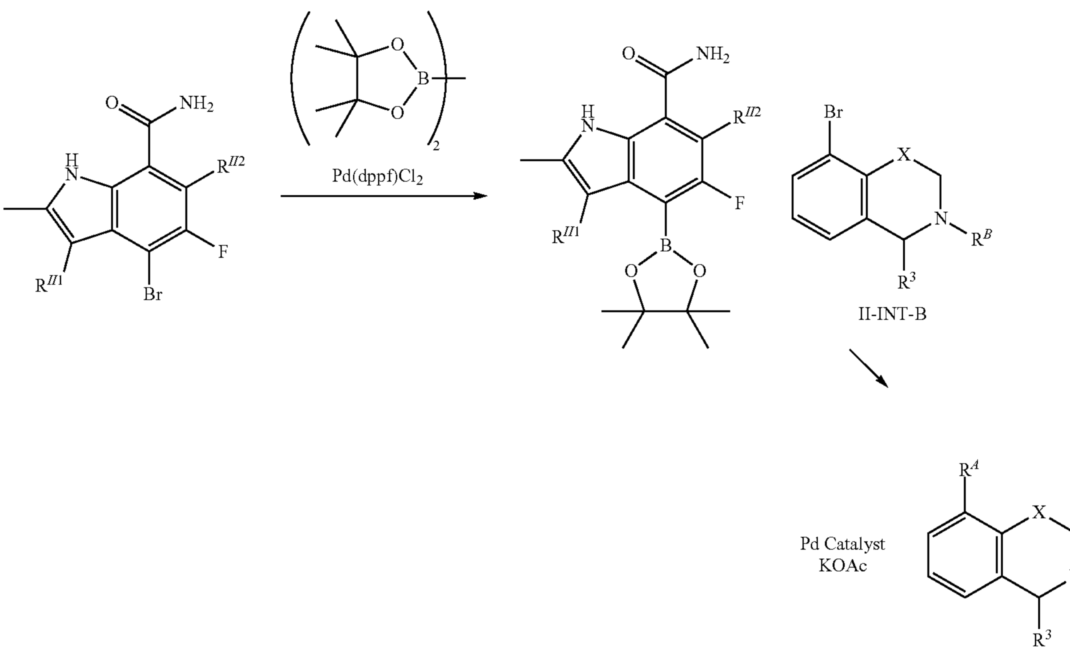

-continued

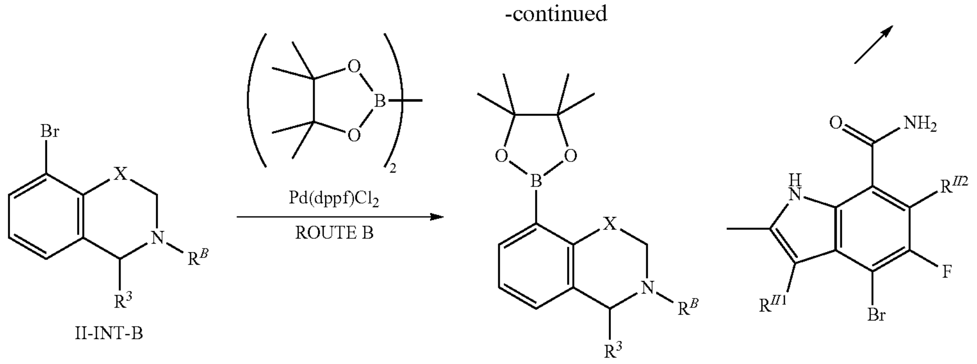

II-INT-B

Compounds of formula (II) may be prepared by conversion of the 4-bromo-1H-indole to the corresponding dioxaborolanyl derivative, followed by Suzuki coupling with II-INT-B (See Scheme 10, ROUTE A).

Alternatively, compounds of formula (II) may be prepared by conversion of (I-INT-B) to the corresponding dioxaborolanyl derivative, followed by Suzuki coupling with the 4-bromo-1H-indole (See Scheme 10, ROUTE B).

Scheme 11: Introduction of $R^{II1}$ as Cl or F

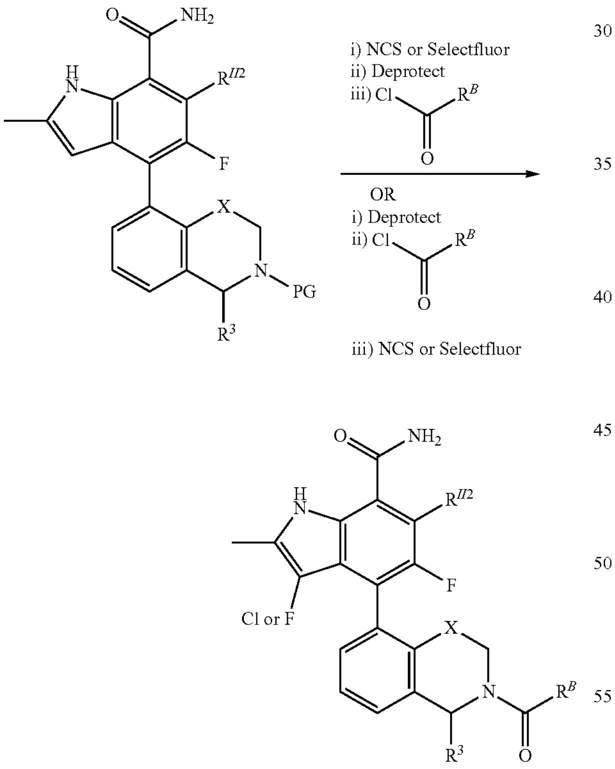

Compounds of formula (II) wherein $R^{II1}$ is H, may be converted to compounds wherein $R^{II1}$ is not H. N-protected compound is treated with N-chlorosuccinimide or selectfluor to introduce Cl or F, respectively. The final compound is achieved by removal of the protecting group, and treatment with the appropriate $R^B$ acid chloride. The sequence of these steps may be altered as required from that shown in Scheme 11.

Scheme 12: Introduction of $R^{II1}$ as I or CN

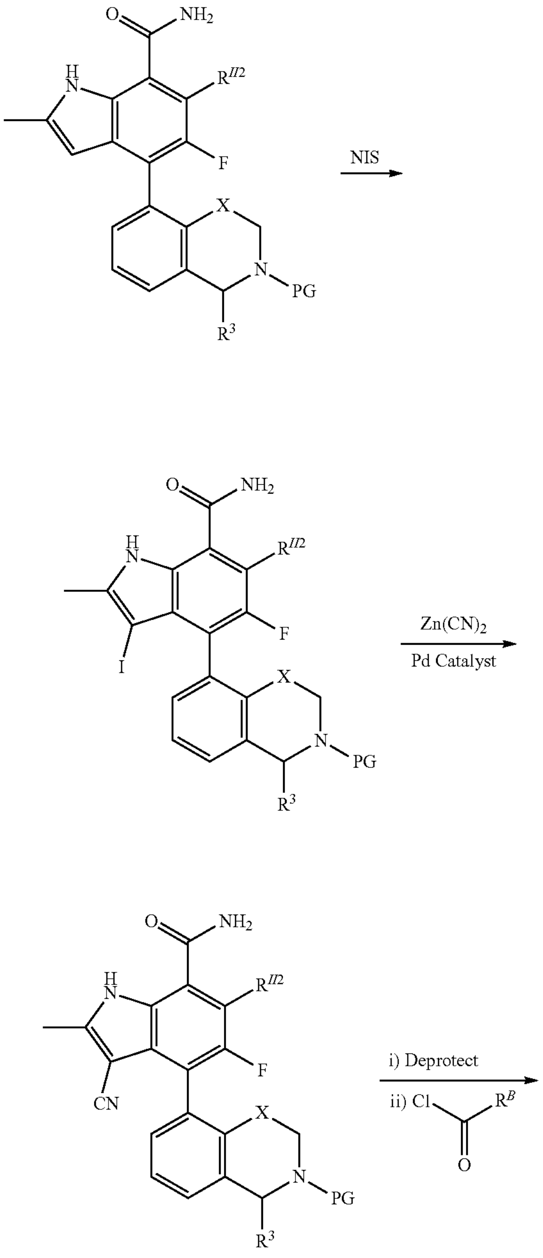

-continued
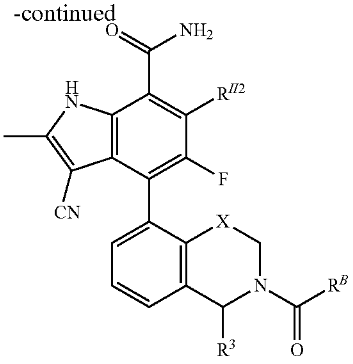
An N-protected compound is treated with N-iodosuccinimide to introduce I. The final compound is achieved by removal of the protecting group, and treatment with the appropriate $R^B$ acid chloride.
Scheme 13: Introduction of $R^{II1}$ as CHO, $CHF_2$ or $CH_2F$
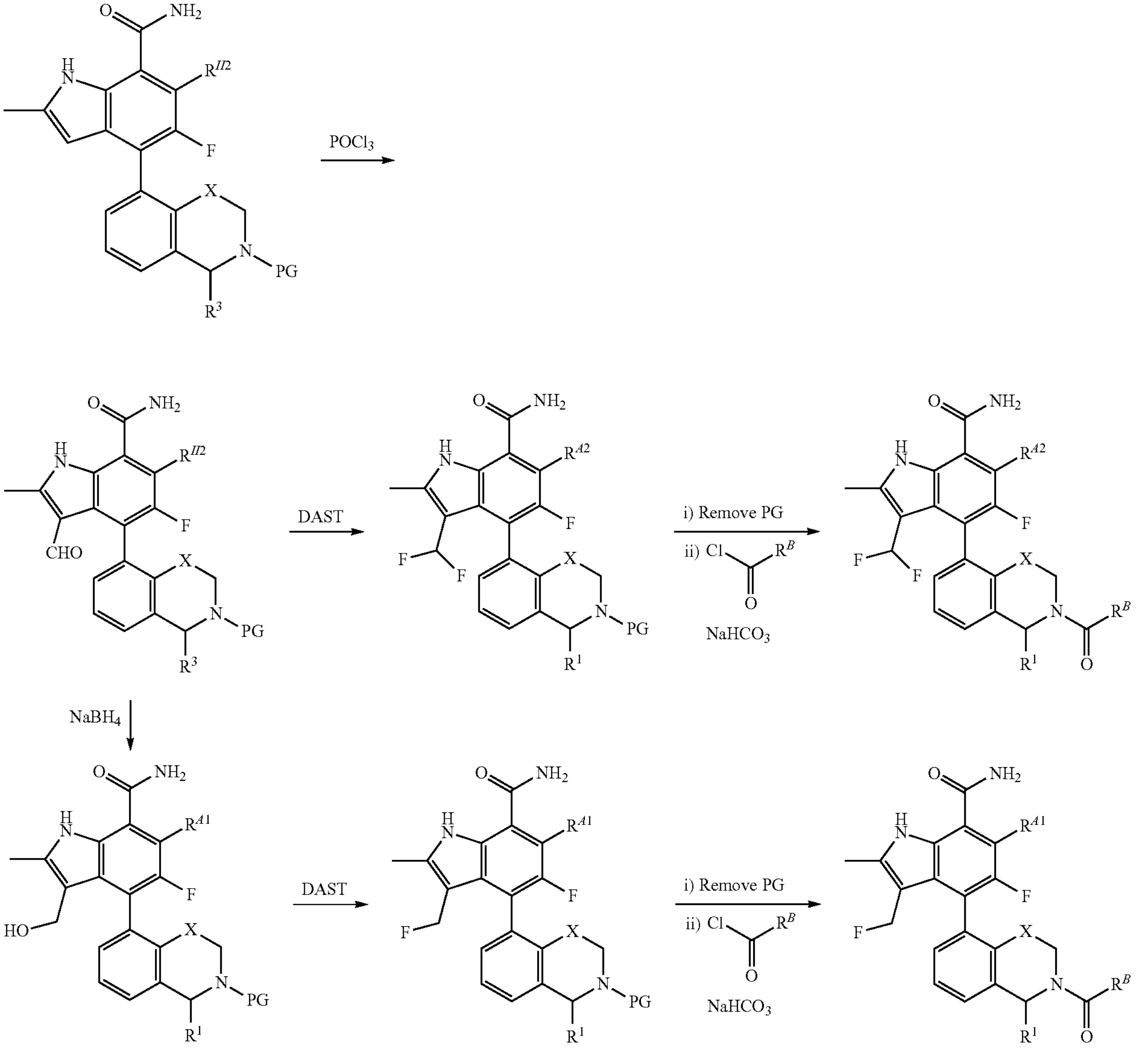

An N-protected compound is treated with $POCl_3$ to introduce an aldehyde group. The aldehyde may be reduced by treatment with a suitable reducing agent (e.g. $NaBH_4$) to the alcohol. Treatment of the aldehyde with DAST provides the $CF_2H$ group, while treatment of the alcohol provides the $CH_2F$ group. Removal of the protecting group followed by reaction with $R^B$ acid chloride provides final compounds of formula (II).

Synthesis of Compounds Having the Structure of Formula (III)

Cyclic Amine Starting Materials

Non-limiting examples of cyclic amines that may be used as starting materials are shown below and are either commercially available or prepared via routes apparent to one of skill in the art. Differential protection of the second amine group is performed as required.

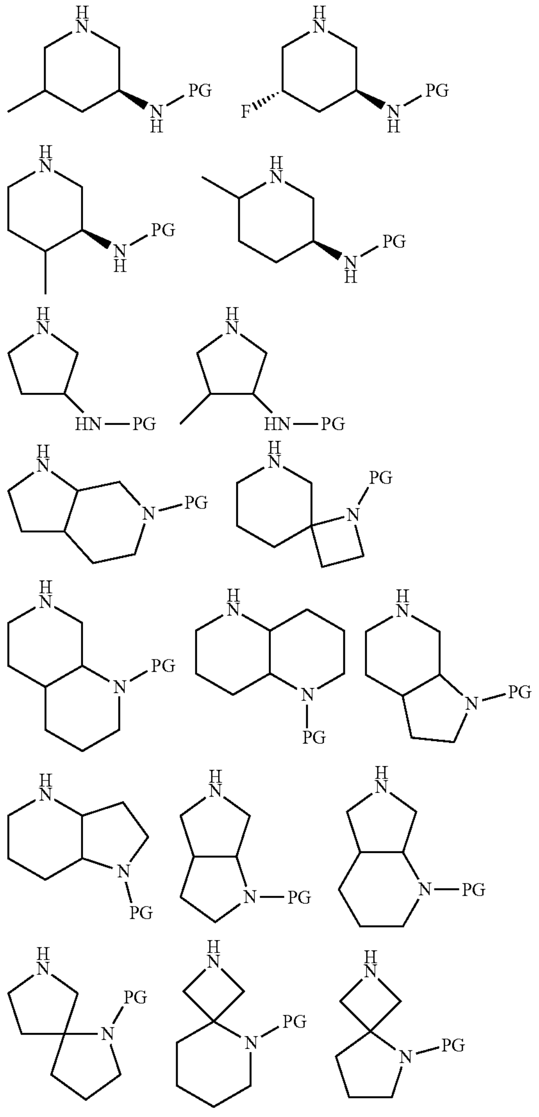

Coupling of cyclic amine with 4-bromo-5-fluoro-2-methyl-3-$R^{II1}$-1H-indole-7-carboxamide ($R^{II2}$=H) or 4-bromo-5,6-difluoro-2-methyl-3-$R^{II1}$-1H-indole-7-carboxamide ($R^{II2}$=F)

Scheme 14: General procedure for preparation of compounds of Formula (III)

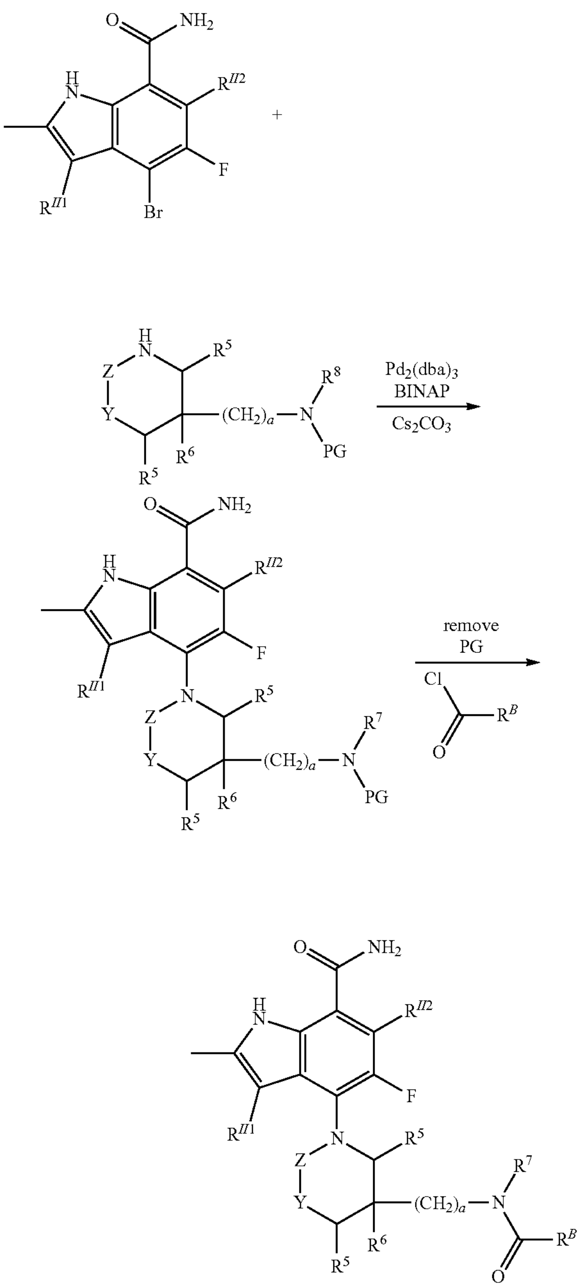

As a general procedure, compounds of Formula (III) are prepared according to Scheme 14. The cyclic amine is coupled (e.g. using Pd catalyst) with the bromo indole. The resulting compound comprising an amine group, is then deprotected, as required, and reacted with $R^B$ acid chloride to provide the desired final compound.

Scheme 15: Preparation of Compounds of Formula (III) - $R^{III1}$ is Cl and $R^{III2}$ is H

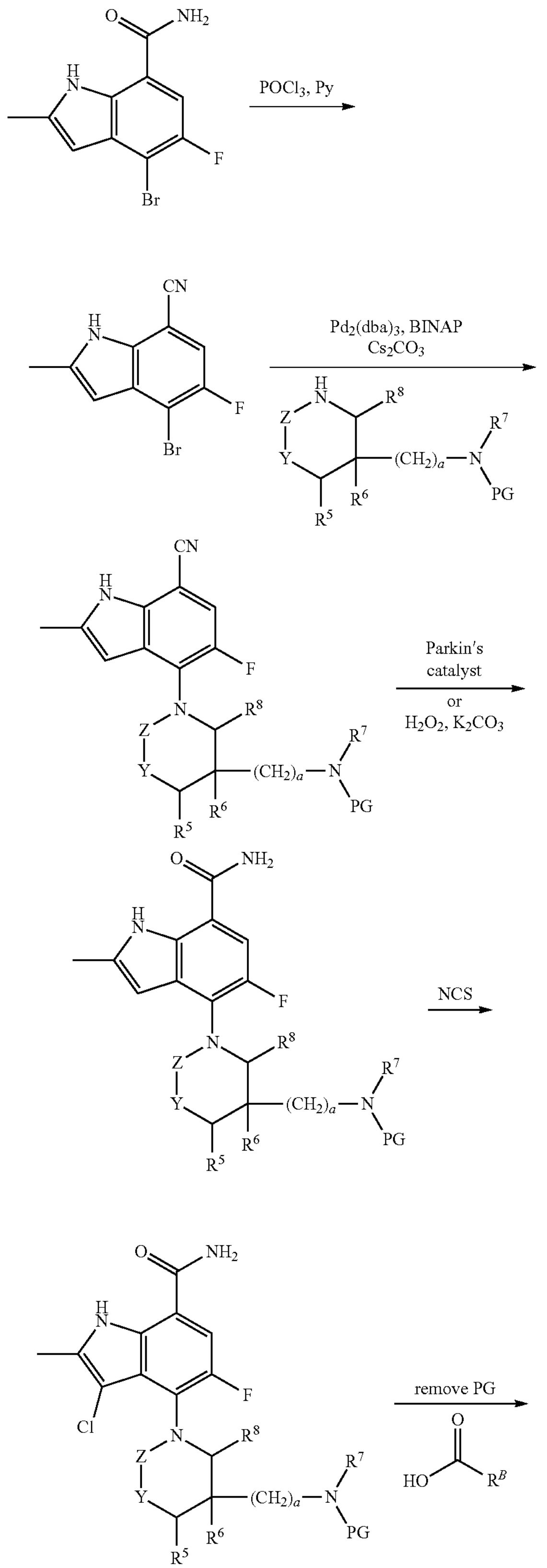

-continued

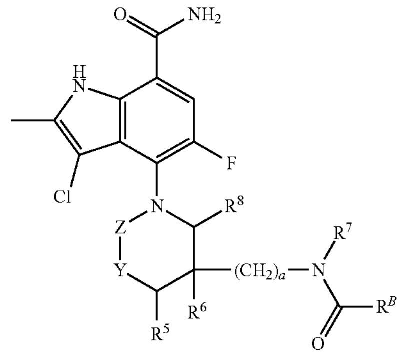

Compounds of Formula (III), wherein $R^{III1}$ is Cl and $R^{III2}$ is H are prepared as shown in Scheme 15. The carboxamide group is first protected, e.g. by conversion to the nitrile group by treatment with phosphoryl chloride. The protected compound is then coupled with the cyclic amine and the carboxamide protecting group removed, e.g. by hydration of the nitrile group. The $R^{III1}$ chloro is then introduced by treatment with N-chloro succinimide. Lastly, the second amine group is deprotected (e.g. removal of a Boc group), and the resulting amine reacted with $R^B$ acid chloride to provide the desired final compound.

Scheme 16: Preparation of Compounds of Formula (III) $R^{III1}$ is Cl, and $R^{III2}$, $R^6$ and $R^7$ are H

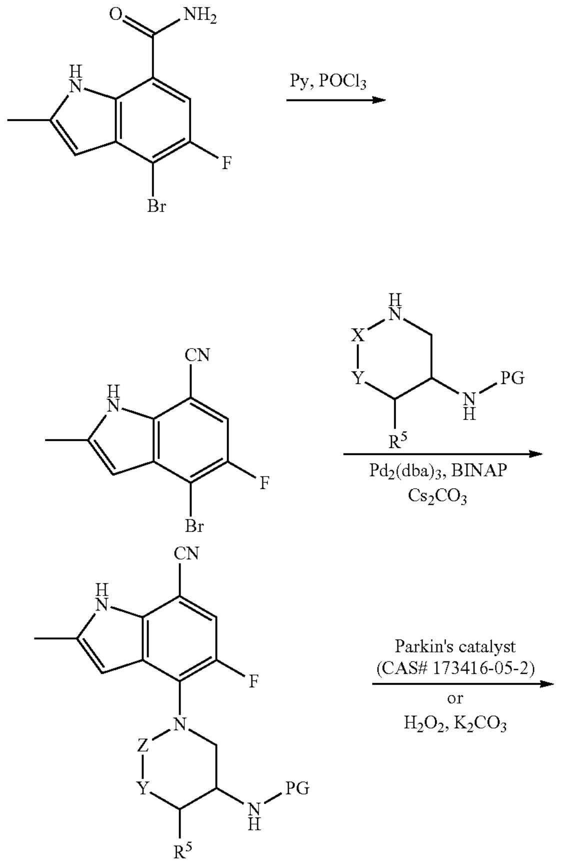

-continued

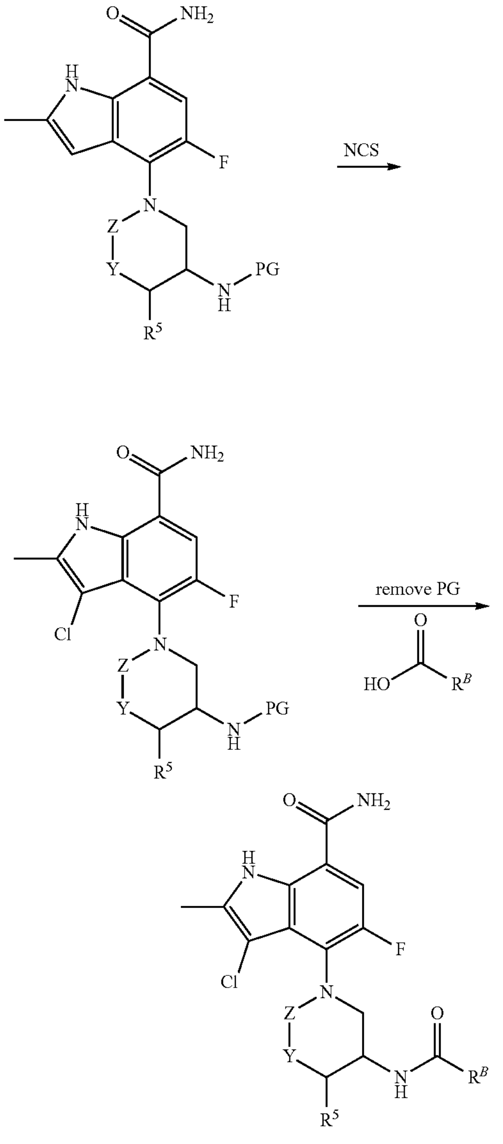

Carboxamide protected bromo indole is coupled with the cyclic amine ($R^6$ is H and $R^7$ is H) and the carboxamide protecting group removed. The $R^{III1}$ chloro is introduced by treatment with N-chloro succinimide. Lastly, the second amine group is deprotected and reacted with $R^B$ acid chloride to provide the desired final compound.

Scheme 17: Preparation of Compounds of Formula (III)
$R^6$ is H, $R^8$ is H, a is 1 and $R^5$ and $R^7$ together form a 5-membered cycle

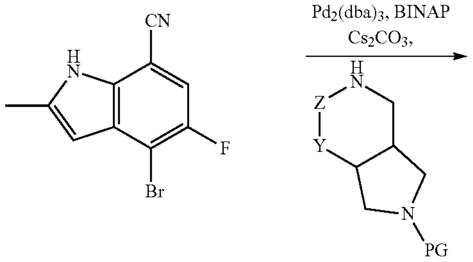

-continued

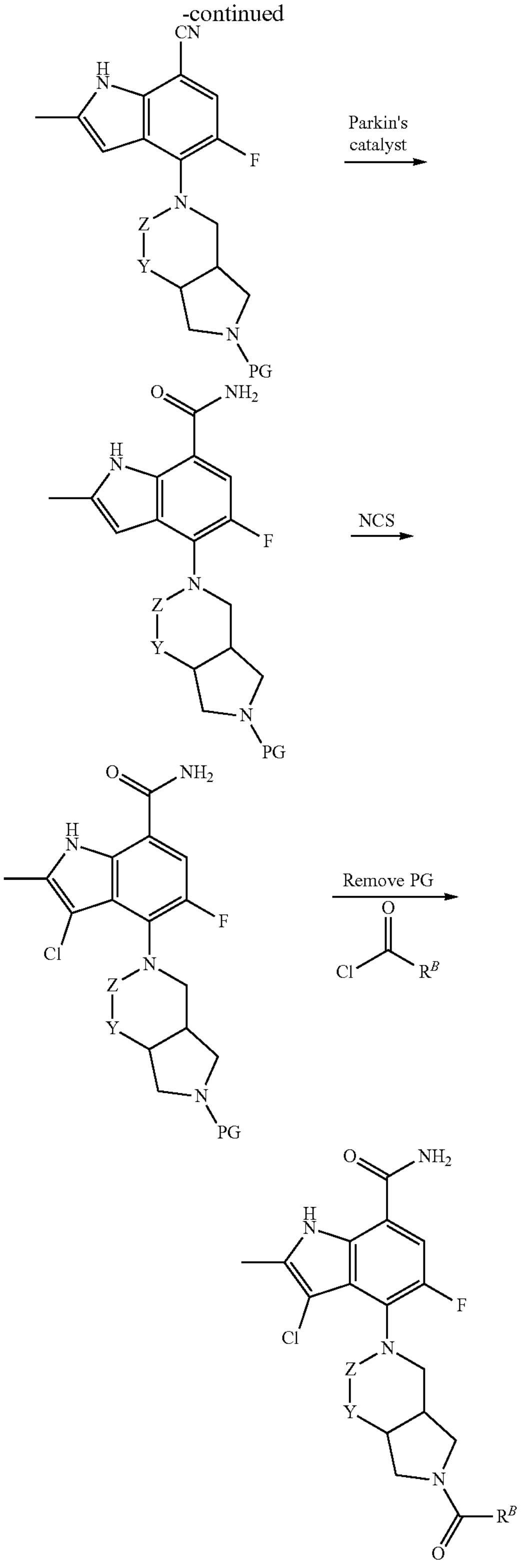

Indole bromide ($R^{III1}$ and $R^{III2}$ both H) is coupled with the cyclic amine ($R^5$ is H, $R^8$ is H, a is 1 and $R^5$ and $R^7$ together form a 5-membered cycle comprising a protected N), as shown in Scheme 17, followed by deprotection of the carboxamide, if required. The $R^{III1}$ chloro is introduced by treatment with N-chloro succinimide. Lastly, the second amine group is deprotected and reacted with $R^B$ acid chloride to provide the desired final compound.

Scheme 18: Preparation of Compounds of Formula (III)
$R^{III1}$ is Me, $R^6$ is H, $R^8$ is H, a is 0 and $R^5$ and $R^7$ together form a 5-membered cycle

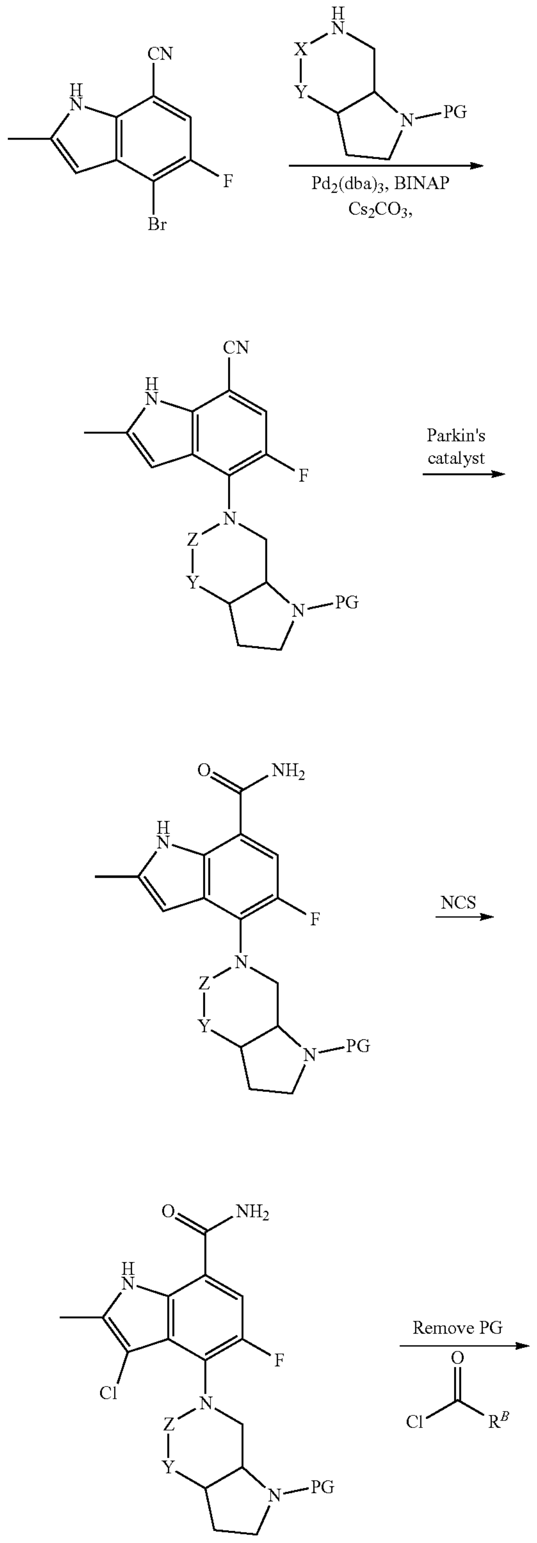

-continued

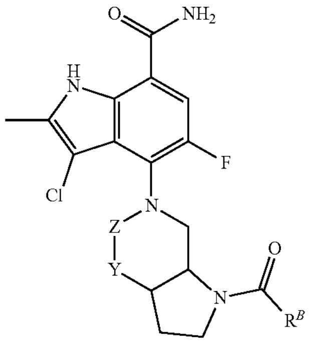

Indole bromide ($R^{III1}$ and $R^{III2}$ both H) is coupled with the bicyclic amine ($R^6$ is H, $R^8$ is H, a is 0 and $R^5$ and $R^7$ together form a 5-membered cycle comprising a protected N), as shown in Scheme 18, followed by deprotection of the carboxamide, if required. The $R^{III1}$ chloro is introduced by treatment with N-chloro succinimide. Lastly, the second amine group is deprotected and reacted with $R^B$ acid chloride to provide the desired final compound.

Scheme 19: Preparation of Compounds of Formula (III)
$R^{III1}$ is Me, $R^6$ is H, $R^8$ is H, a is 0 and $R^5$ and $R^7$ together form a 5-membered cycle

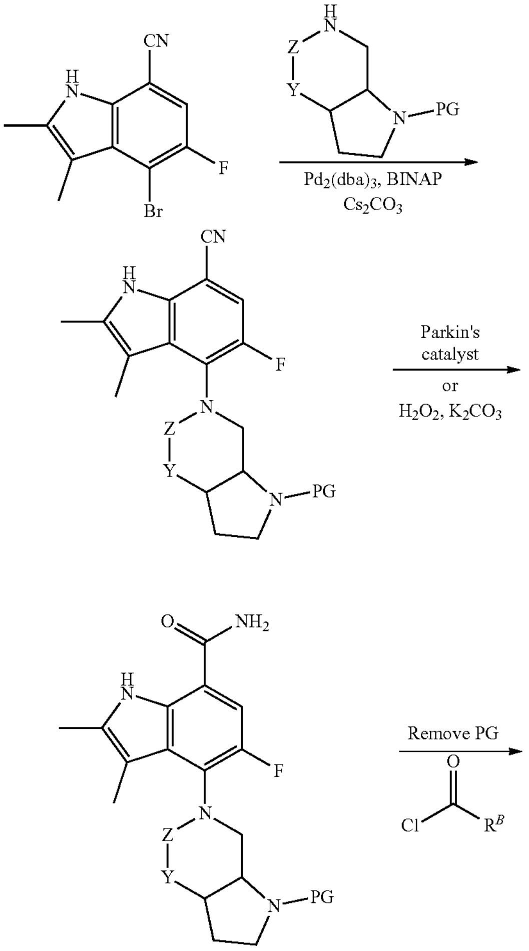

-continued

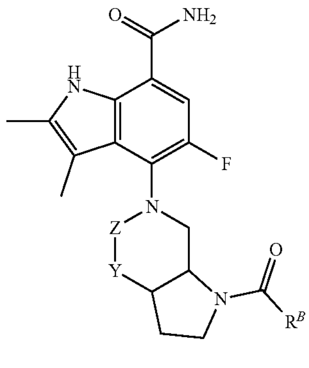

Indole bromide ($R^{III1}$ is Me and $R^{III2}$ is H) is coupled with the bicyclic amine ($R^6$ is H, $R^8$ is H, a is 0 and $R^5$ and $R^7$ together form a 5-membered cycle comprising a protected N), as shown in Scheme 19, followed by deprotection of the carboxamide, if required. The $R^{III1}$ chloro is introduced by treatment with N-chloro succinimide. Lastly, the second amine group is deprotected and reacted with $R^B$ acid chloride to provide the desired final compound.

Scheme 20: Preparation of Compounds of Formula (III) Z is a bond, Y is $CHR^4$, $R^4$, is H $R^6$ is H, $R^8$ is H, a is 0, and $R^5$ and $R^7$ together form a 6-membered cycle

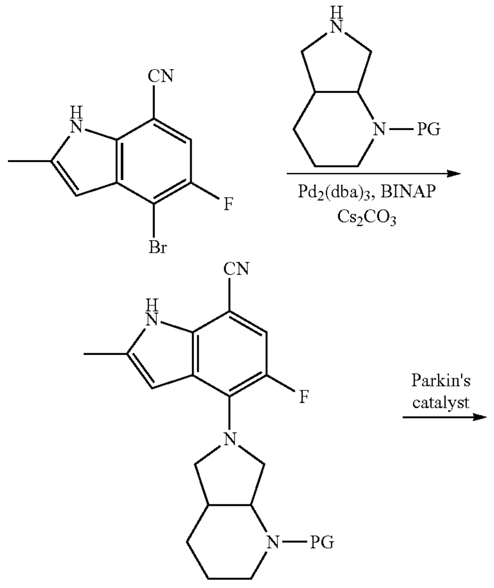

-continued

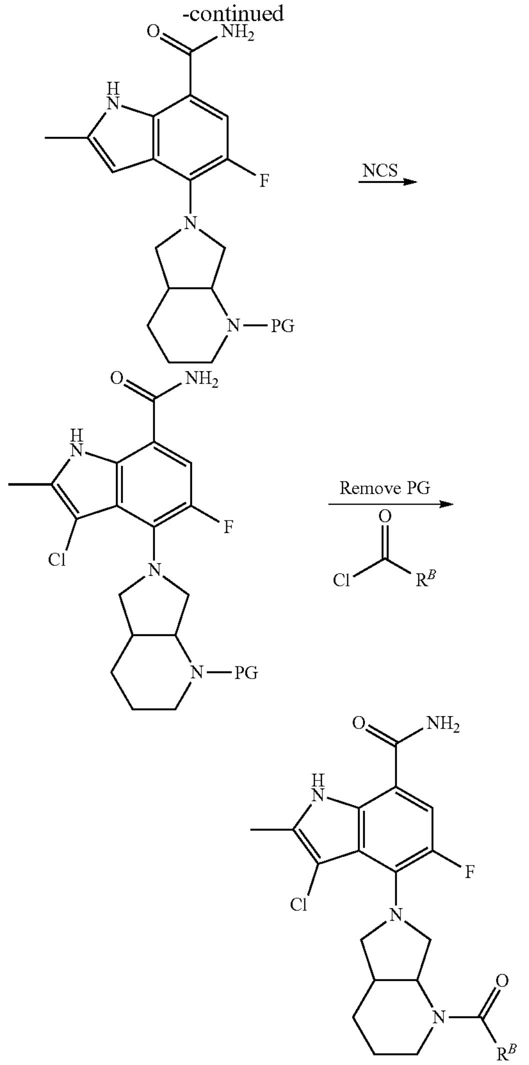

Indole bromide ($R^{III1}$ and $R^{III2}$ both H) is coupled with 1-PG-octahydro-1H-pyrrolo[3,4-b]pyridine (PG is a suitable protecting group, Z is a bond, Y is $CR^4$, $R^4$ is H, $R^6$ is H, $R^8$ is H, a is 0 and $R^5$ and $R^7$ together form a 6-membered cycle comprising a protected N), as shown in Scheme 20, followed by deprotection of the carboxamide, if required. The $R^{III1}$ chloro is introduced by treatment with N-chloro succinimide. Lastly, the second amine group is deprotected and reacted with $R^B$ acid chloride to provide the desired final compound.

Scheme 21: Introduction of $R^{IIII}$

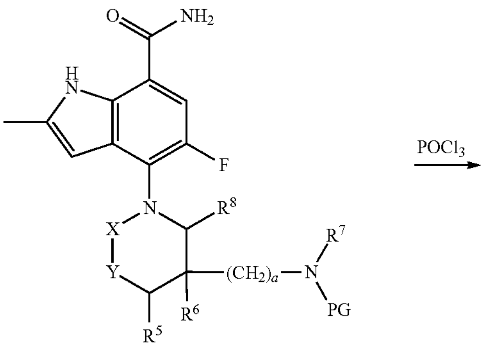

-continued

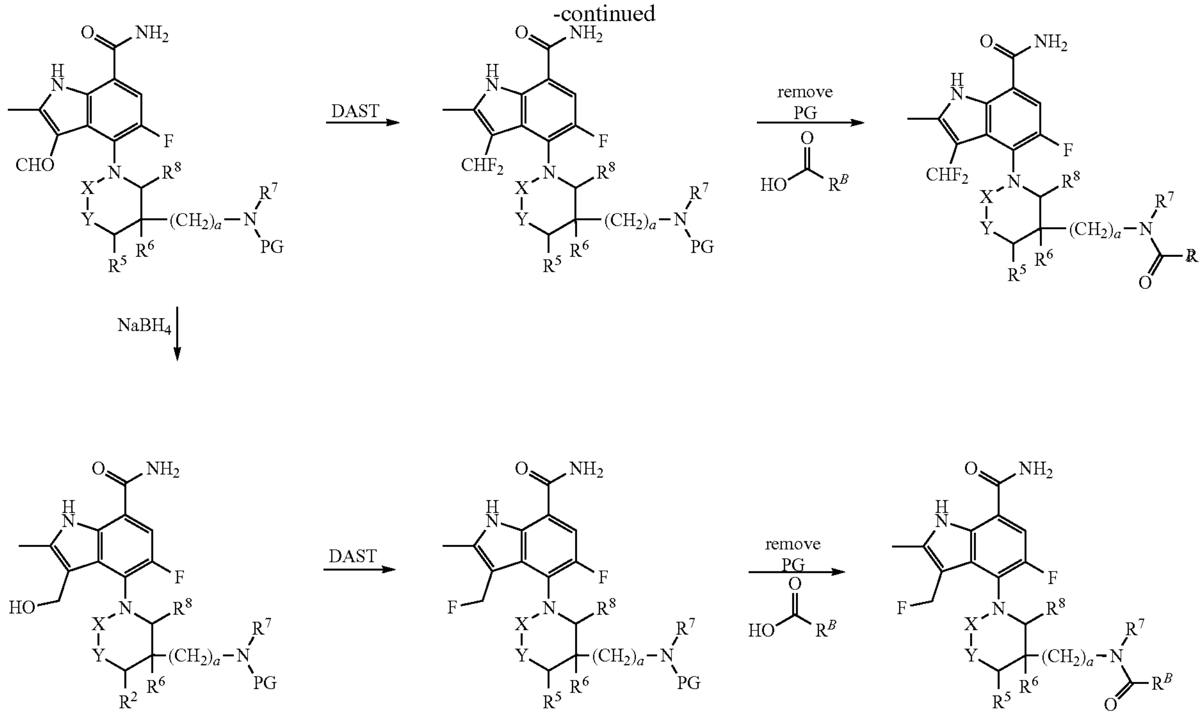

Compounds of formula (III) wherein $R^{III1}$ is H, and as shown in Scheme 21, are treated with:

phosphorus oxychloride to provide the 3-formyl compound which is then treated with diethylaminosulfur trifluoride, ($Et_2NSF_3$; DAST) to provide $R^{III1}$ as $—CHF_2$; or phosphorus oxychloride to provide the 3-formyl compound, which is reduced to the hydroxy methyl and then treated with diethylaminosulfur trifluoride, ($Et_2NSF_3$; DAST) to provide $R^{III1}$ as $—CH_2F$.

The second amine group is then deprotected and reacted with $R^B$ acid chloride to provide the desired final compound.

EXAMPLES

The following examples are provided for illustrative purposes only and not to limit the scope of the claims provided herein. While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Preparation of Compounds of Formula (I)

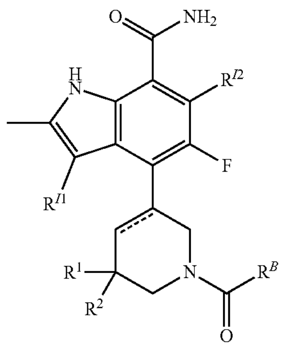

Example 1

Synthesis of 4-(1-acryloyl-1,2,5,6-tetrahydropyridin-3-yl)-3-chloro-5-fluoro-2-methyl-1H-indole-7-carboxamide (Compound 1)

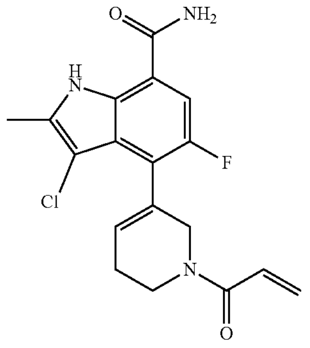 [SMILES: C=CC(=O)N1CCC=C(c2c(F)cc(C(N)=O)c3[nH]c(C)c(Cl)c23)C1]

Step 1: 4-bromo-5-fluoro-2-methyl-1H-indole-7-carboxylic acid

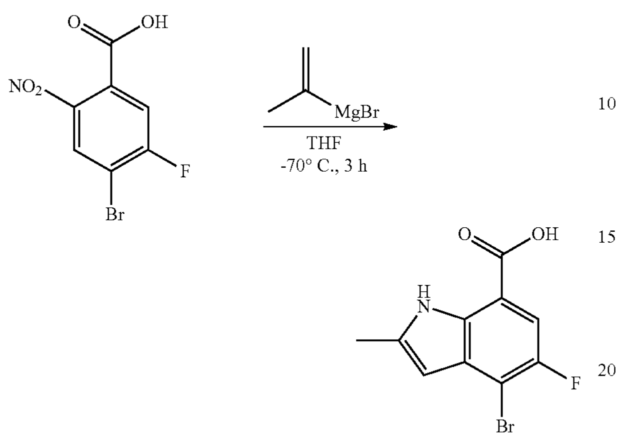

To a stirred solution of 4-bromo-5-fluoro-2-nitrobenzoic acid (17 g, 64.4 mmol) in THE (200 mL) was added dropwise prop-1-en-2-ylmagnesium bromide (451 mL, 225 mmol, 0.5 M in THF) at −70° C. under nitrogen. After addition, the reaction mixture was stirred at −70° C. for 3 h. The reaction mixture was quenched with saturated aqueous ammonium chloride (500 mL) and extracted with ethyl acetate (2×500 mL). The combined extracts were washed with brine (300 mL), dried over anhydrous sodium sulfate, and concentrated under vacuum to give 4-bromo-5-fluoro-2-methyl-1H-indole-7-carboxylic acid (17.5 g) as a brown solid. The solids were taken forward without purification.

ESI-MS $[M-H]^-$ calcd for ($C_{10}H_7BrFNO_2$) 269.96, 271.96 found: 270.25, 272.25.

Step 2: 4-bromo-5-fluoro-2-methyl-1H-indole-7-carboxamide

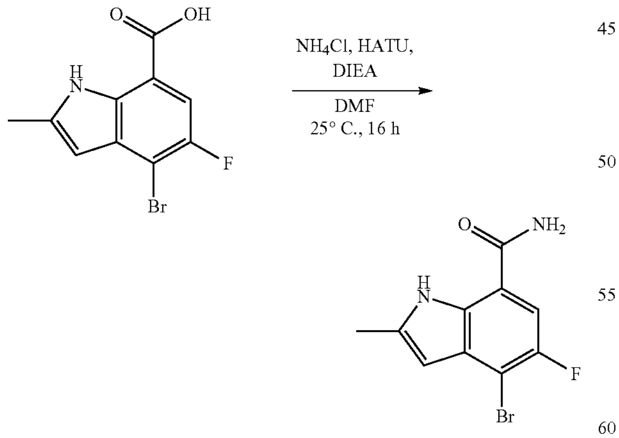

To a stirred solution of 4-bromo-5-fluoro-2-methyl-1H-indole-7-carboxylic acid (17.5 g, 64.4 mmol), ammonia hydrochloride (5.17 g, 96.6 mmol) and HATU (29.4 g, 77.3 mmol) in DMF (200 mL) was added N-ethyl-N-isopropyl-propan-2-amine (25.0 g, 193 mmol). The reaction mixture was stirred at 25° C. for 16 h, quenched with water (300 mL) and extracted with ethyl acetate (3×300 mL). The combined extracts were washed with water (200 mL), brine (200 mL), and then dried over anhydrous sodium sulfate and concentrated under vacuum. The concentrate was purified by column chromatography (50% ethyl acetate in petroleum ether) to give 4-bromo-5-fluoro-2-methyl-1H-indole-7-carboxamide (3.8 g, 22%) as a yellow solid.

$^1H$ NMR (400 MHz, DMSO-$d_6$) δ 11.26 (s, 1H), 8.11 (s, 1H), 7.63-7.53 (m, 2H), 6.19 (s, 1H), 2.42 (s, 3H).

ESI-MS $[M+H]^+$ calcd for ($C_{10}H_8BrFN_2O$) 270.98, 272.98; found: 270.90, 272.90.

Step 3: tert-butyl 5-(7-carbamoyl-5-fluoro-2-methyl-1H-indol-4-yl)-3,6-dihydropyridine-1(2H)-carboxylate

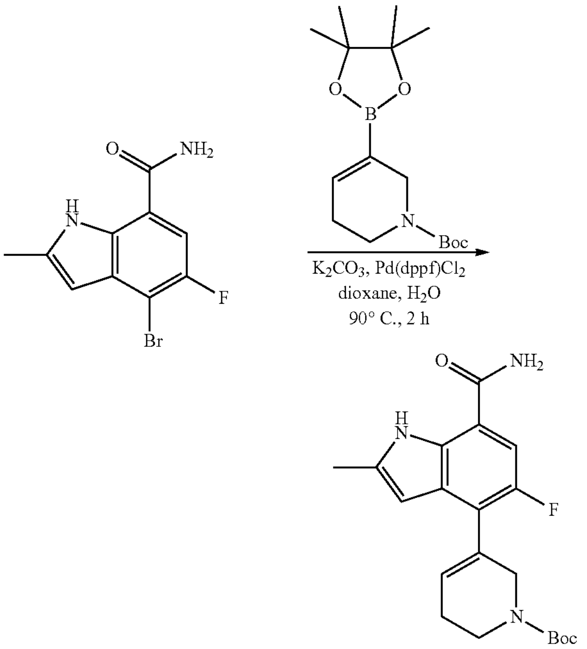

A mixture of 4-bromo-5-fluoro-2-methyl-1H-indole-7-carboxamide (250 mg, 0.922 mmol), tert-butyl 5-(4,4,5,5-tetramethyl-1,3,2-dioxaborolan-2-yl)-3,6-dihydropyridine-1(2H)-carboxylate (314 mg, 1.01 mmol), Pd(dppf)Cl2 (67 mg, 0.092 mmol) and potassium carbonate (382 mg, 2.77 mmol) in 1,4-dioxane (8 mL) and water (2 mL) was degassed and backfilled with nitrogen. The reaction mixture was stirred under nitrogen at 90° C. for 2 h. The reaction mixture was diluted with water (30 mL) and extracted with ethyl acetate (3×20 mL). The combined extracts were washed with brine (20 mL), dried over sodium sulfate, and concentrated under vacuum. The residue was purified by column chromatography on silica gel (50% ethyl acetate in petroleum ether) to give tert-butyl 5-(7-carbamoyl-5-fluoro-2-methyl-1H-indol-4-yl)-3,6-dihydropyridine-1(2H)-carboxylate (330 mg, 96%) as a yellow solid.

$^1H$ NMR (300 MHz, DMSO-$d_6$) δ 7.46 (d, J=11.7 Hz, 1H), 6.17 (s, 1H), 5.98 (s, 1H), 4.12-4.06 (m, 2H), 3.58-3.46 (m, 2H), 2.38 (s, 3H), 2.34-2.21 (m, 2H), 1.40 (s, 9H).

ESI-MS $[M+H]^+$ calcd for ($C_{20}H_{24}FN_3O_3$) 374.18, found: 374.15.

Step 4: tert-butyl 5-(7-carbamoyl-3-chloro-5-fluoro-2-methyl-1H-indol-4-yl)-3,6-dihydropyridine-1(2H)-carboxylate

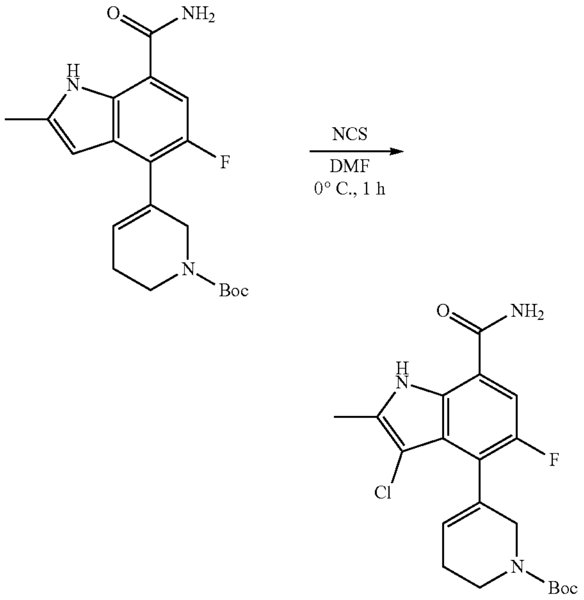

To a solution of tert-butyl 5-(7-carbamoyl-5-fluoro-2-methyl-1H-indol-4-yl)-3,6-dihydropyridine-1(2H)-carboxylate (150 mg, 0.40 mmol) in DMF (5 mL) was added N-chlorosuccinimide (54 mg, 0.40 mmol) at 0° C. The reaction mixture was stirred at 0° C. for 1 h, quenched with water (20 mL) and extracted with ethyl acetate (3×20 mL). The combined extracts were washed with brine (30 mL), dried over sodium sulfate, and concentrated under vacuum. The residue was purified by reversed phase column chromatography eluting with acetonitrile in water (10% to 60%) to afford tert-butyl 5-(7-carbamoyl-3-chloro-5-fluoro-2-methyl-1H-indol-4-yl)-3,6-dihydropyridine-1(2H)-carboxylate (100 mg, 61%) as a yellow solid.

$^1$H NMR (300 MHz, DMSO-$d_6$) δ 7.55 (d, J=10.8 Hz, 1H), 5.78 (s, 1H), 4.04-3.97 (m, 2H), 3.63-3.43 (m, 2H), 2.37 (s, 3H), 2.33-2.18 (m, 2H), 1.39 (s, 9H).

ESI-MS [M+H-tBu]$^+$ calcd for ($C_{20}H_{23}ClFN_3O_3$) 352.14, 352.14; found: 352.10, 352.10.

Step 5: 3-chloro-5-fluoro-2-methyl-4-(1,2,5,6-tetrahydropyridin-3-yl)-1H-indole-7-carboxamide

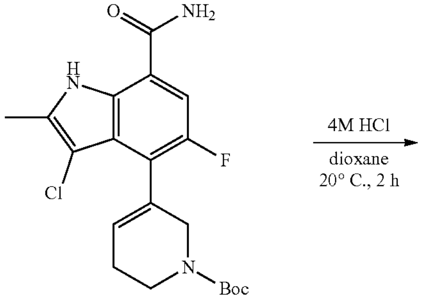

-continued

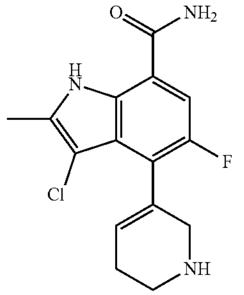

A mixture of tert-butyl 5-(7-carbamoyl-3-chloro-5-fluoro-2-methyl-1H-indol-4-yl)-3,6-dihydropyridine-1(2H)-carboxylate (100 mg, 0.245 mmol) and 4 M hydrogen chloride in dioxane (3 mL) was stirred at 20° C. for 2 h. The reaction mixture was concentrated under vacuum, diluted with saturated aqueous sodium bicarbonate (30 mL) and extracted with ethyl acetate (3×20 mL). The combined extracts were dried over sodium sulfate and concentrated under vacuum to afford 3-chloro-5-fluoro-2-methyl-4-(1,2,5,6-tetrahydropyridin-3-yl)-1H-indole-7-carboxamide (70 mg) as a green solid.

ESI-MS [M+H]$^+$ calcd for ($C_{15}H_{15}ClFN_3O$) 308.09, 310.09; found: 308.05, 310.05.

Step 6: 4-(1-acryloyl-1,2,5,6-tetrahydropyridin-3-yl)-3-chloro-5-fluoro-2-methyl-1H-indole-7-carboxamide

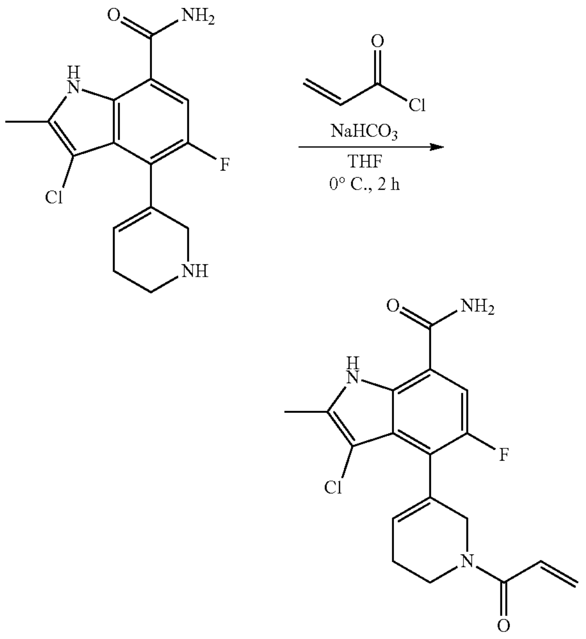

4-(1-Acryloyl-1,2,5,6-tetrahydropyridin-3-yl)-3-chloro-5-fluoro-2-methyl-1H-indole-7-carboxamide: To a mixture of 3-chloro-5-fluoro-2-methyl-4-(1,2,5,6-tetrahydropyridin-3-yl)-1H-indole-7-carboxamide (70 mg, 0.23 mmol) in tetrahydrofuran (4.0 mL) and water (1.0 mL) was added sodium bicarbonate (57 mg, 0.68 mmol) and acryloyl chloride (20 mg, 0.23 mmol) at 0° C. The reaction mixture was stirred at 0° C. for 2 h. The reaction mixture was diluted with water (10 mL) and extracted with ethyl acetate (3×10 mL). The combined extracts were washed with brine (10 mL), dried over sodium sulfate, and concentrated under vacuum. The residue was purified by reversed phase column chromatography eluting with acetonitrile in water (10% to 35%) to afford 4-(1-acryloyl-1,2,5,6-tetrahydropyridin-3-yl)-3-chloro-5-fluoro-2-methyl-1H-indole-7-carboxamide (42.3 mg, 51%) as a green solid.

$^1$H NMR (300 MHz, DMSO-d6) δ 11.37 (s, 1H), 8.12 (s, 1H), 7.68-7.50 (m, 2H), 6.93-6.69 (m, 1H), 6.13 (d, J=17.4 Hz, 1H), 5.83-5.62 (m, 2H), 4.35-4.05 (m, 2H), 3.90-3.60 (m, 2H), 2.41-2.27 (m, 5H).

ESI-MS $[M+H]^+$ calcd for ($C_{18}H_{17}ClFN_3O_2$) 362.10, 364.10; found: 362.05, 362.05.

Example 2

Synthesis of 4-(1-acryloylpiperidin-3-yl)-3-chloro-5-fluoro-2-methyl-1H-indole-7-carboxamide (Compound 2)

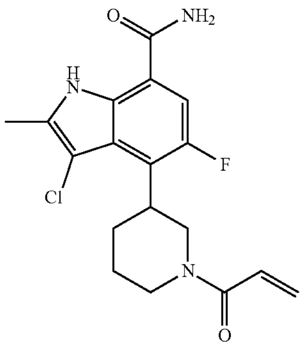 [SMILES: C=CC(=O)N1CCCC(c2c(F)cc(C(N)=O)c3[nH]c(C)c(Cl)c23)C1]

Step 1: tert-butyl 3-(7-carbamoyl-5-fluoro-2-methyl-1H-indol-4-yl) piperidine-1-carboxylate

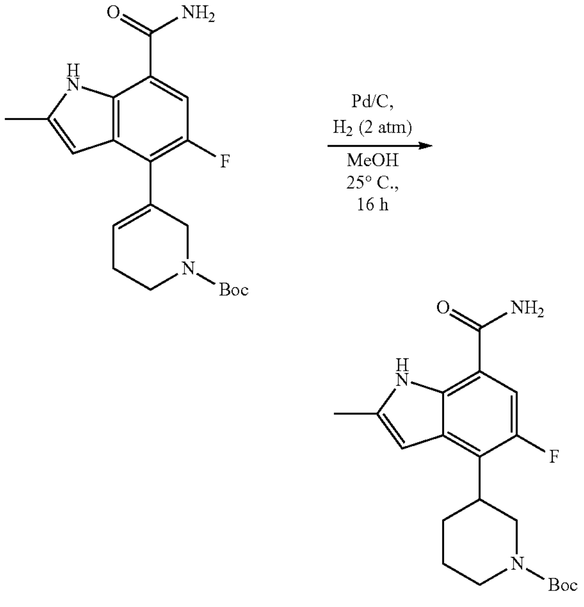

A mixture of tert-butyl 5-(7-carbamoyl-5-fluoro-2-methyl-1H-indol-4-yl)-3,6-dihydropyridine-1(2H)-carboxylate (prepared as described in example 1 herein; 390 mg, 1.04 mmol) and Pd/C (10%, 500 mg) in methanol (20 mL) were stirred under hydrogen (2 atm) at 25° C. for 16 h. The reaction mixture was filtered. The filtrate was concentrated under vacuum to give tert-butyl 3-(7-carbamoyl-5-fluoro-2-methyl-1H-indol-4-yl) piperidine-1-carboxylate (340 mg, 87%) as a white solid.

ESI-MS $[M-H]^-$ calcd for ($C_{20}H_{26}FN_3O_3$) 374.20, found: 374.15.

Step 2: tert-butyl 3-(7-carbamoyl-3-chloro-5-fluoro-2-methyl-1H-indol-4-yl) piperidine-1-carboxylate

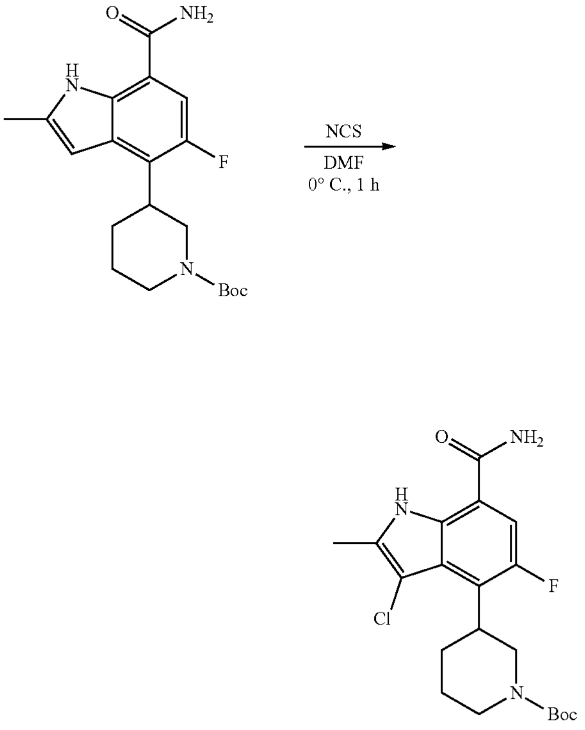

Tert-Butyl 3-(7-carbamoyl-3-chloro-5-fluoro-2-methyl-1H-indol-4-yl) piperidine-1-carboxylate: To a solution of tert-butyl 3-(7-carbamoyl-5-fluoro-2-methyl-1H-indol-4-yl) piperidine-1-carboxylate (340 mg, 0.91 mmol) in DMF (10 mL) was added NCS (133 mg, 0.996 mmol) at 0° C. The reaction mixture was stirred at 0° C. for 1 h. The reaction mixture was quenched with water (30 mL) and extracted with ethyl acetate (3×30 mL). The combined extracts were washed with brine (3×20 mL), dried over sodium sulfate, and concentrated under vacuum. The residue was purified by column chromatography on silica gel (0 to 50% ethyl acetate in petroleum ether) to give tert-butyl 3-(7-carbamoyl-3-chloro-5-fluoro-2-methyl-1H-indol-4-yl)piperidine-1-carboxylate (270 mg, 73%) as a white solid.

$^1$H NMR (400 MHz, DMSO-d6) δ 11.32 (s, 1H), 8.10 (s, 1H), 7.56-7.46 (m, 2H), 4.14-3.96 (m, 3H), 3.30-3.09 (m, 1H), 2.91-2.62 (m, 1H), 2.39 (s, 3H), 1.94-1.87 (m, 2H), 1.79-1.69 (m, 1H), 1.47-1.38 (m, 1H), 1.38 (s, 9H).

ESI-MS [M+H-tBu]+ calcd for ($C_{20}H_{25}ClFN_3O_3$) 354.16, 356.16; found: 354.15, 356.15.

Step 3: 3-chloro-5-fluoro-2-methyl-4-(piperidin-3-yl)-1H-indole-7-carboxamide hydrochloride

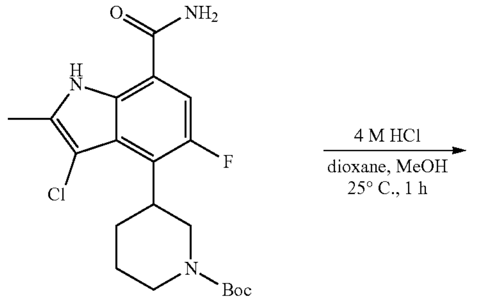

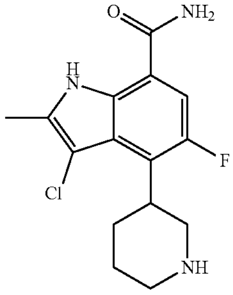

3-Chloro-5-fluoro-2-methyl-4-(piperidin-3-yl)-1H-indole-7-carboxamide hydrochloride: A mixture of tert-butyl 3-(7-carbamoyl-3-chloro-5-fluoro-2-methyl-1H-indol-4-yl) piperidine-1-carboxylate (312 mg, 0.76 mmol) and hydrogen chloride (4 M in dioxane, 6.0 mL) was stirred at 25° C. for 1 h. The reaction mixture was concentrated under vacuum to give 3-chloro-5-fluoro-2-methyl-4-(piperidin-3-yl)-1H-indole-7-carboxamide hydrochloride (260 mg) as a white solid.

ESI-MS [M−H]− calcd for ($C_{15}H_{17}ClFN_3O$) 308.10, 310.10; found: 308.00, 310.00.

Step 4: 4-(1-acryloylpiperidin-3-yl)-3-chloro-5-fluoro-2-methyl-1H-indole-7-carboxamide

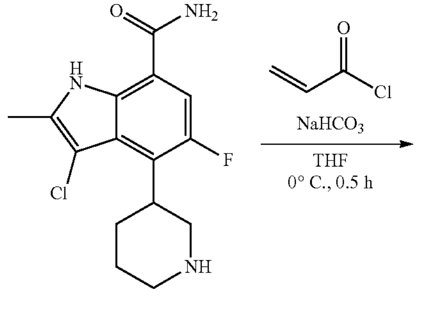

-continued

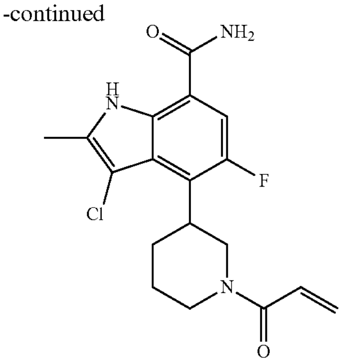

4-(1-Acryloylpiperidin-3-yl)-3-chloro-5-fluoro-2-methyl-1H-indole-7-carboxamide: To a mixture of 3-chloro-5-fluoro-2-methyl-4-(piperidin-3-yl)-1H-indole-7-carboxamide hydrochloride (260 mg, 0.76 mmol) in water (2 mL) and THE (8 mL) were added sodium bicarbonate (382 mg, 4.55 mmol) and acryloyl chloride (65 mg, 0.76 mmol) at 0° C. The reaction mixture was stirred at 0° C. for 0.5 h, diluted with water (20 mL) and extracted with ethyl acetate (3×15 mL). The combined extracts were washed with brine (20 mL), dried over sodium sulfate, and concentrated under vacuum. The residue was purified by Prep-HPLC (Column: XSelect CSH Prep C18 OBD Column, 5 um, 19×150 mm; mobile phase A: water (10 mmol/L $NH_4HCO_3$), mobile phase B: acetonitrile; flow rate: 25 mL/min; gradient: 10% B to 35% B, 7 min; 220 nm; retention time=6.4 minutes) to afford 4-(1-acryloylpiperidin-3-yl)-3-chloro-5-fluoro-2-methyl-1H-indole-7-carboxamide (165 mg, 60%) as a white solid.

$^1$H NMR (300 MHz, DMSO-d6) δ 11.40 (s, 1H), 8.12 (s, 1H), 7.62-7.48 (m, 2H), 6.84-6.76 (m, 1H), 6.16-6.07 (m, 1H), 5.66-5.60 (m, 1H), 4.57 (d, J=12.6 Hz, 1H), 4.23-3.94 (m, 2H), 3.55-3.51 (m, 0.5H), 3.12-3.08 (m, 1H), 2.78-2.60 (m, 0.5H), 2.40 (s, 3H), 2.17-1.77 (m, 3H), 1.60-1.38 (m, 1H).

ESI-MS [M+H]+ calcd for ($C_{18}H_{19}ClFN_3O_2$) 364.11, 366.11; found: 364.10, 366.10.

Step 5: Chiral Separation (Compounds 2a and 2b)

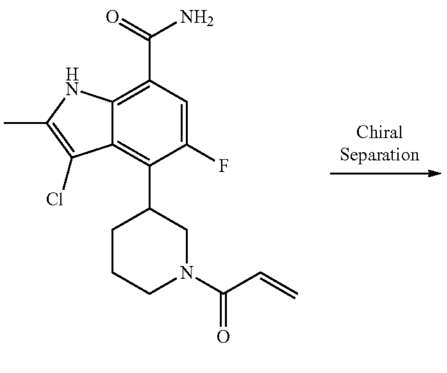

-continued

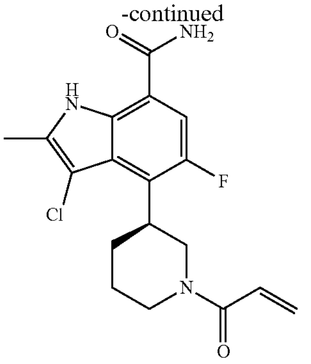

+

(S)-

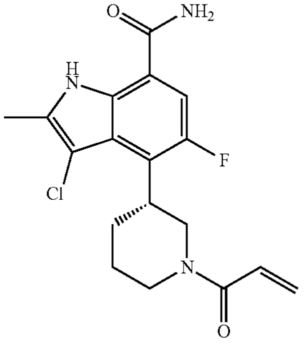

(R)-

The enantiomers of 4-(1-acryloylpiperidin-3-yl)-3-chloro-5-fluoro-2-methyl-1H-indole-7-carboxamide were separated by Prep-Chiral-HPLC (120 mg sample, column: CHIRALPAK IG, 2×25 cm, 5 um; mobile phase A: hexane (0.5% 2 M $NH_3$-MeOH), mobile phase B: EtOH; flow rate: 17 mL/min; gradient: 50% B to 50% B in 14 min; 220/254 nm) to provide compounds 2a (RT=7.106 minutes) and 2b (RT=11.312 minutes).

Compound 2a (Retention Time=7.106 Minutes) 48.6 mg of a White Solid was Obtained $^1$H NMR (300 MHz, DMSO-d6) δ 11.39 (s, 1H), 8.11 (s, 1H), 7.64-7.50 (m, 2H), 6.84-6.80 (m, 1H), 6.11-6.07 (m, 1H), 5.66-5.61 (m, 1H), 4.57 (d, J=12.8 Hz, 1H), 4.26-3.91 (m, 2H), 3.57-3.54 (m, 0.5H), 3.12-3.18 (m, 1H), 2.68-2.64 (m, 0.5H), 2.40 (s, 3H), 1.95-1.83 (m, 3H), 1.70-1.50 (m, 1H).

ESI-MS [M+H]+ calcd for ($C_{18}H_{19}ClFN_3O_2$) 364.11, 366.11; found: 364.05, 366.05.

Compound 2b (Retention Time=11.312 Minutes) 46.7 mg of a White Solid was Obtained $^1$H NMR (300 MHz, DMSO-d6) δ 11.40 (s, 1H), 8.11 (s, 1H), 7.63-7.46 (m, 2H), 6.84-6.80 (m, 1H), 6.11-5.95 (m, 1H), 5.66-5.41 (m, 1H), 4.57 (d, J=12.7 Hz, 1H), 4.23-3.95 (m, 2H), 3.57-3.54 (m, 0.5H), 3.12-3.01 (m, 1H), 2.68-2.55 (m, 0.5H), 2.40 (s, 3H), 1.95-1.73 (m, 3H), 1.70-1.50 (m, 1H).

ESI-MS [M+H]+ calcd for ($C_{18}H_{19}ClFN_3O_2$) 364.11, 366.11; found: 364.10, 366.10.

Example 3

Synthesis of 4-(1-acryloylpiperidin-3-yl)-3-chloro-5,6-difluoro-2-methyl-1H-indole-7-carboxamide (Compound 3)

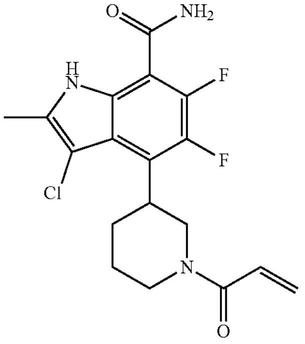 [SMILES: C=CC(=O)N1CCCC(c2c(F)c(F)c(C(N)=O)c3[nH]c(C)c(Cl)c23)C1]

Step 1: 1,4-dibromo-2,3-difluoro-5-nitrobenzene

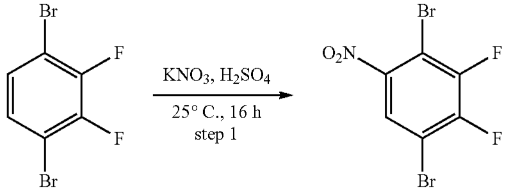

To a solution of 1,4-dibromo-2,3-difluorobenzene (25.0 g, 91.95 mmol) in concentrated sulfuric acid (200 mL) was added potassium nitrate (11.0 g, 108.8 mmol) at 0° C. The reaction mixture was stirred at 25° C. for 16 h. The reaction mixture was poured into ice-water (1 L) and stirred at 0° C. for 30 min. The resulting precipitation was filtered, the filter cake was washed with water and dried under reduced pressure to afford 1,4-dibromo-2,3-difluoro-5-nitro-benzene (27.0 g, 92%) as a yellow solid.

$^1$H NMR (300 MHz, DMSO-$d_6$) δ 8.47 (dd, J=6.0, 2.4 Hz 1H).

Step 2: 2,5-dibromo-3,4-difluoroaniline

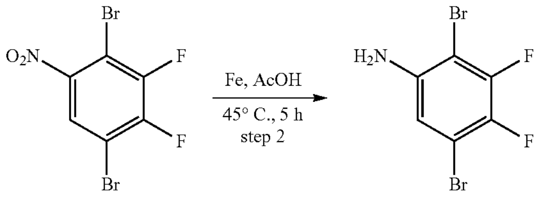

To a solution of 1,4-dibromo-2,3-difluoro-5-nitrobenzene (27.0 g, 85.21 mmol) in acetic acid (260 mL) was added iron powder (47.6 g, 852.0 mmol). The reaction mixture was stirred at 45° C. for 5 h. The cooled reaction mixture was filtered. The filtrate was poured into ice-water (500 mL) and filtered. The filter cake was washed with water (300 mL) and dried under reduced pressure to afford 2,5-dibromo-3,4-difluoroaniline (23.0 g, 94% yield) as a yellow solid.

$^1$H NMR (300 MHz, DMSO-$d_6$) δ 6.88 (dd, J=6.0, 2.4 Hz 1H), 5.74 (brs, 2H).

Step 3: 2,5-dibromo-3,4-difluoro-6-iodoaniline

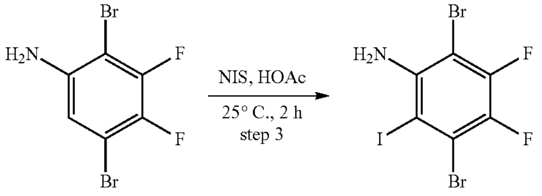

To a solution of 2,5-dibromo-3,4-difluoroaniline (23.0 g, 80.17 mmol) in acetic acid (250 mL) was added N-iodosuccinimide (19.84 g, 88.18 mmol). The reaction mixture was stirred at 25° C. for 2 h. The reaction mixture was poured into ice-water (500 mL) and filtered. The filter cake was washed with water (100 mL) and dried under reduced pressure. The crude product was purified by column chromatography on silica gel eluting with ethyl acetate in petroleum ether (0 to 5%) to give 2,5-dibromo-3,4-difluoro-6-iodoaniline (30.0 g, 90%) as an off-white solid.

$^1$H NMR (300 MHz, DMSO-$d_6$) δ 5.63 (s, 2H).

ESI-MS $[M-H]^-$ calcd for ($C_6H_2Br_2F_2IN$) 409.76, 411.75, 413.75 found: 409.75, 411.75, 413.70.

Step 4: 2,5-dibromo-3,4-difluoro-6-(prop-1-yn-1-yl) aniline

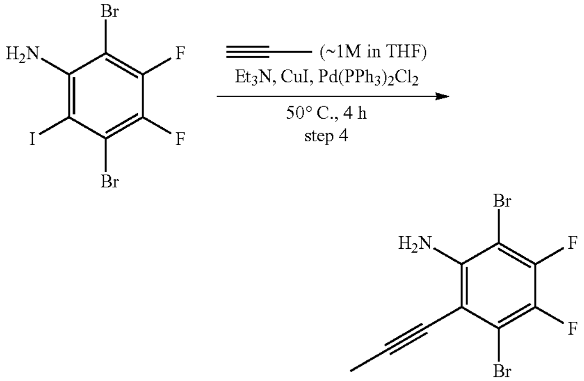

To a mixture of 2,5-dibromo-3,4-difluoro-6-iodoaniline (30.0 g, 72.68 mmol), copper(II) iodide (2.77 g, 14.54 mmol) and $Pd(PPh_3)_2Cl_2$ (5.12 g, 7.27 mmol) in triethylamine (365 mL) was added prop-1-yne (1 M in THF, 364 mL) under nitrogen. The reaction mixture was stirred in a sealed flask at 50° C. for 4 h. The cooled reaction mixture was quenched with water (300 ml) and extracted with ethyl acetate (300 ml×3). The combined organic layers were dried over anhydrous sodium sulfate, filtered and concentrated under vacuum. The residue was purified by column chromatography onto silica gel eluting with ethyl acetate in petroleum ether (0 to 10%) to give 2,5-dibromo-3,4-difluoro-6-(prop-1-yn-1-yl)aniline (20.0 g, 84%) as a yellow solid.

ESI-MS $[M-H]^-$ calcd for ($C_9H_5Br_2F_2N$) 321.88, 323.87, 325.87 found: 322.00, 324.00, 326.00.

$^1$H NMR (300 MHz, DMSO-$d_6$) δ 5.79 (s, 2H), 2.18 (s, 3H).

Step 5: 4,7-dibromo-5,6-difluoro-2-methyl-1H-indole

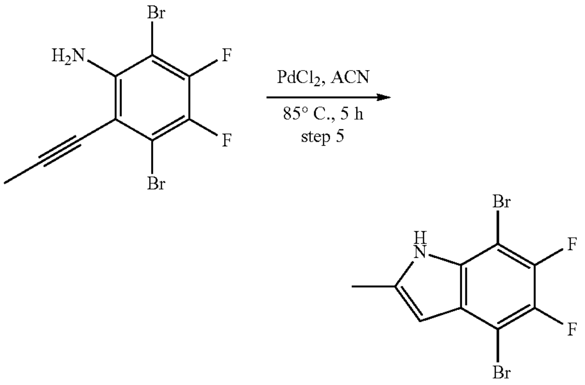

A mixture of 2,5-dibromo-3,4-difluoro-6-(prop-1-yn-1-yl)aniline (20.0 g, 61.55 mmol) and $PdCl_2$ (1.09 g, 6.15 mmol) in acetonitrile (400 mL) was degassed and backfilled with nitrogen for three times and stirred at 85° C. for 5 h. The cooled reaction mixture was concentrated under vacuum. The residue was purified by column chromatography on silica gel eluting with ethyl acetate in petroleum ether (0 to 10%) to afford 4,7-dibromo-5,6-difluoro-2-methyl-1H-indole (17.0 g, 85%) as a yellow solid.

$^1$H NMR (300 MHz, DMSO-$d_6$) δ 11.75 (s, 1H), 6.28 (s, 1H), 2.41 (s, 3H).

ESI-MS $[M-H]^-$ calcd for ($C_9H_5Br_2F_2N$) 321.88, 323.87, 325.87 found: 321.80, 323.80, 325.80.

Step 6: 4,7-dibromo-5,6-difluoro-2-methyl-1-((2-(trimethylsilyl)ethoxy)methyl)-1H-indole

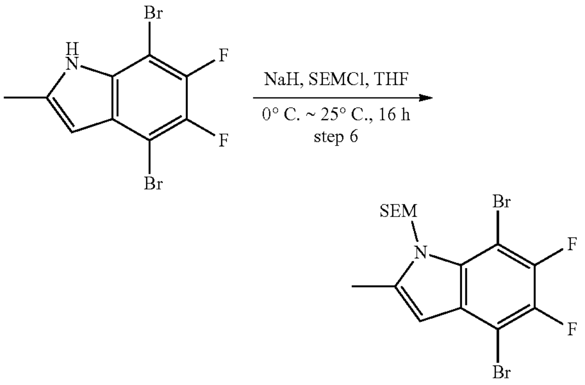

To a stirred solution of 4,7-dibromo-5,6-difluoro-2-methyl-1H-indole (10.0 g, 30.77 mmol) in THE (200 mL) was added sodium hydride (1.60 g, 40.01 mmol, 60%) at 0° C. After stirring at this temperature for 1 h, 2-(Trimethylsilyl)ethoxymethyl chloride (7.70 g, 46.16 mmol) was added at 0° C. The reaction mixture was stirred at 25° C. for 16 h.

The reaction mixture was quenched with water (200 mL) and extracted with ethyl acetate (150 mL×3). The combined organic layers were washed with brine (100 mL), dried over anhydrous sodium sulfate and concentrated under vacuum. The residue was purified by column chromatography on silica gel eluting with ethyl acetate in petroleum ether (0 to 10%) to afford 4,7-dibromo-5,6-difluoro-2-methyl-1-((2-(trimethylsilyl)ethoxy)methyl)-1H-indole (12.3 g, 87%) as a yellow oil.

$^1$H NMR (300 MHz, DMSO-$d_6$) δ 6.42 (s, 1H), 5.78 (s, 2H), 3.55 (t, J=7.8 Hz, 2H), 2.47 (s, 3H), 0.83 (t, J=8.1 Hz, 2H), −0.08 (s, 9H).

Step 7: 4-bromo-5,6-difluoro-2-methyl-1-((2-(trimethylsilyl)ethoxy)methyl)-1H-indole-7-carboxylic acid

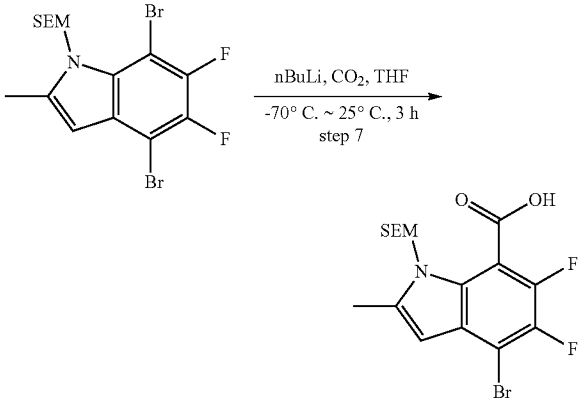

To a solution of 4,7-dibromo-5,6-difluoro-2-methyl-1-((2-(trimethylsilyl)ethoxy) methyl)-1H-indole (12.3 g, 27.03 mmol) in THF (130 mL) was added n-butyllithium (2.5 M in n-hexane, 13 mL, 32.5 mmol) under nitrogen at −70° C. After stirring at this temperature for 0.5 h and 0° C. 0.5 h, the reaction mixture was cooled to −70° C. and bubbled with carbon dioxide for 30 min. After stirring at 25° C. for 1.5 h, the reaction mixture was quenched with saturated aqueous ammonium chloride (100 mL) and extracted with dichloromethane (100 mL×3). The combined organic layers was washed with brine (100 mL), dried over anhydrous sodium sulfate and concentrated under vacuum to afford 4-bromo-5,6-difluoro-2-methyl-1-((2-(trimethylsilyl)ethoxy) methyl)-1H-indole-7-carboxylic acid (11.4 g, crude) as a yellow oil.

ESI-MS [M−H]$^+$ calcd for ($C_{16}H_{20}BrF_2NO_3Si$) 418.04, 420.03 found: 417.95, 419.95.

Step 8: 4-bromo-5,6-difluoro-2-methyl-1-((2-(trimethylsilyl)ethoxy)methyl)-1H-indole-7-carboxamide

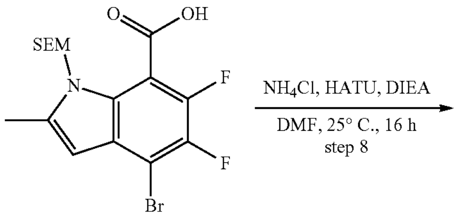

-continued

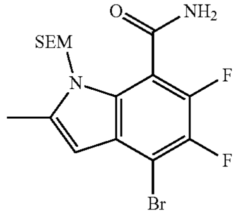

To a stirred mixture of 4-bromo-5,6-difluoro-2-methyl-1-(2-trimethylsilylethoxymethyl)indole-7-carboxylic acid (11.4 g, 27.12 mmol) and ammonium chloride (2.18 g, 40.68 mmol) in DMF (100 mL) were added HATU (12.38 g, 32.55 mmol) and DIPEA (17.53 g, 135.61 mmol) at 0° C. After stirring at 25° C. for 16 h, the reaction mixture was quenched with water (300 ml) and extracted with ethyl acetate (300 ml×3). The combined organic layers were washed with brine (200 ml×3), dried over anhydrous sodium sulfate and concentrated under vacuum. The residue was purified by column chromatography on silica gel eluting with ethyl acetate in petroleum ether (0 to 50%) to afford 4-bromo-5,6-difluoro-2-methyl-1-((2-(trimehylsilyl)ethoxy)methyl)-1H-indole-7-carboxamide (6.3 g, 55%) as a yellow solid.

$^1$H NMR (300 MHz, DMSO-$d_6$) δ 8.34 (s, 1H), 8.10 (s, 1H), 6.40 (s, 1H), 5.50 (s, 2H), 3.42 (t, J=8.1 Hz, 2H), 2.46 (s, 3H), 0.81 (t, J=8.1 Hz, 2H), −0.06 (s, 9H).

ESI-MS [M+H]$^+$ calcd for ($C_{16}H_{20}BrF_2N_2O_2Si$) 419.05, 421.05 found: 419.20, 421.20.

Step 9: 4-bromo-5,6-difluoro-2-methyl-1H-indole-7-carboxamide

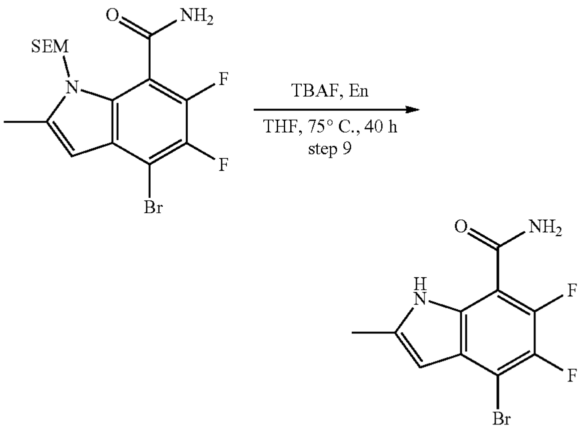

A mixture of 4-bromo-5,6-difluoro-2-methyl-1-((2-(trimethylsilyl)ethoxy) methyl)-1H-indole-7-carboxamide (6.3 g, 15.02 mmol), TBAF (1 M in THF, 150 mL, 150.2 mmol), and ethane-1,2-diamine (30 mL, 450.6 mmol) in THF (60 mL) was stirred at 75° C. for 40 h. The reaction mixture was cooled to 0° C. and acidified with 2 M hydrochloric acid until pH=4. The precipitate was collected by filtration, washed with water (100 mL) and dried under reduced pressure to afford 4-bromo-5,6-difluoro-2-methyl-1H-indole-7-carboxamide (3.5 g, 80%) as a yellow solid.

ESI-MS [M+H]+ calcd for ($C_{10}H_7BrF_2N_2O$) 288.97, 290.97 found: 288.95, 290.95.

1H NMR (300 MHz, DMSO-d6) δ 11.38 (s, 1H), 7.97 (s, 1H), 7.90 (s, 1H), 6.20 (s, 1H), 2.40 (s, 3H).

Step 10: tert-butyl 5-(7-carbamoyl-5,6-difluoro-2-methyl-1H-indol-4-yl)-3,6-dihydropyridine-1(2H)-carboxylate

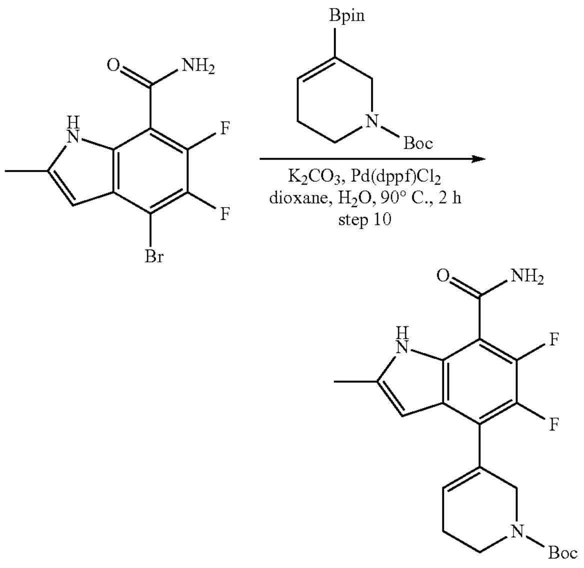

A mixture of 4-bromo-5,6-difluoro-2-methyl-1H-indole-7-carboxamide (600 mg, 2.1 mmol), tert-butyl 5-(4,4,5,5-tetramethyl-1,3,2-dioxaborolan-2-yl)-3,6-dihydro-2H-pyridine-1-carboxylate (706 mg, 2.3 mmol), Pd(dppf)Cl2·DCM (169 mg, 0.21 mmol) and potassium carbonate (860 mg, 6.23 mmol) in dioxane (12 mL) and Water (3 mL) was degassed and backfilled with nitrogen for five times and stirred at 90° C. for 2 h. The cooled reaction mixture was diluted with water (60 mL) and extracted with dichloromethane (3×50 mL). The combined organic layers were washed with brine (60 mL), dried over sodium sulfate and concentrated under vacuum. The residue was purified by column chromatography on silica gel eluting with ethyl acetate in dichloromethane (0 to 7%) to afford tert-butyl 5-(7-carbamoyl-5,6-difluoro-2-methyl-1H-indol-4-yl)-3,6-dihydropyridine-1(2H)-carboxylate (700 mg, 86%) as a yellow solid.

ESI-MS [M−H]− calcd for ($C_{20}H_{23}F_2N_3O_3$) 390.17 found: 390.05.

1H NMR (400 MHz, DMSO-d6) δ 11.07 (s, 1H), 7.86 (s, 1H), 7.77 (s, 1H), 6.18 (s, 1H), 6.08-5.98 (m, 1H), 4.17-4.07 (m, 2H), 3.55 (t, J=5.8 Hz, 2H), 2.37 (s, 3H), 2.35-2.27 (m, 2H), 1.42 (s, 9H).

Step 11: tert-butyl 3-(7-carbamoyl-5,6-difluoro-2-methyl-1H-indol-4-yl) piperidine-1-carboxylate

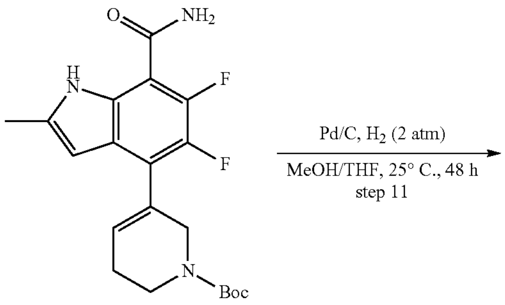

-continued

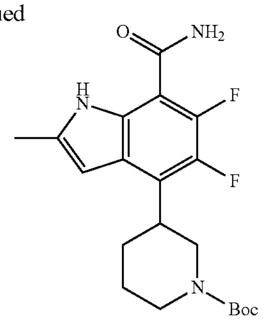

To a stirred solution of tert-butyl 5-(7-carbamoyl-5,6-difluoro-2-methyl-1H-indol-4-yl)-3,6-dihydropyridine-1(2H)-carboxylate (450 mg, 1.15 mmol) in methanol (60 mL) and tetrahydrofuran (30 mL) was added Pd/C (300 mg, 10%). The reaction mixture was stirred under hydrogen (2 atm) at 25° C. for 48 h. The reaction mixture was filtered, the filtrate was concentrated under vacuum. The residue was purified by column chromatography on silica gel eluting with ethyl acetate in dichloromethane (0 to 7%) to afford tert-butyl 3-(7-carbamoyl-5,6-difluoro-2-methyl-1H-indol-4-yl) piperidine-1-carboxylate (400 mg, 88%) as a yellow solid.

$^1$H NMR (400 MHz, DMSO-$d_6$) δ 11.02 (s, 1H), 7.82 (s, 1H), 7.71 (s, 1H), 6.38 (s, 1H), 4.04-3.82 (m, 2H), 3.31-3.04 (m, 2H), 3.01-2.63 (m, 1H), 2.38 (s, 3H), 2.14-1.99 (m, 1H), 1.90-1.68 (m, 2H), 1.59-1.44 (m, 1H), 1.40 (s, 9H).

ESI-MS [M+H-tBu]$^-$ calcd for ($C_{20}H_{25}F_2N_3O_3$) 338.19 found: 338.10.

Step 12: tert-butyl 3-(7-carbamoyl-3-chloro-5,6-difluoro-2-methyl-1H-indol-4-yl) piperidine-1-carboxylate

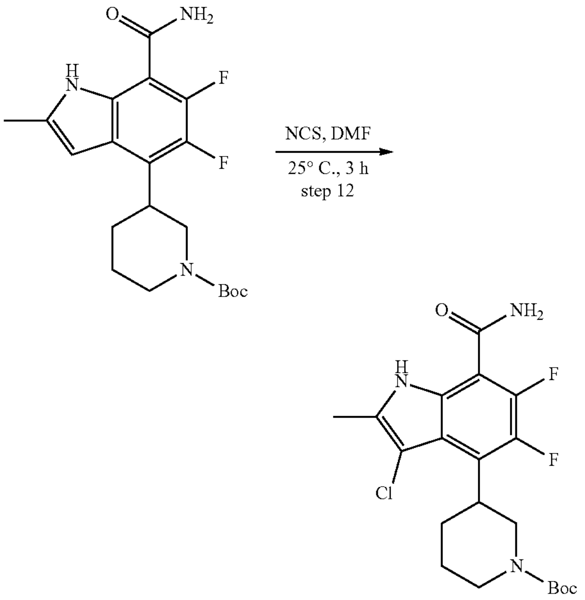

To a stirred solution of tert-butyl 3-(7-carbamoyl-5,6-difluoro-2-methyl-1H-indol-4-yl) piperidine-1-carboxylate (400 mg, 1.02 mmol) in DMF (10 mL) was added NCS (136 mg, 1.02 mmol) at 0° C. The reaction mixture was stirred at 25° C. for 3 h. The reaction mixture was quenched with water (50 mL) and extracted with ethyl acetate (3×40 mL). The combined organic layers were washed with brine (50 mL), dried over sodium sulfate and concentrated under vacuum. The residue was purified by column chromatography on silica gel eluting with methanol in dichloromethane (0 to 8%) to afford tert-butyl 3-(7-carbamoyl-3-chloro-5,6-difluoro-2-methyl-1H-indol-4-yl) piperidine-1-carboxylate (350 mg, 80%) as a yellow solid.

$^{1}$H NMR (400 MHz, DMSO-$d_6$) δ 11.45 (s, 1H), 7.92 (s, 1H), 7.85 (s, 1H), 4.13-4.04 (m, 2H), 3.27-3.06 (m, 2H), 2.90-2.65 (m, 1H), 2.36 (s, 3H), 1.98-1.88 (m, 2H), 1.80-1.71 (m, 1H), 1.57-1.42 (m, 1H), 1.39 (s, 9H).

ESI-MS [M+H-tBu]$^{-}$ calcd for ($C_{20}H_{24}ClF_2N_3O_3$) 372.15, 374.14 found: 372.10, 374.10.

Step 13: 3-chloro-5,6-difluoro-2-methyl-4-(piperidin-3-yl)-1H-indole-7-carboxamide hydrochloride

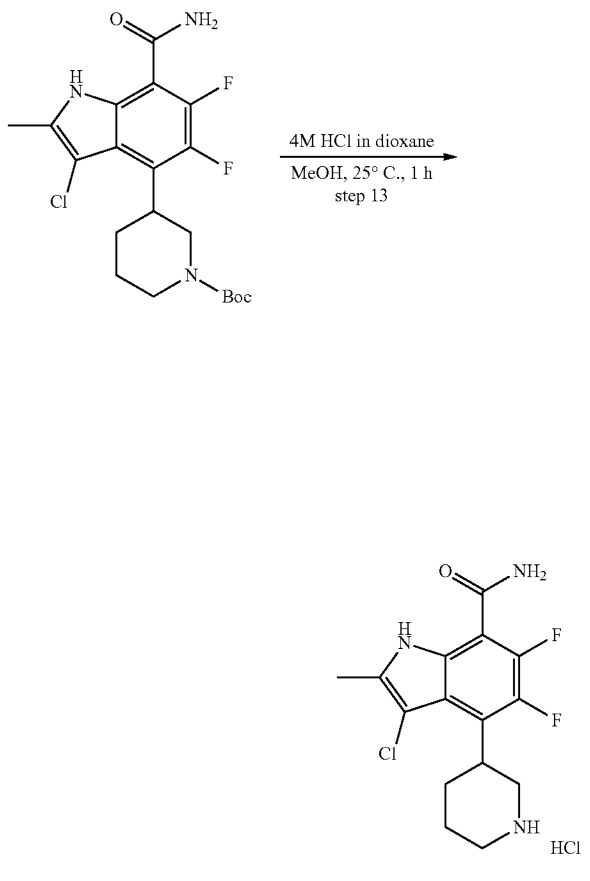

To a stirred solution of tert-butyl 3-(7-carbamoyl-3-chloro-5,6-difluoro-2-methyl-1H-indol-4-yl) piperidine-1-carboxylate (350 mg, 0.82 mmol) in methanol (1 mL) was added hydrogen chloride (4 M in dioxane, 5 mL). The reaction mixture was stirred at 25° C. for 1 h. The mixture was concentrated under vacuum to give 3-chloro-5,6-difluoro-2-methyl-4-(piperidin-3-yl)-1H-indole-7-carboxamide hydrochloride (280 mg, 94%) as a yellow solid.

ESI-MS [M+H]$^{+}$ calcd for ($C_{15}H_{16}ClF_2N_3O$) 328.09, 330.09 found: 328.15, 330.15.

Step 14: 4-(1-acryloylpiperidin-3-yl)-3-chloro-5,6-difluoro-2-methyl-1H-indole-7-carboxamide

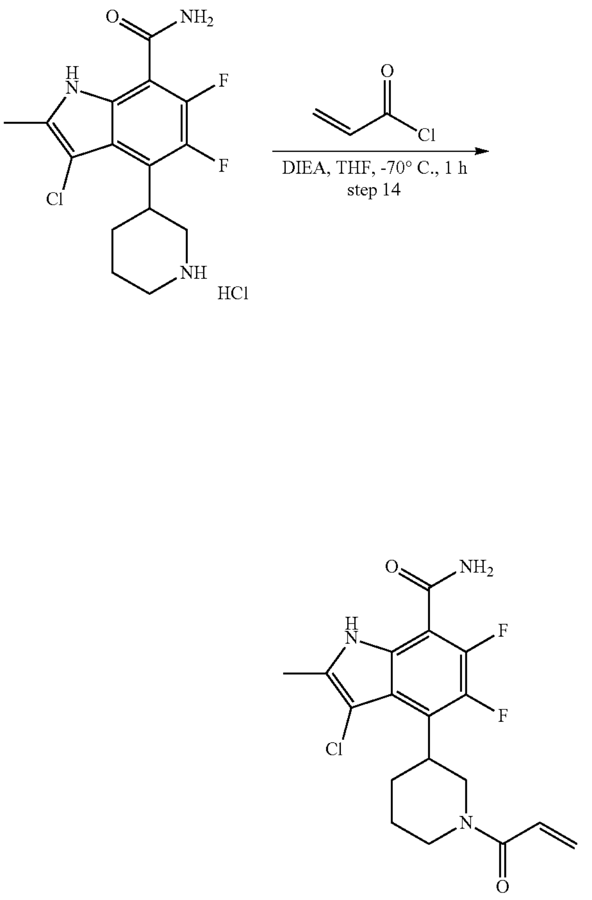

To a stirred solution of 3-chloro-5,6-difluoro-2-methyl-4-(3-piperidyl)-1H-indole-7-carboxamide (280 mg, 0.76 mmol) in THF (4 mL) were added DIEA (294 mg, 2.28 mmol) and acryloyl chloride ((98 mg, 0.76 mmol) at −70° C. The reaction mixture was stirred for 1 h at −70° C. The reaction mixture was quenched with water (30 mL) and extracted with ethyl acetate (3×30 mL). The combined organic layers were washed with brine (30 mL), dried over sodium sulfate and concentrated under vacuum. The residue was purified by Prep-HPLC with the following conditions: Column: XBridge Prep OBD C18 Column, 30×150 mm 5 um; Mobile Phase A: Water (10 MMOL/L $NH_4HCO_3$+0.1% $NH_3 \cdot H_2O$), Mobile Phase B: Acetonitrile; Flow rate: 60 mL/min; Gradient: 30% B to 52% B in 7 min; 220 nm; Rt: 6.32 min to give 4-(1-acryloylpiperidin-3-yl)-3-chloro-5,6-difluoro-2-methyl-1H-indole-7-carboxamide (123.7 mg, 42%) as an off-white solid.

$^{1}$H NMR (400 MHz, DMSO-$d_6$) δ 11.46 (s, 1H), 7.95 (s, 1H), 7.88 (s, 1H), 6.96-6.70 (m, 1H), 6.20-6.03 (m, 1H), 5.81-5.57 (m, 1H), 4.74-4.45 (m, 1H), 4.28-3.94 (m, 2H), 3.60-3.45 (m, 0.5H), 3.19-3.00 (m, 1H), 2.77-2.63 (m, 0.5H), 2.35 (s, 3H), 2.13-1.91 (m, 2H), 1.89-1.77 (m, 1H), 1.64-1.40 (m, 1H).

ESI-MS [M+H]$^{+}$ calcd for ($C_{18}H_{18}ClF_2N_3O_2$) 382.11, 384.11 found: 382.25, 384.25.

Example 4

Synthesis of 4-(1-acryloyl-1,2,5,6-tetrahydropyridin-3-yl)-3-chloro-5,6-difluoro-2-methyl-1H-indole-7-carboxamide (Compound 4)

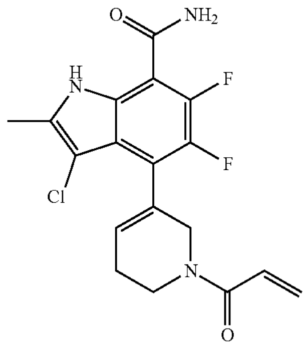 [SMILES: C=CC(=O)N1CCC=C(c2c(F)c(F)c(C(N)=O)c3[nH]c(C)c(Cl)c23)C1]

Step 1: Tert-butyl 5-(7-carbamoyl-3-chloro-5,6-difluoro-2-methyl-1H-indol-4-yl)-3,6-dihydropyridine-1(2H)-carboxylate

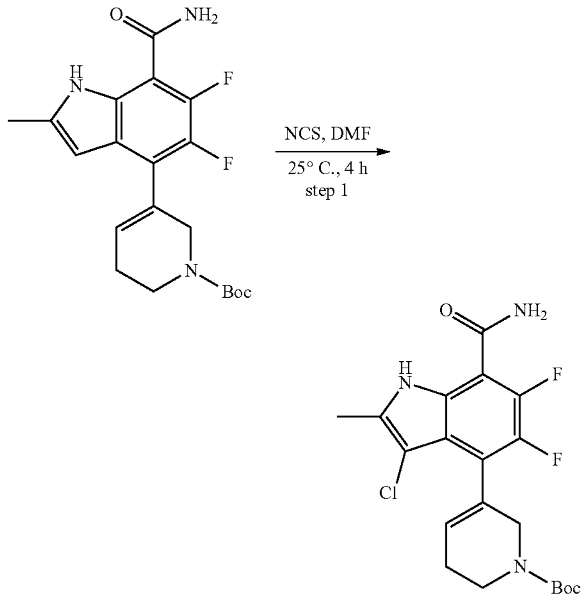

To a stirred solution of tert-butyl 5-(7-carbamoyl-5,6-difluoro-2-methyl-1H-indol-4-yl)-3,6-dihydropyridine-1(2H)-carboxylate (150 mg, 0.38 mmol) was added NCS (52 mg, 0.38 mmol) at 0° C. The reaction mixture was stirred at 25° C. for 4 h. The reaction mixture was quenched with water (20 mL) and extracted with ethyl acetate (3×20 mL). The combined organic layers were washed with brine (30 mL), dried over sodium sulfate and concentrated under vacuum. The residue was purified by column chromatography on aluminum oxide eluting with methanol in dichloromethane (0 to 10%) to give tert-butyl 5-(7-carbamoyl-3-chloro-5,6-difluoro-2-methyl-1H-indol-4-yl)-3,6-dihydropyridine-1(2H)-carboxylate (140 mg, 85%) as a yellow solid.

$^1H$ NMR (400 MHz, DMSO-$d_6$) δ 11.46 (s, 1H), 7.95 (s, 1H), 7.89 (s, 1H), 5.85 (s, 1H), 4.16-3.91 (m, 2H), 3.60-3.46 (m, 2H), 2.35 (s, 3H), 2.31-2.24 (m, 2H), 1.40 (s, 9H).

ESI-MS $[M+H]^+$ calcd for ($C_{20}H_{22}ClF_2N_3O_3$) 426.13, 426.13 found: 426.15, 428.15.

Step 2: 3-chloro-5,6-difluoro-2-methyl-4-(1,2,5,6-tetrahydropyridin-3-yl)-1H-indole-7-carboxamide hydrochloride

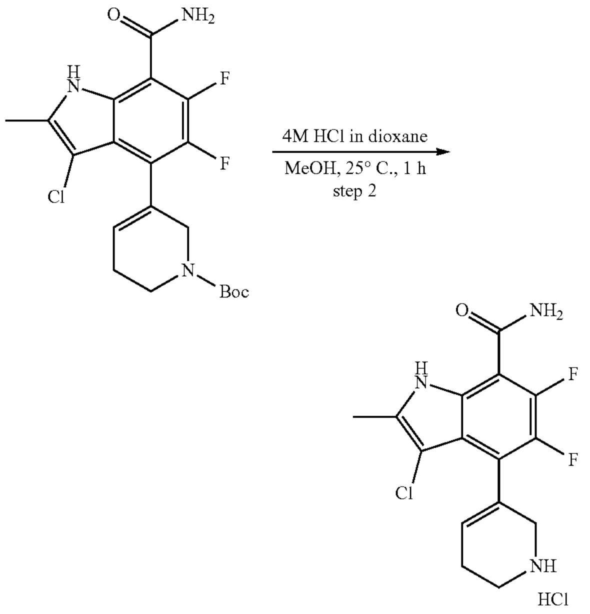

To a stirred solution of tert-butyl 5-(7-carbamoyl-3-chloro-5,6-difluoro-2-methyl-1H-indol-4-yl)-3,6-dihydropyridine-1(2H)-carboxylate (140 mg, 0.33 mmol) in methanol (1 mL) was added hydrogen chloride (4 M in dioxane, 2 mL). The reaction mixture was stirred at 25° C. for 1 h. The mixture was concentrated under vacuum to give 3-chloro-5,6-difluoro-2-methyl-4-(1,2,5,6-tetrahydropyridin-3-yl)-1H-indole-7-carboxamide hydrochloride (125 mg, crude) as a yellow solid.

ESI-MS $[M+H]^+$ calcd for ($C_{15}H_{14}ClF_2N_3O$) 326.08, 328.08, found: 326.10, 328.10.

Step 3: 4-(1-acryloyl-1,2,5,6-tetrahydropyridin-3-yl)-3-chloro-5,6-difluoro-2-methyl-1H-indole-7-carboxamide

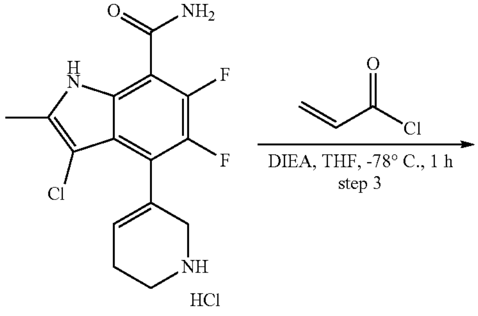

-continued

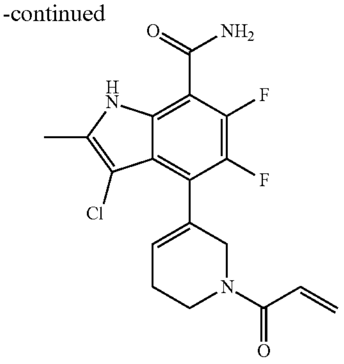

To a stirred solution of 3-chloro-5,6-difluoro-2-methyl-4-(1,2,5,6-tetrahydropyridin-3-yl)-1H-indole-7-carboxamide hydrochloride (125 mg, 0.34 mmol) in THF (4 mL) were added DIEA (140 mg, 1.08 mmol) and acryloyl chloride (33 mg, 0.36 mmol) at −78° C. The reaction mixture was stirred for 1 h at −78° C. The reaction mixture was quenched with water (20 mL) and extracted with ethyl acetate (3×20 mL). The combined organic layers was washed with brine (30 mL), dried over sodium sulfate and concentrated under vacuum. The residue was purified by prep-HPLC with the following conditions: Column: Xselect CSH OBD Column 30×150 mm 5 um; Mobile Phase A: Water (10 MMOL/L $NH_4HCO_3$+0.1% $NH_3 \cdot H_2O$), Mobile Phase B: Acetonitrile; Flow rate: 60 mL/min; Gradient: 33% B to 53% B in 7 min; 220 nm; Rt: 5.53 min to give 4-(1-acryloyl-1,2,5,6-tetrahydropyridin-3-yl)-3-chloro-5,6-difluoro-2-methyl-1H-indole-7-carboxamide (66.3 mg, 48%) as an off-white solid.

$^1$H NMR (400 MHz, DMSO-$d_6$) δ 11.47 (s, 1H), 7.99 (s, 1H), 7.93 (s, 1H), 6.95-6.68 (m, 1H), 6.19-6.08 (m, 1H), 5.95-5.84 (m, 1H), 5.75-5.61 (m, 1H), 4.40-4.09 (m, 2H), 3.93-3.57 (m, 2H), 2.44-2.16 (m, 5H).

ESI-MS $[M+H]^+$ calcd for ($C_{18}H_{16}ClF_2N_3O_2$) 380.09, 382.09 found: 380.05, 382.05.

Example 5

Synthesis of 4-(1-acryloyl-1,2,5,6-tetrahydropyridin-3-yl)-3-cyano-5,6-difluoro-2-methyl-1H-indole-7-carboxamide (Compound 5)

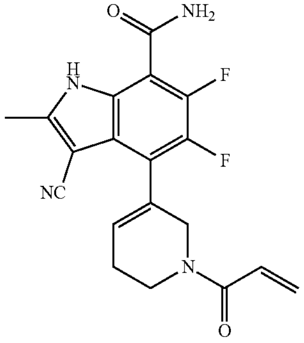 [SMILES: C=CC(=O)N1CCC=C(c2c(F)c(F)c(C(N)=O)c3[nH]c(C)c(C#N)c23)C1]

Step 1: tert-butyl 5-(3-bromo-7-carbamoyl-5,6-difluoro-2-methyl-1H-indol-4-yl)-3,6-dihydropyridine-1(2H)-carboxylate

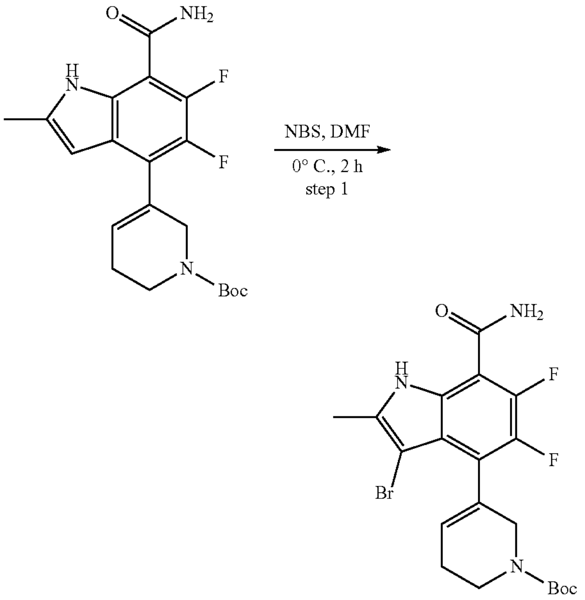

To a stirred solution of tert-butyl 5-(7-carbamoyl-5,6-difluoro-2-methyl-1H-indol-4-yl)-3,6-dihydropyridine-1(2H)-carboxylate (600 mg, 1.53 mmol) in DMF (15 mL) was added N-Bromosuccinimide (273 mg, 1.53 mmol) at 0° C. After stirring at 0° C. for 2 h, the reaction mixture was quenched with water (60 mL) and extracted with ethyl acetate (3×50 mL). The combined organic layers were washed with brine (50 mL), dried over sodium sulfate and concentrated under vacuum. The residue was purified by column chromatography on silica gel eluting with ethyl acetate in petroleum ether (0 to 33%) to give tert-butyl 5-(3-bromo-7-carbamoyl-5,6-difluoro-2-methyl-1H-indol-4-yl)-3,6-dihydropyridine-1(2H)-carboxylate (530 mg, 73%) as a yellow solid.

$^1$H NMR (400 MHz, DMSO-$d_6$) δ 11.57 (s, 1H), 7.94 (s, 1H), 7.89 (s, 1H), 5.90-5.82 (m, 1H), 4.15-3.86 (m, 2H), 3.72-3.44 (m, 2H), 2.36 (s, 3H), 2.32-2.24 (m, 2H), 1.41 (s, 9H).

ESI-MS $[M+H-Boc]^+$ calcd for ($C_{20}H_{22}BrF_2N_3O_3$) 370.08, 372.08 found: 370.10, 372.10.

Step 2: tert-butyl 5-(7-carbamoyl-3-cyano-5,6-difluoro-2-methyl-1H-indol-4-yl)-3,6-dihydropyridine-1(2H)-carboxylate

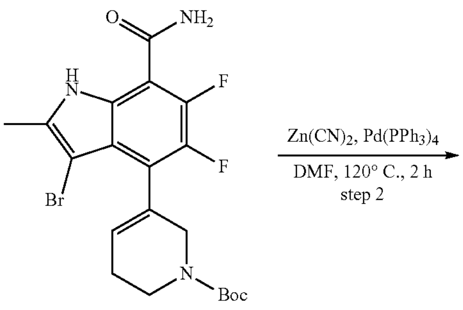

-continued

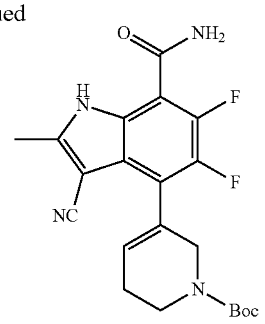

A mixture of tert-butyl 5-(3-bromo-7-carbamoyl-5,6-difluoro-2-methyl-1H-indol-4-yl)-3,6-dihydropyridine-1(2H)-carboxylate (530 mg, 1.13 mmol), $Pd(PPh_3)_4$ (130 mg, 0.112 mmol) and $Zn(CN)_2$ (132 mg, 1.13 mmol) in DMF (15 mL) was degassed and backfilled with nitrogen for five times. The reaction mixture was heated at 120° C. for 2 h. The cooled reaction mixture was quenched with water (60 mL) and extracted with ethyl acetate (3×50 mL). The combined organic layers were washed with brine (50 mL), dried over sodium sulfate and concentrated under vacuum. The residue was purified by column chromatography on silica gel eluting with ethyl acetate in petroleum ether (0 to 43%) to give tert-butyl 5-(7-carbamoyl-3-cyano-5,6-difluoro-2-methyl-1H-indol-4-yl)-3,6-dihydropyridine-1(2H)-carboxylate (220 mg, 46%) as a yellow solid.

ESI-MS $[M+H-Boc]^+$ calcd for $(C_{21}H_{22}F_2N_4O_3)$ 317.17 found: 317.15.

Step 3: 3-cyano-5,6-difluoro-2-methyl-4-(1,2,5,6-tetrahydropyridin-3-yl)-1H-indole-7-carboxamide hydrochloride

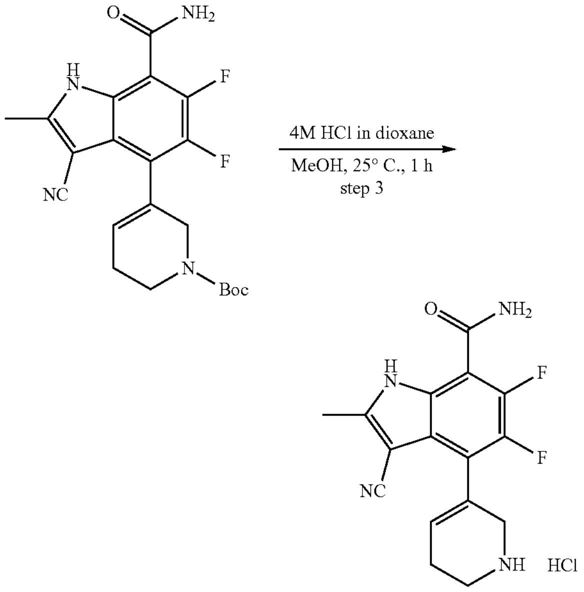

To a stirred solution of tert-butyl 5-(7-carbamoyl-3-cyano-5,6-difluoro-2-methyl-1H-indol-4-yl)-3,6-dihydropyridine-1(2H)-carboxylate (220 mg, 0.528 mmol) in MeOH (2 mL) was added 4 M hydrogen chloride in dioxane (5.00 mL). The reaction mixture was stirred at 25° C. for 1 h. The resulting mixture was concentrated under vacuum to give 3-cyano-5,6-difluoro-2-methyl-4-(1,2,5,6-tetrahydropyridin-3-yl)-1H-indole-7-carboxamide hydrochloride (182 mg, crude) as a brown solid.

ESI-MS $[M+H]^+$ calcd for $(C_{16}H_{14}F_2N_4O)$ 317.11 found: 317.15.

Step 4: 4-(1-acryloyl-1,2,5,6-tetrahydropyridin-3-yl)-3-cyano-5,6-difluoro-2-methyl-1H-indole-7-carboxamide

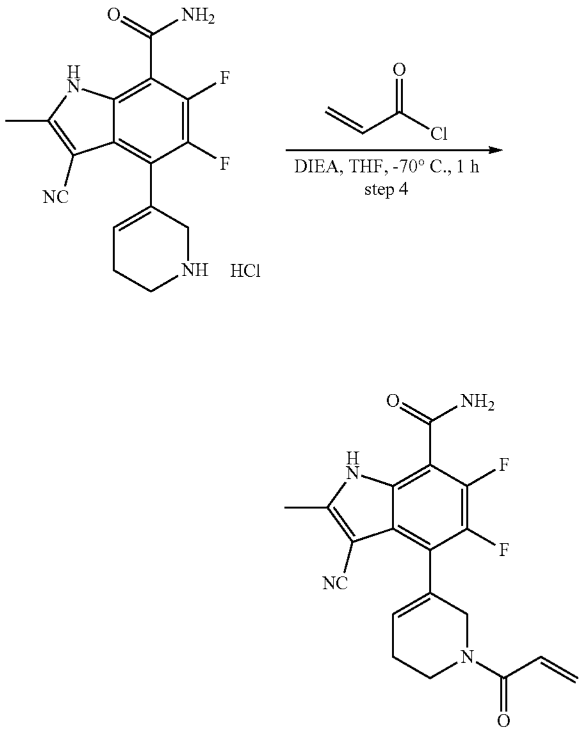

To a solution of 3-cyano-5,6-difluoro-2-methyl-4-(1,2,5,6-tetrahydropyridin-3-yl)-1H-indole-7-carboxamide hydrochloride (160 mg, 0.453 mmol) in THF (6 mL) were added DIEA (293 mg, 2.27 mmol) and acryloyl chloride (41 mg, 0.453 mmol) at −70° C. The reaction mixture was stirred at −70° C. for 1 h. The reaction mixture was quenched with water (40 mL) and extracted with ethyl acetate (3×30 mL). The combined organic layers were washed with brine (30 mL), dried over sodium sulfate and concentrated under vacuum. The residue was purified by Prep-HPLC with the following conditions: Column: XBridge Prep OBD C18 Column, 30×150 mm 5 um; Mobile Phase A: Water (50 mmol/L $NH_4HCO_3$), Mobile Phase B: Acetonitrile; Flow rate: 60 mL/min; Gradient: 5% B to 95% B in 12 min; 254 nm; RT: 4.33 min to give 4-(1-acryloyl-1,2,5,6-tetrahydropyridin-3-yl)-3-cyano-5,6-difluoro-2-methyl-1H-indole-7-carboxamide (88 mg, 52%) as a white solid.

$^1H$ NMR (400 MHz, DMSO-$d_6$) δ 12.19 (s, 1H), 8.16-7.94 (m, 2H), 6.98-6.70 (m, 1H), 6.17-6.01 (m, 2H), 5.80-5.63 (m, 1H), 4.41-4.20 (m, 2H), 3.88-3.67 (m, 2H), 2.54 (s, 3H), 2.44-2.28 (m, 2H).

ESI-MS $[M+H]^+$ calcd for $(C_{19}H_{16}F_2N_4O_2)$ 371.12 found: 371.05.

Example 6

Synthesis of (S)-4-(1-acryloylpiperidin-3-yl)-3,5,6-trifluoro-2-methyl-1H-indole-7-carboxamide and (R)-4-(1-acryloylpiperidin-3-yl)-3,5,6-trifluoro-2-methyl-1H-indole-7-carboxamide (Compound 6a and 6b)

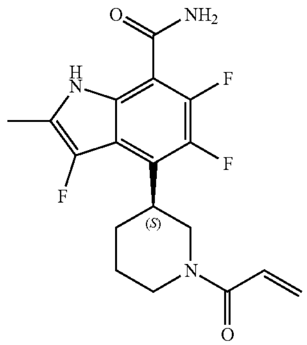

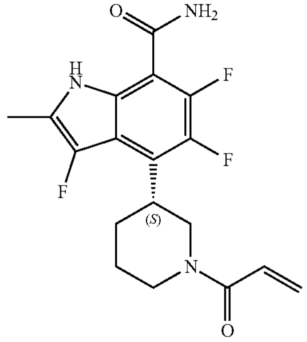

Step 1: tert-butyl 3-(7-carbamoyl-3,5,6-trifluoro-2-methyl-1H-indol-4-yl) piperidine-1-carboxylate

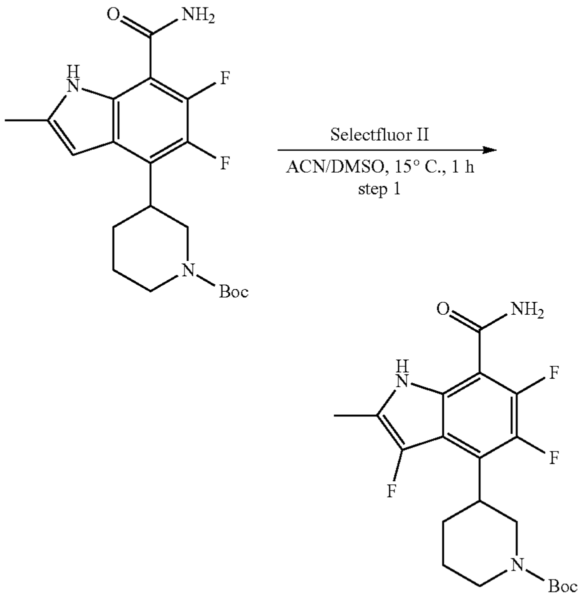

To a stirred solution of tert-butyl 3-(7-carbamoyl-5,6-difluoro-2-methyl-1H-indol-4-yl) piperidine-1-carboxylate (500 mg, 1.27 mmol) in acetonitrile (8 mL) and DMSO (2 mL) was added selectfluor II (407 mg, 1.27 mmol) in portions at 15° C. The reaction mixture was stirred at 15° C. for 1 h. The reaction mixture was quenched with water (30 mL) and extracted with dichloromethane (3x30 mL). The combined organic layers were washed with brine (30 mL), dried over sodium sulfate and concentrated under vacuum. The residue was purified by column chromatography on silica gel eluting with ethyl acetate in petroleum ether (0 to 53%) to give tert-butyl 3-(7-carbamoyl-3,5,6-trifluoro-2-methyl-1H-indol-4-yl) piperidine-1-carboxylate (300 mg, crude) as a yellow solid.

ESI-MS $[M+H-tBu]^+$ calcd for ($C_{20}H_{24}F_3N_3O_3$) 356.18 found: 356.10.

Step 2: 3,5,6-trifluoro-2-methyl-4-(piperidin-3-yl)-1H-indole-7-carboxamide hydrochloride

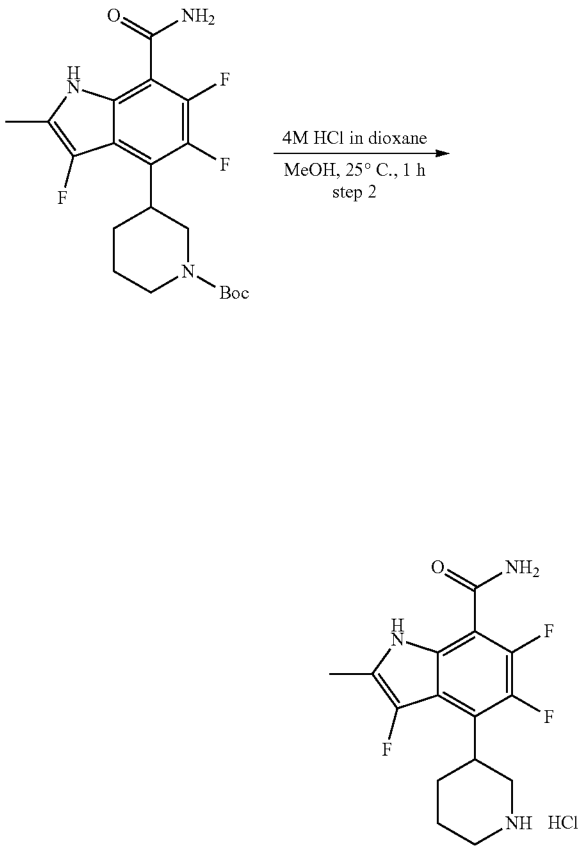

To a stirred solution of tert-butyl 3-(7-carbamoyl-3,5,6-trifluoro-2-methyl-1H-indol-4-yl) piperidine-1-carboxylate (300 mg, crude) in methanol (1 mL) was added hydrogen chloride (4 M in dioxane, 4 mL). The reaction mixture was stirred at 25° C. for 1 h. The reaction mixture was concentrated under vacuum to give 3,5,6-trifluoro-2-methyl-4-(3-piperidyl)-1H-indole-7-carboxamide (220 mg, crude) as a yellow solid.

ESI-MS $[M+H]^+$ calcd for ($C_{15}H_{16}F_3N_3O$) 312.12 found: 312.10.

Step 3: 4-(1-acryloylpiperidin-3-yl)-3,5,6-trifluoro-2-methyl-1H-indole-7-carboxamide

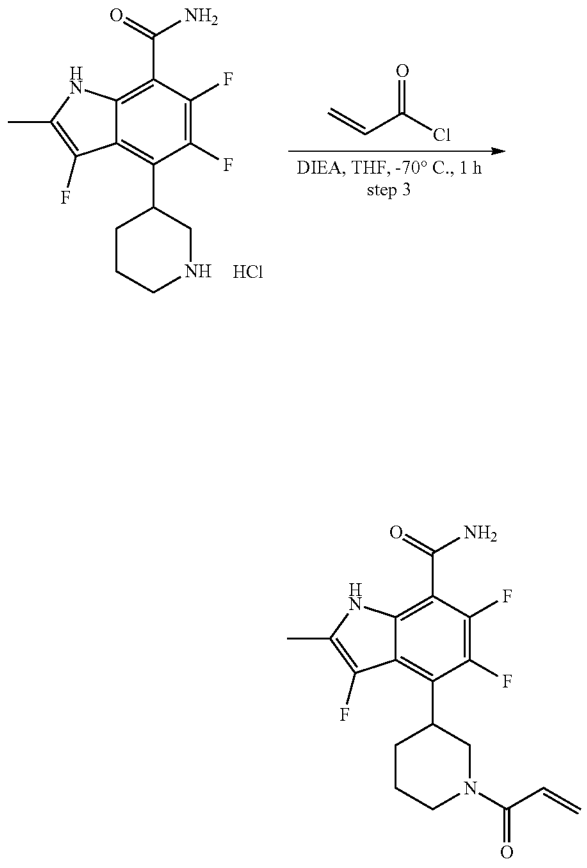

To a stirred solution of 3,5,6-trifluoro-2-methyl-4-(3-piperidyl)-1H-indole-7-carboxamide (200 mg, crude) in THF (6 mL) were added DIEA (223 mg, 1.73 mmol) and acryloyl chloride (52 mg, 0.58 mmol) at −70° C. The reaction mixture was stirred at −70° C. for 1 h. The reaction mixture was quenched with water (20 mL) and extracted with ethyl acetate (3×20 mL). The combined organic layers were washed with brine (20 mL), dried over sodium sulfate and concentrated under vacuum. The residue was purified by Prep-HPLC with the following conditions: Column: Xselect CSH OBD Column 30×150 mm, 5 um; Mobile Phase A: Water (10 mmol/L $NH_4HCO_3$+0.1% $NH_3{\cdot}H_2O$), Mobile Phase B: Acetonitrile; Flow rate: 60 mL/min; Gradient: 32% B to 53% B in 7 min; 220 nm; RT: 5.43 min to give 4-(1-acryloylpiperidin-3-yl)-3,5,6-trifluoro-2-methyl-1H-indole-7-carboxamide (107 mg, 23% over three steps) as an off-white solid.

$^1$H NMR (400 MHz, DMSO-$d_6$) δ 10.96 (s, 1H), 7.92 (s, 1H), 7.84 (s, 1H), 6.96-6.71 (m, 1H), 6.19-6.03 (m, 1H), 5.78-5.52 (m, 1H), 4.54 (t, J=12.4 Hz, 1H), 4.15 (d, J=13.2 Hz, 1H), 3.49 (t, J=12.4 Hz, 0.5H), 3.31-3.22 (m, 1H), 3.16-2.97 (m, 1H), 2.64 (t, J=13.4 Hz, 0.5H), 2.31 (s, 3H), 2.12-1.97 (m, 1H), 1.96-1.87 (m, 1H), 1.86-1.76 (m, 1H), 1.56-1.36 (m, 1H).

ESI-MS [M+H]$^+$ calcd for ($C_{18}H_{18}F_3N_3O_2$) 366.14 found: 366.15.

Step 4: (S)-4-(1-Acryloylpiperidin-3-Yl)-3,5,6-Trifluoro-2-Methyl-1H-Indole-7-carboxamide and (R)-4-(1-acryloylpiperidin-3-yl)-3,5,6-trifluoro-2-methyl-1H-indole-7-carboxamide

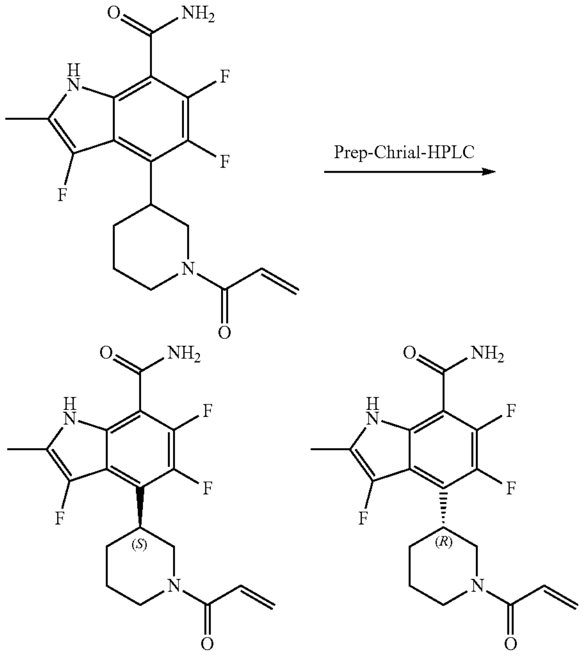

4-(1-acryloylpiperidin-3-yl)-3,5,6-trifluoro-2-methyl-1H-indole-7-carboxamide (90 mg) was separated by Prep-Chiral-HPLC with the following conditions: Column: CHIRALPAK IG, 2×25 cm, 5 m; Mobile Phase A: Hexane (0.5% 2 M $NH_3$-MeOH)-HPLC, Mobile Phase B: EtOH-HPLC; Flow rate: 20 mL/min; Gradient: 50% B to 50% B in 26 min; 220/254 nm.

Retention Time: 12.231 Min $^1$H NMR (300 MHz, DMSO-$d_6$) δ 10.96 (s, 1H), 7.92 (s, 1H), 7.84 (s, 1H), 7.00-6.72 (m, 1H), 6.22-6.05 (m, 1H), 5.79-5.58 (m, 1H), 4.67-4.47 (m, 1H), 4.17 (d, J=13.2 Hz, 1H), 3.50 (t, J=12.6 Hz, 0.5H), 3.31-3.22 (m, 1H), 3.18-2.98 (m, 1H), 2.66 (t, J=12.6 Hz, 0.5H), 2.33 (s, 3H), 2.17-1.79 (m, 3H), 1.62-1.41 (m, 1H).

ESI-MS [M+H]$^+$ calcd for ($C_{18}H_{18}F_3N_3O_2$) 366.14 found: 366.15.

Retention Time: 20.421; Min $^1$H NMR (300 MHz, DMSO-$d_6$) δ 10.96 (s, 1H), 7.92 (s, 1H), 7.84 (s, 1H), 6.97-6.63 (m, 1H), 6.24-6.01 (m, 1H), 5.80-5.55 (m, 1H), 4.66-4.45 (m, 1H), 4.17 (d, J=13.2 Hz, 1H), 3.51 (t, J=12.6 Hz, 0.5H), 3.30-3.21 (m, 1H), 3.19-2.97 (m, 1H), 2.66 (t, J=12.6 Hz, 0.5H), 2.33 (s, 3H), 2.16-1.77 (m, 3H), 1.65-1.41 (m, 1H).

ESI-MS [M+H]$^+$ calcd for ($C_{18}H_{18}F_3N_3O_2$) 366.14 found: 366.15.

(S)-4-(1-acryloylpiperidin-3-yl)-3,5,6-trifluoro-2-methyl-1H-indole-7-carboxamide (32.6 mg 36%) as a white solid; (R)-4-(1-acryloylpiperidin-3-yl)-3,5,6-trifluoro-2-methyl-1H-indole-7-carboxamide (32.2 mg, 36%) as a white solid.

Examples 7-19

Synthesis of Compounds 7-19

Compounds 7-19, as shown in Table 5, below, were prepared according to similar methods as described in the preceding schemes and examples by employing correspondingly appropriate starting materials.

TABLE 5
| COMPOUNDS 7-19 | | | |
|---|---|---|---|
| Cmpd. No. | Structure | $^1$HNMR | LC-MS: m/z (M + H) |
| 7 | 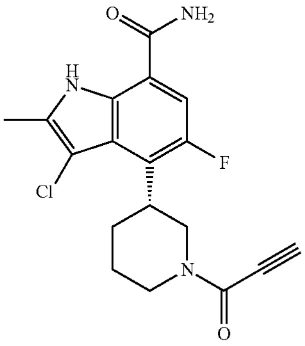 [SMILES: C#CC(=O)N1CCC[C@H](c2c(F)cc(C(N)=O)c3[nH]c(C)c(Cl)c23)C1] | (400 MHz, DMSO-$d_6$) δ 11.48-11.33 (m, 1H), 8.11 (s, 1H), 7.65-7.47 (m, 2H), 4.63-4.43 (m, 1H), 4.46-4.29 (m, 2H), 4.22-3.93 (m, 1H), 3.71-3.57 (m, 0.5H), 3.31-3.12 (m, 1H), 2.83-2.71 (m, 0.5H), 2.44-2.37 (m, 3H), 2.17-1.78 (m, 3H), 1.64-1.36 (m, 1H). | 362.00, 364.00 |
| 8 | 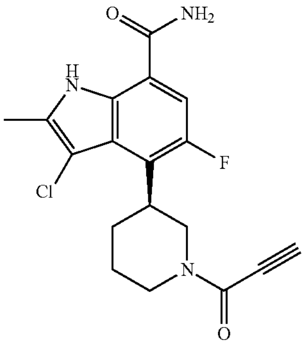 [SMILES: C#CC(=O)N1CCC[C@@H](c2c(F)cc(C(N)=O)c3[nH]c(C)c(Cl)c23)C1] | (400 MHz, DMSO-$d_6$) δ 11.50-11.35 (m, 1H), 8.11 (s, 1H), 7.62-7.50 (m, 2H), 4.63-4.46 (m, 1H), 4.47-4.29 (m, 2H), 4.23-3.92 (m, 1H), 3.69-3.55 (m, 0.5H), 3.30-3.11 (m, 1H), 2.82-2.69 (m, 0.5H), 2.43-2.37 (m, 3H), 2.17-1.74 (m, 3H), 1.64-1.36 (m, 1H). | 362.30, 364.30 |
| 9 | 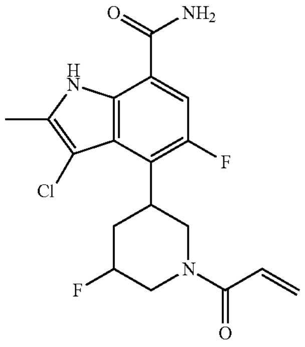 [SMILES: C=CC(=O)N1CC(F)CC(c2c(F)cc(C(N)=O)c3[nH]c(C)c(Cl)c23)C1] | (300 MHz, DMSO-$d_6$) δ 11.44 (s, 1H), 8.13 (s, 1H), 7.79-740 (m, 2H), 7.12-6.73 (m, 1H), 6.32-5.99 (m, 1H), 5.87-5.48 (m, 1H), 4.90-4.38 (m, 2.5H), 4.27-3.99 (m, 1.5H), 3.62-3.42 (m, 0.5H), 3.29-3.02 (m, 1H), 2.95-2.77 (m, 0.5H), 2.47-2.35 (m, 4H), 2.35-2.07 (m, 1H). | 382.30 |
| 10 | 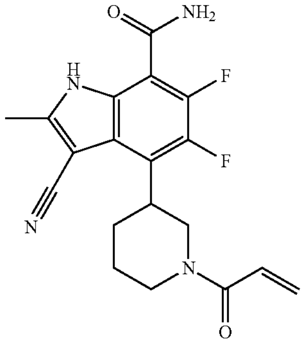 [SMILES: C=CC(=O)N1CCCC(c2c(F)c(F)c(C(N)=O)c3[nH]c(C)c(C#N)c23)C1] | (300 MHz, DMSO-$d_6$) δ 12.18 (s, 1H), 8.11-7.94 (m, 2H), 6.95-6.75 (m, 1H), 6.19-6.03 (m, 1H), 5.75-5.59 (m, 1H), 4.59 (t, J = 9.0 Hz, 1H), 4.33-4.04 (m, 1H), 3.70-3.49 (m, 1.5H), 3.27-3.09 (m, 1H), 2.80-2.65 (m, 0.5H), 2.55 (s, 3H), 2.02 (s, 2H), 1.93-1.78 (m, 1H), 1.52 (s, 1H). | 373.10 |

TABLE 5-continued
| COMPOUNDS 7-19 | | | |
|---|---|---|---|
| Cmpd. No. | Structure | $^1$HNMR | LC-MS: m/z (M + H) |
| 11 | 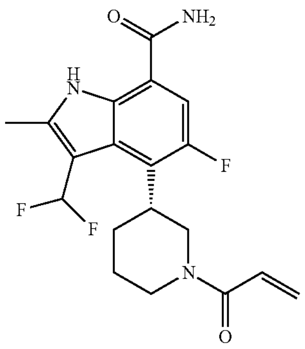 [SMILES: C=CC(=O)N1CCC[C@H](c2c(F)cc(C(N)=O)c3[nH]c(C)c(C(F)F)c23)C1] | (300 MHz, DMSO-$d_6$) δ 11.28 (s, 1H), 8.21 (s, 1H), 7.91 (s, 1H), 7.27-6.69 (m, 1), 6.97-6.68 (m, 1H), 6.51 (s, 1H), 6.11 (t, J = 14.4 Hz, 1H), 5.82-5.53 (m, 1H), 4.65-4.37 (m, 1H), 4.25-3.91 (m, 1H), 3.63 (t, J = 12.3 Hz, 0.5H), 3.27-3.05 (m, 2H), 2.76 (t, J = 12.0 Hz, 0.5H), 2.41 (s, 3H), 2.29-2.04 (m, 1H), 1.95-1.74 (m, 2H), 1.65-1.42 (m, 1H). | 379.15 |
| 12 | 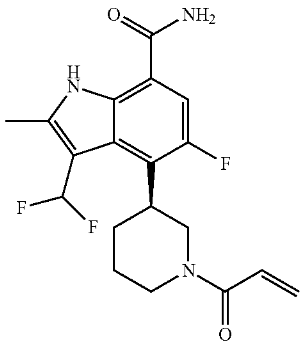 [SMILES: C=CC(=O)N1CCC[C@@H](c2c(F)cc(C(N)=O)c3[nH]c(C)c(C(F)F)c23)C1] | (300 MHz, DMSO-$d_6$) δ 11.28 (s, 1H), 8.21 (s, 1H), 7.91 (s, 1H), 7.25-6.98 (m, 1H), 6.97-6.67 (m, 1H), 6.51 (s, 1H), 6.11 (t, J = 14.7 Hz, 1H), 5.80-5.55 (m, 1H), 4.68-4.36 (m, 1H), 4.28-3.97 (m, 1H), 3.63 (t, J = 12.0 Hz, 0.5H), 3.28-3.00 (m, 2H), 2.76 (t, J = 12.0 Hz, 0.5H), 2.41 (s, 3H), 2.30-2.06 (m, 1H), 1.94-1.74 (m, 2H), 1.64-1.42 (m, 1H). | 379.15 |
| 13 | 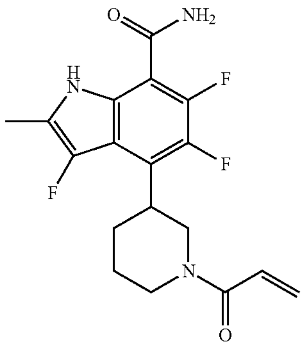 [SMILES: C=CC(=O)N1CCCC(c2c(F)c(F)c(C(N)=O)c3[nH]c(C)c(F)c23)C1] | (400 MHz, DMSO-$d_6$) δ 10.96 (s, 1H), 8.02-7.73 (m, 2H), 6.96-6.71 (m, 1H), 6.19-6.03 (m, 1H), 5.78-5.52 (m, 1H), 4.54 (t, J = 12.4 Hz, 1H), 4.15 (d, J = 13.2 Hz, 1H), 3.49 (t, J = 12.4 Hz, 0.5H), 3.16-2.97 (m, 1H), 2.64 (t, J = 13.4 Hz, 0.5H), 2.31 (s, 3H), 2.12-1.97 (m, 1H), 1.96-1.87 (m, 1H), 1.86-1.76 (m, 1H), 1.56-1.36 (m, 1H). | 366.15 |
| 14 | 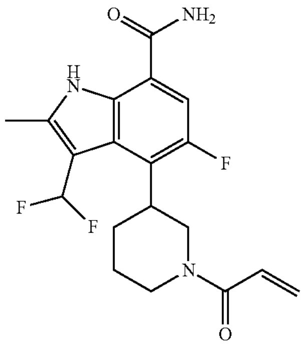 [SMILES: C=CC(=O)N1CCCC(c2c(F)cc(C(N)=O)c3[nH]c(C)c(C(F)F)c23)C1] | (300 MHz, DMSO-$d_6$) δ 11.28 (s, 1H), 8.21 (s, 1H), 7.91 (s, 1H), 7.19-6.69 (m, 2H), 6.51 (s, 1H), 6.20-6.03 (m, 1H) 5.80-5.52 (m, 1H), 4.69-4.37 (m, 1H), 4.22-3.96 (m, 1H), 3.63 (t, J = 12.0 Hz, 0.5H), 3.27-3.05 (m, 2H), 2.76 (t, J = 12.0 Hz, 1H, 0.5H), 2.41 (s, 3H), 2.24-2.08 (m, 1H), 1.94-1.74 (m, 2H), 1.62-1.45 (m, 1H). | 380.15 |

TABLE 5-continued
| COMPOUNDS 7-19 | | | |
|---|---|---|---|
| Cmpd. No. | Structure | $^1$HNMR | LC-MS: m/z (M + H) |
| 15 | 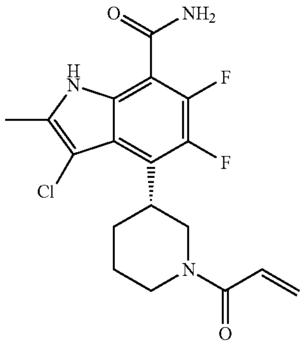 [SMILES: C=CC(=O)N1CCC[C@H](c2c(F)c(F)c(C(N)=O)c3[nH]c(C)c(Cl)c23)C1] | (400 MHz, DMSO-$d_6$) δ 11.45 (s, 1H), 8.06-7.71 (m, 2H), 6.99-6.65 (m, 1H), 6.18-5.96 (m, 1H), 5.74-5.57 (m, 1H), 4.71-4.46 (m, 1H), 4.31-3.96 (m, 2H), 3.52 (t, J = 11.4 Hz, 0.5H) 3.13 (t, J = 12.4 Hz, 1H), 2.69 (t, J = 12.4 Hz, 0.5H), 2.35 (s, 3H), 2.16-1.89 (m, 2H), 1.88-1.75 (m, 1H), 1.62-1.38 (m, 1H). | 382.10, 384.10 |
| 16 | 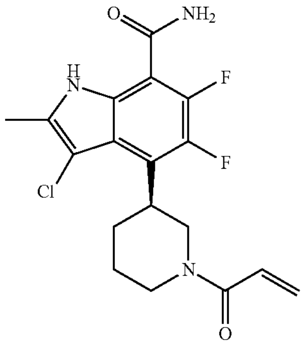 [SMILES: C=CC(=O)N1CCC[C@@H](c2c(F)c(F)c(C(N)=O)c3[nH]c(C)c(Cl)c23)C1] | (400 MHz, DMSO-$d_6$) δ 11.45 (s, 1H), 8.07-7.74 (m, 2H), 6.96-6.73 (m, 1H), 6.21-6.01 (m, 1H), 5.77-5.58 (m, 1H), 4.70-4.48 (m, 1H), 4.30-3.96 (m, 2H), 3.53 (t, J = 11.5 Hz, 0.5H), 3.13 (t, J = 12.4 Hz, 1H), 2.69 (t, J = 12.4 Hz, 0.5H), 2.35 (s, 3H), 2.14-1.91 (m, 2H), 1.90-1.76 (m, 1H), 1.59-1.35 (m, 1H). | 382.05, 384.05 |
| 17 | 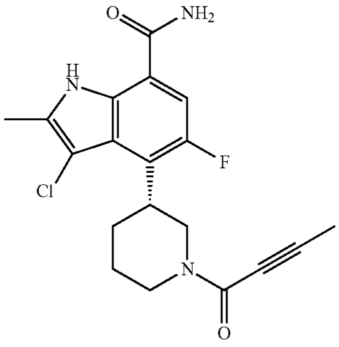 [SMILES: CC#CC(=O)N1CCC[C@H](c2c(F)cc(C(N)=O)c3[nH]c(C)c(Cl)c23)C1] | (300 MHz, DMSO-$d_6$) δ 11.41 (d, J = 6.3 Hz, 1H), 8.11 (s, 1H), 7.69-7.41 (m, 2H), 4.54-4.25 (m, 2H), 4.19-3.84 (m, 1H), 3.67-3.47 (m, 0.5H), 3.26-3.00 (m, 1H), 2.71 (t, J = 12.6 Hz, 0.5H), 2.39 (d, J = 3.9 Hz, 3H), 2.13-1.76 (m, 6H), 1.63-1.27 (m, 1H). | 376.10, 378.10 |
| 18 | 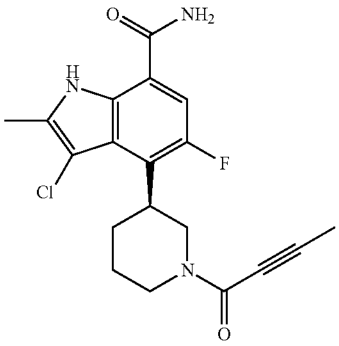 [SMILES: CC#CC(=O)N1CCC[C@@H](c2c(F)cc(C(N)=O)c3[nH]c(C)c(Cl)c23)C1] | (300 MHz, DMSO-$d_6$) δ 11.41 (d, J = 6.3 Hz, 1H), 8.11 (s, 1H), 7.66-7.46 (m, 2H), 4.54-4.29 (m, 2H), 4.26-3.88 (m, 1H), 3.59 (t, J = 11.4 Hz, 1H, 0.5H), 3.30-3.01 (m, 1H), 2.71 (t, J = 10.8 Hz, 0.5H), 2.40 (d, J = 3.9 Hz, 3H), 2.14-1.74 (m, 6H), 1.65-1.33 (m, 1H). | 376.10, 378.10 |

TABLE 5-continued

| COMPOUNDS 7-19 | | | |
|---|---|---|---|
| Cmpd. No. | Structure | $^1$HNMR | LC-MS: m/z (M + H) |
| 19 | 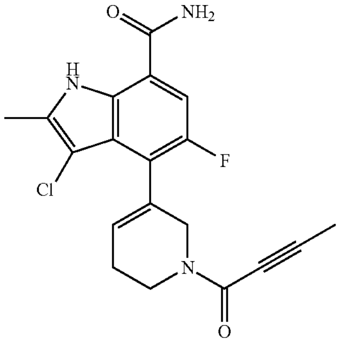 [SMILES: CC#CC(=O)N1CCC=C(c2c(F)cc(C(N)=O)c3[nH]c(C)c(Cl)c23)C1] | (400 MHz, DMSO-$d_6$) δ 11.47-11.30 (m, 1H), 8.11 (s, 1H), 7.70-7.42 (m, 2H), 5.89-5.71 (m, 1H), 4.36 (s, 1H), 4.13 (s, 1H), 3.89 (s, 1H), 3.69 (t, J = 6.0 Hz, 1H), 2.40-2.15 (m, 5H), 2.07 (s, 2H), 1.96 (s, 1H). | 374.10, 376.10 |

Preparation of Compounds of Formula (II)

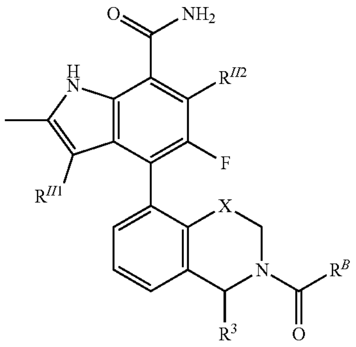

Preparation of Compounds of Formula (II) Wherein X is $CH_2$, $R^3$ is H and $R^{II2}$ is H

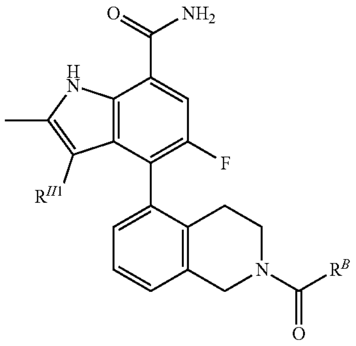

Example 20

Synthesis of 4-(2-acryloyl-1,2,3,4-tetrahydroisoquinolin-5-yl)-3-chloro-5-fluoro-2-methyl-1H-indole-7-carboxamide (Compound 20a)

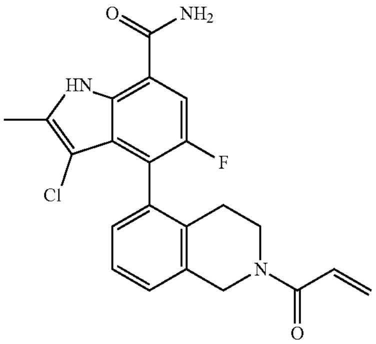 [SMILES: C=CC(=O)N1CCc2c(cccc2-c2c(F)cc(C(N)=O)c3[nH]c(C)c(Cl)c23)C1]

Step 1: tert-butyl 5-(7-carbamoyl-5-fluoro-2-methyl-1H-indol-4-yl)-3,4-dihydroisoquinoline-2 (1H)-carboxylate

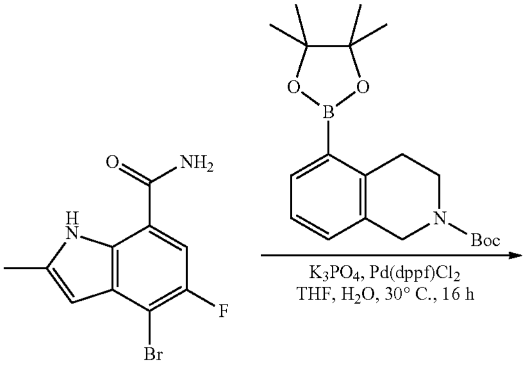

-continued

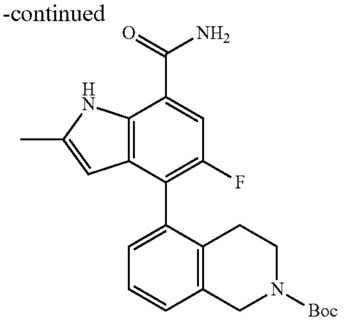

A mixture of 4-bromo-5-fluoro-2-methyl-1H-indole-7-carboxamide (2.0 g, 7.38 mmol), tert-butyl-5-(4,4,5,5-tetramethyl-1,3,2-dioxaborolan-2-yl)-3,4-dihydroisoquinoline-2(1H)-carboxylate (2.70 g, 7.38 mmol), potassium phosphate (4.70 g, 22.1 mmol) and Pd(dppf)Cl2 (540 mg, 0.738 mmol) in tetrahydrofuran (16 mL) and water (4.0 mL) was degassed and backfilled with nitrogen. The reaction mixture was stirred under nitrogen at 30° C. for 16 h and then diluted with water (50 mL) and extracted with ethyl acetate (3×50 mL). The combined extracts were washed with brine (50 mL), dried over sodium sulfate, and concentrated under vacuum. The residue was purified by column chromatography on silica gel (45% ethyl acetate in petroleum ether) to afford tert-butyl 5-(7-carbamoyl-5-fluoro-2-methyl-1H-indol-4-yl)-3,4-dihydroisoquinoline-2(1H)-carboxylate (2.50 g, 80%) as a yellow solid.

$^1$H NMR (300 MHz, DMSO-d6) δ 11.03 (s, 1H), 8.10 (s, 1H), 7.60-7.47 (m, 2H), 7.32-7.23 (m, 2H), 7.16-7.13 (m, 1H), 5.71 (s, 1H), 4.64-4.49 (m, 2H), 3.55-3.43 (m, 2H), 2.39-2.30 (m, 5H), 1.05 (s, 9H).

ESI-MS [M+H]+ calcd for ($C_{24}H_{26}FN_3O_3$) 424.20, found: 424.15.

Step 2: tert-butyl 5-(7-carbamoyl-3-chloro-5-fluoro-2-methyl-1H-indol-4-yl)-3,4-dihydroisoquinoline-2(1H)-carboxylate

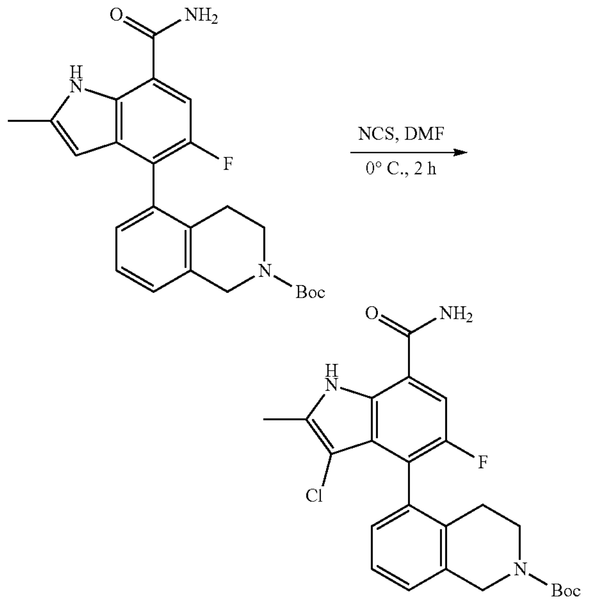

To a solution of tert-butyl 5-(7-carbamoyl-5-fluoro-2-methyl-1H-indol-4-yl)-3,4-dihydro-isoquinoline-2(1H)-carboxylate (3.0 g, 7.08 mmol) in N,N-dimethylformamide (30.0 mL) was added N-chlorosuccinimide (1.00 g, 7.79 mmol) at 0° C. The reaction mixture was stirred at 0° C. for 2 h. The reaction mixture was quenched with water (80 mL) and extracted with ethyl acetate (3×60 mL). The combined extracts were washed with brine (60 mL), dried over sodium sulfate, and concentrated under vacuum. The residue was purified by column chromatography on silica gel (45% ethyl acetate in petroleum ether) to afford tert-butyl 5-(7-carbamoyl-3-chloro-5-fluoro-2-methyl-1H-indol-4-yl)-3,4-dihydroisoquinoline-2(1H)-carboxylate (2.30 g, 71%) as a yellow solid.

$^1$H NMR (400 MHz, DMSO-d6) δ 11.42 (s, 1H), 8.16 (s, 1H), 7.70-7.56 (m, 2H), 7.28-7.20 (m, 2H), 7.09-7.06 (m, 1H), 4.56 (s, 2H), 3.49-3.34 (m, 2H), 2.40-2.22 (m, 5H), 1.38 (s, 9H).

ESI-MS [M+H-Boc]+ calcd for ($C_{24}H_{25}ClFN_3O_3$) 358.16, 360.16; found: 358.05, 360.05.

Step 3: 3-chloro-5-fluoro-2-methyl-4-(1,2,3,4-tetrahydroisoquinolin-5-yl)-1H-indole-7-carboxamide

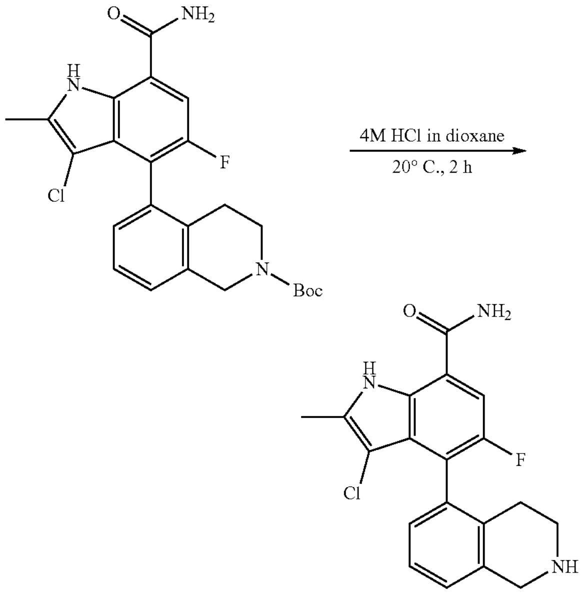

A mixture of tert-butyl 5-(7-carbamoyl-3-chloro-5-fluoro-2-methyl-1H-indol-4-yl)-3,4-dihydroisoquinoline-2(1H)-carboxylate (2.30 g, 5.02 mmol) and 4.0 M hydrogen chloride in dioxane (20 mL) was stirred at 20° C. for 2 h. The reaction mixture was concentrated under vacuum. The residue diluted with saturated aqueous sodium bicarbonate (150 mL) and extracted with ethyl acetate (3×100 mL). The combined extracts were dried over sodium sulfate and concentrated under vacuum to afford 3-chloro-5-fluoro-2-methyl-4-(1,2,3,4-tetrahydroisoquinolin-5-yl)-1H-indole-7-carboxamide (1.70 g) as a brown solid.

ESI-MS [M+H]+ calcd for ($C_{19}H_{17}ClFN_3O$) 358.16, 360.16; found: 358.10, 360.10.

Step 4: 4-(2-acryloyl-1,2,3,4-tetrahydroisoquinolin-5-yl)-3-chloro-5-fluoro-2-methyl-1H-indole-7-carboxamide (Compound 20a)

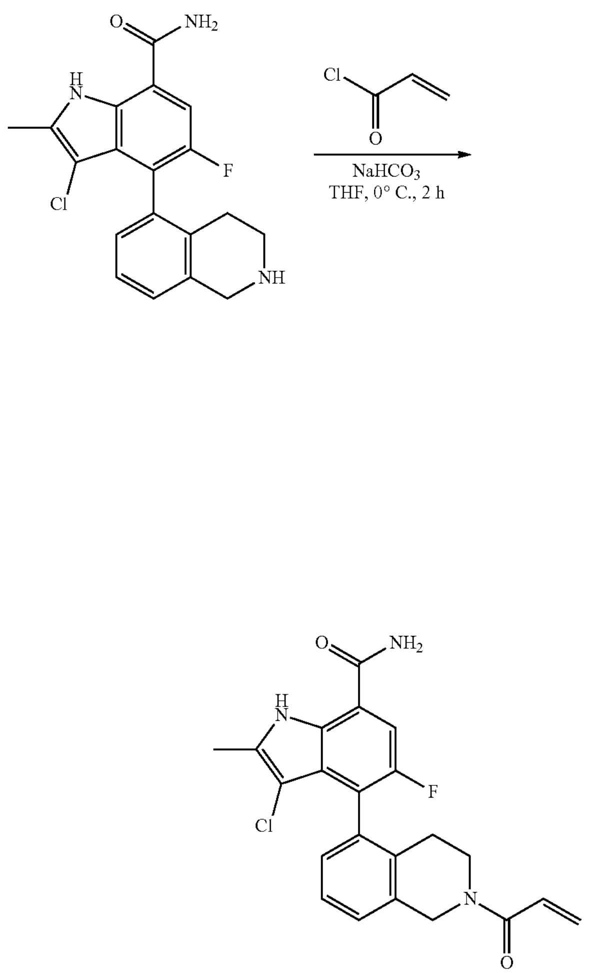

To a mixture of 3-chloro-5-fluoro-2-methyl-4-(1,2,3,4-tetrahydroisoquinolin-5-yl)-1H-indole-7-carboxamide (1.70 g, 4.75 mmol) in tetrahydrofuran (16 mL) and water (4.0 mL) were added sodium bicarbonate (1.20 g, 14.3 mmol) and acryloyl chloride (430 mg, 4.75 mmol) at 0° C. The reaction mixture was stirred at 0° C. for 2 h. The reaction mixture was diluted with water (50 mL) and extracted with ethyl acetate (3x50 mL). The combined extracts were washed with brine (50 mL), dried over sodium sulfate, and concentrated under vacuum. The residue was purified by column chromatography on silica gel (75% ethyl acetate in petroleum ether) to afford 4-(2-acryloyl-1,2,3,4-tetrahydroisoquinolin-5-yl)-3-chloro-5-fluoro-2-methyl-1H-indole-7-carboxamide (1.20 g, 51%) as a white solid.

$^1$H NMR (300 MHz, DMSO-d6) δ 11.45 (s, 1H), 8.19 (s, 1H), 7.73-7.56 (m, 2H), 7.38-7.22 (m, 2H), 7.17-7.08 (m, 1H), 6.98-6.75 (m, 1H), 6.17-6.11 (m, 1H), 5.78-5.62 (m, 1H), 4.87 (s, 0.8H), 4.76 (s, 1.2H), 3.77-3.56 (m, 2H), 2.43-2.35 (m, 5H).

ESI-MS [M+H]+ calcd for ($C_{22}H_{19}ClFN_3O_2$) 412.11, 414.11; found: 412.05, 414.05.

Step 5: Separation of Isomers (R)-4-(2-acryloyl-1,2,3,4-tetrahydroisoquinolin-5-yl)-3-chloro-5-fluoro-2-methyl-1H-indole-7-carboxamide (Compound 20b) and (S)-4-(2-acryloyl-1,2,3,4-tetrahydroisoquinolin-5-yl)-3-chloro-5-fluoro-2-methyl-1H-indole-7-carboxamide (Compound 20c)

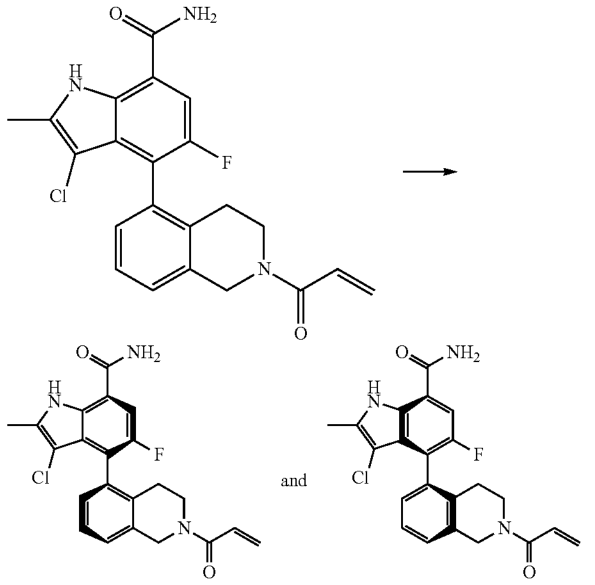

and

Compound 20b (R)

Compound 20c (S)

The two atropisomers were separated by Prep-Chiral-HPLC (sample amount=1.2 g, column: CHIRALPAK IC (2x25 cm, 5 um); mobile phase A: hexane (0.5% 2 M $NH_3$-MeOH), mobile phase B: EtOH; flow rate: 20 mL/min; gradient: 30% B, isocratic, 16 min; 220/254 nm).

Compound 20b: Retention Time=9.807 Minutes (530 mg)

1H NMR (400 MHz, DMSO-d6) δ 11.45 (s, 1H), 8.19 (s, 1H), 7.67-7.63 (m, 2H), 7.32-7.25 (m, 2H), 7.13-7.11 (m, 1H), 6.98-6.75 (m, 1H), 6.17-6.11 (m, 1H), 5.75-5.65 (m, 1H), 4.87 (s, 0.8H), 4.76 (s, 1.2H), 3.78-3.59 (m, 2H), 2.41-2.35 (m, 5H).

ESI-MS [M+H]+ calcd for ($C_{22}H_{19}ClFN_3O_2$) 412.11, 414.11; found: 412.10, 414.10.

Compound 20c: Retention Time=12.634 Minutes (515 mg)

1H NMR (400 MHz, DMSO-d6) δ 11.45 (s, 1H), 8.19 (s, 1H), 7.68-7.64 (m, 2H), 7.30-7.25 (m, 2H), 7.13-7.11 (m, 1H), 6.94-6.75 (m, 1H), 6.17-6.11 (m, 1H), 5.75-5.65 (m, 1H), 4.87 (s, 0.8H), 4.76 (s, 1.2H), 3.76-3.59 (m, 2H), 2.41-2.35 (m, 5H).

ESI-MS [M+H]+ calcd for ($C_{22}H_{19}ClFN_3O_2$) 412.11, 414.11; found: 412.10, 414.10.

Compounds 20d-20i

Compounds 20d-20i listed below were prepared according to similar methods as described in the preceding schemes and examples by employing correspondingly appropriate starting materials (NA=not available).

TABLE 6
| COMPOUNDS 20d-20i | | | |
|---|---|---|---|
| Cmpd. No. | Structure | $^1$H NMR | ESI-MS: m/z [M + H]+ |
| 20d | 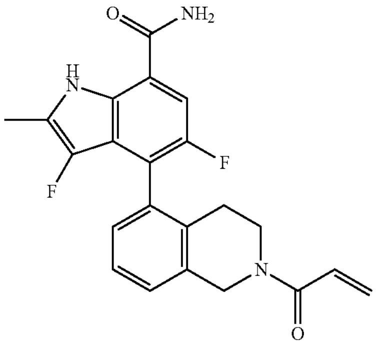 [SMILES: C=CC(=O)N1CCc2c(cccc2-c2c(F)cc(C(N)=O)c3[nH]c(C)c(F)c23)C1] | NA | 396.10 |
| 20e | 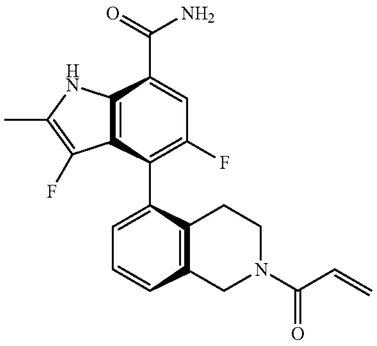 | (400 MHz, DMSO-$d_6$) δ 10.93 (s, 1H), 8.15 (s, 1H), 7.64-7.58 (m, 2H), 7.31-7.19 (m, 3H), 6.97-6.80 (m, 1H), 6.17-6.12 (m, 1H), 5.75-5.67 (m, 1H), 4.87-4.71 (m, 2H), 3.76-3.57 (m, 2H), 2.54-2.47 (m, 2H), 2.33 (s, 3H) | 396.10 |
| 20f | 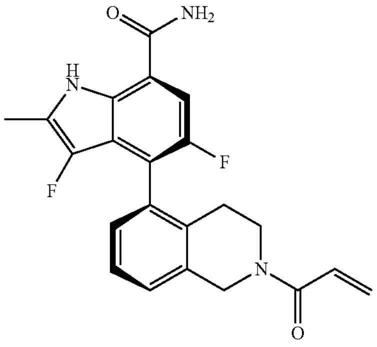 | (400 MHz, DMSO-$d_6$) δ 10.93 (s, 1H), 8.16 (s, 1H), 7.64-7.58 (m, 2H), 7.31-7.19 (m, 3H), 6.97-6.80 (m, 1H), 6.17-6.12 (m, 1H), 5.75-5.67 (m, 1H), 4.87-4.71 (m, 2H), 3.76-3.55 (m, 2H), 2.54-2.46 (m, 2H), 2.32 (s, 3H) | 396.10 |
| 20g | 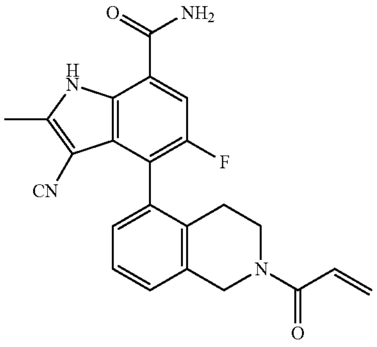 | (300 MHz, DMSO-$d_6$) δ 12.14 (s, 1H), 8.28 (s, 1H), 7.83-7.69 (m, 2H), 7.41-7.25 (m, 2H), 7.22-7.12 (m, 1H), 6.97-6.75 (m, 1H), 6.15 (dd, J = 16.5, 2.1 Hz, 1H), 5.75-5.60 (m, 1H), 4.96-4.61 (m, 2H), 3.83-3.51 (m, 2H), 2.54 (s, 3H), 2.46-2.27 (m, 2H). | 403.15 |

TABLE 6-continued

COMPOUNDS 20d-20i

| Cmpd. No. | Structure | $^1$H NMR | ESI-MS: m/z [M + H]+ |
|---|---|---|---|
| 20h | 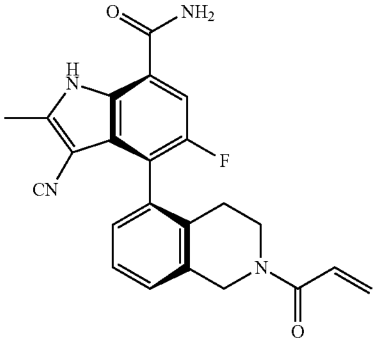 | (300 MHz, DMSO-$d_6$) δ 12.14 (s, 1H), 8.28 (s, 1H), 7.86-7.70 (m, 2H), 7.40-7.26 (m, 2H), 7.18-7.11 (m, 1H), 6.97-6.75 (m, 1H), 6.15 (dd, J = 16.5, 2.4 Hz, 1H), 5.80-5.64 (m, 1H), 4.96-4.60 (m, 2H), 3.84-3.51 (m, 2H), 2.53 (s, 3H), 2.47-2.30 (m, 2H). | 403.15, 405.15 |
| 20i | 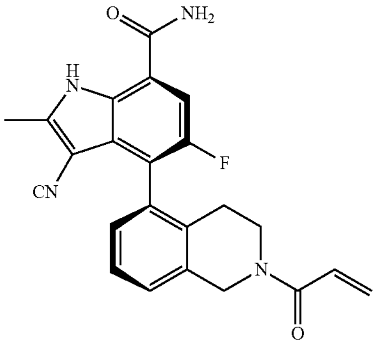 | (300 MHz, DMSO-$d_6$) δ 12.14 (s, 1H), 8.28 (s, 1H), 7.85-7.70 (m, 2H), 7.37-7.26 (m, 2H), 7.22-7.11 (m, 1H), 6.97-6.75 (m, 1H), 6.15 (dd, J = 16.5, 2.4 Hz, 1H), 5.79-5.63 (m, 1H), 4.97-4.62 (m, 2H), 3.83-3.53 (m, 2H), 2.53 (s, 3H), 2.46-2.38 (m, 2H). | 403.10, 405.10 |

Compound 20j: 5-fluoro-2,3-dimethyl-4-(2-propioloyl-1,2,3,4-tetrahydroisoquinolin-5-yl)-1H-indole-7-carboxamide

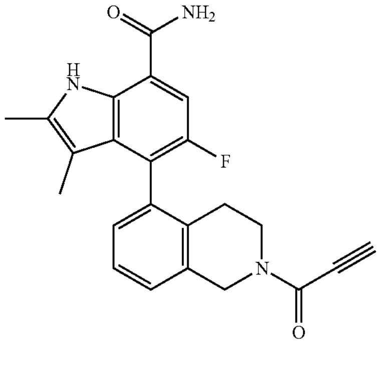 [SMILES: C#CC(=O)N1CCc2c(cccc2-c2c(F)cc(C(N)=O)c3[nH]c(C)c(C)c23)C1]

Compound 1j was prepared according to similar procedures and using propioloyl chloride in place of acryloyl chloride.

$^1$H NMR (400 MHz, DMSO-$d_6$) δ 10.84 (s, 1H), 8.08 (s, 1H), 7.60-7.45 (m, 2H), 7.38-7.28 (m, 2H), 7.17-7.10 (m, 1H), 4.97 (s, 1H), 4.81-4.70 (m, 1H), 4.68-4.50 (m, 1H), 4.00-3.51 (m, 2H), 2.47-2.32 (m, 2H), 2.29 (s, 3H), 1.46-1.35 (m, 3H).

ESI-MS [M+H]+ m/z=390.15

Preparation of Compounds of Formula (II) Wherein X is $CH_2$, $R^3$ is H and $R^{II2}$ is F

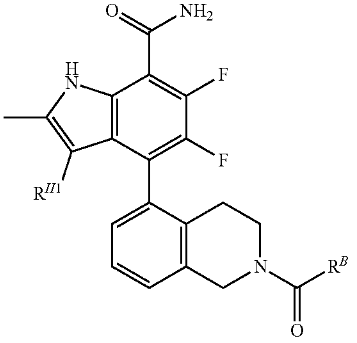

Example 21

Preparation of 4-(2-acryloyl-1,2,3,4-tetrahydroisoquinolin-5-yl)-3-chloro-5,6-difluoro-2-methyl-1H-indole-7-carboxamide (Compound 21a)

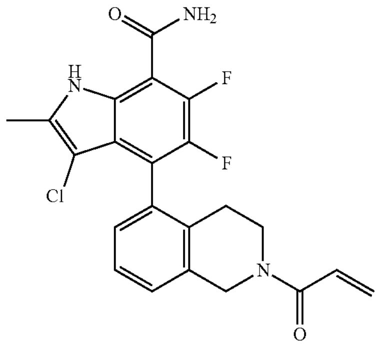 [SMILES: C=CC(=O)N1CCc2c(cccc2-c2c(F)c(F)c(C(N)=O)c3[nH]c(C)c(Cl)c23)C1]

Step 1: 1,4-dibromo-2,3-difluoro-5-nitrobenzene

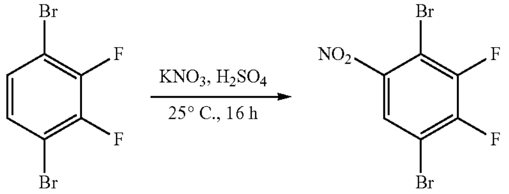

To a solution of 1,4-dibromo-2,3-difluorobenzene (25.0 g, 91.95 mmol) in concentrated sulfuric acid (200 mL) was added potassium nitrate (11.0 g, 108.8 mmol) at 0° C. The reaction mixture was stirred at 25° C. for 16 h. The reaction mixture was poured into ice-water (1 L) and stirred at 0° C. for 30 min. The resulting precipitation was filtered, the filter cake was washed with water and dried under reduced pressure to afford 1,4-dibromo-2,3-difluoro-5-nitro-benzene (27.0 g, 92%) as a yellow solid.

$^1$H NMR (300 MHz, DMSO-$d_6$) δ 8.47 (dd, J=6.0, 2.4 Hz 1H).

Step 2: 2,5-dibromo-3,4-difluoroaniline

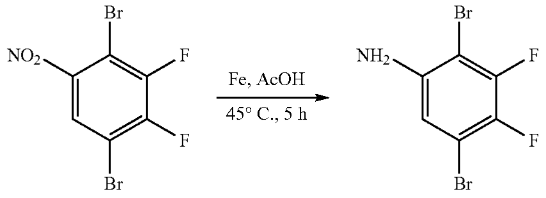

To a solution of 1,4-dibromo-2,3-difluoro-5-nitrobenzene (27.0 g, 85.21 mmol) in acetic acid (260 mL) was added iron powder (47.6 g, 852.0 mmol). The reaction mixture was stirred at 45° C. for 5 h. The cooled reaction mixture was filtered. The filtrate was poured into ice-water (500 mL) and filtered. The filter cake was washed with water (300 mL) and dried under reduced pressure to afford 2,5-dibromo-3,4-difluoroaniline (23.0 g, 94% yield) as a yellow solid.

$^1$H NMR (300 MHz, DMSO-$d_6$) δ 6.88 (dd, J=6.0, 2.4 Hz 1H), 5.74 (brs, 2H).

Step 3: 2,5-dibromo-3,4-difluoro-6-iodoaniline

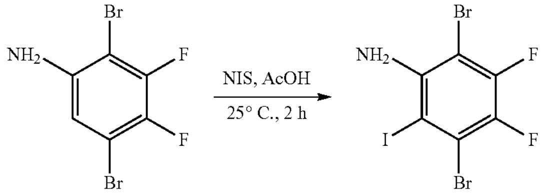

To a solution of 2,5-dibromo-3,4-difluoroaniline (23.0 g, 80.17 mmol) in acetic acid (250 mL) was added N-iodosuccinimide (19.84 g, 88.18 mmol). The reaction mixture was stirred at 25° C. for 2 h. The reaction mixture was poured into ice-water (500 mL) and filtered. The filter cake was washed with water (100 mL) and dried under reduced pressure. The crude product was purified by column chromatography on silica gel eluting with ethyl acetate in petroleum ether (0 to 5%) to give 2,5-dibromo-3,4-difluoro-6-iodoaniline (30.0 g, 90%) as an off-white solid.

$^1$H NMR (300 MHz, DMSO-$d_6$) δ 5.63 (s, 2H).

ESI-MS [M−H]$^-$ calcd for ($C_6H_2Br_2F_2IN$) 409.76, 411.75, 413.75 found: 409.75, 411.75, 413.70.

Step 4: 2,5-dibromo-3,4-difluoro-6-(prop-1-yn-1-yl) aniline

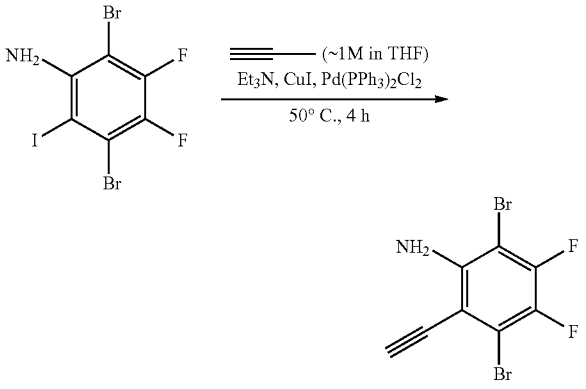

To a mixture of 2,5-dibromo-3,4-difluoro-6-iodoaniline (30.0 g, 72.68 mmol), copper(I) iodide (2.77 g, 14.54 mmol) and $Pd(PPh_3)_2Cl_2$ (5.12 g, 7.27 mmol) in triethylamine (365 mL) was added prop-1-yne (1M in THF, 364 mL) under nitrogen. The reaction mixture was stirred in a sealed flask at 50° C. for 4 h. The cooled reaction mixture was quenched with water (300 ml) and extracted with ethyl acetate (300 ml×3). The combined organic layers were dried over anhydrous sodium sulfate, filtered and concentrated under vacuum. The residue was purified by column chromatography onto silica gel eluting with ethyl acetate in petroleum ether (0 to 10%) to give 2,5-dibromo-3,4-difluoro-6-(prop-1-yn-1-yl)aniline (20.0 g, 84%) as a yellow solid.

$^1$H NMR (300 MHz, DMSO-$d_6$) δ 5.79 (s, 2H), 2.18 (s, 3H).

ESI-MS [M−H]$^+$ calcd for ($C_9H_5Br_2F_2N$) 321.88, 323.87, 325.87 found: 322.00, 324.00, 326.00.

Step 5: 4,7-dibromo-5,6-difluoro-2-methyl-1H-indole

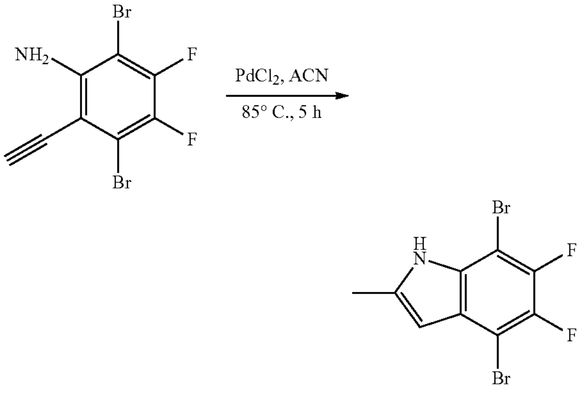

A mixture of 2,5-dibromo-3,4-difluoro-6-(prop-1-yn-1-yl)aniline (20.0 g, 61.55 mmol) and $PdCl_2$ (1.09 g, 6.15 mmol) in acetonitrile (400 mL) was degassed and backfilled with nitrogen for three times and stirred at 85° C. for 5 h. The cooled reaction mixture was concentrated under vacuum. The residue was purified by column chromatography on silica gel eluting with ethyl acetate in petroleum ether (0 to 10%) to afford 4,7-dibromo-5,6-difluoro-2-methyl-1H-indole (17.0 g, 85%) as a yellow solid.

$^1$H NMR (300 MHz, DMSO-$d_6$) δ 11.75 (s, 1H), 6.28 (s, 1H), 2.41 (s, 3H).

ESI-MS $[M-H]^-$ calcd for ($C_9H_5Br_2F_2N$) 321.88, 323.87, 325.87 found: 321.80, 323.80, 325.80.

Step 6: 4,7-dibromo-5,6-difluoro-2-methyl-1-((2-(trimethylsilyl)ethoxy)methyl)-1H-indole

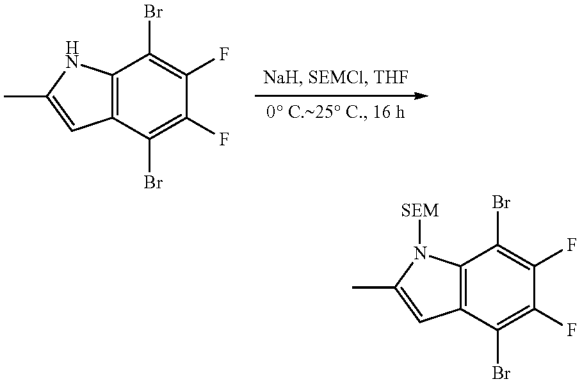

To a stirred solution of 4,7-dibromo-5,6-difluoro-2-methyl-1H-indole (10.0 g, 30.77 mmol) in THE (200 mL) was added sodium hydride (1.60 g, 40.01 mmol, 60%) at 0° C. After stirring at this temperature for 1 h, 2-(trimethylsilyl) ethoxymethyl chloride (7.70 g, 46.16 mmol) was added at 0° C. The reaction mixture was stirred at 25° C. for 16 h. The reaction mixture was quenched with water (200 mL) and extracted with ethyl acetate (150 mL×3). The combined organic layers were washed with brine (100 mL), dried over anhydrous sodium sulfate and concentrated under vacuum. The residue was purified by column chromatography on silica gel eluting with ethyl acetate in petroleum ether (0 to 10%) to afford 4,7-dibromo-5,6-difluoro-2-methyl-1-((2-(trimethylsilyl)ethoxy)methyl)-1H-indole (12.3 g, 87%) as a yellow oil.

$^1$H NMR (300 MHz, DMSO-$d_6$) δ 6.42 (s, 1H), 5.78 (s, 2H), 3.55 (t, J=7.8 Hz, 2H), 2.47 (s, 3H), 0.83 (t, J=8.1 Hz, 2H), −0.08 (s, 9H).

Step 7: 4-bromo-5,6-difluoro-2-methyl-1-((2-(trimethylsilyl)ethoxy)methyl)-1H-indole-7-carboxylic acid

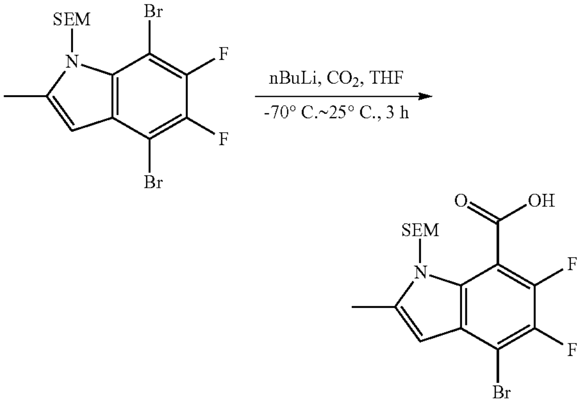

To a solution of 4,7-dibromo-5,6-difluoro-2-methyl-1-((2-(trimethylsilyl)ethoxy)methyl)-1H-indole (12.3 g, 27.03 mmol) in THF (130 mL) was added n-butyllithium (2.5 M in n-hexane, 13 mL, 32.5 mmol) under nitrogen at −70° C. After stirring at this temperature for 0.5 h and 0° C. 0.5 h, the reaction mixture was cooled to −70° C. and bubbled with carbon dioxide for 30 min. After stirring at 25° C. for 1.5 h, the reaction mixture was quenched with saturated aqueous ammonium chloride (100 mL) and extracted with dichloromethane (100 mL×3). The combined organic layers was washed with brine (100 mL), dried over anhydrous sodium sulfate and concentrated under vacuum to afford 4-bromo-5,6-difluoro-2-methyl-1-((2-(trimethylsilyl)ethoxy)methyl)-1H-indole-7-carboxylic acid (11.4 g, crude) as a yellow oil.

ESI-MS $[M-H]^-$ calcd for ($C_{16}H_{20}BrF_2NO_3Si$) 418.04, 420.03 found: 417.95, 419.95.

Step 8: 4-bromo-5,6-difluoro-2-methyl-1-((2-(trimethylsilyl)ethoxy)methyl)-1H-indole-7-carboxamide

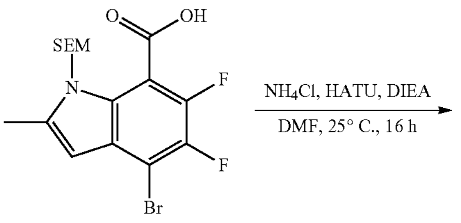

-continued

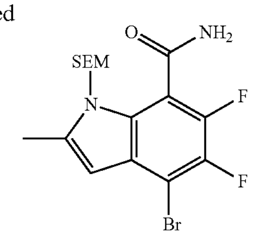

To a stirred mixture of 4-bromo-5,6-difluoro-2-methyl-1-(2-trimethylsilylethoxy methyl)indole-7-carboxylic acid (11.4 g, 27.12 mmol) and ammonium chloride (2.18 g, 40.68 mmol) in DMF (100 mL) were added HATU (12.38 g, 32.55 mmol) and DIPEA (17.53 g, 135.61 mmol) at 0° C. After stirring at 25° C. for 16 h, the reaction mixture was quenched with water (300 ml) and extracted with ethyl acetate (300 ml×3). The combined organic layers were washed with brine (200 ml×3), dried over anhydrous sodium sulfate and concentrated under vacuum. The residue was purified by column chromatography on silica gel eluting with ethyl acetate in petroleum ether (0 to 50%) to afford 4-bromo-5,6-difluoro-2-methyl-1-((2-(trimethylsilyl)ethoxy)methyl)-1H-indole-7-carboxamide (6.3 g, 55%) as a yellow solid.

$^1$H NMR (300 MHz, DMSO-$d_6$) δ 8.34 (s, 1H), 8.10 (s, 1H), 6.40 (s, 1H), 5.50 (s, 2H), 3.42 (t, J=8.1 Hz, 2H), 2.46 (s, 3H), 0.81 (t, J=8.1 Hz, 2H), −0.06 (s, 9H).

ESI-MS $[M+H]^+$ calcd for ($C_{16}H_{21}BrF_2N_2O_2Si$) 419.05, 421.05 found: 419.20, 421.20.

Step 9: 4-bromo-5,6-difluoro-2-methyl-1H-indole-7-carboxamide

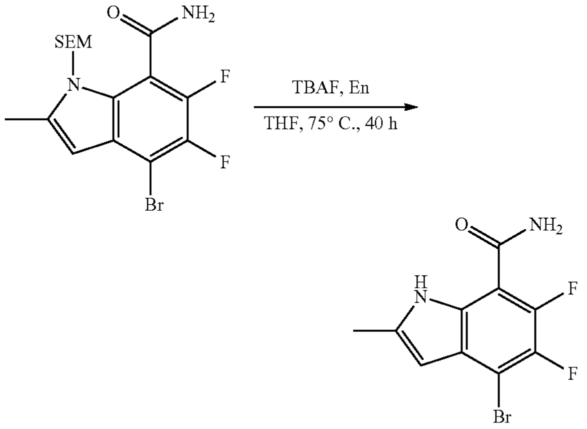

A mixture of 4-bromo-5,6-difluoro-2-methyl-1-((2-(trimethylsilyl)ethoxy)methyl)-1H-indole-7-carboxamide (6.3 g, 15.02 mmol), TBAF (1 M in THF, 150 mL, 150.2 mmol), and ethane-1,2-diamine (30 mL, 450.6 mmol) in THF (60 mL) was stirred at 75° C. for 40 h. The reaction mixture was cooled to 0° C. and acidified with 2 M hydrochloric acid until pH=4. The precipitate was collected by filtration, washed with water (100 mL) and dried under reduced pressure to afford 4-bromo-5,6-difluoro-2-methyl-1H-indole-7-carboxamide (3.5 g, 80%) as a yellow solid.

$^1$H NMR (300 MHz, DMSO-$d_6$) δ 11.38 (s, 1H), 7.97 (s, 1H), 7.90 (s, 1H), 6.20 (s, 1H), 2.40 (s, 3H).

ESI-MS $[M+H]^+$ calcd for ($C_{10}H_7BrF_2N_2O$) 288.97, 290.97 found: 288.95, 290.95.

Step 10: tert-butyl 5-(7-carbamoyl-5,6-difluoro-2-methyl-1H-indol-4-yl)-3,4-dihydroisoquinoline-2(1H)-carboxylate

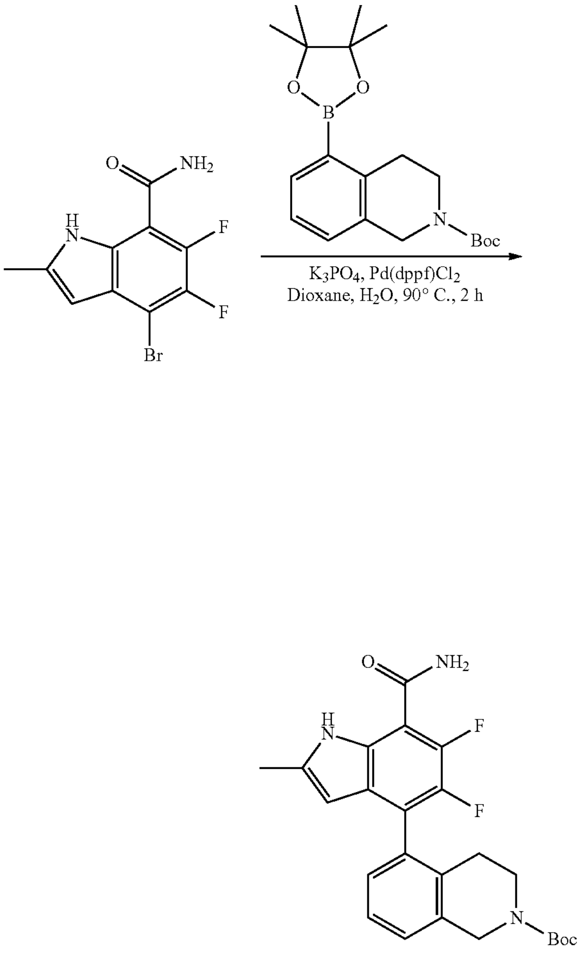

A mixture of 4-bromo-5,6-difluoro-2-methyl-1H-indole-7-carboxamide (250 mg, 0.864 mmol), tert-butyl 5-(4,4,5,5-tetramethyl-1,3,2-dioxaborolan-2-yl)-3,4-dihydroisoquinoline-2(1H)-carboxylate (373 mg, 1.04 mmol), potassium carbonate (359 mg, 2.59 mmol) and Pd(dppf)$Cl_2$. DCM (71 mg, 0.086 mmol) in dioxane (8 mL) and water (2 mL) was degassed and backfilled with nitrogen for five times and stirred at 90° C. for 2 h. The cooled reaction mixture was quenched with water (30 mL) and extracted with ethyl acetate (3×30 mL). The combined organic layers were washed with brine (30 mL), dried over sodium sulfate and concentrated under vacuum. The residue was purified by column chromatography on silica gel eluting with ethyl acetate in petroleum ether (0 to 38%) to give tert-butyl 5-(7-carbamoyl-5,6-difluoro-2-methyl-1H-indol-4-yl)-3,4-dihydroisoquinoline-2(1H)-carboxylate (340 mg, 89%) as a white solid.

$^1$H NMR (300 MHz, DMSO-$d_6$) δ 11.11 (s, 1H), 7.90 (s, 1H), 7.82 (s, 1H), 7.40-7.22 (m, 2H), 7.17 (dd, J=6.9, 2.1 Hz, 1H), 5.70 (s, 1H), 4.70-4.44 (m, 2H), 3.91 (s, 1H), 3.56-3.44 (m, 1H), 3.40-3.35 (m, 1H), 2.43-2.38 (m, 1H), 2.32 (s, 3H), 1.41 (s, 9H).

ESI-MS $[M+H-tBu]^+$ calcd for ($C_{24}H_{25}F_2N_3O_3$) 386.19 found: 386.15.

Step 11: tert-butyl 5-(7-carbamoyl-3-chloro-5,6-difluoro-2-methyl-1H-indol-4-yl)-3,4-dihydroisoquinoline-2(1H)-carboxylate

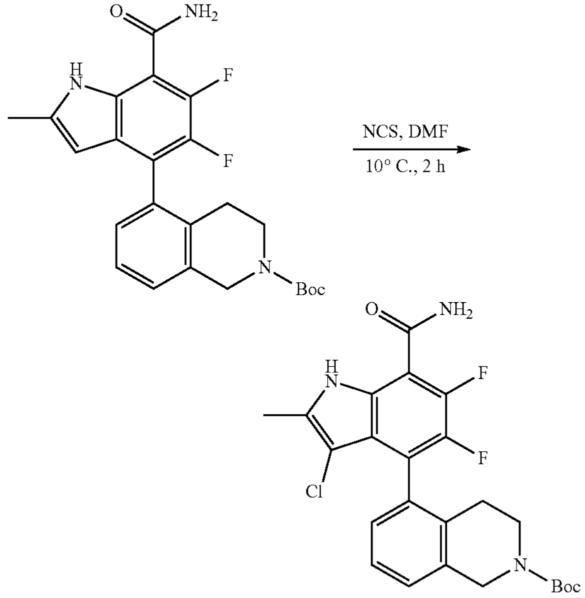

To a solution of tert-butyl 5-(7-carbamoyl-5,6-difluoro-2-methyl-1H-indol-4-yl)-3,4-dihydroisoquinoline-2(1H)-carboxylate (250 mg, 0.566 mmol) in DMF (5 mL) was added NCS (91 mg, 0.679 mmol) at 0° C. After stirring at 10° C. for 2 h, the reaction mixture was quenched with water (30 mL) and extracted with ethyl acetate (3x30 mL). The combined organic layers were washed with brine (30 mL), dried over sodium sulfate and concentrated under vacuum. The residue was purified by Prep-TLC (30% ethyl acetate in petroleum ether) to give tert-butyl 5-(7-carbamoyl-3-chloro-5,6-difluoro-2-methyl-1H-indol-4-yl)-3,4-dihydroisoquinoline-2(1H)-carboxylate (200 mg, 74%) as a yellow solid.

$^1$H NMR (300 MHz, DMSO-$d_6$) δ 11.52 (s, 1H), 8.01-7.95 (m, 2H), 7.32-7.28 (m, 2H), 7.17-7.11 (m, 1H), 4.66-4.52 (m, 2H), 3.52-3.43 (m, 2H), 2.45-2.34 (m, 2H), 2.31 (s, 3H), 1.41 (s, 9H).

ESI-MS [M+H-tBu]$^+$ calcd for ($C_{24}H_{24}ClF_2N_3O_3$) 420.15, 422.15 found: 420.05, 422.05.

Step 12: 3-chloro-5,6-difluoro-2-methyl-4-(1,2,3,4-tetrahydroisoquinolin-5-yl)-1H-indole-7-carboxamide hydrochloride

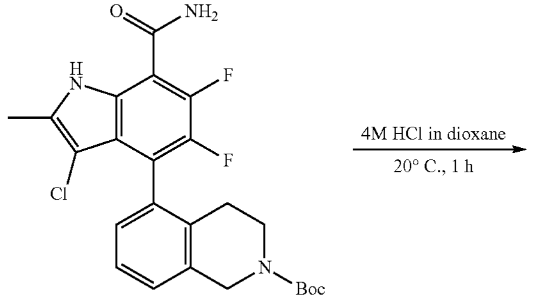

-continued

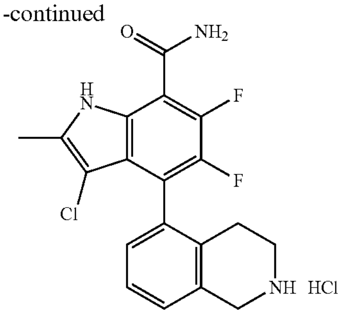

A mixture of tert-butyl 5-(7-carbamoyl-3-chloro-5,6-difluoro-2-methyl-1H-indol-4-yl)-3,4-dihydroisoquinoline-2(1H)-carboxylate (240 mg, 0.504 mmol) and hydrogen chloride (4 M in dioxane, 5 mL) was stirred for 2 h at 20° C. The mixture was concentrated under vacuum to give 3-chloro-5,6-difluoro-2-methyl-4-(1,2,3,4-tetrahydroisoquinolin-5-yl)-1H-indole-7-carboxamide hydrochloride (200 mg, crude) as a brown solid.

ESI-MS [M+H]$^+$ calcd for ($C_{19}H_{16}ClF_2N_3O$) 376.09, 378.09 found: 376.05, 378.05.

Step 13: 4-(2-acryloyl-1,2,3,4-tetrahydroisoquinolin-5-yl)-3-chloro-5,6-difluoro-2-methyl-1H-indole-7-carboxamide

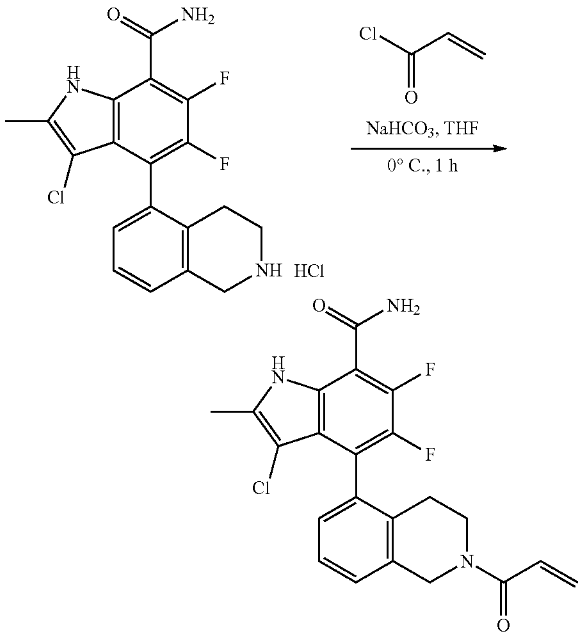

To a mixture of 3-chloro-5,6-difluoro-2-methyl-4-(1,2,3,4-tetrahydroisoquinolin-5-yl)-1H-indole-7-carboxamide hydrochloride (200 mg, 0.485 mmol) in tetrahydrofuran (4 mL) and water (1 mL) were added sodium bicarbonate (204 mg, 2.43 mmol) and acryloyl chloride (44 mg, 0.485 mmol) at 0° C. After stirring for 1 h at 0° C., the reaction mixture was quenched with water (30 mL) and extracted with ethyl acetate (3x30 mL). The combined organic layers were washed with brine (30 mL), dried over sodium sulfate and concentrated under vacuum. The residue was purified Prep-HPLC with the following conditions: Column: XBridge Prep OBD C18 Column, 30×150 mm 5 um; Mobile Phase A: Water (10 MMOL/L $NH_4HCO_3$+0.1% $NH_3 \cdot H_2O$), Mobile Phase B: Acetonitrile; Flow rate: 60 mL/min; Gradient: 30% B to 60% B in 7 min; 220 nm; Rt: 6.32 min to give 4-(2-acryloyl-1,2,3,4-tetrahydroisoquinolin-5-yl)-3-chloro-5,6-difluoro-2-methyl-1H-indole-7-carboxamide (80 mg, 38%) as a white solid.

$^1$H NMR (400 MHz, DMSO-$d_6$) δ 11.54 (s, 1H), 8.03 (s, 1H), 7.99 (s, 1H), 7.35-7.29 (m, 2H), 7.17-7.14 (m, 1H), 6.97-6.77 (m, 1H), 6.15 (dd, J=17.2, 1.6 Hz, 1H), 5.74-5.66 (m, 1H), 4.89-4.75 (m, 2H), 3.78-3.60 (m, 2H), 2.46-2.34 (m, 2H), 2.31 (s, 3H).

ESI-MS $[M+H]^+$ calcd for ($C_{22}H_{18}ClF_2N_3O_2$) 430.11, 432.11 found: 430.05, 432.05.

Step 14: Separation of Isomers (R)-4-(2-acryloyl-1,2,3,4-tetrahydroisoquinolin-5-yl)-3-chloro-5,6-difluoro-2-methyl-1H-indole-7-carboxamide (compound 21b) and (S)-4-(2-acryloyl-1,2,3,4-tetrahydroisoquinolin-5-yl)-3-chloro-5,6-difluoro-2-methyl-1H-indole-7-carboxamide (Compound 21c)

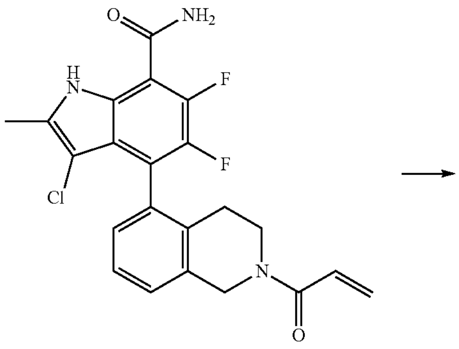

-continued

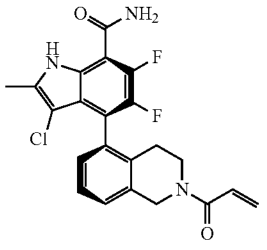

Compound 21b (R)

and

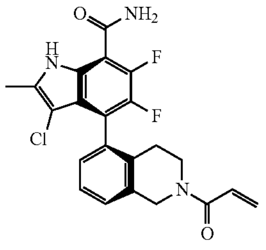

Compound 21c (S)

The two atropisomers of 4-(2-acryloyl-1,2,3,4-tetrahydroisoquinolin-5-yl)-3-chloro-5,6-difluoro-2-methyl-1H-indole-7-carboxamide were separated by Prep-Chiral-HPLC according to procedures as described herein:

$^1$H NMR (300 MHz, DMSO-$d_6$) δ 11.54 (s, 1H), 8.05-7.96 (m, 2H), 7.37-7.29 (m, 2H), 7.18-7.13 (m, 1H), 6.98-6.75 (m, 1H), 6.20-6.10 (m, 1H), 5.75-5.65 (m, 1H), 4.95-4.67 (m, 2H), 3.81-3.57 (m, 2H), 2.46-2.36 (m, 2H), 2.31 (s, 3H). LC-MS: m/z=430.05, 432.05 $[M+H]^+$.

$^1$H NMR (300 MHz, DMSO-$d_6$) δ 11.54 (s, 1H), 8.02-7.97 (m, 2H), 7.37-7.29 (m, 2H), 7.18-7.13 (m, 1H), 6.98-6.76 (m, 1H), 6.15 (dd, J=16.5, 1.8 Hz, 1H), 5.75-5.66 (m, 1H), 4.88-4.77 (m, 2H), 3.77-3.62 (m, 2H), 2.46-2.36 (m, 2H), 2.31 (s, 3H). LC-MS: m/z=430.05, 432.05 $[M+H]^+$.

Compounds 21d-21e

Compounds 21d and 21e were prepared according to similar methods as described in the preceding schemes and examples by employing correspondingly appropriate starting materials.

TABLE 7

COMPOUNDS 21D AND 21E

| Cmpd. No. | Structure | $^1$H NMR | LC-MS: m/z [M + H] |
|---|---|---|---|
| 21d | 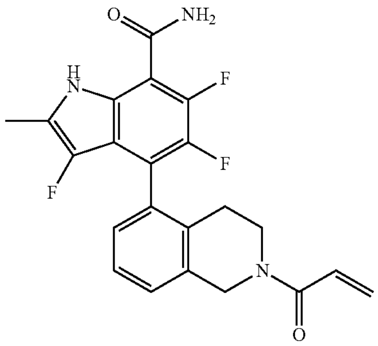 [SMILES: C=CC(=O)N1CCc2c(cccc2-c2c(F)c(F)c(C(N)=O)c3[nH]c(C)c(F)c23)C1] | (400 MHz, DMSO-$d_6$) δ 11.02 (s, 1H), 8.07-7.84 (m, 2H), 7.39-7.28 (m, 2H), 7.27-7.17 (m, 1H), 7.01-6.75 (m, 1H), 6.24-6.09 (m, 1H), 5.81-5.62 (m, 1H), 4.96-4.70 (m, 2H), 3.81-3.53 (m, 2H), 2.69-2.51 (m, 2H), 2.27 (s, 3H). | 414.10 |

TABLE 7-continued

COMPOUNDS 21D AND 21E

| Cmpd. No. | Structure | $^1$H NMR | LC-MS: m/z [M + H] |
|---|---|---|---|
| 21e | 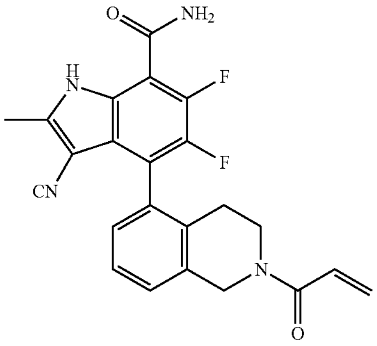 | (300 MHz, DMSO-$d_6$) δ 12.26 (s, 1H), 8.09 (d, J = 6.0 Hz, 2H), 7.43-7.30 (m, 2H), 7.23-7.16 (m, 1H), 6.99-6.74 (m, 1H), 6.15 (dd, J = 16.5, 2.1 Hz, 1H), 5.77-5.66 (m, 1H), 4.96-4.64 (m, 2H), 3.88-3.56 (m, 2H), 2.50-2.38 (m, 5H). | 421.35 |

Preparation of Compounds of Formula (II) Wherein X is $CH_2$, $R^3$ is Me

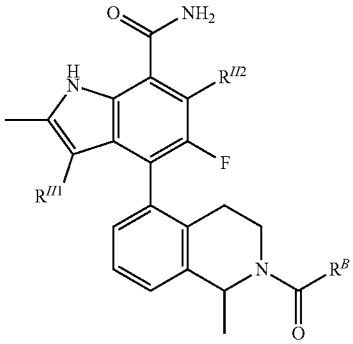

Example 22

Synthesis of 4-(2-acryloyl-1-methyl-1,2,3,4-tetrahydroisoquinolin-5-yl)-3-chloro-5-fluoro-2-methyl-1H-indole-7-carboxamide (Compound 22a)

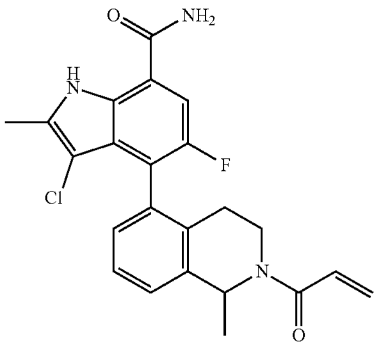 [SMILES: C=CC(=O)N1CCc2c(-c3c(F)cc(C(N)=O)c4[nH]c(C)c(Cl)c34)cccc2C1C]

Step 1: N-(2-bromophenethyl) acetamide

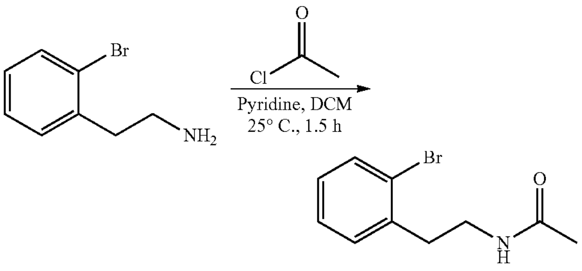

To a stirred solution of 2-(2-bromophenyl) ethan-1-amine (5.0 g, 25.0 mmol) in DCM (25 mL) and pyridine (50 mL) was added dropwise acetyl chloride (1.96 g, 24.99 mmol) at 0° C. After addition, the reaction mixture was stirred for 1.5 h at 25 C. The reaction mixture was diluted with water (50 mL) and extracted with ethyl acetate (3x20 mL). The combined extracts were washed with water (30 mL) and brine (30 mL), dried over sodium sulfate and concentrated under vacuum. The concentrate was purified by column chromatography on silica gel (5% methanol in dichloromethane) to give N-(2-bromophenethyl) acetamide (4.8 g, 79%) as a yellow oil.

$^1$H NMR (300 MHz, DMSO-$d_6$) δ 7.96 (s, 1H), 7.59 (d, J=6.0 Hz, 1H), 7.35-7.28 (m, 2H), 7.19-7.13 (m, 1H), 3.31-3.20 (m, 2H), 2.84-2.80 (m, 2H), 1.78 (s, 3H).

ESI-MS $[M+H]^+$ calcd for ($C_{10}H_{12}BrNO$) 242.01, 244.01; found: 242.10, 244.10.

Step 2: 7-bromo-10b-methyl-6,10b-dihydro-5H-oxazolo[2,3-a] isoquinoline-2,3-dione

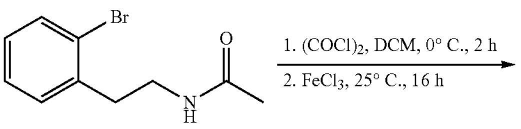

-continued

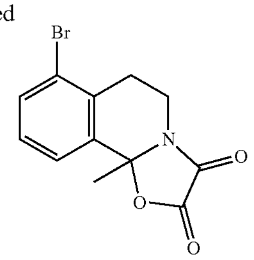

To a solution of N-(2-bromophenethyl) acetamide (5.0 g, 20.7 mmol) in DCM (70 mL) was added dropwise oxalyl chloride (4.72 g, 37.2 mmol) at 0° C. The mixture was stirred at 0° C. for 2 h, then at 25° C. for 3 h. The reaction mixture was cooled to 0° C. and $FeCl_3$ (4.02 g, 24.8 mmol) was added in portions. The reaction mixture was allowed to warm to 25° C. and stirred for 16 h. The reaction mixture was diluted with 12 M aqueous ammonia (50 mL) and extracted with DCM (3x30 mL). The combined extracts were washed with brine (50 mL), dried over sodium sulfate and concentrated under vacuum to give 7-bromo-10b-methyl-6,10b-dihydro-5H-oxazolo[2,3-a] isoquinoline-2,3-dione (6.0 g) as a brown solid that was used without purification.

ESI-MS $[M+H]^+$ calcd for ($C_{12}H_{10}BrNO_3$) 295.98, 297.98; found: 296.05, 298.05.

Step 3: 5-bromo-1-methyl-3,4-dihydroisoquinoline

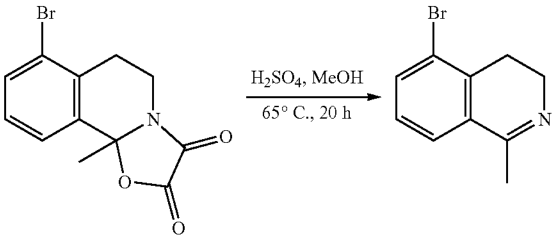 [SMILES: CC12OC(=O)C(=O)N1CCc1c(Br)cccc12 ; CC1=NCCc2c(Br)cccc21]

To a solution of 7-bromo-10b-methyl-6,10b-dihydro-5H-oxazolo[2,3-a]isoquinoline-2,3-dione (6.0 g, 20.3 mmol) in methanol (150 mL) was added concentrated sulfuric acid (1.99 g, 20.3 mmol). The reaction mixture was heated at 65 C for 20 h. The reaction mixture was diluted with 12 M aqueous ammonia at 0 C. The methanol was removed under reduced pressure. The residue was diluted with water (30 mL) and extracted with DCM (3x50 mL). The combined extracts were washed with brine (50 mL), dried over sodium sulfate, and concentrated under vacuum to give 5-bromo-1-methyl-3,4-dihydroisoquinoline (3.9 g, 86%) as a brown oil.

$^1H$ NMR (400 MHz, DMSO-$d_6$) δ 7.68 (d, J=8.0 Hz, 1H), 7.59 (d, J=8.0 Hz, 1H), 7.32-7.28 (m, 1H), 3.58-3.54 (m, 2H), 2.71-2.67 (m, 2H), 2.31-2.30 (m, 3H).

ESI-MS $[M+H]^+$ calcd for ($C_{12}H_{10}BrNO_3$) 224.00, 226.00; found: 224.10, 226.10.

Step 4: 5-bromo-1-methyl-1,2,3,4-tetrahydroisoquinoline

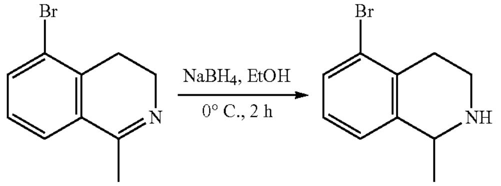

To a solution of 5-bromo-1-methyl-3,4-dihydroisoquinoline (3.9 g, 17.4 mmol) in ethanol (100 mL) was added sodium borohydride (658 mg, 17.4 mmol) at 0° C. The reaction mixture was stirred at 0° C. for 2 h, diluted with water (100 mL) and extracted with DCM (3x100 mL). The combined extracts were washed with brine (100 mL), dried over sodium sulfate, and concentrated under vacuum to give 5-bromo-1-methyl-1,2,3,4-tetrahydroisoquinoline (2.75 g, 70%) as a brown solid.

$^1H$ NMR (300 MHz, DMSO-$d_6$) δ 7.40 (d, J=7.8 Hz, 1H), 7.18 (d, J=7.5 Hz, 1H), 7.12-7.01 (mf, 1H), 3.93-3.87 (m, 1H), 3.30 (brs, 1H), 3.15-3.11 (m, 1H), 2.88-2.76 (m, 1H), 2.61-2.57 (m, 2H), 1.33 (d, J=6.6 Hz, 3H).

ESI-MS $[M+H]^+$ calcd for ($C_{10}H_{12}BrN$) 226.02, 228.02; found: 226.15, 228.11.

Step 5: tert-butyl 5-bromo-1-methyl-3,4-dihydroisoquinoline-2(1H)-carboxylate

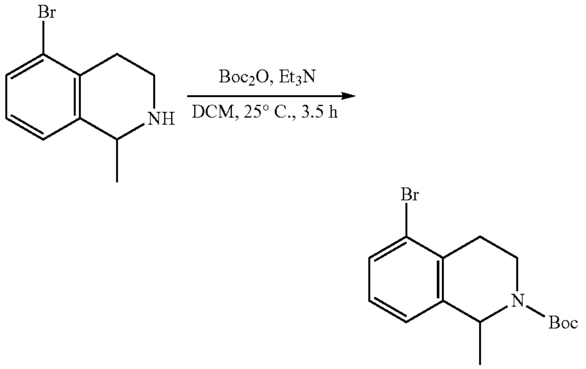

To a solution of 5-bromo-1-methyl-1,2,3,4-tetrahydroisoquinoline (2.75 g, 12.2 mmol) and triethylamine (3.69 g, 36.5 mmol) in DCM (75 mL) was added di-tert-butyl dicarbonate (2.65 g, 12.2 mmol). The reaction mixture was stirred for 3 h at 25° C., quenched with water (50 mL) and extracted with ethyl acetate (3x50 mL). The combined organic layers were washed with brine (50 mL), dried over sodium sulfate, and concentrated under vacuum. The residue was purified by column chromatography on silica gel (7% ethyl acetate in petroleum ether) to give tert-butyl 5-bromo-1-methyl-3,4-dihydroisoquinoline-2(1H)-carboxylate (3.1 g, 78%) as a white solid.

$^1H$ NMR (300 MHz, DMSO-$d_6$) δ 7.48 (d, J=7.8 Hz, 1H), 7.28 (d, J=7.5 Hz, 1H), 7.21-7.10 (m, 1H), 5.24-4.96 (m, 1H), 4.13-3.97 (m, 1H), 3.27-3.06 (m, 1H), 2.86-2.73 (m, 1H), 2.69-2.57 (m, 1H), 1.46-1.37 (m, 12H).

ESI-MS [M+H-Boc]$^+$ calcd for ($C_{15}H_{20}BrNO_2$) 226.07, 228.07; found: 226.05, 228.05.

Step 6: tert-butyl 1-methyl-5-(4,4,5,5-tetramethyl-1,3,2-dioxaborolan-2-yl)-3,4-dihydroisoquinoline-2(1H)-carboxylate

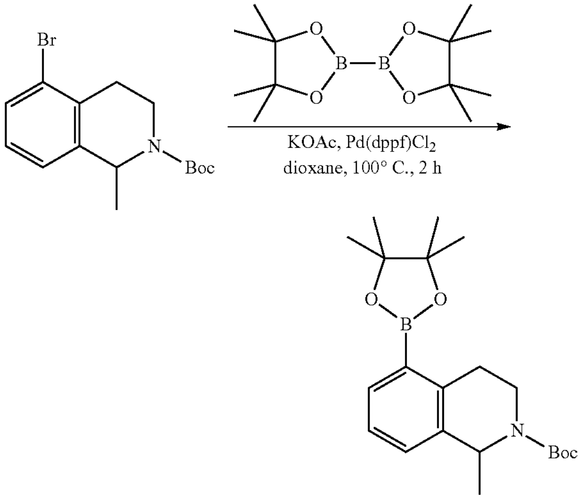

A mixture of tert-butyl 5-bromo-1-methyl-3,4-dihydroisoquinoline-2(1H)-carboxylate (3.5 g, 10.7 mmol), 4,4,4',4',5,5,5',5'-octamethyl-2,2'-bi(1,3,2-dioxaborolane) (3.27 g, 12.9 mmol), Pd(dppf)$Cl_2$. DCM (876 mg, 1.07 mmol), and potassium acetate (3.16 g, 32.2 mmol) in 1,4-dioxane (100 mL) was degassed and backfilled with nitrogen. The reaction mixture was heated under nitrogen at 100° C. for 2 h. The cooled reaction mixture was quenched with water (50 mL) and extracted with ethyl acetate (3×50 mL). The combined extracts were washed with brine (50 mL), dried over sodium sulfate, and concentrated under vacuum. The residue was purified by column chromatography on silica gel (60% ethyl acetate in petroleum ether) to give tert-butyl 1-methyl-5-(4,4,5,5-tetramethyl-1,3,2-dioxaborolan-2-yl)-3,4-dihydro-1H-isoquinoline-2-carboxylate (4.0 g, 89%) as a yellow oil.

$^1$H NMR (300 MHz, DMSO-$d_6$) δ 7.52 (d, J=7.5 Hz, 1H), 7.30 (d, J=7.2 Hz, 1H), 7.21-7.14 (m, 1H), 5.12-4.96 (m, 1H), 3.97-3.81 (m, 1H), 3.29-3.03 (m, 2H), 2.93-2.88 (m, 1H), 1.43 (s, 9H), 1.36 (d, J=6.0 Hz, 3H), 1.29 (s, 12H).

ESI-MS [M+H-Boc]$^+$ calcd for ($C_{21}H_{32}BNO_4$) 274.24, found: 274.25.

Step 7: 4-bromo-5-fluoro-2-methyl-1H-indole-7-carboxylic acid

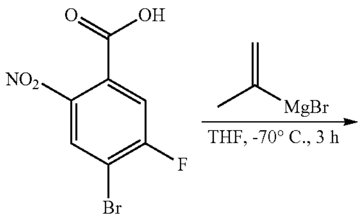

-continued

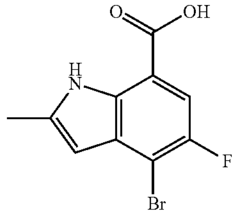

To a stirred solution of 4-bromo-5-fluoro-2-nitrobenzoic acid (17 g, 64.4 mmol) in THF (200 mL) was added dropwise prop-1-en-2-ylmagnesium bromide (451 mL, 225 mmol, 0.5 M in THF) at −70° C. under nitrogen. After addition, the reaction mixture was stirred at −70° C. for 3 h. The reaction mixture was quenched with saturated aqueous ammonium chloride (500 mL) and extracted with ethyl acetate (2×500 mL). The combined extracts were washed with brine (300 mL), dried over anhydrous sodium sulfate, and concentrated under vacuum to give 4-bromo-5-fluoro-2-methyl-1H-indole-7-carboxylic acid (17.5 g) as a brown solid. The solids were taken forward without purification.

ESI-MS [M−H]$^-$ calcd for ($C_{10}H_7BrFNO_2$) 269.96, 271.96; found: 270.25, 272.25.

Step 8: 4-bromo-5-fluoro-2-methyl-1H-indole-7-carboxamide

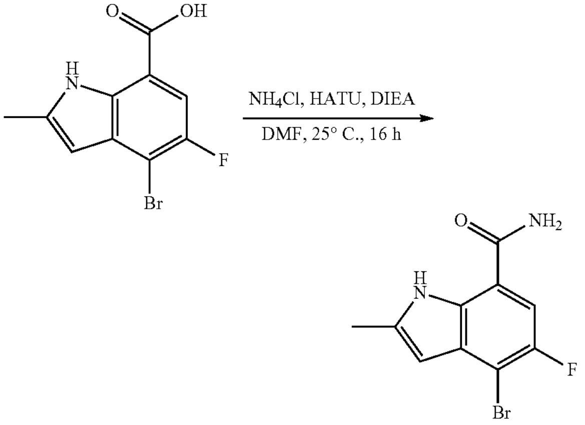

To a stirred solution of 4-bromo-5-fluoro-2-methyl-1H-indole-7-carboxylic acid (17.5 g, 64.4 mmol), ammonia hydrochloride (5.17 g, 96.6 mmol) and HATU (29.4 g, 77.3 mmol) in DMF (200 mL) was added N-ethyl-N-isopropylpropan-2-amine (25.0 g, 193 mmol). The reaction mixture was stirred at 25° C. for 16 h. The reaction mixture was quenched with water (300 mL) and extracted with ethyl acetate (3×300 mL). The combined extracts were washed with water (200 mL), brine (200 mL), and then dried over anhydrous sodium sulfate and concentrated under vacuum. The concentrate was purified by column chromatography (50% ethyl acetate in petroleum ether) to give 4-bromo-5-fluoro-2-methyl-1H-indole-7-carboxamide (3.8 g, 22%) as a yellow solid.

$^1$H NMR (400 MHz, DMSO-$d_6$) δ 11.26 (s, 1H), 8.11 (s, 1H), 7.63-7.53 (m, 2H), 6.19 (s, 1H), 2.42 (s, 3H).

ESI-MS [M+H]$^+$ calcd for ($C_{10}H_8BrFN_2O$) 270.98, 272.98; found: 270.90, 272.90.

Step 9: tert-butyl 5-(7-carbamoyl-5-fluoro-2-methyl-1H-indol-4-yl)-1-methyl-3,4-dihydroisoquinoline-2(1H)-carboxylate

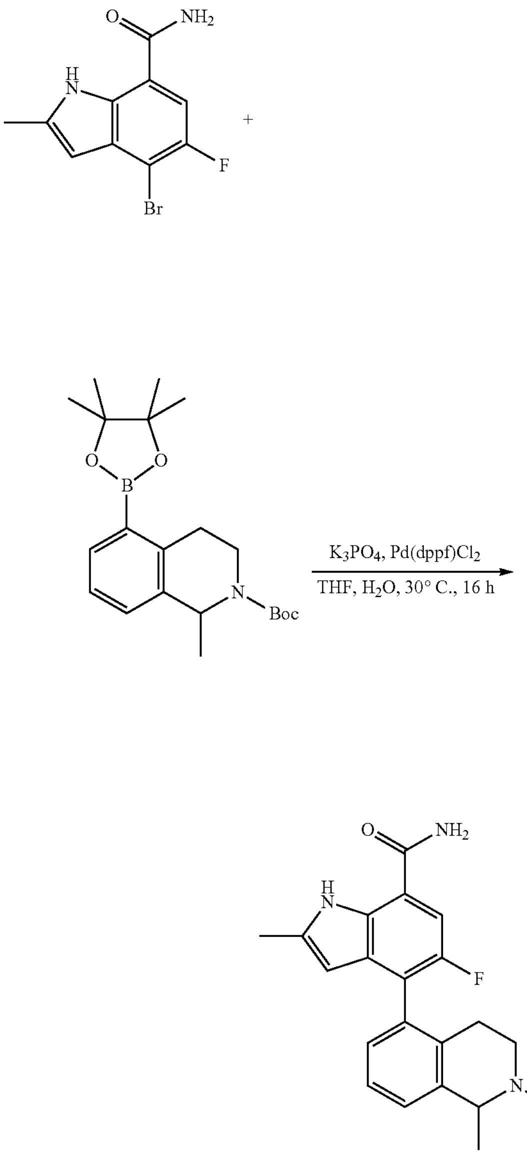

A mixture of 4-bromo-5-fluoro-2-methyl-1H-indole-7-carboxamide (400 mg, 1.47 mmol), tert-butyl 1-methyl-5-(4,4,5,5-tetramethyl-1,3,2-dioxaborolan-2-yl)-3,4-dihydro-1H-isoquinoline-2-carboxylate (550 mg, 1.47 mmol), potassium phosphate (938 mg, 4.42 mmol), and $Pd(dppf)Cl_2$ (108 mg, 0.147 mmol) in THF (12 mL) and water (3 mL) was degassed and backfilled with nitrogen. The reaction mixture was stirred under nitrogen at 30° C. for 16 h, quenched with water (60 mL) and extracted with ethyl acetate (3×50 mL). The combined extracts were washed with brine (30 mL), dried over sodium sulfate and concentrated under vacuum. The concentrate was purified by column chromatography on silica gel (55% ethyl acetate in petroleum ether) to give tert-butyl 5-(7-carbamoyl-5-fluoro-2-methyl-1H-indol-4-yl)-1-methyl-3,4-dihydroisoquinoline-2(1H)-carboxylate (500 mg, 78%) as a yellow solid.

$^1H$ NMR (300 MHz, DMSO-$d_6$) δ 11.05 (s, 1H), 7.62-7.52 (m, 2H), 7.36-7.26 (m 3H), 7.17-7.11 (m, 1H), 5.78-5.76 (m, 1H), 5.18-5.13 (m, 1H), 3.92-3.61 (m, 1H), 3.19-2.98 (m, 1H), 2.43-2.40 (m, 1H), 2.39-2.33 (m, 3H), 2.30-2.24 (m, 1H), 1.43 (s, 12H).

ESI-MS $[M+H]^+$ calcd for ($C_{25}H_{28}FN_3O_3$) 438.21, found: 438.30.

Step 10: 5-fluoro-2-methyl-4-(1-methyl-1,2,3,4-tetrahydroisoquinolin-5-yl)-1H-indole-7-carboxamide

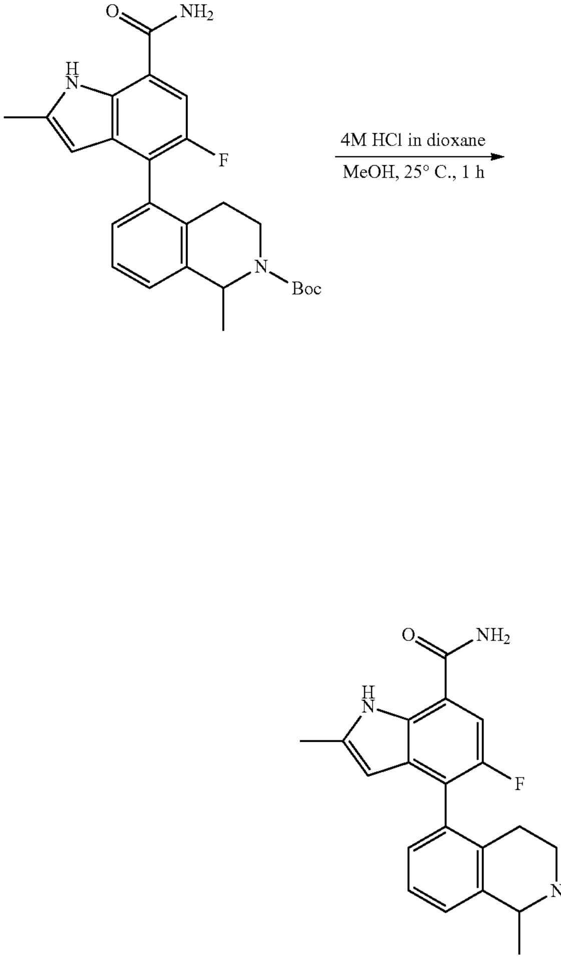

A mixture of tert-butyl 5-(7-carbamoyl-5-fluoro-2-methyl-1H-indol-4-yl)-1-methyl-3,4-dihydroisoquinoline-2(1H)-carboxylate (500 mg, 1.14 mmol) and hydrogen chloride (4 M in dioxane, 10 mL) was stirred at 25° C. for 1 h. The reaction mixture was concentrated under vacuum. The residue was diluted with saturated aqueous sodium bicarbonate (50 mL) and extracted with ethyl acetate (3×50 mL). The combined extracts were dried over sodium sulfate and concentrated under vacuum to give 5-fluoro-2-methyl-4-(1-methyl-1,2,3,4-tetrahydroisoquinolin-5-yl)-1H-indole-7-carboxamide (370 mg, 89%) as a yellow solid.

ESI-MS $[M+H]^+$ calcd for ($C_{20}H_{20}FN_3O$) 338.16, found: 338.15.

Step 11: 4-(2-acryloyl-1-methyl-1,2,3,4-tetrahydroisoquinolin-5-yl)-5-fluoro-2-methyl-1H-indole-7-carboxamide

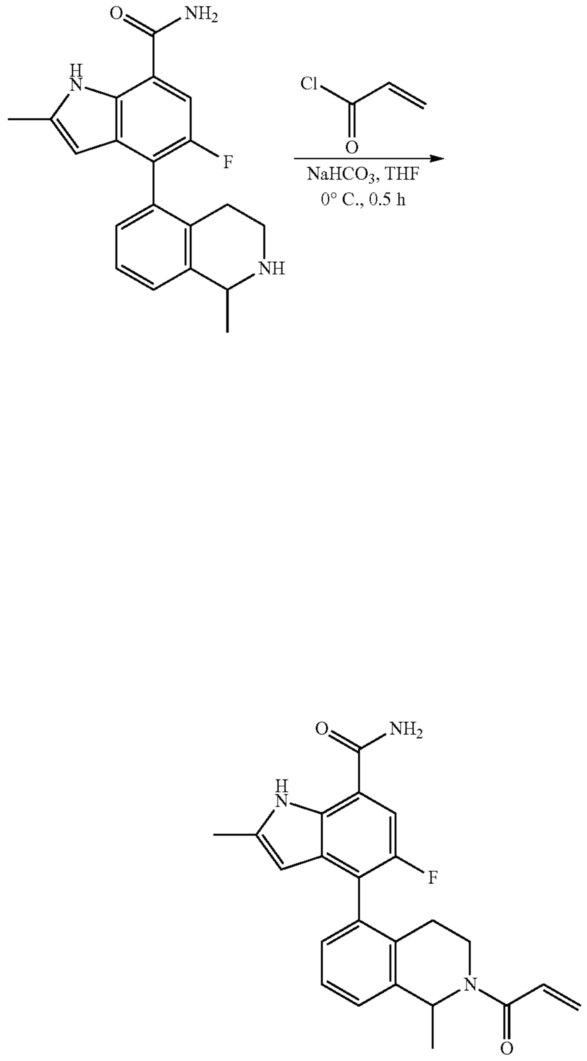

To a stirred mixture of 5-fluoro-2-methyl-4-(1-methyl-1,2,3,4-tetrahydroisoquinolin-5-yl)-1H-indole-7-carboxamide (370 mg, 1.10 mmol) and sodium bicarbonate (276 mg, 3.29 mmol) in THE (8 mL) and water (2 mL) was added acryloyl chloride (99 mg, 1.10 mmol) at 0° C. The reaction mixture was stirred at 0° C. for 0.5 h. The reaction mixture was diluted with water (30 mL) and extracted with ethyl acetate (3x30 mL). The combined extracts were washed with brine (30 mL), dried over sodium sulfate and concentrated under vacuum. The residue was purified by column chromatography on silica gel (75-100% ethyl acetate in petroleum ether) to afford 4-(2-acryloyl-1-methyl-1,2,3,4-tetrahydroisoquinolin-5-yl)-5-fluoro-2-methyl-1H-indole-7-carboxamide (290 mg, 67%) as a yellow solid.

$^1$H NMR (300 MHz, DMSO-d$_6$) δ 11.09-11.00 (m, 1H), 8.11 (s, 1H), 7.63-7.49 (m, 2H), 7.43-7.28 (m, 2H), 7.19-7.14 (m, 1H), 7.03-6.71 (m, 1H), 6.25-6.08 (m, 1H), 5.83-5.55 (m, 3H), 4.36-3.85 (m, 1H), 3.54-3.36 (m, 1H), 2.76-2.53 (m, 1H), 2.46-2.23 (m, 4H), 1.56-1.47 (m, 3H).

ESI-MS [M+H]$^+$ calcd for ($C_{23}H_{22}FN_3O_2$) 392.17, found: 392.15.

Step 12: 4-(2-acryloyl-1-methyl-1,2,3,4-tetrahydroisoquinolin-5-yl)-3-chloro-5-fluoro-2-methyl-1H-indole-7-carboxamide

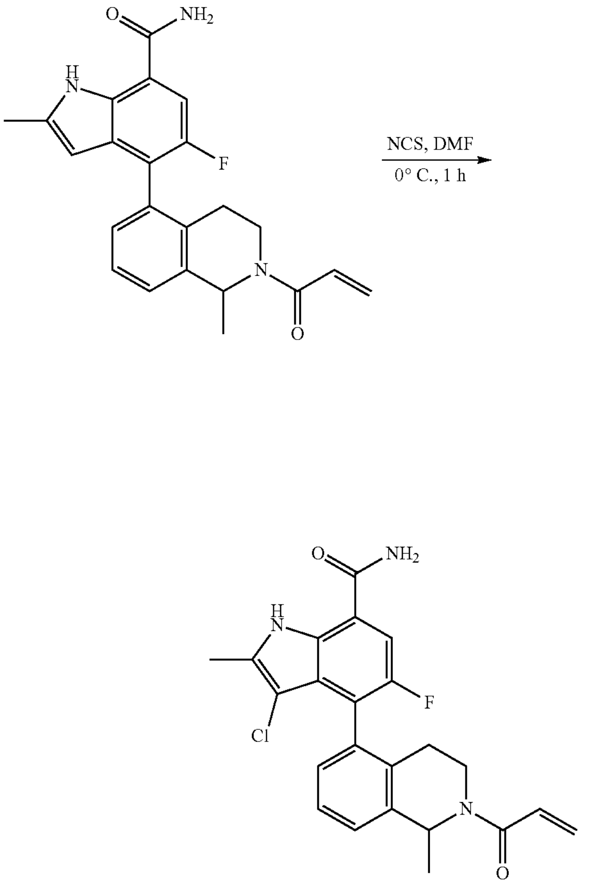

To a stirred solution of 4-(2-acryloyl-1-methyl-1,2,3,4-tetrahydroisoquinolin-5-yl)-5-fluoro-2-methyl-1H-indole-7-carboxamide (230 mg, 0.59 mmol) in DMF (5.0 mL) was added 1-chloropyrrolidine-2,5-dione (78 mg, 0.59 mmol) at 0° C. The reaction mixture was stirred at 0° C. for 1 h. The reaction mixture was diluted with water (25 mL) and extracted with ethyl acetate (3x20 mL). The combined extracts were washed with brine (30 mL), dried over sodium sulfate, and concentrated under vacuum. The concentrate was purified by preparative HPLC (Column: XBridge Prep OBD C18 Column, 19x250 mm, 5 um; Mobile Phase A: Water (10 mmol/L $NH_4HCO_3$+0.1% $NH_3 \cdot H_2O$), Mobile Phase B: Acetonitrile; Flow rate: 25 mL/min; Gradient: 40% B to 60% B in 7 min; 220 nm; RT: 6.00 minute) to give 4-(2-acryloyl-1-methyl-1,2,3,4-tetrahydroisoquinolin-5-yl)-3-chloro-5-fluoro-2-methyl-1H-indole-7-carboxamide (110 mg, 44%) as a white solid.

$^1$H NMR (400 MHz, DMSO-d$_6$) δ 11.55-11.40 (m, 1H), 8.19 (s, 1H), 7.72-7.59 (m, 2H), 7.38-7.24 (m, 2H), 7.15-7.07 (m, 1H), 7.01-6.73 (m, 1H), 6.18-6.11 (m, 1H), 5.77-5.36 (m, 2H), 4.31-3.93 (m, 1H), 3.48-3.05 (m, 1H), 2.44-2.18 (m, 5H), 1.54-1.43 (m, 3H).

ESI-MS [M+H]$^+$ calcd for ($C_{23}H_{21}ClFN_3O_2$) 426.13, found: 426.25.

Step 13: Separation of Isomers

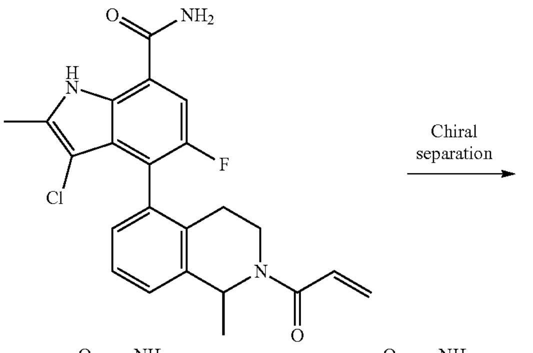

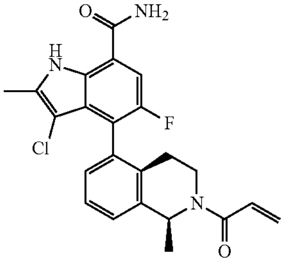

(S)-(S)-

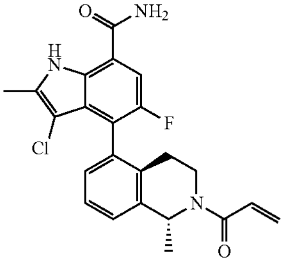

(S)-(R)-

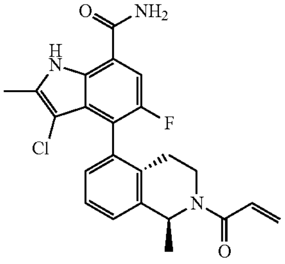

(R)-(S)-

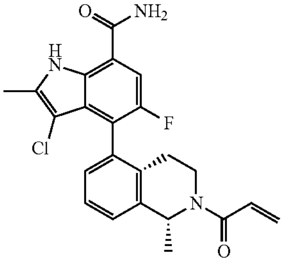

(R)-(R)-

4-(2-Acryloyl-1-methyl-1,2,3,4-tetrahydroisoquinolin-5-yl)-3-chloro-5-fluoro-2-methyl-1H-indole-7-carboxamide (100 mg) was separated into four isomers by Prep-Chiral-HPLC. The crude material was run through a CHIRALPAK IG (2×25 cm, 5 um); mobile phase A: hexane (0.5% 2M $NH_3$-MeOH), mobile phase B: EtOH; flow rate: 20 mL/min; gradient: 25% B, isocratic, 24 min; 220/254 nm, to provide four compounds with retention times as follows:

Compound 22b: Retention Time=11.342 Minutes (16.4 mg)

$^1$H NMR (400 MHz, Methanol-d4) δ 7.55 (d, J=10.4 Hz, 1H), 7.38-7.28 (m, 2H), 7.19-7.10 (m, 1H), 6.96-6.73 (m, 1H), 6.34-6.24 (m, 1H), 5.83-5.68 (m, 1.6H), 5.42-5.37 (m, 0.4H), 4.42-3.96 (m, 1H), 3.61-3.54 (m, 0.6H), 3.28-3.21 (m, 0.4H), 2.70-2.35 (m, 2H), 2.38 (s, 3H), 1.66 (d, J=6.8 Hz, 1H), 1.58 (d, J=6.8 Hz, 2H).

ESI-MS $[M+H]^+$ calcd for ($C_{23}H_{21}ClFN_3O_2$) 426.13, found: 426.05.

Compound 22c: Retention Time=18.98 Minutes (19.5 mg)

$^1$H NMR (400 MHz, Methanol-d4) δ 7.51 (d, J=10.4 Hz, 1H), 7.30-7.28 (m, 2H), 7.14-7.11 (m, 1H), 6.96-6.73 (m, 1H), 6.29-6.20 (m, 1H), 5.82-5.35 (m, 2H), 4.36-3.92 (m, 1H), 3.59-3.52 (m, 0.6H), 3.25-3.18 (m, 0.4H), 2.65-2.47 (m, 2H), 2.38 (s, 3H), 1.62 (d, J=6.8 Hz, 1H), 1.54 (d, J=6.8 Hz, 2H).

ESI-MS $[M+H]^+$ calcd for ($C_{23}H_{21}ClFN_3O_2$) 426.13, found: 426.05.

Compound 22d

The material eluting at 14.331 minutes was then chromatographed by CHIRAL ART Cellulose-SC (2×25 cm, 5 um); mobile phase A: hexane (0.5% 2M $NH_3$-MeOH), mobile phase B: EtOH; flow rate: 20 mL/min; gradient: 25% B, isocratic, 18 min; 220/254 nm. Retention time=10.855 minutes (14.9 mg).

$^1$H NMR (400 MHz, Methanol-d4) δ 7.51 (d, J=10.4 Hz, 1H), 7.30-7.29 (m, 2H), 7.14-7.11 (m, 1H), 6.96-6.72 (m, 1H), 6.29-6.19 (m, 1H), 5.81-5.66 (m, 1.6H), 5.39-5.34 (m, 0.4H), 4.35-3.92 (m, 1H), 3.59-3.52 (m, 0.6H), 3.24-3.18 (m, 0.4H), 2.55-2.47 (m, 2H), 2.38 (s, 3H), 1.62 (d, J=6.8 Hz, 1H), 1.54 (d, J=6.8 Hz, 2H).

ESI-MS $[M+H]^+$ calcd for ($C_{23}H_{21}ClFN_3O_2$) 426.13, found: 426.05.

Compound 22e

The material eluting at 15.677 minutes was then chromatographed by CHIRAL ART Cellulose-SC (2×25 cm, 5 um); mobile phase A: hexane (0.5% 2M $NH_3$-MeOH), mobile phase B: EtOH; flow rate: 20 mL/min; Gradient: 25% B, isocratic, 18 min; 220/254 nm. Retention time=14.665 minutes (19.0 mg).

$^1$H NMR (400 MHz, Methanol-d4) δ 7.51 (d, J=10.4 Hz, 1H), 7.31-7.28 (m, 2H), 7.14-7.11 (m, 1H), 6.96-6.72 (m, 1H), 6.29-6.18 (m, 1H), 5.82-5.65 (m, 1.6H), 5.39-5.32 (m, 0.4H), 4.36-3.90 (m, 1H), 3.60-3.50 (m, 0.6H), 3.24-3.18 (m, 0.4H), 2.55-2.47 (m, 2H), 2.37 (s, 3H), 1.62 (d, J=6.4 Hz, 1H), 1.54 (d, J=6.8 Hz, 2H).

ESI-MS [M+H]+ calcd for ($C_{23}H_{21}ClFN_3O_2$) 426.13, found: 426.05.

Compounds 22f-22i

The compounds listed in Table 8 were prepared according to similar methods as described in the preceding schemes and examples by employing correspondingly appropriate starting materials.

TABLE 8
| COMPOUNDS 22F-22I | | | |
|---|---|---|---|
| Cmpd. No. | Structure | $^1$H NMR | LC-MS: m/z [M + H] |
| 22f | 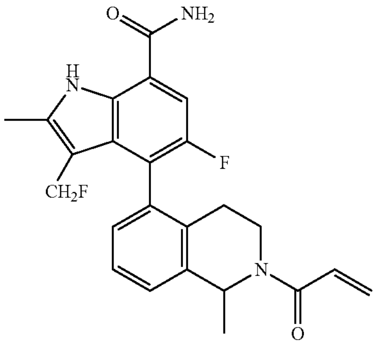 | | |
| 22g | 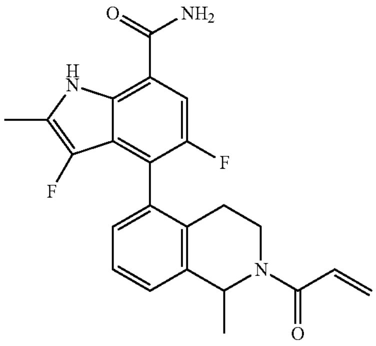 [SMILES: C=CC(=O)N1CCc2c(-c3c(F)cc(C(N)=O)c4[nH]c(C)c(F)c34)cccc2C1C] | | |
| 22h | 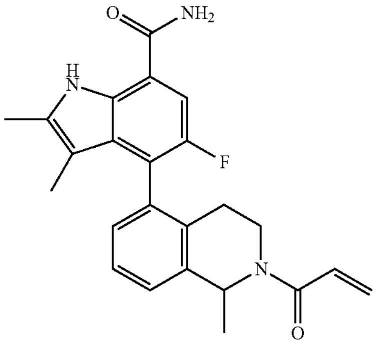 [SMILES: C=CC(=O)N1CCc2c(-c3c(F)cc(C(N)=O)c4[nH]c(C)c(C)c34)cccc2C1C] | | |
| 22i | 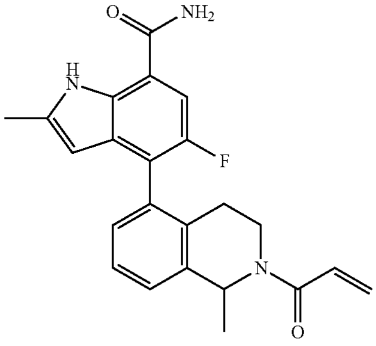 [SMILES: C=CC(=O)N1CCc2c(-c3c(F)cc(C(N)=O)c4[nH]c(C)cc34)cccc2C1C] | (300 MHz, DMSO-$d_6$) δ 11.16-10.94 (m, 1H), 8.11 (s, 1H), 7.67-7.44 (m, 2H), 7.41-7.26 (m, 2H), 7.23-7.08 (m, 1H), 7.02-6.70 (m, 1H), 6.25-6.07 (m, 1H), 5.83-5.34 (m, 3H), 4.38-3.82 (m, 1H), 3.53-2.92 (m, 1H), 2.70-2.23 (m, 5H), 1.61-1.37 (m, 3H). | 392.15 |

Preparation of Compounds of Formula (II) Wherein X is $CH_2$, $R^3$ is Cyclopropyl

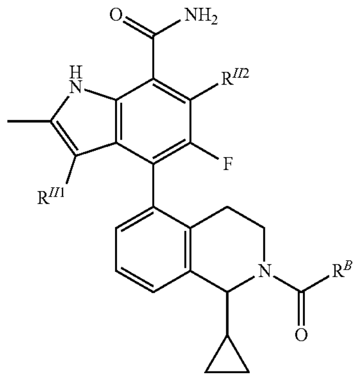

Example 23

Synthesis of 4-(2-acryloyl-1-cyclopropyl-1,2,3,4-tetrahydroisoquinolin-5-yl)-5-fluoro-2-methyl-1H-indole-7-carboxamide (Compound 23)

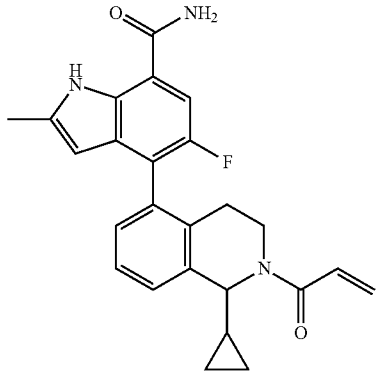 [SMILES: C=CC(=O)N1CCc2c(-c3c(F)cc(C(N)=O)c4[nH]c(C)cc34)cccc2C1C1CC1]

Compound 23 was prepared according to similar procedures as described herein.

$^1$H NMR (400 MHz, DMSO-$d_6$) δ 11.18-10.92 (m, 1H), 8.12 (s, 1H), 7.63-7.49 (m, 2H), 7.48-7.37 (m, 1H), 7.36-7.27 (m, 1H), 7.23-7.11 (m, 1H), 7.04-6.68 (m, 1H), 6.23-6.04 (m, 1H), 5.85-5.58 (m, 2H), 5.02-4.67 (m, 1H), 4.41-3.85 (m, 1H), 3.75-3.15 (m, 1H), 2.70-2.28 (m, 5H), 1.48-1.19 (m, 1H), 0.99-0.32 (m, 4H).

LC-MS: m/z=418.15 $[M+H]^+$.

Preparation of Compounds of Formula (II) Wherein X is $—CR^{x1}R^{x2}—$, and $R^{x1}$ and $R^{x2}$ Together with the C Atom to which there are Attached Form a $C_{3-6}$-Membered Carbocyclic Ring

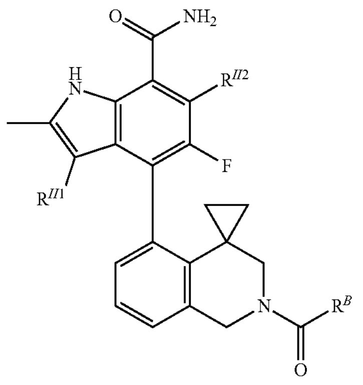

Example 24

Synthesis of 4-(2'-Acryloyl-2',3'-dihydro-1'H-spiro[cyclopropane-1,4'-isoquinolin]-5'-yl)-3-chloro-5-fluoro-2-methyl-1H-indole-7-carboxamide (Compound 24a)

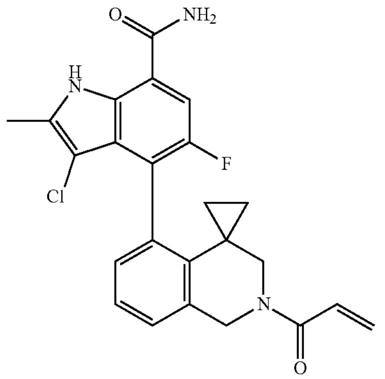 [SMILES: C=CC(=O)N1Cc2cccc(-c3c(F)cc(C(N)=O)c4[nH]c(C)c(Cl)c34)c2C2(CC2)C1]

Step 1: 3-bromo-2-(3-cyanopropoxy) benzonitrile

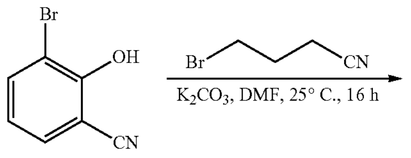

-continued

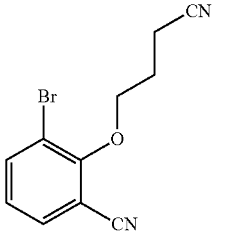

A mixture of 3-bromo-2-hydroxybenzonitrile (10 g, 50.5 mmol), 4-bromobutanenitrile (11.2 g, 75.8 mmol) and potassium carbonate (10.5 g, 75.8 mmol) in DMF (100 mL) was stirred at 25° C. for 16 h. The reaction mixture was diluted with water (200 mL) and extracted with ethyl acetate (3×100 mL). The combined extracts were washed with brine (120 mL), dried over sodium sulfate, and concentrated under vacuum. The residue was purified by column chromatography on silica gel (0 to 40% ethyl acetate in petroleum ether) to give 3-bromo-2-(3-cyanopropoxy) benzonitrile (12.0 g, 89%) as a colorless oil.

$^1$H NMR (300 MHz, DMSO-d6) δ 8.03 (dd, J=8.1, 1.5 Hz, 1H), 7.88 (dd, J=7.8, 1.5 Hz, 1H), 7.28-6.98 (m, 1H), 4.22 (t, J=6.0 Hz, 2H), 2.77 (t, J=7.2 Hz, 2H), 2.20-2.06 (m, 2H).

Step 2: 9-bromo-1,2-dihydrofuro[2,3-c] isoquinolin-5-amine

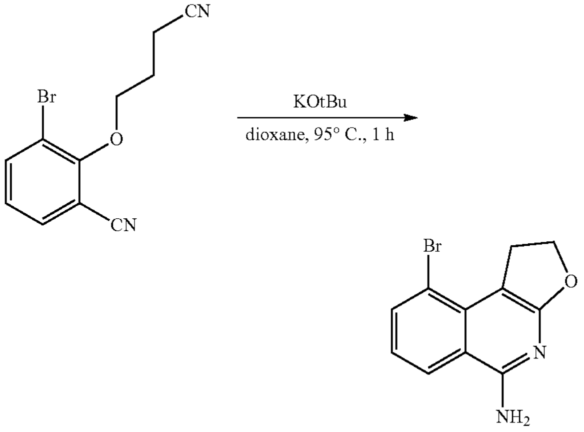

A mixture of 3-bromo-2-(3-cyanopropoxy) benzonitrile (1.0 g, 3.77 mmol) and potassium 2-methylpropan-2-olate (847 mg, 7.54 mmol) in dioxane (30 mL) was heated at 95° C. for 1 h. The reaction mixture was diluted with water (60 mL) and extracted with ethyl acetate (3×50 mL). The combined extracts were washed with brine (50 mL), dried over sodium sulfate, and concentrated under vacuum. The residue was purified by column chromatography on silica gel (0 to 50% ethyl acetate in petroleum ether) to give 9-bromo-1,2-dihydrofuro[2,3-c]isoquinolin-5-amine (300 mg, 30%) as a yellow solid.

$^1$H NMR (400 MHz, DMSO-d6) δ 8.11 (d, J=8.4 Hz, 1H), 7.79 (d, J=7.6 Hz, 1H), 7.09 (s, 2H), 7.06-6.95 (m, 1H), 4.50 (t, J=6.6 Hz, 2H), 3.73 (t, J=6.6 Hz, 2H).

ESI-MS $[M+H]^+$ calcd for ($C_{11}H_9BrN_2O$) 265.11, 267.11; found: 265.10, 267.10.

Step 3: 5'-bromo-1'H-spiro[cyclopropane-1,4'-isoquinoline]-1',3'(2'H)-dione

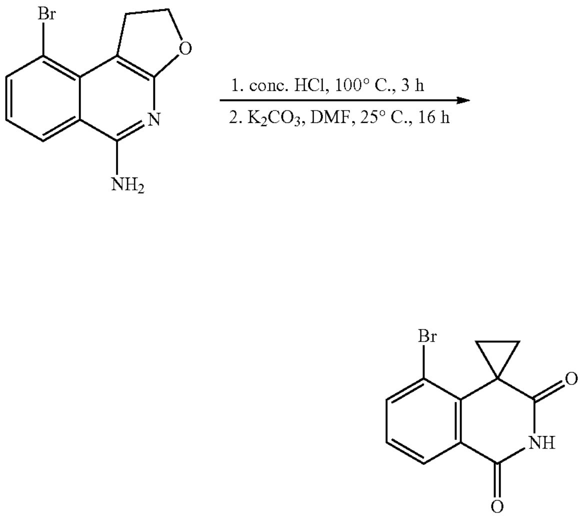

A mixture of 5'-bromo-1'H-spiro[cyclopropane-1,4'-isoquinoline]-1',3'(2'H)-dione and 9-bromo-1,2-dihydrofuro[2,3-c] isoquinolin-5-amine (1.80 g, 6.78 mmol) in concentrated hydrochloric acid (100 mL) was heated at 100° C. for 3 h. The reaction mixture was diluted with water (200 mL) and extracted with ethyl acetate (3×150 mL). The combined extracts were washed with brine (150 mL), dried over sodium sulfate, and concentrated under vacuum. The residue was dissolved into DMF (25 mL) and potassium carbonate (1.90 g, 13.9 mmol) was added. The reaction mixture was stirred at 25° C. for 16 h. The reaction mixture was quenched with water (50 mL) and extracted with ethyl acetate (3×40 mL). The combined extracts were washed with brine (50 mL), dried over sodium sulfate, and concentrated under vacuum. The residue was purified by column chromatography on silica gel (0 to 60% ethyl acetate in petroleum ether) to give 5'-bromo-1'H-spiro[cyclopropane-1,4'-isoquinoline]-1',3'(2'H)-dione (1.0 g, 55%) as a white solid.

$^1$H NMR (300 MHz, DMSO-d6) δ 7.43 (d, J=8.1 Hz, 1H), 7.20 (d, J=8.4 Hz, 1H), 7.11-7.01 (m, 1H), 1.93-1.81 (m, 2H), 0.86-0.77 (m, 2H).

ESI-MS [M−H]− calcd for ($C_{11}H_8BrNO_2$) 263.97, 265.97; found: 264.00, 266.00.

Step 4: 5'-bromo-2',3'-dihydro-1'H-spiro [cyclopropane-1,4'-isoquinoline

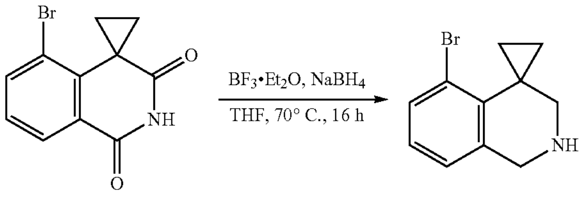

To a mixture of sodium borohydride (600 mg, 15.8 mmol) in THF (30 mL) was added $BF_3 \cdot Et_2O$ (3.00 g, 21.1 mmol) at 0° C. After stirring at this temperature for 1 h, a solution of 5'-bromo-1'H-spiro[cyclopropane-1,4'-isoquinoline]-1',3'(2'H)-dione (1.40 g, 5.26 mmol) in THF (50 mL) was added dropwise. The reaction mixture was heated at 70° C. for 16 h. The reaction mixture was quenched with water (60 mL) and extracted with ethyl acetate (3×50 mL). The combined extracts were washed with brine (50 mL), dried over sodium sulfate, and concentrated under vacuum. The residue was purified by column chromatography on silica gel (80% ethyl acetate in petroleum ether) to give 5'-bromo-2',3'-dihydro-1'H-spiro[cyclopropane-1,4'-isoquinoline (480 mg, 38%) as a white solid.

ESI-MS [M+H]+ calcd for ($C_{11}H_{12}BrN$) 238.02, 240.02; found: 238.10, 240.10.

Step 5: 1-(5'-bromo-1'H-spiro[cyclopropane-1,4'-isoquinolin]-2'(3'H)-yl) prop-2-en-1-one

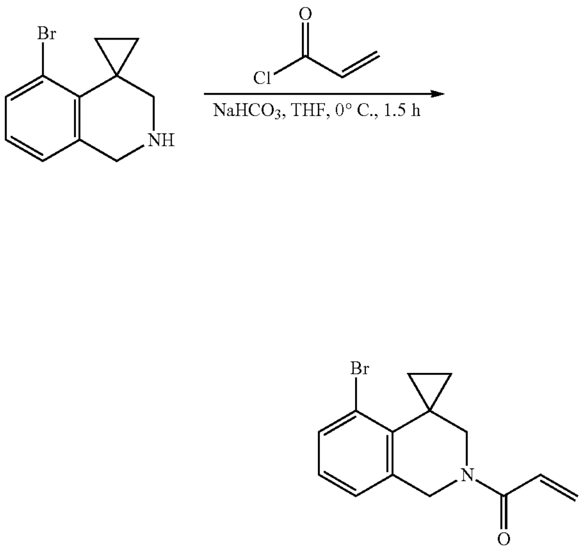

To a stirred mixture of 5'-bromo-2',3'-dihydro-1'H-spiro[cyclopropane-1,4'-isoquinoline] (480 mg, 2.02 mmol) in water (2.0 mL) and THF (8.0 mL) were added sodium bicarbonate (850 mg, 10.1 mmol) and acryloyl chloride (180 mg, 2.02 mmol) at 0° C. The reaction mixture was stirred at 0° C. for 1.5 h. The reaction mixture was diluted with water (30 mL) and extracted with ethyl acetate (3×25 mL). The combined extracts were washed with brine (30 mL), dried over sodium sulfate, and concentrated under vacuum. The residue was purified by column chromatography on silica gel (40% ethyl acetate in petroleum ether) to give 1-(5'-bromo-1'H-spiro[cyclopropane-1,4'-isoquinolin]-2'(3'H)-yl) prop-2-en-1-one (350 mg, 59%) as a yellow solid.

$^1$H NMR (400 MHz, DMSO-d6) δ 7.47 (d, J=8.4 Hz, 1H), 7.39-7.31 (m, 1H), 7.18-7.10 (m, 1H), 7.00-6.59 (m, 1H), 6.19-6.13 (m, 1H), 5.76-5.67 (m, 1H), 4.87 (s, 0.8H), 4.78 (s, 1.2H), 3.49 (s, 1.2H), 3.33 (s, 0.8H), 1.58-1.54 (m, 2H), 1.08-1.02 (m, 2H).

ESI-MS [M+H]+ calcd for ($C_{14}H_{14}BrNO$) 292.03, 294.03; found: 292.00, 294.00.

Step 6: 4-(2'-acryloyl-2',3'-dihydro-1'H-spiro[cyclopropane-1,4'-isoquinolin]-5'-yl)-5-fluoro-2-methyl-1H-indole-7-carboxamide (Compound 5b)

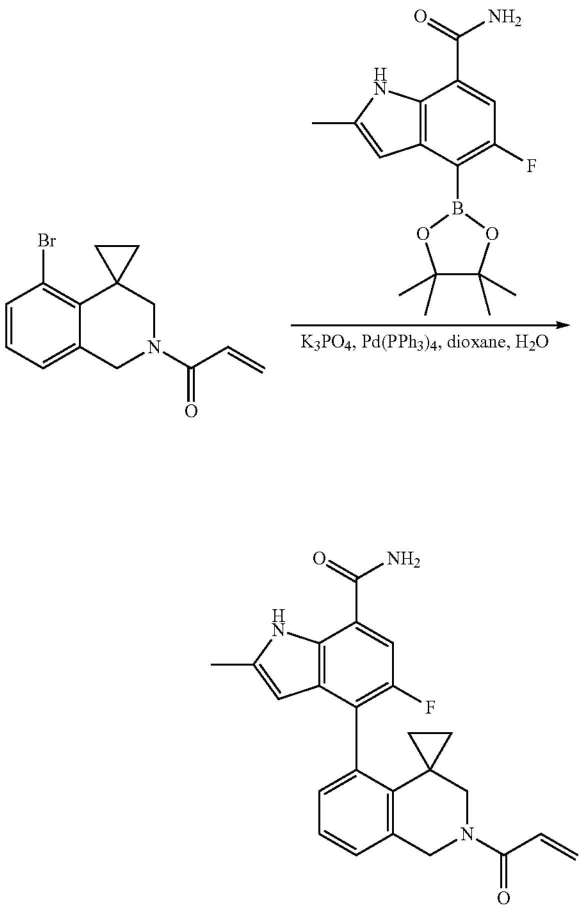

A mixture of 5-fluoro-2-methyl-4-(4,4,5,5-tetramethyl-1,3,2-dioxaborolan-2-yl)-1H-indole-7-carboxamide (350 mg, 1.10 mmol), 1-(5'-bromo-1'H-spiro[cyclopropane-1,4'-isoquinolin]-2'(3'H)-yl) prop-2-en-1-one (230 mg, 0.787 mmol) and potassium phosphate (500 mg, 2.36 mmol) and Pd(PPh3)4 (90 mg, 0.078 mmol) in water (2.5 mL) and dioxane (10 mL) was degassed and backfilled with nitrogen. The reaction mixture was heated under nitrogen at 80° C. for 16 h. The cooled reaction mixture was diluted with water (30 mL) and extracted with ethyl acetate (3×30 mL). The combined extracts were washed with brine (30 mL), dried over sodium sulfate, and concentrated under vacuum. The residue was purified by column chromatography on silica gel (80% ethyl acetate in petroleum ether) to give 4-(2'-acryloyl-2',3'-dihydro-1'H-spiro[cyclopropane-1,4'-isoquinolin]-5'-yl)-5-fluoro-2-methyl-1H-indole-7-carboxamide (170 mg, 56%) as a green solid.

$^1$H NMR (400 MHz, DMSO-$d_6$) δ 11.06 (s, 1H), 8.13 (s, 1H), 7.65-7.48 (m, 2H), 7.46-7.36 (m, 1H), 7.35-7.29 (m, 1H), 7.19-7.10 (m, 1H), 7.06-6.96 (m, 0.5H), 6.67-6.58 (m, 0.5H), 6.22-6.10 (m, 1H), 5.82-5.60 (m, 2H), 5.09-4.96 (m, 1H), 4.85-4.55 (m, 1H), 3.65-3.42 (m, 1H), 3.37-3.13 (m, 1H), 2.38 (s, 3H), 0.72-0.59 (m, 2H), 0.32-0.14 (m, 2H).

ESI-MS $[M+H]^+$ calcd for ($C_{24}H_{22}FN_3O_2$) 404.17, found: 404.30.

Step 7: 4-(2'-acryloyl-2',3'-dihydro-1'H-spiro[cyclopropane-1,4'-isoquinolin]-5'-yl)-3-chloro-5-fluoro-2-methyl-1H-indole-7-carboxamide (Compound 5a)

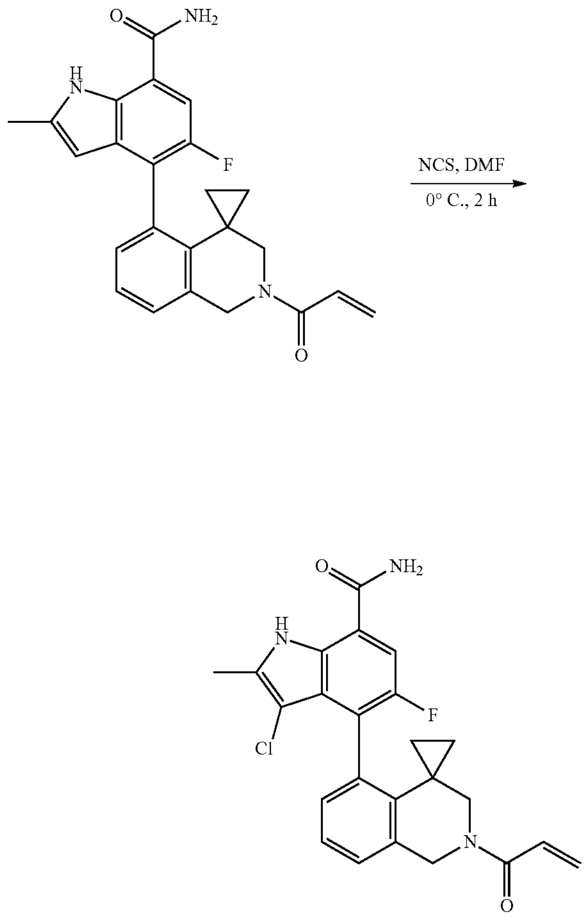

To a solution of 4-(2'-acryloyl-2',3'-dihydro-1'H-spiro[cyclopropane-1,4'-isoquinolin]-5'-yl)-5-fluoro-2-methyl-1H-indole-7-carboxamide (170 mg, 0.421 mmol) in DMF (6.0 mL) was added NCS (56.0 mg, 0.421 mmol) at 0° C. The reaction mixture was stirred at 0° C. for 2 h. The reaction mixture was quenched with water (20 mL) and extracted with ethyl acetate (3×15 mL). The combined extracts were washed with brine (3×20 mL), dried over sodium sulfate, and concentrated under vacuum. The residue was purified by Prep-HPLC (Column: Xselect CSH OBD Column 30×150 mm 5 um; mobile phase A: water (10 mmol/L $NH_4HCO_3$+ 0.1% $NH_3 \cdot H_2O$), mobile phase B: acetonitrile; flow rate: 60 mL/min; gradient: 38% B to 58% B, 7 min; 220 nm; retention time=5.32 minutes) to give 4-(2'-acryloyl-2',3'-dihydro-1'H-spiro[cyclopropane-1,4'-isoquinolin]-5'-yl)-3-chloro-5-fluoro-2-methyl-1H-indole-7-carboxamide (32.6 mg, 17%) as a white solid.

$^1H$ NMR (400 MHz, DMSO-d6) δ 11.43 (s, 1H), 8.18 (s, 1H), 7.68-7.56 (m, 2H), 7.38-7.35 (m, 1H), 7.24-7.21 (m, 1H), 7.05-6.54 (m, 2H), 6.14-6.08 (m, 1H), 5.69-5.60 (m, 1H), 4.98-4.65 (m, 2H), 3.42-3.20 (m, 2H), 2.34 (s, 3H), 0.67-0.53 (m, 2H), 0.36-0.22 (m, 2H).

ESI-MS [M+H]+ calcd for ($C_{24}H_{21}ClN_3O_2$) 438.13, found: 438.15.

Step 8: Separation of Isomers (R)-4-(2'-acryloyl-2',3'-dihydro-1'H-spiro[cyclopropane-1,4'-isoquinolin]-5'-yl)-3-chloro-5-fluoro-2-methyl-1H-indole-7-carboxamide (Compound 24c) and (S)-4-(2'-acryloyl-2',3'-dihydro-1'H-spiro[cyclopropane-1,4'-isoquinolin]-5'-yl)-3-chloro-5-fluoro-2-methyl-1H-indole-7-carboxamide (Compound 24d)

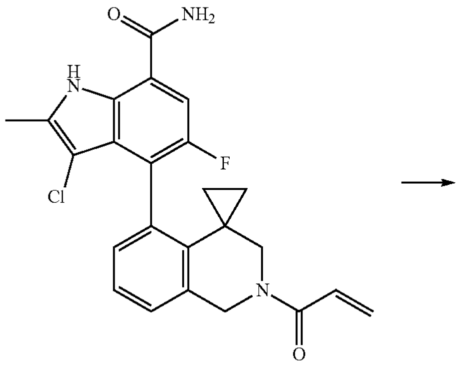

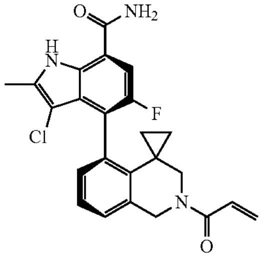

and

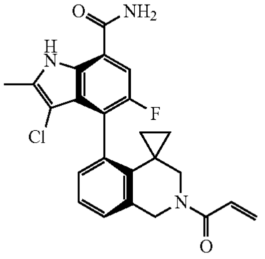

Compound 24c (R)

Compound 24d (S)

The two atropisomers were separated by Prep-Chiral-HPLC (sample amount=24 mg, column: CHIRALPAK IE, 2×25 cm, 5 um; mobile phase A: MTBE (0.5% 2 M $NH_3$-MeOH), mobile phase B: EtOH; flow rate: 20 mL/min; gradient: 5% B, 12 min; 220/254 nm):

Compound 24c: Retention Time=8.078 Minutes (7.9 mg)

$^1H$ NMR (400 MHz, Methanol-$d_4$) δ 7.50 (d, J=10.0 Hz, 1H), 7.36-7.34 (m, 1H), 7.27-7.25 (m, 1H), 7.09-7.07 (m, 1H), 6.99-6.55 (m, 1H), 6.26-6.23 (m, 1H), 5.83-5.72 (m, 1H), 5.03-4.78 (m, 2H), 3.59-3.37 (m, 2H), 2.38 (s, 3H), 0.68-0.58 (m, 2H), 0.48-0.40 (m, 2H).

ESI-MS $[M+H]^+$ calcd for ($C_{24}H_{21}ClN_3O_2$) 438.13, found: 438.10.

Compound 24d: Retention Time=9.991 Minutes (7.6 mg)

$^1H$ NMR (400 MHz, Methanol-$d_4$) δ 7.50 (d, J=10.0 Hz, 1H), 7.36-7.34 (m, 1H), 7.30-7.25 (m, 1H), 7.09-7.07 (m, 1H), 6.98-6.56 (m, 1H), 6.26-6.23 (m, 1H), 5.77-5.72 (m, 1H), 5.02-4.78 (m, 2H), 3.56-3.41 (m, 2H), 2.38 (s, 3H), 0.66-0.58 (m, 2H), 0.47-0.41 (m, 2H).

ESI-MS $[M+H]^+$ calcd for ($C_{24}H_{21}ClN_3O_2$) 438.13, found: 438.10.

Preparation of Compounds of Formula (II) Wherein X is $-CH_2CH_2-$

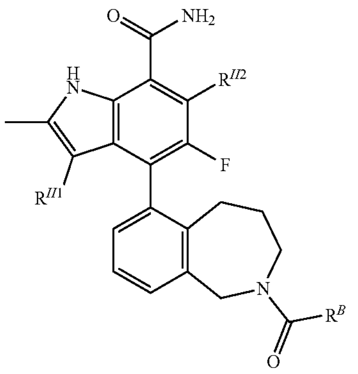

Example 25

Synthesis of 4-(2-Acryloyl-2,3,4,5-tetrahydro-1H-benzo[c]azepin-6-yl)-3-chloro-5-fluoro-2-methyl-1H-indole-7-carboxamide (Compound 25a)

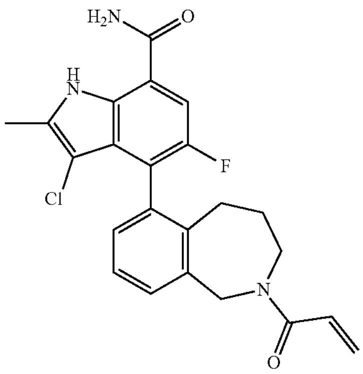 [SMILES: C=CC(=O)N1CCCc2c(cccc2-c2c(F)cc(C(N)=O)c3[nH]c(C)c(Cl)c23)C1]

Step 1: 5-fluoro-2-methyl-4-(4,4,5,5-tetramethyl-1,3,2-dioxaborolan-2-yl)-1H-indole-7-carboxamide

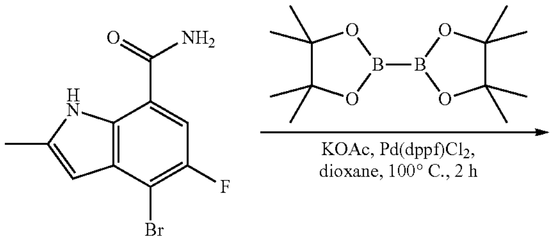

-continued

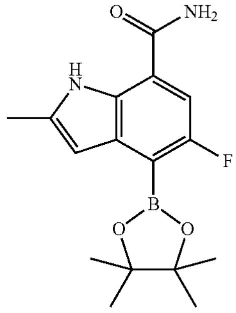

A mixture of 4-bromo-5-fluoro-2-methyl-1H-indole-7-carboxamide (prepared as described in example 1, 1.30 g, 4.80 mmol), 4,4,4',4',5,5,5',5'-octamethyl-2,2'-bi(1,3,2-dioxaborolane) (1.34 g, 5.28 mmol), potassium acetate (941 mg, 9.59 mmol) and Pd(dppf)$Cl_2$·DCM (196 mg, 0.24 mmol) in dioxane (16 mL) was degassed and backfilled with nitrogen. The reaction mixture was heated under nitrogen for 2 h at 100° C. The cooled reaction mixture was concentrated under vacuum. The residue was purified by column chromatography on silica gel (0 to 30% ethyl acetate in petroleum ether) to give 5-fluoro-2-methyl-4-(4,4,5,5-tetramethyl-1,3,2-dioxaborolan-2-yl)-1H-indole-7-carboxamide (660 mg) as a yellow solid.

ESI-MS $[M+H]^+$ calcd for ($C_{16}H_{20}BFN_2O_3$) 319.16, found: 319.25.

Step 2: 6-bromo-2,3,4,5-tetrahydro-1H-benzo[c]azepin-1-one

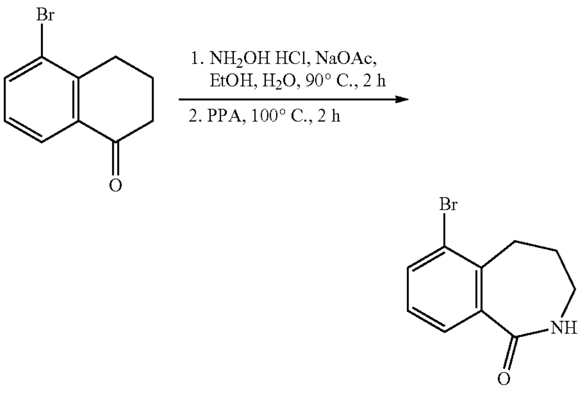

A mixture of 5-bromotetralin-1-one (5.2 g, 23.10 mmol), hydroxylamine hydrochloride (2.41 g, 34.7 mmol) and sodium acetate (2.84 g, 34.7 mmol) in ethanol (100 mL) and water (40 mL) was heated under nitrogen at 90° C. for 2 h. The cooled reaction mixture was diluted with water (150 mL) and extracted with ethyl acetate (3×100 mL). The combined extracts were washed with brine (100 mL), dried over sodium sulfate, and concentrated under vacuum. The residue was dissolved in polyphosphoric acid (100 mL) and stirred for 2 h at 100° C. The cooled reaction mixture was basified with aqueous sodium hydroxide and extracted with ethyl acetate (4×150 mL). The combined extracts were washed with brine (200 mL), dried over sodium sulfate and concentrated under vacuum. The residue was purified by column chromatography on silica gel (0 to 10% ethyl acetate in petroleum ether) to give 6-bromo-2,3,4,5-tetrahydro-2-benzazepin-1-one (2.7 g, 48%) as a brown solid.

ESI-MS $[M+H]^+$ calcd for ($C_{10}H_{10}BrNO$) 239.99, 241.99; found: 240.00, 242.00.

Step 3: 6-bromo-2,3,4,5-tetrahydro-1H-benzo[c]azepine

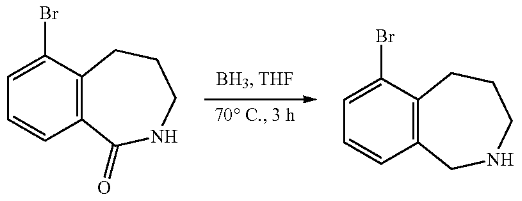

To a solution of 6-bromo-2,3,4,5-tetrahydro-2-benzazepin-1-one (2.7 g, 11.3 mmol) in THE (54 mL) was added borane (1 M in THF, 112 mL, 112 mmol). The reaction mixture was heated for 3 h at 70° C. The cooled reaction mixture was diluted with methanol (100 mL) and concentrated under vacuum. The residue was purified by column chromatography on silica gel (0 to 12% ethyl acetate in petroleum ether) to give 6-bromo-2,3,4,5-tetrahydro-1H-benzo[c]azepine (2.4 g, 94%) as a colorless oil.

$^1$H NMR (400 MHz, DMSO-$d_6$) δ 6.96 (dd, J=7.6, 1.2 Hz, 1H), 6.87-6.75 (m, 2H), 5.44 (s, 1H), 2.97-2.90 (m, 2H), 2.89-2.82 (m, 2H), 1.70-1.60 (m, 2H), 1.59-1.49 (m, 2H).

ESI-MS $[M+H]^+$ calcd for ($C_{10}H_{12}BrN$) 226.02, 228.02; found: 226.15, 228.15.

Step 4: 1-(6-bromo-1,3,4,5-tetrahydro-2H-benzo[c]azepin-2-yl)prop-2-en-1-one

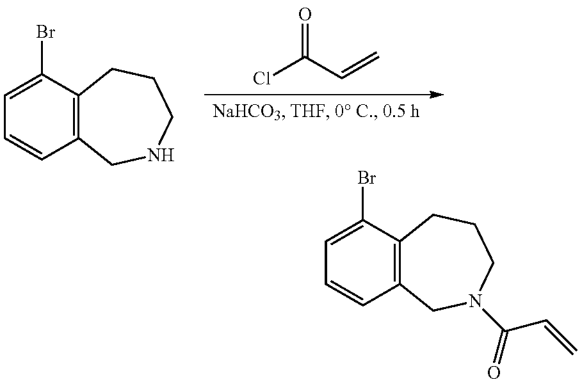

To a mixture of 6-bromo-2,3,4,5-tetrahydro-1H-benzo[c]azepine (1.6 g, 7.08 mmol) in THF (8 mL) and water (2 mL) were added sodium bicarbonate (1.78 g, 21.2 mmol) and acryloyl chloride (769 mg, 8.49 mmol) at 0° C. The reaction mixture was stirred for 0.5 h at 0° C. Water (20 mL) was added. The mixture was extracted with ethyl acetate (3×20 mL). The combined extracts were washed with brine (40 mL), dried over sodium sulfate, and concentrated under vacuum. The residue was purified by column chromatography on silica gel (0 to 15% ethyl acetate in petroleum ether) to give 1-(6-bromo-4,5-dihydro-1H-benzo[c]azepin-2(3H)-yl)prop-2-en-1-one (1.6 g, 80%) as a white solid.

$^1$H NMR (300 MHz, DMSO-$d_6$) δ 7.63 (dd, J=7.5, 2.1 Hz, 1H), 7.27-7.11 (m, 2H), 6.25-6.13 (m, 1H), 6.07-5.92 (m, 1H), 5.58 (dd, J=10.2, 2.4 Hz, 1H), 4.58-4.46 (m, 1H), 3.27-3.14 (m, 1H), 2.79-2.55 (m, 2H), 1.99-1.85 (m, 1H), 1.82-1.63 (m, 2H), 1.45-1.14 (m, 1H).

ESI-MS $[M+H]^+$ calcd for ($C_{13}H_{14}BrNO$) 280.03, 282.03; found: 280.10, 282.10.

Step 5: 4-(2-acryloyl-2,3,4,5-tetrahydro-1H-benzo[c]azepin-6-yl)-5-fluoro-2-methyl-1H-indole-7-carboxamide (Compound 25b)

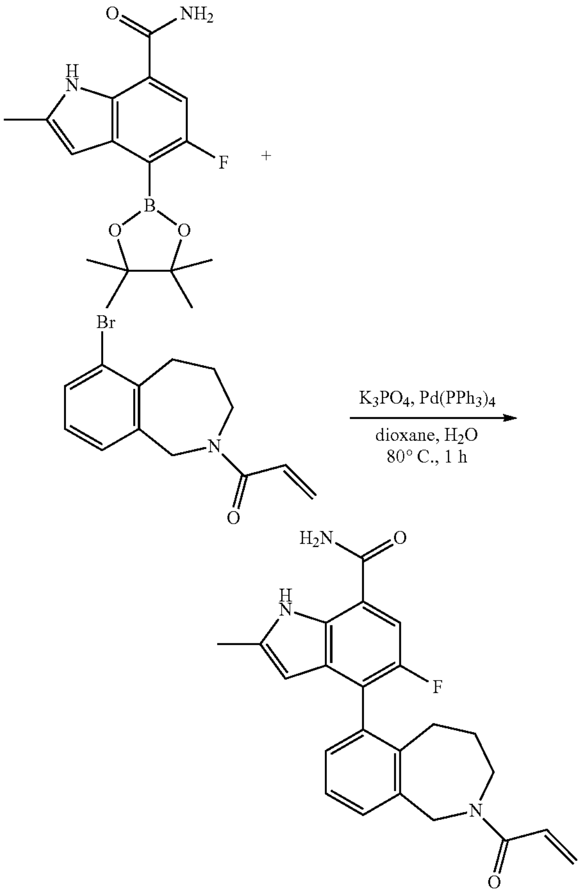

A mixture of 1-(6-bromo-1,3,4,5-tetrahydro-2-benzazepin-2-yl)prop-2-en-1-one (581 mg, 2.07 mmol), 5-fluoro-2-methyl-4-(4,4,5,5-tetramethyl-1,3,2-dioxaborolan-2-yl)-1H-indole-7-carboxamide (660 mg, 2.07 mmol), potassium phosphate (1.32 g, 6.22 mmol) and tetrakis(triphenylphosphine)palladium (240 mg, 0.21 mmol) in dioxane (8 mL) and water (2 mL) was degassed and backfilled with nitrogen. The reaction mixture was heated under nitrogen for 16 h at 80° C. The reaction mixture was diluted with water (30 mL) and extracted with ethyl acetate (3×30 mL). The combined extracts were washed with brine (40 mL), dried over sodium sulfate, and concentrated under vacuum. The residue was purified by column chromatography on silica gel (0 to 70% with ethyl acetate in petroleum ether) to give 5-fluoro-2-methyl-4-(2-prop-2-enoyl-1,3,4,5-tetrahydro-2-benzazepin-6-yl)-1H-indole-7-carboxamide (500 mg, 61%) as a white solid.

$^1H$ NMR (400 MHz, DMSO-d6) δ 11.08 (s, 1H), 8.12 (s, 1H), 7.65-7.48 (m, 2H), 7.42-7.36 (m, 1H), 7.29-7.18 (m, 2H), 6.25-6.15 (m, 1H), 6.14-6.00 (m, 1H), 5.88-5.68 (m, 1H), 5.67-5.59 (m, 1H), 4.69-4.52 (m, 1H), 2.82-2.66 (m, 1H), 2.45-2.25 (m, 5H), 1.89-1.55 (m, 3H), 1.48-1.08 (m, 1H).

ESI-MS $[M+H]^+$ calcd for ($C_{23}H_{22}FN_3O_2$) 392.17, found: 392.30.

Step 6: 4-(2-acryloyl-2,3,4,5-tetrahydro-1H-benzo[c]azepin-6-yl)-3-chloro-5-fluoro-1H-indole-7-carboxamide (Compound 25a)

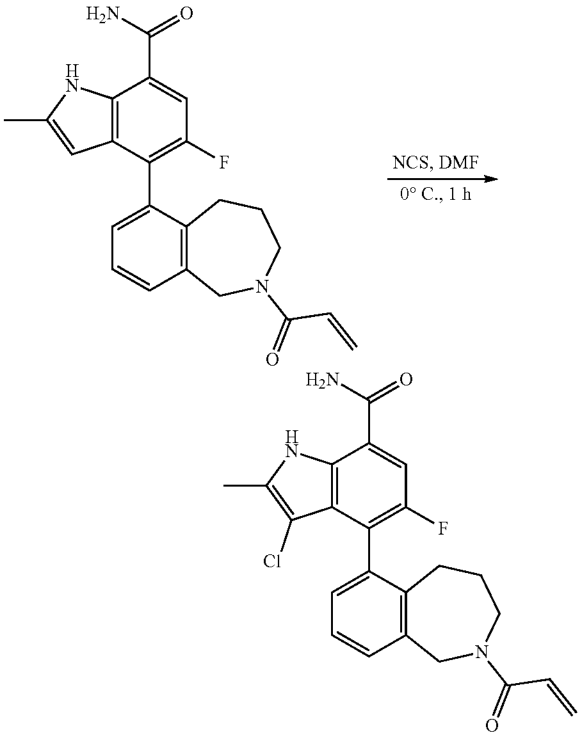

To a stirred solution of 5-fluoro-2-methyl-4-(2-prop-2-enoyl-1,3,4,5-tetrahydro-2-benzazepin-6-yl)-1H-indole-7-carboxamide (150 mg, 0.38 mmol) in N,N-dimethylformamide (5.0 mL) was added N-chlorosuccinimide (51 mg, 0.38 mmol) at 0° C. The reaction mixture was stirred at 0° C. for 1 h. The reaction mixture was diluted with water (30 mL) and extracted with ethyl acetate (3×25 mL). The combined extracts were washed with brine (30 mL), dried over sodium sulfate, and concentrated under vacuum. The residue was purified by Prep-HPLC with the following conditions: Column: Xselect CSH OBD Column 30×150 mm, 5 um; Mobile Phase A: Water (10 mmol/L $NH_4HCO_3$+0.1% $NH_3 \cdot H_2O$), Mobile Phase B: Acetonitrile; Flow rate: 60 mL/min; Gradient: 40% B to 60% B in 7 min; 220 nm; RT: 5.45 min) to give 3-chloro-5-fluoro-2-methyl-4-(2-prop-2-enoyl-1,3,4,5-tetrahydro-2-benzazepin-6-yl)-1H-indole-7-carboxamide (80 mg, 49%) as a mixture of atropisomers.

$^1H$ NMR (400 MHz, DMSO-d6) δ 11.46 (s, 1H), 8.19 (s, 1H), 7.70-7.57 (m, 2H), 7.43-7.29 (m, 1H), 7.28-7.19 (m, 2H), 6.28-5.96 (m, 2H), 5.68-5.57 (m, 1H), 4.66-4.52 (m, 1H), 2.80-2.65 (m, 1H), 2.45-2.25 (m, 5H), 1.77-1.51 (m, 3H), 1.33-1.10 (m, 1H).

ESI-MS $[M+H]^+$ calcd for ($C_{23}H_{21}ClFN_3O_2$) 426.13, 428.13; found: 426.25, 428.25.

Step 7: Separation of Isomers (R)-3-chloro-5-fluoro-2-methyl-4-(2-prop-2-enoyl-1,3,4,5-tetrahydro-2-benzazepin-6-yl)-1H-indole-7-carboxamide (compound 25c) and (S)-3-chloro-5-fluoro-2-methyl-4-(2-prop-2-enoyl-1,3,4,5-tetrahydro-2-benzazepin-6-yl)-1H-indole-7-carboxamide (Compound 25d)

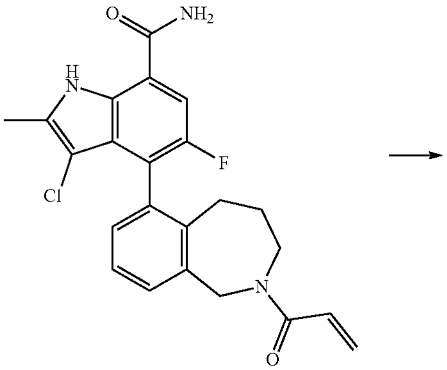

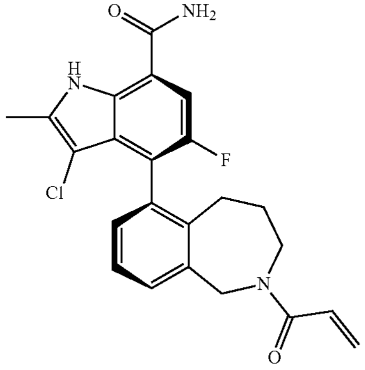

and

Compound 25c (R)

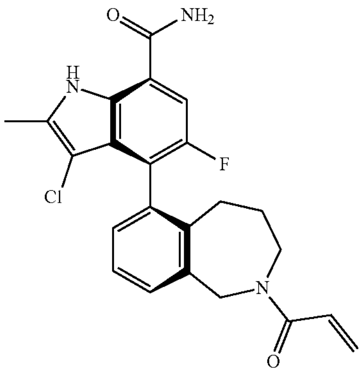

Compound 25d (S)

The two atropisomers were separated by Chiral-HPLC (sample amount=45 mg, CHIRAL ART Cellulose-SB, 2×25 cm, 5 um; mobile phase A: MTBE (0.5% 2 M $NH_3$-MeOH), mobile phase B: IPA; flow rate: 20 mL/min; gradient: 5% B, 14 min; 220/254 nm).

Compound 25c: Retention Time=8.502 Minutes (19.1 mg)

$^1$H NMR (400 MHz, DMSO-d6) δ 11.44 (s, 1H), 8.18 (s, 1H), 7.70-7.54 (m, 2H), 7.40-7.29 (m, 1H), 7.29-7.16 (m, 2H), 6.26-5.98 (m, 2H), 5.67-5.55 (m, 1H), 4.64-4.53 (m, 1H), 2.80-2.65 (m, 1H), 2.45-2.25 (m, 5H), 1.81-1.62 (m, 3H), 1.32-1.14 (m, 1H).

ESI-MS [M+H]+ calcd for ($C_{23}H_{21}ClFN_3O_2$) 426.13, 428.13; found: 426.10, 428.10.

Compound 25d: Retention Time=11.588 Minutes (19.3 mg)

$^1$H NMR (400 MHz, DMSO-d6) δ 11.44 (s, 1H), 8.18 (s, 1H), 7.70-7.60 (m, 2H), 7.38-7.29 (m, 1H), 7.27-7.17 (m, 2H), 6.26-6.00 (m, 2H), 5.67-5.56 (m, 1H), 4.64-4.53 (m, 1H), 2.80-2.65 (m, 1H), 2.43-2.30 (m, 5H), 1.77-1.65 (m, 3H), 1.33-1.15 (m, 1H).

ESI-MS [M+H]+ calcd for ($C_{23}H_{21}ClFN_3O_2$) 426.13, 428.13; found: 426.05, 428.05.

Synthesis of 4-(2-acryloyl-2,3,4,5-tetrahydro-1H-benzo[c]azepin-6-yl)-3,5-difluoro-2-methyl-1H-indole-7-carboxamide (Compound 25e)

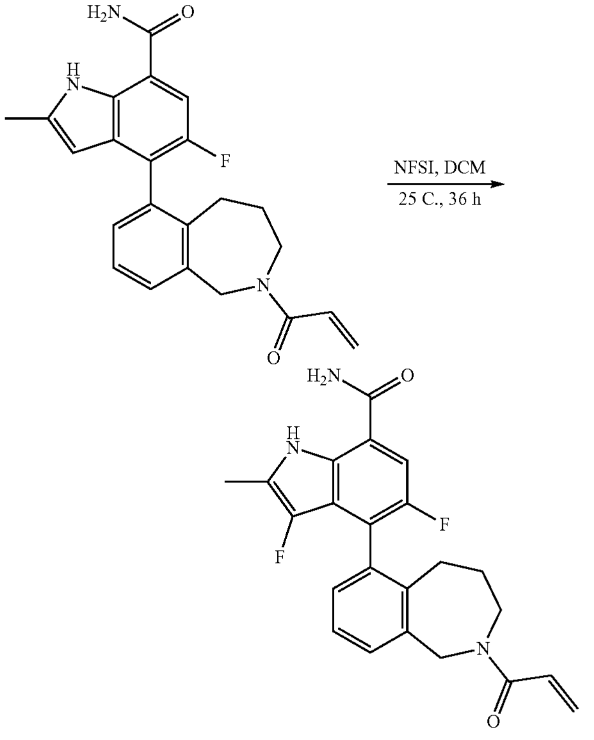

To a stirred solution of 4-(2-acryloyl-2,3,4,5-tetrahydro-1H-benzo[c]azepin-6-yl)-5-fluoro-2-methyl-1H-indole-7-carboxamide (80 mg, 0.20 mmol) in dichloromethane (10 mL) was added N-Fluorobenzenesulfonimide (126 mg, 0.51 mmol). The reaction mixture was stirred for 36 h at 25° C. The reaction mixture was diluted with water (30 mL) and extracted with dichloromethane (3×30 mL). The combined extracts were washed with brine (100 mL), dried over sodium sulfate, and concentrated under vacuum. The residue was purified by Prep-HPLC (Column: YMC-Actus Triart C18, 30×250 mm, 5 um; mobile phase A: water (10 mmol/L $NH_4HCO_3$+0.1% $NH_3 \cdot H_2O$), mobile phase B: acetonitrile; flow rate: 60 mL/min; gradient: 40% B to 50% B, 8 min; 254 nm; retention time=7.95) to give 4-(2-acryloyl-2,3,4,5-tetrahydro-1H-benzo[c]azepin-6-yl)-3,5-difluoro-2-methyl-1H-indole-7-carboxamide (8.0 mg, 9%) as a white solid.

$^1$H NMR (400 MHz, DMSO-d6) δ 10.87 (s, 1H), 8.09 (s, 1H), 7.65-7.43 (m, 2H), 7.37-7.12 (m, 3H), 6.20-6.05 (m, 1H), 6.03-5.80 (m, 1H), 5.59-5.52 (m, 1H), 4.60-4.45 (m, 1H), 2.75-2.58 (m, 1H), 2.42-2.28 (m, 2H), 2.24 (s, 3H), 1.75-1.52 (m, 3H), 1.30-1.05 (m, 1H).

ESI-MS [M+H]+ calcd for ($C_{23}H_{21}F_2N_3O_2$) 410.16, found: 410.30.

Preparation of Compounds of Formula (II) Wherein X is —$CR^{x1}R^{x2}$—, and $R^{x1}$ is H and $R^{x2}$ and $R^3$ Together Form an Alkylene Bridge

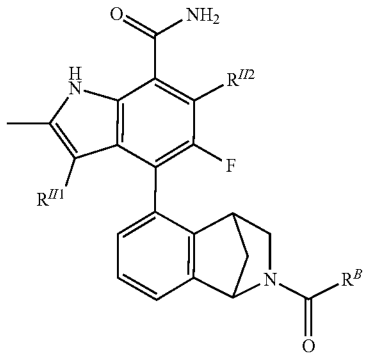

Example 26

Synthesis of 4-(2-acryloyl-1,2,3,4-tetrahydro-1,4-methanoisoquinolin-5-yl)-3-chloro-5-fluoro-2-methyl-1H-indole-7-carboxamide (Compound 26)

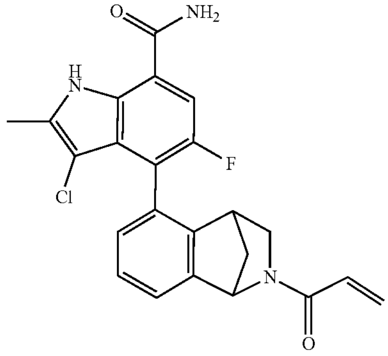 [SMILES: C=CC(=O)N1CC2CC1c1cccc(-c3c(F)cc(C(N)=O)c4[nH]c(C)c(Cl)c34)c12]

Step 1: 4-ethyl 1-methyl 2-(2-bromophenyl)succinate

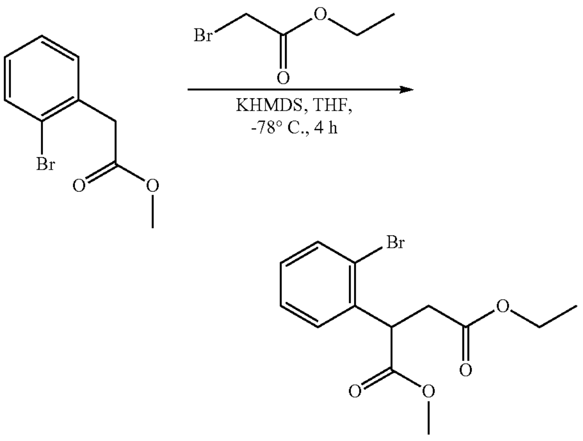

To a stirred solution of methyl 2-(2-bromophenyl)acetate (10.0 g, 43.7 mmol) in THF (120 mL) was added dropwise potassium bis(trimethylsilyl)amide (1.0 M, 65.5 mL, 65.5 mmol) at −78° C. under nitrogen. After stirring at this temperature for 1 h, ethyl 2-bromoacetate (50.00 g, 299 mmol) was added dropwise. The reaction mixture was stirred for 1 h at −78° C., then at −40° C. for 3 h. The reaction mixture was diluted with water (200 mL) and extracted with ethyl acetate (3×100 mL). The combined extracts were washed with brine (100 mL), dried over sodium sulfate, and concentrated under vacuum. The residue was purified by column chromatography on silica gel (0 to 30% ethyl acetate in petroleum ether) to give 4-ethyl 1-methyl 2-(2-bromophenyl)succinate (11.9 g, 86%) as a white solid.

$^1$H NMR (400 MHz, DMSO-d6) δ 7.63-7.59 (m, 1H), 7.38-7.28 (m, 2H), 7.24-7.19 (m, 1H), 4.52-4.45 (m, 1H), 4.03-4.00 (m, 2H), 3.59 (s, 3H), 3.03-2.99 (m, 1H), 2.69-2.66 (m, 1H), 1.12 (t, J=6.8 Hz, 3H).

ESI-MS [M+H]+ calcd for ($C_{13}H_{15}BrO_4$) 315.02, 317.02; found: 314.95, 316.95.

Step 2: 2-(2-bromophenyl)succinic acid

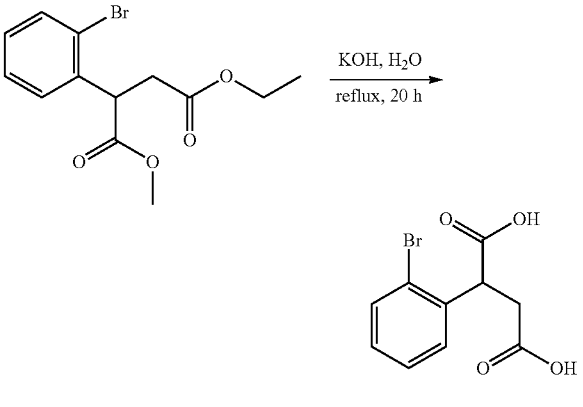

To a stirred mixture of 4-ethyl 1-methyl 2-(2-bromophenyl)succinate (11.9 g, 37.8 mmol) in water (150 mL) was added potassium hydroxide (21.2 g, 378 mmol). The reaction mixture was heated under reflux for 20 h. The pH of the cooled reaction mixture was adjusted to 3-4 with 1 M aq. HCl. The solid was collected by filtration and dried under reduced pressure to give 2-(2-bromophenyl)succinic acid (9.80 g) as a white solid.

$^1$H NMR (300 MHz, DMSO-d6) δ 12.49 (brs, 2H), 7.63 (dd, J=8.1, 1.5 Hz, 1H), 7.40-7.13 (m, 3H), 4.35-4.30 (m, 1H), 2.89-2.85 (m, 1H), 2.59-2.50 (m, 1H).

ESI-MS [M+H]+ calcd for ($C_{10}H_9BrO_4$) 272.97, 274.97; found: 272.85, 274.85.

Step 3: 3-(2-bromophenyl)dihydrofuran-2,5-dione

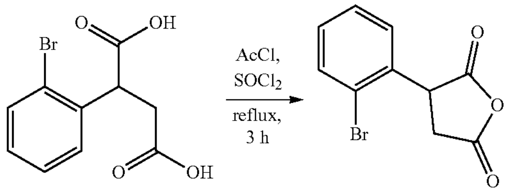 [SMILES: O=C(O)CC(C(=O)O)c1ccccc1Br ; O=C1CC(c2ccccc2Br)C(=O)O1]

A mixture of 2-(2-bromophenyl)succinic acid (9.80 g, crude) and sulfurous dichloride (4.30 g, 35.9 mmol) in acetyl chloride (84.0 g) was stirred under reflux for 3 h. The cooled reaction mixture was concentrated under vacuum to give 3-(2-bromophenyl)dihydrofuran-2,5-dione (9.0 g) as a yellow solid.

$^1$H NMR (400 MHz, DMSO-d6) δ 7.67 (dd, J=8.0, 1.2 Hz, 1H), 7.55 (dd, J=7.6, 1.6 Hz, 1H), 7.48-7.36 (m, 1H), 7.34-7.24 (m, 1H), 5.00-4.87 (m, 1H), 3.51-3.35 (m, 1H), 3.21-3.09 (m, 1H).

ESI-MS [M−H]− calcd for ($C_{10}H_7BrO_3$) 252.96, 254.96; found: 252.85, 254.85.

Step 4: 7-bromo-3-oxo-2,3-dihydro-1H-indene-1-carboxylic acid

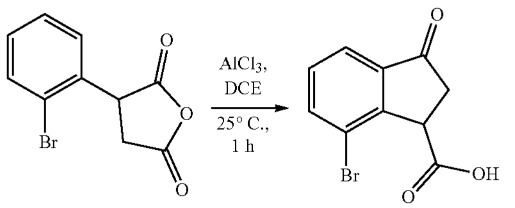 [SMILES: O=C1CC(c2ccccc2Br)C(=O)O1 ; O=C1CC(C(=O)O)c2c(Br)cccc21]

To a solution of 3-(2-bromophenyl)dihydrofuran-2,5-dione (9.0 g) in 1,2-dichloroethane (125 mL) was added dropwise a solution of aluminum chloride (11.0 g, 82.5 mmol) in 1,2-dichloroethane (32 mL) at 0° C. The reaction mixture was stirred at 25° C. for 1 h. The reaction mixture was diluted with water (100 mL) and was extracted with DCM (3×100 mL). The combined extracts were washed with brine (100 mL), dried over sodium sulfate, and concentrated under vacuum to give 7-bromo-3-oxo-2,3-dihydro-1H-indene-1-carboxylic acid (8.30 g) as a yellow solid.

$^1$H NMR (300 MHz, DMSO-d6) δ 12.81 (brs, 1H), 7.96 (dd, J=7.8, 1.2 Hz, 1H), 7.70 (dd, J=7.5, 0.9 Hz, 1H), 7.48-7.42 (m, 1H), 4.18-4.09 (m, 1H), 3.23-3.10 (m, 1H), 2.72-2.67 (m, 1H).

Step 5: methyl 7-bromo-3-oxo-2,3-dihydro-1H-indene-1-carboxylate

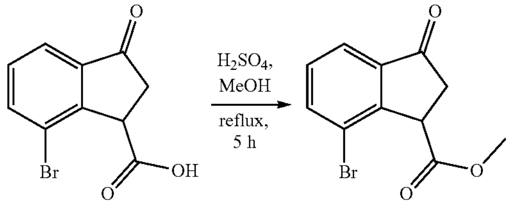

To a solution of 7-bromo-3-oxo-2,3-dihydro-1H-indene-1-carboxylic acid (8.00 g, 31.4 mmol) in methanol (130 mL) was added concentrated sulfuric acid (4.0 mL). The reaction mixture was heated under reflux for 5 h. The reaction mixture was concentrated under vacuum. The residue was diluted with water (150 mL) and extracted with ethyl acetate (3×100 mL). The combined extracts were washed with brine (100 mL), dried over anhydrous sodium sulfate, and concentrated under vacuum. The residue was purified by column chromatography on silica gel (0 to 20% ethyl acetate in petroleum ether) to give methyl 7-bromo-3-oxo-2,3-dihydro-1H-indene-1-carboxylate (7.30 g, 86%) as a yellow solid.

$^1$H NMR (300 MHz, DMSO-d6) δ 7.99 (d, J=7.8, 1.2 Hz, 1H), 7.74 (dd, J=7.5, 1.2 Hz, 1H), 7.64-7.49 (m, 1H), 4.33 (dd, J=8.7, 2.9 Hz, 1H), 3.67 (s, 3H), 3.17 (dd, J=19.1, 8.7 Hz, 1H), 2.79 (dd, J=19.1, 2.9 Hz, 1H).

ESI-MS [M+H+ACN]+ calcd for ($C_{11}H_9BrO_3$) 309.97, 311.97; found: 309.95, 311.95.

Step 6: methyl (Z)-7-bromo-3-(hydroxyimino)-2,3-dihydro-1H-indene-1-carboxylate

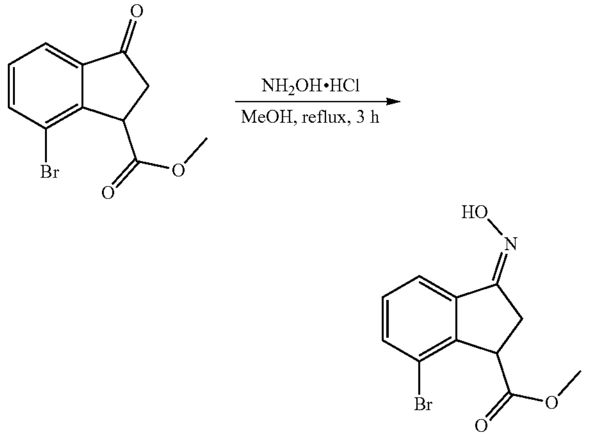

To a solution of methyl 7-bromo-3-oxo-2,3-dihydro-1H-indene-1-carboxylate (7.30 g, 27.1 mmol) in MeOH (50 mL) was added hydroxylamine hydrochloride (2.60 g, 36.8 mmol). The reaction mixture was stirred under reflux for 3 h. The cooled reaction mixture was diluted with water (150 mL) and extracted with ethyl acetate (3×100 mL). The combined extracts were washed with brine (2×100 mL), dried over anhydrous sodium sulfate, and concentrated under vacuum to give methyl (Z)-7-bromo-3-(hydroxyimino)-2,3-dihydro-1H-indene-1-carboxylate (7.5 g) as a yellow solid.

$^1$H NMR (300 MHz, DMSO-d6) δ 11.32 (s, 1H), 7.66-7.58 (m, 2H), 7.39-7.31 (m, 1H), 4.21 (dd, J=9.6, 3.3 Hz, 1H), 3.65 (s, 3H), 3.23 (dd, J=18.9, 9.6 Hz, 1H), 2.88 (dd, J=18.9, 3.3 Hz, 1H).

ESI-MS [M+H]+ calcd for ($C_{11}H_{10}BrNO_3$) 283.98, 285.98; found: 284.00, 286.00.

Step 7: Methyl 3-amino-7-bromo-2,3-dihydro-1H-indene-1-carboxylate

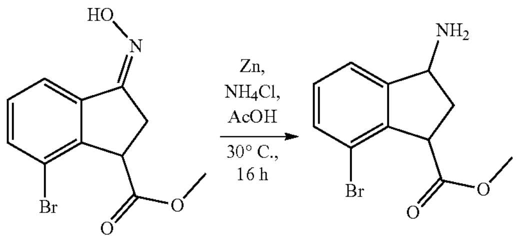 [SMILES: COC(=O)C1C/C(=N/O)c2cccc(Br)c21 ; COC(=O)C1CC(N)c2cccc(Br)c21]

To a solution of methyl (Z)-7-bromo-3-(hydroxyimino)-2,3-dihydro-1H-indene-1-carboxylate (1.0 g, 3.52 mmol) in acetic acid (30 mL) were added zinc powder (2.30 g, 35.2 mmol) and ammonium chloride (1.88 g, 35.2 mmol). The reaction mixture was stirred for 16 h at 30° C. The reaction mixture was basified with saturated aqueous $NaHCO_3$ and extracted with ethyl acetate (3×60 mL). The combined extracts were washed with brine (50 mL), dried over sodium sulfate, and concentrated under vacuum to give methyl 3-amino-7-bromo-2,3-dihydro-1H-indene-1-carboxylate (700 mg) as a white solid.

ESI-MS [M+H]+ calcd for ($C_{11}H_{12}BrNO_2$) 270.01, 272.01; found: 270.00, 272.00.

Step 8: 3-amino-7-bromo-2,3-dihydro-1H-indene-1-carboxylic acid

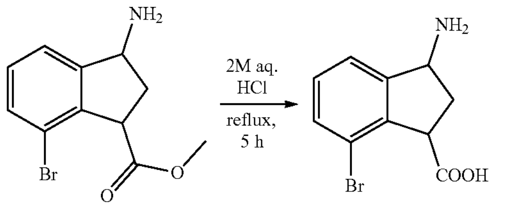

A mixture of methyl 3-amino-7-bromo-2,3-dihydro-1H-indene-1-carboxylate (6.00 g, 22.2 mmol) in 2 M hydrochloric acid (300 mL) was heated under reflux for 5 h. The pH of the cooled reaction mixture was adjusted to 7 with saturated aqueous sodium bicarbonate and the mixture was extracted with ethyl acetate (4×150 mL). The combined extracts were washed with brine (150 mL), dried over sodium sulfate, and concentrated under vacuum to give 3-amino-7-bromo-2,3-dihydro-1H-indene-1-carboxylic acid (5.50 g) as a white solid.

$^1$H NMR (300 MHz, DMSO-d6) δ 12.94 (s, 1H), 8.57 (s, 2H), 7.69-7.62 (m, 2H), 7.36-7.32 (m, 1H), 4.92-4.74 (m, 1H), 3.99-3.94 (m, 1H), 2.95-2.85 (m, 1H), 2.14-2.08 (m, 1H).

ESI-MS [M+H]+ calcd for ($C_{10}H_{10}BrNO_2$) 255.99, 257.99; found: 255.95, 257.95.

Step 9: 5-bromo-1,4-dihydro-1,4-methanoisoquinolin-3(2H)-one

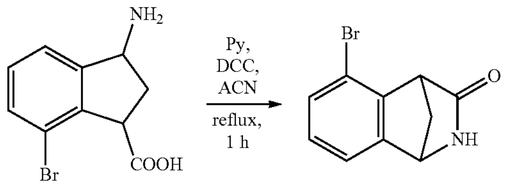 [SMILES: NC1CC(C(=O)O)c2c(Br)cccc21 ; O=C1NC2CC1c1c(Br)cccc12]

To a solution of 3-amino-7-bromo-2,3-dihydro-1H-indene-1-carboxylic acid (5.50 g, crude) and pyridine (9.30 g, 117 mmol) in acetonitrile (150 mL) was added dicyclohexylcarbodiimide (5.3 g, 25.8 mmol). The reaction mixture was heated under reflux for 1 hr. The cooled reaction mixture was quenched with water (200 mL) and extracted with ethyl acetate (3×150 mL). The combined extracts were washed with brine (100 mL), dried over sodium sulfate, and concentrated under vacuum. The residue was purified by column chromatography on silica gel (0 to 50% ethyl acetate in petroleum ether) to give 5-bromo-1,4-dihydro-1,4-methanoisoquinolin-3(2H)-one (2.40 g, 43%) as a yellow solid.

ESI-MS [M+H]+ calcd for ($C_{10}H_8BrNO$) 237.98, 239.98; found: 238.00, 240.00.

Step 10: 5-bromo-1,2,3,4-tetrahydro-1,4-methanoisoquinoline

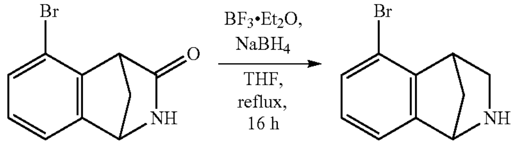 [SMILES: O=C1NC2CC1c1c(Br)cccc12 ; Brc1cccc2c1C1CNC2C1]

To a solution of sodium borohydride (596 mg, 15.8 mmol) in THF (10 mL) was added $BF_3{\cdot}Et_2O$ (2.98 g, 21.0 mmol) at 0° C. After stirring at this temperature for 1 h, a solution of 5-bromo-1,4-dihydro-1,4-methanoisoquinolin-3(2H)-one (1.25 g, 5.25 mmol) in THF (10 mL) was added dropwise. The reaction mixture was stirred under reflux for 16 h. The cooled reaction mixture was quenched with water (40 mL) and extracted with ethyl acetate (3×30 mL). The combined extracts were washed with brine (40 mL), dried over sodium sulfate, and concentrated under vacuum to give 5-bromo-1,2,3,4-tetrahydro-1,4-methanoisoquinoline (1.00 g) as a yellow solid.

ESI-MS [M+H]+ calcd for ($C_{10}H_{10}BrN$) 224.00, 226.00; found: 224.00, 226.00.

Step 11: 1-(5-bromo-3,4-dihydro-1,4-methanoisoquinolin-2(1H)-yl)prop-2-en-1-one

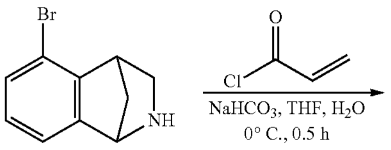

-continued

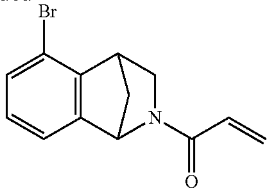

To a mixture of 5-bromo-1,2,3,4-tetrahydro-1,4-methanoisoquinoline (800 mg, 3.57 mmol) in water (2 mL) and THF (8 mL) were added sodium bicarbonate (1.50 g, 17.9 mmol) and acryloyl chloride (323 mg, 3.57 mmol) at 0° C. The reaction mixture was stirred at 0° C. for 0.5 h. The reaction mixture was diluted with water (30 mL) and extracted with ethyl acetate (3×30 mL). The combined extracts were washed with brine (30 mL), dried over anhydrous sodium sulfate, and concentrated under vacuum. The residue was purified by column chromatography on silica gel (0 to 50% ethyl acetate in petroleum ether) to give 1-(5-bromo-3,4-dihydro-1,4-methanoisoquinolin-2(1H)-yl)prop-2-en-1-one (400 mg, 40%) as a white solid.

ESI-MS [M+H]+ calcd for ($C_{13}H_{12}BrNO$) 278.01, 280.01; found: 277.95, 279.95.

Step 12: 4-(2-acryloyl-1,2,3,4-tetrahydro-1,4-methanoisoquinolin-5-yl)-5-fluoro-2-methyl-1H-indole-7-carboxamide

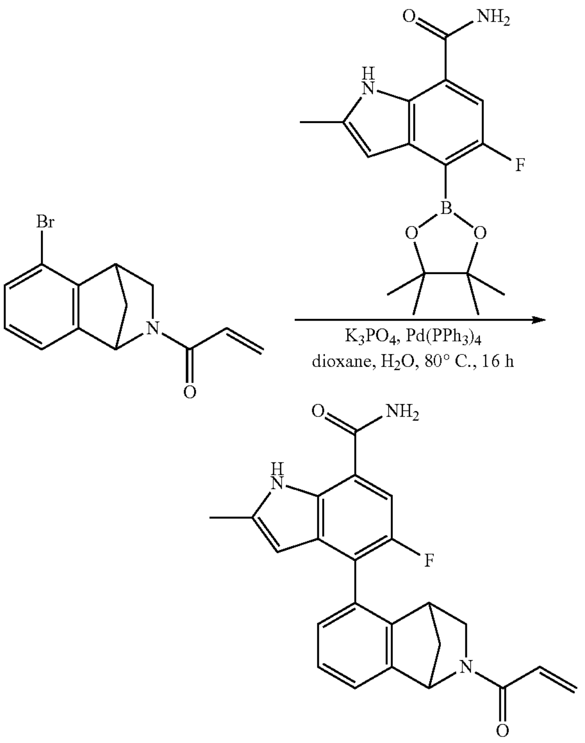

A mixture of 1-(5-bromo-3,4-dihydro-1,4-methanoisoquinolin-2(1H)-yl)prop-2-en-1-one (755 mg, 2.37 mmol), 5-fluoro-2-methyl-4-(4,4,5,5-tetramethyl-1,3,2-dioxaborolan-2-yl)-1H-indole-7-carboxamide (600 mg, 2.16 mmol), potassium phosphate (1.37 g, 6.47 mmol) and $Pd(PPh_3)_4$ (250 mg, 0.216 mmol) in water (3.0 mL) and dioxane (12 mL) was degassed and backfilled with nitrogen. The reaction mixture was heated under nitrogen at 80° C. for 16 h. The cooled reaction mixture was diluted with water (30 mL) and extracted with ethyl acetate (3x30 mL). The combined extracts were washed with brine (50 mL), dried over sodium sulfate, and concentrated under vacuum. The residue was purified by column chromatography on silica gel (0 to 10% methanol in dichloromethane) to give 4-(2-acryloyl-1,2,3,4-tetrahydro-1,4-methanoisoquinolin-5-yl)-5-fluoro-2-methyl-1H-indole-7-carboxamide (440 mg, 52%) as a green solid.

$^1$H NMR (300 MHz, DMSO-d6) δ 11.09 (s, 1H), 8.14 (s, 1H), 7.67-7.21 (m, 5H), 7.08-6.24 (m, 1H), 6.17-5.43 (m, 4H), 3.94-3.45 (m, 2H), 3.03-2.60 (m, 1H), 2.46-2.34 (m, 3H), 2.05-1.92 (m, 2H).

ESI-MS [M+H]+ calcd for ($C_{23}H_{20}FN_3O_2$) 390.15, found: 390.30.

Step 13: 4-(2-acryloyl-1,2,3,4-tetrahydro-1,4-methanoisoquinolin-5-yl)-3-chloro-5-fluoro-2-methyl-1H-indole-7-carboxamide (Compound 26)

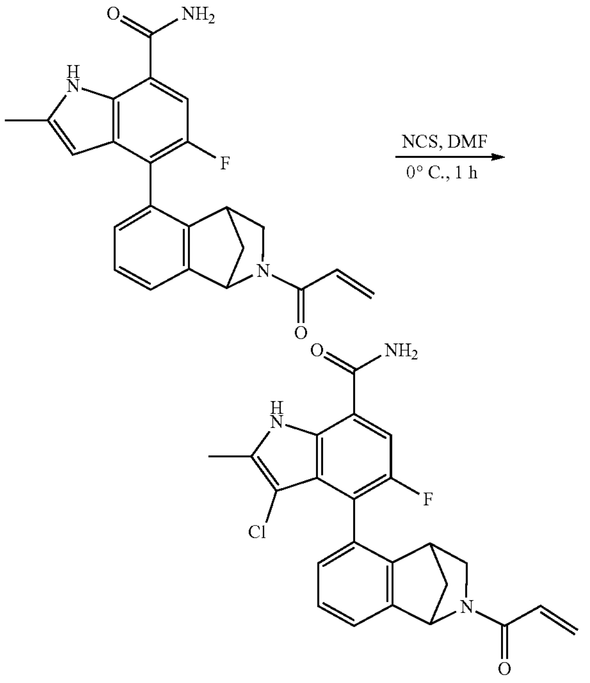

To a solution of 4-(2-acryloyl-1,2,3,4-tetrahydro-1,4-methanoisoquinolin-5-yl)-5-fluoro-2-methyl-1H-indole-7-carboxamide (200 mg, 0.51 mmol) in DMF (6 mL) was added NCS (83 mg, 0.62 mmol) at 0° C. The reaction mixture was stirred at 0° C. for 1 h. The reaction mixture was quenched with water (15 mL) and extracted with ethyl acetate (3x15 mL). The combined extracts were washed with brine (3x20 mL), dried over anhydrous sodium sulfate, and concentrated under vacuum. The residue was purified by Prep-HPLC (Column: Xselect CSH OBD Column 30x150 mm 5 um; mobile phase A: water (10 mmol/L $NH_4HCO_3$+0.1% $NH_3 \cdot H_2O$), mobile phase B: acetonitrile; flow rate: 60 mL/min; Gradient: 38% B to 58% B, 7 min; 220 nm; retention time=5.32 minutes) to give 4-(2-acryloyl-1,2,3,4-tetrahydro-1,4-methanoisoquinolin-5-yl)-3-chloro-5-fluoro-2-methyl-1H-indole-7-carboxamide (91 mg, 42%) as a white solid.

$^1$H NMR (300 MHz, DMSO-d6) δ 11.49 (s, 1H), 8.21 (s, 1H), 7.71-7.66 (m, 2H), 7.40-7.32 (m, 1H), 7.26-6.20 (m, 3H), 6.18-6.01 (m, 1H), 5.75-5.47 (m, 2H), 3.79-3.40 (m, 1H), 3.31-3.20 (m, 1H), 2.81-2.76 (m, 1H), 2.40-2.31 (m, 3H), 1.96-1.88 (m, 2H).

ESI-MS [M+H]+ calcd for ($C_{23}H_{19}ClN_3O_2$) 424.11, found: 424.10.

Preparation of Compounds of Formula (III)

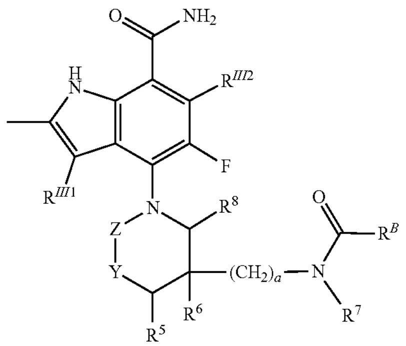

Example 27

Synthesis of 4-((3S,5R)-3-(but-2-ynamido)-5-fluoropiperidin-1-yl)-3-chloro-5-fluoro-2-methyl-1H-indole-7-carboxamide (Compound 27)

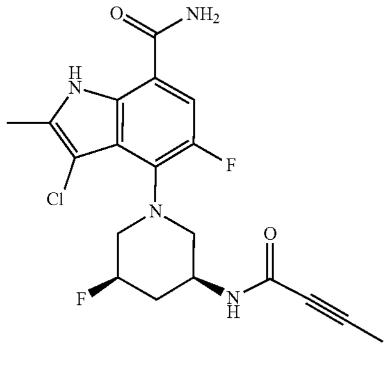 [SMILES: CC#CC(=O)N[C@H]1C[C@@H](F)CN(c2c(F)cc(C(N)=O)c3[nH]c(C)c(Cl)c23)C1]

Step 1: 4-bromo-5-fluoro-2-methyl-1H-indole-7-carboxylic acid

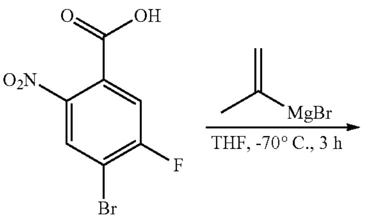

-continued

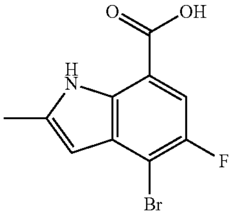

To a stirred solution of 4-bromo-5-fluoro-2-nitrobenzoic acid (17 g, 64.4 mmol) in THF (200 mL) was added dropwise prop-1-en-2-ylmagnesium bromide (451 mL, 225 mmol, 0.5 M in THF) at −70° C. under nitrogen. After addition, the reaction mixture was stirred at −70° C. for 3 h. The reaction mixture was quenched with saturated aqueous ammonium chloride (500 mL) and extracted with ethyl acetate (2×500 mL). The combined extracts were washed with brine (300 mL), dried over anhydrous sodium sulfate, and concentrated under vacuum to give 4-bromo-5-fluoro-2-methyl-1H-indole-7-carboxylic acid (17.5 g) as a brown solid. The solids were taken forward without purification.

ESI-MS [M−H]− calcd for ($C_{10}H_7BrFNO_2$) 269.96, 271.96 found: 270.25, 272.25.

Step 2: 4-bromo-5-fluoro-2-methyl-1H-indole-7-carboxamide

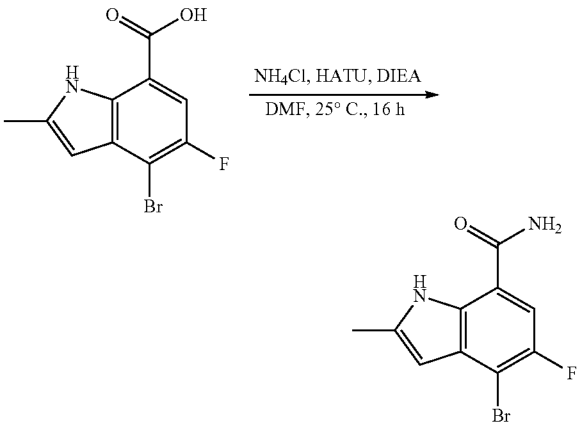

To a stirred solution of 4-bromo-5-fluoro-2-methyl-1H-indole-7-carboxylic acid (17.5 g, 64.4 mmol), ammonia hydrochloride (5.17 g, 96.6 mmol) and HATU (29.4 g, 77.3 mmol) in DMF (200 mL) was added N-ethyl-N-isopropyl-propan-2-amine (25.0 g, 193 mmol). The reaction mixture was stirred at 25° C. for 16 h. The reaction mixture was quenched with water (300 mL) and extracted with ethyl acetate (3×300 mL). The combined extracts were washed with water (200 mL), brine (200 mL), and then dried over anhydrous sodium sulfate and concentrated under vacuum. The concentrate was purified by column chromatography (50% ethyl acetate in petroleum ether) to give 4-bromo-5-fluoro-2-methyl-1H-indole-7-carboxamide (3.8 g, 22%) as a yellow solid.

$^1$H NMR (400 MHz, DMSO-$d_6$) δ 11.26 (s, 1H), 8.11 (s, 1H), 7.63-7.53 (m, 2H), 6.19 (s, 1H), 2.42 (s, 3H).

ESI-MS [M+H]$^+$ calcd for ($C_{10}H_8BrFN_2O$) 270.98, 272.98 found: 270.90, 272.90.

Step 3: 4-bromo-5-fluoro-2-methyl-1H-indole-7-carbonitrile

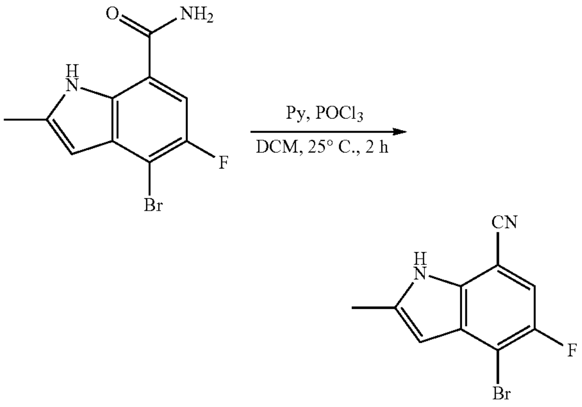

To a mixture of 4-bromo-5-fluoro-2-methyl-1H-indole-7-carboxamide (2.00 g, 7.38 mmol) in DCM (40 mL) were added pyridine (1.46 g, 18.4 mmol) and phosphorus oxychloride (1.70 g, 11.1 mmol) at 0° C. The reaction mixture was stirred for 2 h at 25° C. The reaction mixture was concentrated under vacuum. The residue was purified by column chromatography on silica gel (0-10% ethyl acetate in petroleum ether) to afford 4-bromo-5-fluoro-2-methyl-1H-indole-7-carbonitrile (1.50 g, 80%) as a white solid.

$^1$H NMR (400 MHz, DMSO-$d_6$) δ 12.26 (s, 1H), 7.63 (d, J=9.2 Hz, 1H), 6.34-6.31 (m, 1H), 2.42 (s, 3H).

ESI-MS [M−H]− calcd for ($C_{10}H_6BrFN_2$) 250.97, 252.97; found: 250.95, 252.95.

Step 4: tert-butyl ((3S,5R)-1-(7-cyano-5-fluoro-2-methyl-1H-indol-4-yl)-5-fluoropiperidin-3-yl)carbamate

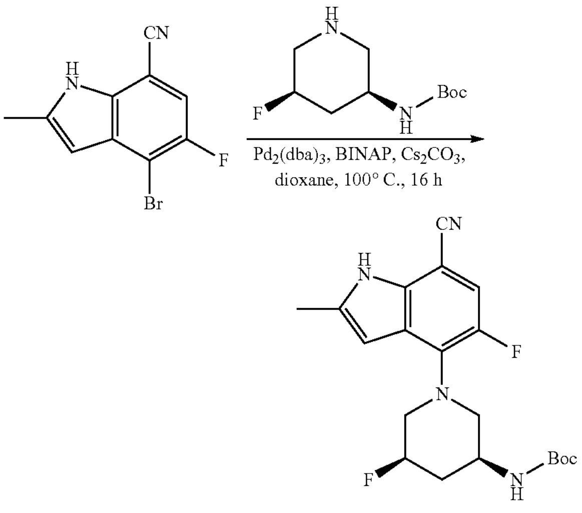

A mixture of 4-bromo-5-fluoro-2-methyl-1H-indole-7-carbonitrile (500 mg, 1.74 mmol), tert-butyl ((3S,5R)-5-fluoropiperidin-3-yl)carbamate (418 mg, 1.91 mmol), benzyl-[1-[2-[benzyl(phenyl)phosphanyl]-1-naphthyl]-2-naphthyl]-phenyl-phosphane (453 mg, 696 μmol), tris (dibenzylideneacetone)dipalladium (360 mg, 348 μmol) and cesium carbonate (1.70 g, 5.22 mmol) in dioxane (10 mL) was degassed and backfilled with nitrogen. The reaction mixture was heated under nitrogen for 16 h at 100° C. The cooled reaction mixture was concentrated under vacuum. The residue was purified by column chromatography on silica gel (0 to 16% ethyl acetate in petroleum ether) to afford tert-butyl ((3 S,5R)-1-(7-cyano-5-fluoro-2-methyl-1H-indol-4-yl)-5-fluoropiperidin-3-yl)carbamate (380 mg) as a yellow solid.

ESI-MS $[M+H]^+$ calcd for ($C_{20}H_{24}F_2N_4O_2$) 391.19, found: 391.15.

Step 5: tert-butyl ((3S,5R)-1-(7-carbamoyl-5-fluoro-2-methyl-1H-indol-4-yl)-5-fluoropiperidin-3-yl)carbamate

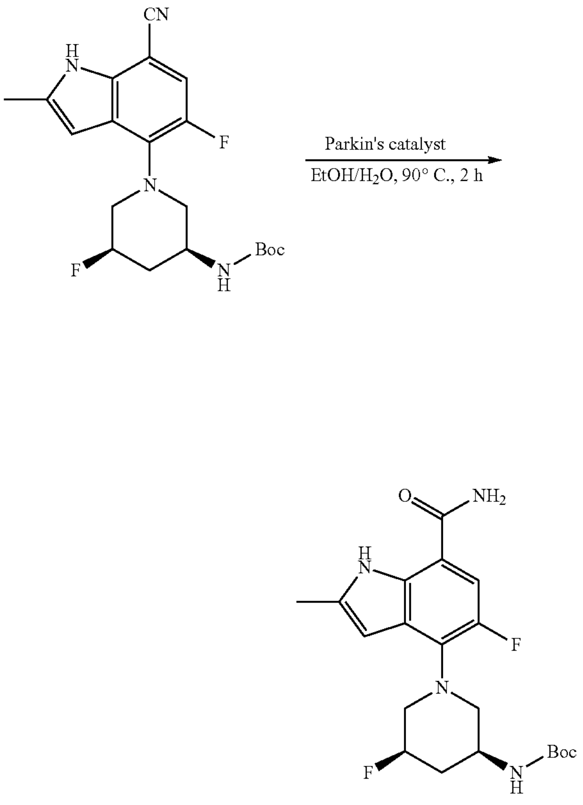

To a mixture of tert-butyl ((3S,5R)-1-(7-cyano-5-fluoro-2-methyl-1H-indol-4-yl)-5-fluoropiperidin-3-yl)carbamate (350 mg, 0.89 mmol) in ethanol (16 mL) and water (4 mL) was added Parkin's catalyst (19 mg, 0.045 mmol). The reaction was stirred for 2 h at 90° C. The cooled reaction mixture was diluted with water (30 mL) and extracted with ethyl acetate (3x30 mL). The combined extracts were washed with brine (50 mL), dried over sodium sulfate, and concentrated under vacuum. The residue was purified by column chromatography on silica gel (0 to 50% ethyl acetate in petroleum ether) to afford tert-butyl ((3S,5R)-1-(7-carbamoyl-5-fluoro-2-methyl-1H-indol-4-yl)-5-fluoropiperidin-3-yl)carbamate (320 mg) as a yellow solid.

ESI-MS $[M+H]^+$ calcd for ($C_{20}H_{26}F_2N_4O_3$) 409.20, found: 409.10.

Step 6: tert-butyl ((3S,5R)-1-(7-carbamoyl-3-chloro-5-fluoro-2-methyl-1H-indol-4-yl)-5-fluoropiperidin-3-yl)carbamate

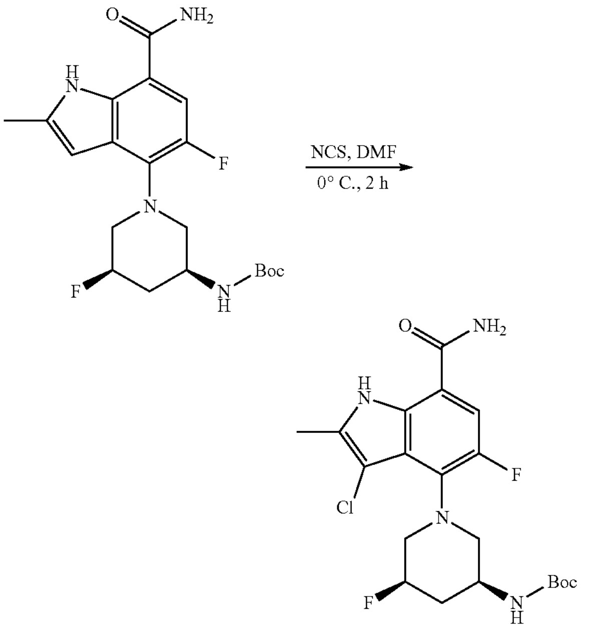

tert-butyl ((3S,5R)-1-(7-carbamoyl-3-chloro-5-fluoro-2-methyl-1H-indol-4-yl)-5-fluoropiperidin-3-yl)carbamate: To a solution of tert-butyl ((3S,5R)-1-(7-carbamoyl-5-fluoro-2-methyl-1H-indol-4-yl)-5-fluoropiperidin-3-yl)carbamate (250 mg, 0.61 mmol) in N,N-dimethylformamide (8 mL) was added N-Chlorosuccinimide (82 mg, 0.61 mmol) at 0° C. The reaction mixture was stirred for 2 h at 0° C. The reaction mixture was diluted with water (30 mL) and extracted with ethyl acetate (3x30 mL). The combined extracts were washed with brine (50 mL), dried over sodium sulfate, and concentrated under vacuum. The residue was purified by column chromatography on silica gel eluting with (0 to 50% ethyl acetate in petroleum ether) to afford tert-butyl ((3S,5R)-1-(7-carbamoyl-3-chloro-5-fluoro-2-methyl-1H-indol-4-yl)-5-fluoropiperidin-3-yl)carbamate (240 mg).

ESI-MS $[M+H]^+$ calcd for ($C_{15}H_{17}ClF_2N_4O$) 443.16, 445.16; found: 443.15, 445.15.

Step 7: 4-((3S,5R)-3-amino-5-fluoropiperidin-1-yl)-3-chloro-5-fluoro-2-methyl-1H-indole-7-carboxamide hydrochloride

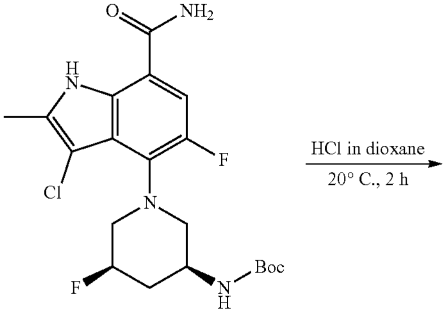

-continued

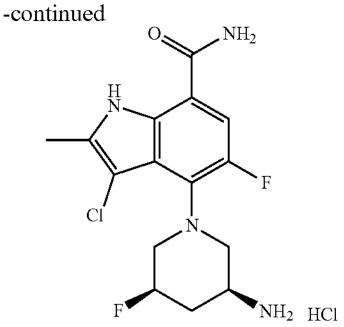

A mixture of tert-butyl ((3S,5R)-1-(7-carbamoyl-3-chloro-5-fluoro-2-methyl-1H-indol-4-yl)-5-fluoropiperidin-3-yl)carbamate (200 mg, 0.45 mmol) and 4 M hydrogen chloride in dioxane (10 mL) was stirred for 2 h at 20° C. The reaction mixture was concentrated under vacuum to afford 44-((3S,5R)-3-amino-5-fluoropiperidin-1-yl)-3-chloro-5-fluoro-2-methyl-1H-indole-7-carboxamide hydrochloride (170 mg).

ESI-MS $[M+H]^+$ calcd for ($C_{15}H_{17}ClF_2N_4O$) 343.11, 345.11; found: 343.05, 345.05.

Step 8: 4-((3S,5R)-3-(but-2-ynamido)-5-fluoropiperidin-1-yl)-3-chloro-5-fluoro-2-methyl-1H-indole-7-carboxamide

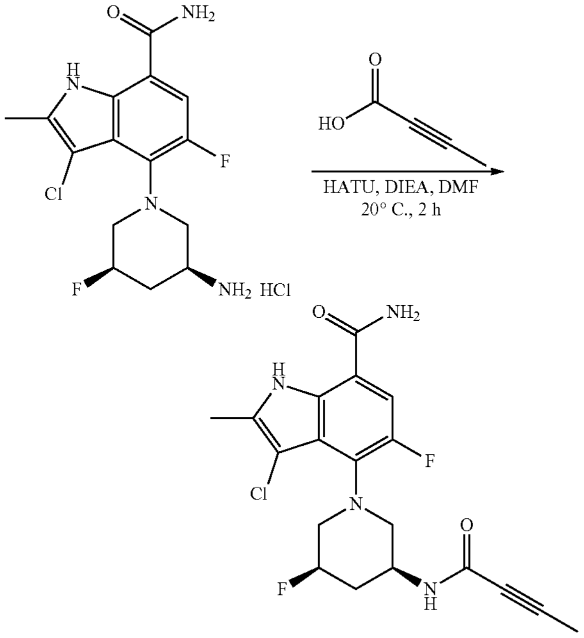

To a mixture of 4-((3S,5R)-3-amino-5-fluoropiperidin-1-yl)-3-chloro-5-fluoro-2-methyl-1H-indole-7-carboxamide hydrochloride (170 mg, 0.49 mmol), but-2-ynoic acid (42 mg, 0.49 mmol) and N,N,N',N'-tetramethyl-O-(7-azabenzotriazol-1-yl)uronium hexafluorophospate (207 mg, 0.55 mmol) in N,N-dimethylformamide (8 mL) was added N,N-diisopropylethylamine (321 mg, 2.48 mmol). The reaction mixture was stirred for 2 h at 20° C. The reaction mixture was diluted with water (30 mL) and extracted with ethyl acetate (3×30 mL). The combined extracts were washed with brine (3×30 mL), dried over sodium sulfate, and concentrated under vacuum. The residue was purified by Prep-HPLC (column: YMC-Actus Triart C18, 30×250 mm, 5 um; mobile phase A: water (10 MMOL/L $NH_4HCO_3$+0.1% $NH_3 \cdot H_2O$), mobile phase B: acetonitrile; flow rate: 60 mL/min; gradient: 36% B to 47% B in 8 min; 254 nm; RT1: 7.5 min to afford 4-((3S,5R)-3-(but-2-ynamido)-5-fluoropiperidin-1-yl)-3-chloro-5-fluoro-2-methyl-1H-indole-7-carboxamide (14.4 mg) as an off-white solid.

1H NMR (400 MHz, DMSO-d6) δ 11.27 (s, 1H), 8.43 (s, 1H), 8.03 (s, 1H), 7.61-7.42 (m, 2H), 5.15-4.85 (m, 1H), 4.49 (s, 1H), 3.32-3.15 (m, 2H), 2.90-2.70 (m, 1H), 2.45-2.35 (m, 4H), 2.20-2.08 (m, 1H), 1.94 (s, 3H), 1.75-1.50 (m, 1H).

ESI-MS $[M+H]^+$ calcd for ($C_{19}H_{19}ClF_2N_4O_2$) 409.12, 411.12; found: 409.05, 411.05.

Example 28

Synthesis of 4-((3S,5S)-3-(but-2-ynamido)-5-fluoropiperidin-1-yl)-3-chloro-5-fluoro-2-methyl-1H-indole-7-carboxamide (Compound 28)

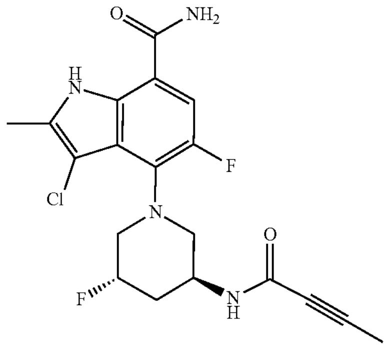 [SMILES: CC#CC(=O)N[C@H]1C[C@H](F)CN(c2c(F)cc(C(N)=O)c3[nH]c(C)c(Cl)c23)C1]

Step 1: tert-butyl ((3S,5S)-1-(7-cyano-5-fluoro-2-methyl-1H-indol-4-yl)-5-fluoropiperidin-3-yl)carbamate

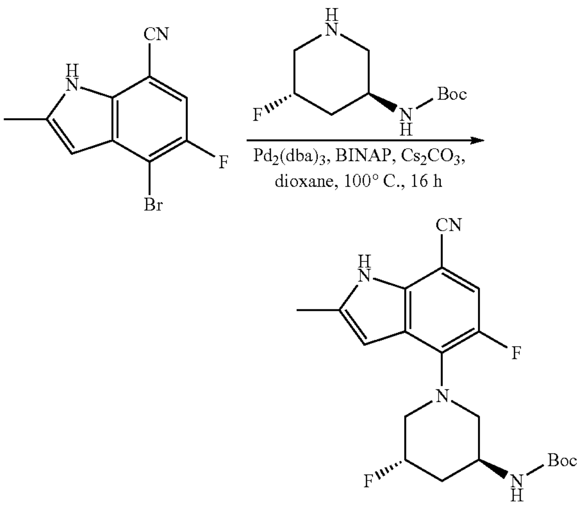

A mixture of 4-bromo-5-fluoro-2-methyl-1H-indole-7-carbonitrile (500 mg, 1.74 mmol), tert-butyl ((3S,5S)-5-fluoropiperidin-3-yl)carbamate (418 mg, 1.91 mmol), benzyl-[1-[2-[benzyl(phenyl)phosphanyl]-1-naphthyl]-2-naphthyl]-phenyl-phosphane (453 mg, 0.696 mmol), tris(dibenzylideneacetone)dipalladium (360 mg, 0.348 mmol) and cesium carbonate (1.70 g, 5.22 mmol) in dioxane (10 mL) was degassed and backfilled with nitrogen. The reaction mixture was heated under nitrogen at 100° C. for 16 h. The cooled reaction mixture was concentrated under vacuum. The residue was purified by column chromatography on silica gel (0 to 16% ethyl acetate in petroleum ether) to afford tert-butyl ((3S,5S)-1-(7-cyano-5-fluoro-2-methyl-1H-indol-4-yl)-5-fluoropiperidin-3-yl)carbamate (320 mg) as a yellow solid.

ESI-MS $[M+H]^+$ calcd for ($C_{20}H_{24}F_2N_4O_2$) 391.19, found: 391.10.

Step 2: tert-butyl ((3S,5S)-1-(7-carbamoyl-5-fluoro-2-methyl-1H-indol-4-yl)-5-fluoropiperidin-3-yl)carbamate

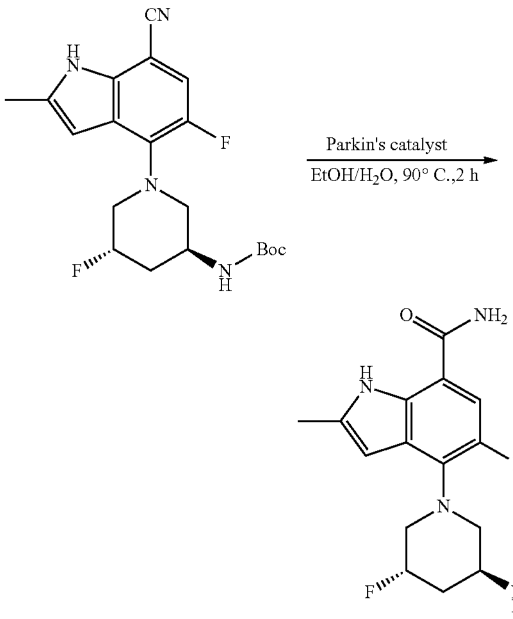

To a mixture of tert-butyl ((3S,5S)-1-(7-cyano-5-fluoro-2-methyl-1H-indol-4-yl)-5-fluoropiperidin-3-yl)carbamate (320 mg, 0.82 mmol) in water (4 mL) and ethanol (16 mL) was added Parkin's catalyst (18 mg, 0.041 mmol). The reaction mixture was heated for 2 h at 90° C. The cooled reaction mixture was diluted with water (30 mL) and extracted with ethyl acetate (3×30 mL). The combined extracts were washed with brine (50 mL), dried over sodium sulfate, and concentrated under vacuum. The residue was purified by column chromatography on silica gel (0 to 50% ethyl acetate in petroleum ether) to afford tert-butyl ((3S,5S)-1-(7-carbamoyl-5-fluoro-2-methyl-1H-indol-4-yl)-5-fluoropiperidin-3-yl)carbamate (350 mg) as a yellow solid.

ESI-MS $[M+H]^+$ calcd for ($C_{20}H_{26}F_2N_4O_3$) 409.20, found: 409.10.

Step 3: tert-butyl ((3S,5S)-1-(7-carbamoyl-3-chloro-5-fluoro-2-methyl-1H-indol-4-yl)-5-fluoropiperidin-3-yl)carbamate

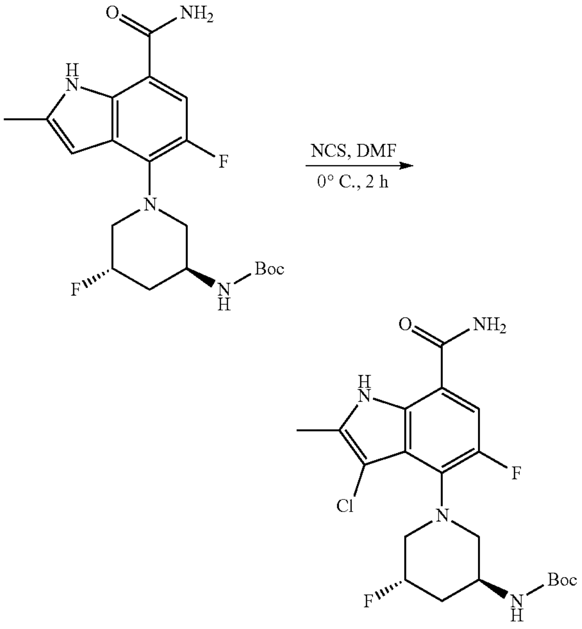

To a solution of tert-butyl ((3S,5S)-1-(7-carbamoyl-5-fluoro-2-methyl-1H-indol-4-yl)-5-fluoropiperidin-3-yl)carbamate (250 mg, 0.61 mmol) in DMF (6 mL) was added N-chlorosuccinimide (82 mg, 0.61 mmol) at 0° C. The reaction mixture was stirred for 2 h at 0° C. The reaction mixture was diluted with water (30 mL) and extracted with ethyl acetate (3×30 mL). The combined extracts were washed with brine (5 mL), dried over sodium sulfate, and concentrated under vacuum. The residue was purified by column chromatography on silica gel eluting with (0 to 50% ethyl acetate in petroleum ether) to afford tert-butyl ((3S,5S)-1-(7-carbamoyl-3-chloro-5-fluoro-2-methyl-1H-indol-4-yl)-5-fluoropiperidin-3-yl)carbamate (250 mg).

ESI-MS $[M+H]^+$ calcd for ($C_{20}H_{25}ClF_2N_4O_3$) 443.16, 445.16; found: 443.15, 445.15.

Step 4: 4-((3S,5S)-3-amino-5-fluoropiperidin-1-yl)-3-chloro-5-fluoro-2-methyl-1H-indole-7-carboxamide hydrochloride

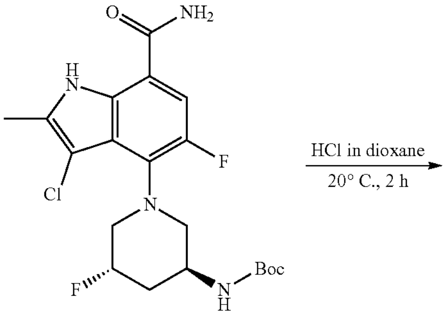

-continued

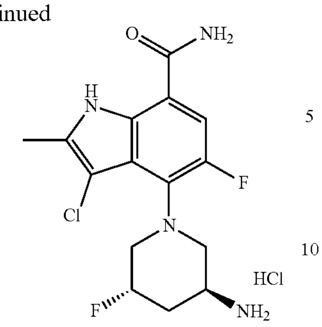

A mixture of tert-butyl (3S,5S)-1-(7-carbamoyl-3-chloro-5-fluoro-2-methyl-1H-indol-4-yl)-5-fluoropiperidin-3-ylcarbamate (250 mg, crude) and 4 M hydrogen chloride in dioxane (10 mL) was stirred for 2 h at 20° C. The reaction mixture was concentrated under vacuum to afford 4-((3S,5S)-3-amino-5-fluoropiperidin-1-yl)-3-chloro-5-fluoro-2-methyl-1H-indole-7-carboxamide hydrochloride (200 mg).

ESI-MS $[M+H]^+$ calcd for $(C_{15}H_{17}ClF_2N_4O)$ 343.11, 345.11; found: 343.10, 345.10.

Step 5: 4-((3S,5S)-3-(but-2-ynamido)-5-fluoropiperidin-1-yl)-3-chloro-5-fluoro-2-methyl-1H-indole-7-carboxamide

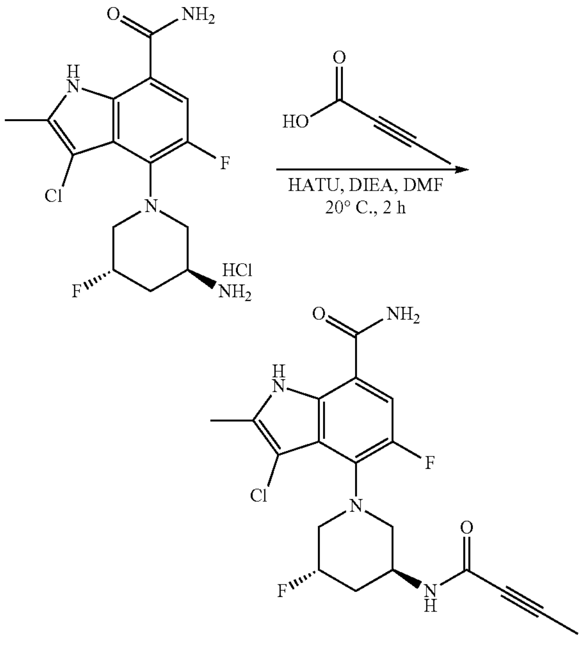

To a solution of 4-((3S,5S)-3-amino-5-fluoropiperidin-1-yl)-3-chloro-5-fluoro-2-methyl-1H-indole-7-carboxamide hydrochloride (200 mg, 0.527 mmol), but-2-ynoic acid (44 mg, 0.527 mmol) and N,N,N',N'-tetramethyl-O-(7-azabenzotriazol-1-yl)uronium hexafluorophospate (221 mg, 0.58 mmol) in N,N-dimethylformamide (8 mL) was added N,N-diisopropylethylamine (341 mg, 2.64 mmol). The mixture was stirred for 2 h at 20° C. The reaction mixture was quenched with water (30 mL) and extracted with ethyl acetate (3×30 mL). The combined extracts were washed with brine (50 mL), dried over sodium sulfate, and concentrated under vacuum. The residue was purified by Prep-HPLC (column: XBridge Prep OBD C18 Column, 19×250 mm, 5 um; mobile phase A: water (10 MMOL/L $NH_4HCO_3$+0.1% $NH_3 \cdot H_2O$), mobile phase B: acetonitrile; flow rate: 25 mL/min; gradient: 38% B to 58% B in 7 min; 220 nm; RT: 5.12 min to afford 4-((3S,5S)-3-but-2-ynamido-5-fluoropiperidin-1-yl)-3-chloro-5-fluoro-2-methyl-1H-indole-7-carboxamide (34.9 mg, 16%) as a white solid.

$^1$H NMR (400 MHz, DMSO-$d_6$) δ 11.28 (s, 1H), 8.45 (s, 1H), 8.03 (s, 1H), 7.62-7.44 (m, 2H), 5.12-4.88 (m, 1H), 4.62-4.40 (m, 1H), 3.51-3.35 (m, 1H), 3.32-3.15 (m, 2H), 2.90-2.70 (m, 1H), 2.37 (s, 3H), 2.21-2.03 (m, 1H), 1.94 (s, 3H), 1.78-1.44 (m, 1H).

Example 29

Synthesis of 4-(1-acryloyloctahydro-6H-pyrrolo[2,3-c]pyridin-6-yl)-3-chloro-5-fluoro-2-methyl-1H-indole-7-carboxamide (Compound 29)

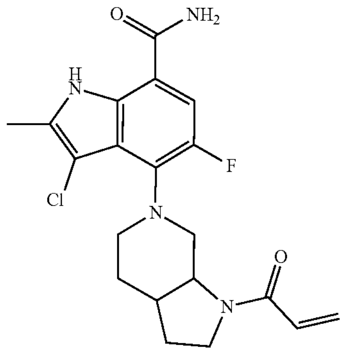 [SMILES: C=CC(=O)N1CCC2CCN(c3c(F)cc(C(N)=O)c4[nH]c(C)c(Cl)c34)CC21]

Step 1: tert-butyl 6-(7-cyano-5-fluoro-2-methyl-1H-indol-4-yl)octahydro-1H-pyrrolo[2,3-c]pyridine-1-carboxylate

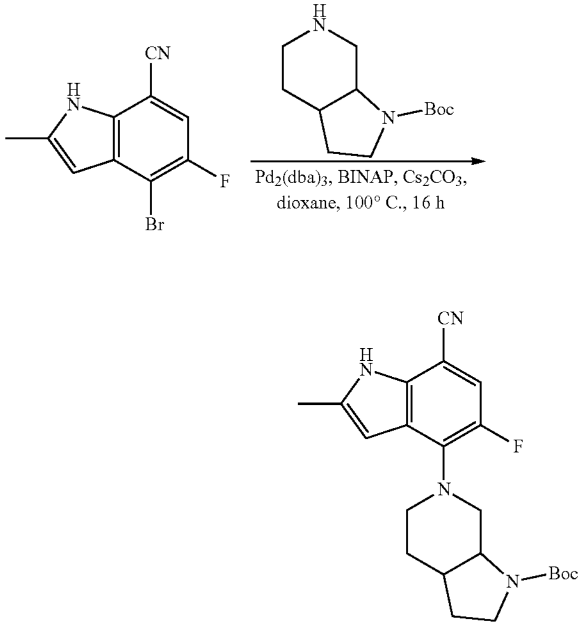

A mixture of 4-bromo-5-fluoro-2-methyl-1H-indole-7-carbonitrile (500 mg, 1.74 mmol), tert-butyl octahydro-1H-pyrrolo[2,3-c]pyridine-1-carboxylate (cis-enantiomeric mixture, 433 mg, 1.91 mmol), benzyl-[1-[2-[benzyl(phenyl) phosphanyl]-1-naphthyl]-2-naphthyl]-phenyl-phosphane (453 mg, 0.696 mmol), tris(dibenzylideneacetone)dipalladium (360 mg, 0.348 mmol) and cesium carbonate (1.70 g, 5.22 mmol) in dioxane (15 mL) was degassed and backfilled with nitrogen. The reaction mixture was heated under nitrogen at 100° C. for 16 h. The cooled reaction mixture was concentrated under vacuum. The residue was purified by column chromatography on silica gel eluting with (0 to 16% ethyl acetate in petroleum ether) to give tert-butyl 6-(7-cyano-5-fluoro-2-methyl-1H-indol-4-yl)octahydro-1H-pyrrolo[2,3-c]pyridine-1-carboxylate (400 mg) as a yellow solid.

ESI-MS $[M+H]^+$ calcd for $(C_{22}H_{27}FN_4O_2)$ 399.21, found: 399.20.

Step 2: tert-butyl 6-(7-carbamoyl-5-fluoro-2-methyl-1H-indol-4-yl)octahydro-1H-pyrrolo[2,3-c]pyridine-1-carboxylate

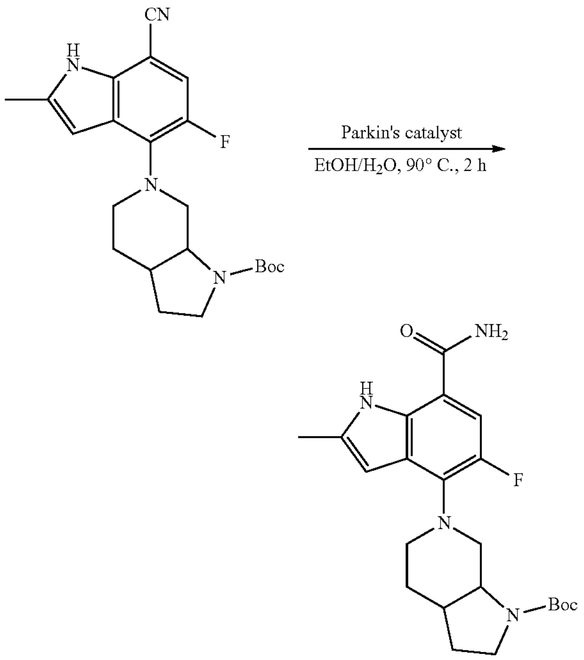

To a mixture of tert-butyl 6-(7-cyano-5-fluoro-2-methyl-1H-indol-4-yl)octahydro-1H-pyrrolo[2,3-c]pyridine-1-carboxylate (350 mg, 0.88 mmol) in water (4 mL) and ethanol (16 mL) was added Parkin's catalyst (19 mg, 0.044 mmol). The reaction mixture was stirred for 2 h at 90° C. The cooled reaction mixture was diluted with water (60 mL) and extracted with ethyl acetate (3×50 mL). The combined extracts were washed with brine (50 mL), dried over sodium sulfate, and concentrated under vacuum. The residue was purified by column chromatography on silica gel eluting with (0 to 50% ethyl acetate in petroleum ether) to afford tert-butyl 6-(7-carbamoyl-5-fluoro-2-methyl-1H-indol-4-yl) octahydro-1H-pyrrolo[2,3-c]pyridine-1-carboxylate (350 mg) as a yellow solid.

ESI-MS $[M+H]^+$ calcd for $(C_{22}H_{29}FN_4O_3)$ 417.22, found: 417.20.

Step 3: tert-butyl 6-(7-carbamoyl-3-chloro-5-fluoro-2-methyl-1H-indol-4-yl)octahydro-1H-pyrrolo[2,3-c]pyridine-1-carboxylate

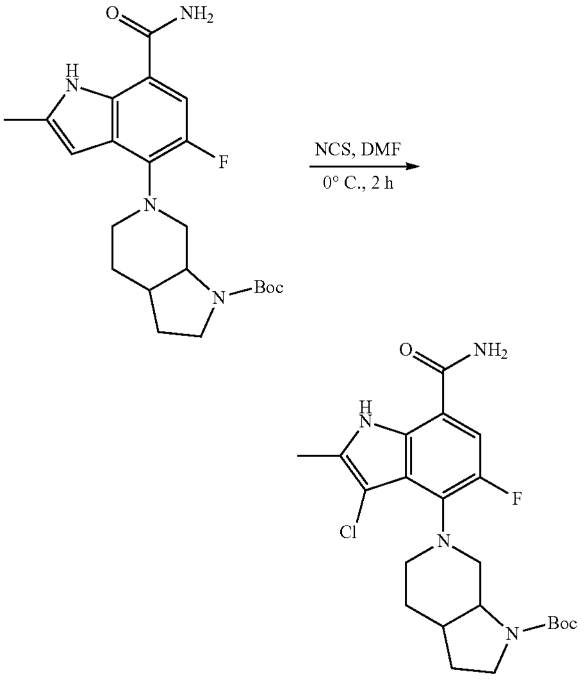

To a solution of tert-butyl 6-(7-carbamoyl-5-fluoro-2-methyl-1H-indol-4-yl)octahydro-1H-pyrrolo[2,3-c]pyridine-1-carboxylate (330 mg, 0.792 mmol) in DMF (6 mL) was added N-chlorosuccinimide (106 mg, 0.792 mmol) at 0° C. The reaction mixture was stirred for 2 h at 0° C. The reaction mixture was quenched with water (30 mL) and extracted with ethyl acetate (3×30 mL). The combined extracts were washed with brine (50 mL), dried over sodium sulfate, and concentrated under vacuum. The residue was purified by column chromatography on silica gel (0 to 50% ethyl acetate in petroleum ether) to afford tert-butyl 6-(7-carbamoyl-3-chloro-5-fluoro-2-methyl-1H-indol-4-yl)octahydro-1H-pyrrolo[2,3-c]pyridine-1-carboxylate (350 mg).

ESI-MS $[M+H]^+$ calcd for $(C_{22}H_{28}ClFN_4O_3)$ 451.18, 453.18; found: 451.05, 453.05.

Step 4: 3-chloro-5-fluoro-2-methyl-4-(octahydro-6H-pyrrolo[2,3-c]pyridin-6-yl)-1H-indole-7-carboxamide 2,2,2-trifluoroacetate

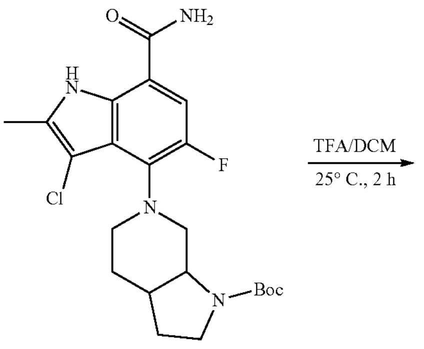

-continued

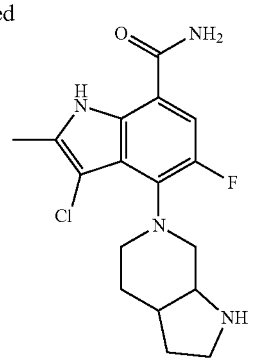

To a solution of tert-butyl 6-(7-carbamoyl-3-chloro-5-fluoro-2-methyl-1H-indol-4-yl)octahydro-1H-pyrrolo[2,3-c]pyridine-1-carboxylate (300 mg, 0.665 mmol) in dichloromethane (5 mL) was added trifluoroacetic acid (5 mL). The reaction mixture was stirred for 2 h at 25° C. The reaction mixture was concentrated under vacuum to give 3-chloro-5-fluoro-2-methyl-4-(octahydro-6H-pyrrolo[2,3-c]pyridin-6-yl)-1H-indole-7-carboxamide 2,2,2-trifluoroacetate (310 mg).

ESI-MS $[M+H]^+$ calcd for $(C_{17}H_{20}ClFN_4O)$ 351.13, 353.13; found: 351.05, 353.05.

Step 5: 4-(1-acryloyloctahydro-6H-pyrrolo[2,3-c]pyridin-6-yl)-3-chloro-5-fluoro-2-methyl-1H-indole-7-carboxamide

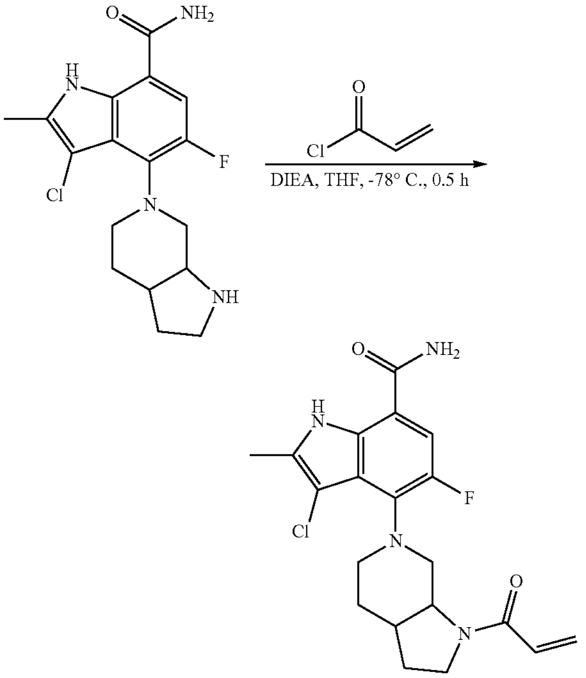

To a mixture of 3-chloro-5-fluoro-2-methyl-4-(octahydro-6H-pyrrolo[2,3-c]pyridin-6-yl)-1H-indole-7-carboxamide 2,2,2-trifluoroacetate (310 mg, 0.667 mmol) in tetrahydrofuran (3 mL) was added N,N-diisopropylethylamine (517 mg, 4.00 mmol) and acryloyl chloride (66 mg, 0.734 mmol) at −78° C. The reaction mixture was stirred for 0.5 h at −78° C. The reaction mixture was quenched with water (30 mL) and extracted with ethyl acetate (3×30 mL). The combined extracts were washed with brine (50 mL), dried over sodium sulfate, and concentrated under vacuum. The residue was purified by Prep-HPLC (column: XBridge Prep OBD C18 Column, 19×250 mm, 5 um; mobile phase A: water (10 MMOL/L $NH_4HCO_3$+0.1% $NH_3 \cdot H_2O$), mobile phase B: acetonitrile; flow rate: 25 mL/min; gradient: 40% B to 60% B in 7 min; 220 nm; retention time=5.78 minutes) to afford 4-(1-acryloyloctahydro-6H-pyrrolo[2,3-c]pyridin-6-yl)-3-chloro-5-fluoro-2-methyl-1H-indole-7-carboxamide (110 mg, 40%) as a white racemic mixture.

$^1H$ NMR (400 MHz, DMSO-$d_6$) δ 11.26 (d, J=12.0 Hz, 1H), 8.01 (s, 1H), 7.60-7.35 (m, 2H), 6.63-6.48 (m, 1H), 6.15-6.05 (m, 1H), 5.69-5.58 (m, 1H), 4.38-4.27 (m, 1H), 3.77-3.69 (m, 0.5H), 3.58-3.49 (m, 1H), 3.49-3.36 (m, 1H), 3.32-3.10 (m, 2H), 3.05-2.87 (m, 2H), 2.58-2.52 (m, 0.5H), 2.39 (d, J=5.2 Hz, 3H), 2.28-2.06 (m, 2H), 1.95-1.63 (m, 2H).

ESI-MS $[M+H]^+$ calcd for $(C_{20}H_{22}ClFN_4O_2)$ 405.14, 407.14; found: 405.10, 407.10.

Step 6: Separation of Isomers

Racemic 4-(1-acryloyloctahydro-6H-pyrrolo[2,3-c]pyridin-6-yl)-3-chloro-5-fluoro-2-methyl-1H-indole-7-carboxamide was separated to its respective enantiomers by Prep-Chiral-HPLC (sample amount=90 mg; column: Chiralpak IA, 2×25 cm, 5 um; mobile phase A: MTBE (0.5% 2 M $NH_3$-MeOH), mobile phase B: EtOH; flow rate: 18 mL/min; gradient: 50% B, isocratic; 220/254 nm).

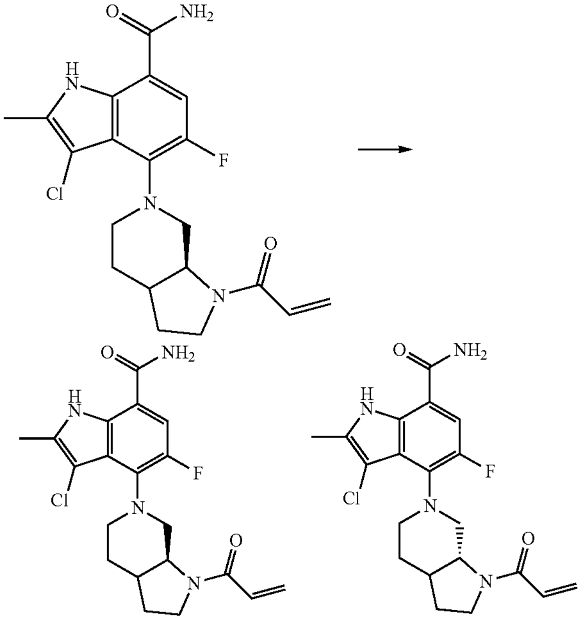

(7aS)- (7aR)-

Compound 29a: Retention Time=8.163 Minutes (29.1 mg). Isolated as a White Solid $^1H$ NMR (400 MHz, DMSO-$d_6$) δ 11.27 (d, J=12.0 Hz, 1H), 8.02 (s, 1H), 7.58-7.39 (m, 2H), 6.65-6.48 (m, 1H), 6.16-6.06 (m, 1H), 5.69-5.59 (m, 1H), 4.39-4.23 (m, 1H), 3.77-3.69 (m, 0.5H), 3.58-3.49 (m, 1H), 3.49-3.35 (m, 1H), 3.32-3.10 (m, 2H), 3.06-2.88 (m, 2H), 2.58-2.54 (m, 0.5H), 2.39 (d, J=5.2 Hz, 3H), 2.27-2.06 (m, 2H), 1.95-1.76 (m, 1H), 1.75-1.61 (m, 1H). ESI-MS $[M+H]^+$ calcd for ($C_{20}H_{22}ClFN_4O_2$) 405.14, 407.14; found: 405.10, 407.10.

Compound 29b: Retention Time=11.102 Minutes (30.9 mg). Isolated as a White Solid $^1$H NMR (400 MHz, DMSO-$d_6$) δ 11.27 (d, J=12.0 Hz, 1H), 8.02 (s, 1H), 7.61-7.31 (m, 2H), 6.64-6.48 (m, 1H), 6.15-6.07 (m, 1H), 5.69-5.57 (m, 1H), 4.41-4.24 (m, 1H), 3.77-3.69 (m, 0.5H), 3.61-3.49 (m, 1H), 3.48-3.37 (m, 1H), 3.31-3.11 (m, 2H), 3.06-2.85 (m, 2H), 2.60-2.51 (m, 0.5H), 2.39 (d, J=5.2 Hz, 3H), 2.28-2.06 (m, 2H), 1.93-1.65 (m, 2H).

ESI-MS $[M+H]^+$ calcd for ($C_{20}H_{22}ClFN_4O_2$) 405.14, 407.14; found: 405.10, 407.10.

Example 30

Synthesis of 4-((3S,4S)-3-acrylamido-4-fluoropiperidin-1-yl)-5-fluoro-2,3-dimethyl-1H-indole-7-carboxamide (Compound 30)

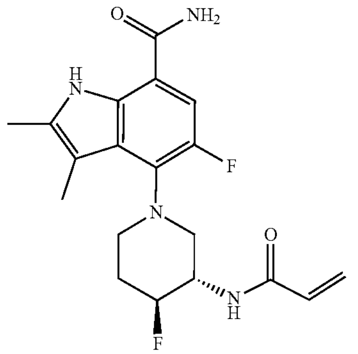 [SMILES: C=CC(=O)N[C@H]1CN(c2c(F)cc(C(N)=O)c3[nH]c(C)c(C)c23)CC[C@@H]1F]

Step 1: Tert-butyl ((3S,4S)-1-(7-cyano-5-fluoro-2,3-dimethyl-1H-indol-4-yl)-4-fluoropiperidin-3-yl)carbamate

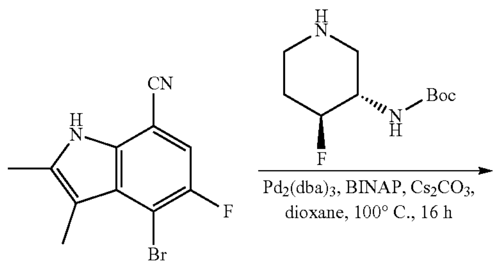

-continued

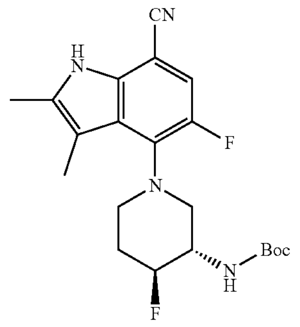

To a mixture of 4-bromo-5-fluoro-2,3-dimethyl-1H-indole-7-carbonitrile (250 mg, 0.94 mmol) and tert-butyl ((3S,4S)-4-fluoropiperidin-3-yl)carbamate (225 mg, 1.03 mmol) in 1,4-dioxane (10 mL) were added 1.1'-binaphthyl-2.2'-diphenyl phosphine (61 mg, 0.09 mmol), tris(dibenzylidene-acetone)dipalladium (86 mg, 0.09 mmol) and cesium carbonate (457 mg, 1.40 mmol) at 20° C. under nitrogen atmosphere. The mixture was degassed and back-filled with nitrogen three times and stirred for 16 hours at 100° C. The cooled mixture was diluted with water (50 mL) and extracted with ethyl acetate (50 mL×3). The combined extracts were washed with water (50 mL×2) and brine (50 mL), dried over anhydrous sodium sulfate, filtered and concentrated under vacuum. The residue was purified by column chromatography on silica (0 to 25% ethyl acetate in petroleum ether) to give tert-butyl ((3S,4S)-1-(7-cyano-5-fluoro-2,3-dimethyl-1H-indol-4-yl)-4-fluoropiperidin-3-yl) carbamate (290 mg, 77%) as a light yellow solid.

$^1$H NMR (400 MHz, DMSO-d6) δ 11.59 (s, 1H), 7.36 (d, J=12.7 Hz, 1H), 7.12 (s, 1H), 4.64-4.35 (m, 1H), 3.85-3.67 (m, 1H), 3.18-3.04 (m, 3H), 2.83 (t, J=11.0 Hz, 1H), 2.37 (s, 3H), 2.30 (s, 3H), 2.21-2.08 (m, 1H), 1.91-1.74 (m, 1H), 1.34 (s, 9H).

Step 2: Tert-butyl ((3S,4S)-1-(7-carbamoyl-5-fluoro-2,3-dimethyl-1H-indol-4-yl)-4-fluoropiperidin-3-yl)carbamate

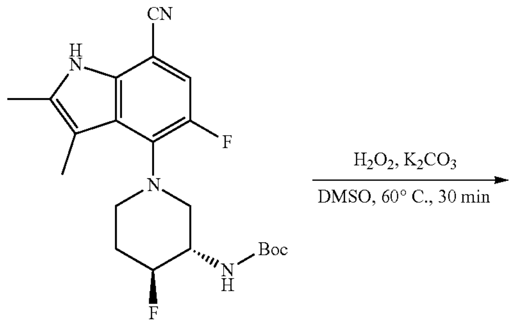

-continued

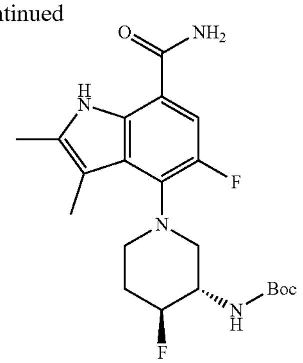

To a mixture of tert-butyl ((3S,4S)-1-(7-cyano-5-fluoro-2,3-dimethyl-1H-indol-4-yl)-4-fluoropiperidin-3-yl)carbamate (290 mg, 0.72 mmol) and potassium carbonate (297 mg, 2.15 mmol) in DMSO (5 mL) was added hydrogen peroxide (30%, 813 mg, 7.17 mmol). The reaction mixture was stirred for 30 min at 60° C. The cooled mixture was diluted with water (50 mL) and extracted with ethyl acetate (40 mL×3). The combined extracts were washed water (50 mL×3) and brine (50 mL), dried over anhydrous sodium sulfate, filtered and concentrated under vacuum to give tert-butyl ((3S,4S)-1-(7-carbamoyl-5-fluoro-2,3-dimethyl-1H-indol-4-yl)-4-fluoropiperidin-3-yl)carbamate (300 mg, 99%) as a yellow solid.

$^1$H NMR (400 MHz, DMSO-d6) δ 10.64 (s, 1H), 7.91 (s, 1H), 7.39 (d, J=14.0 Hz, 1H), 7.34 (s, 1H), 7.10 (s, 1H), 4.63-4.36 (m, 1H), 3.85-3.69 (m, 1H), 3.19-3.01 (m, 3H), 2.84 (t, J=1.09 Hz, 1H), 2.37 (s, 3H), 2.31 (s, 3H), 2.20-2.09 (m, 1H), 1.91-1.76 (m, 1H), 1.34 (s, 9H).

Step 3: 4-((3S,4S)-3-amino-4-fluoropiperidin-1-yl)-5-fluoro-2,3-dimethyl-1H-indole-7-carboxamide hydrochloride

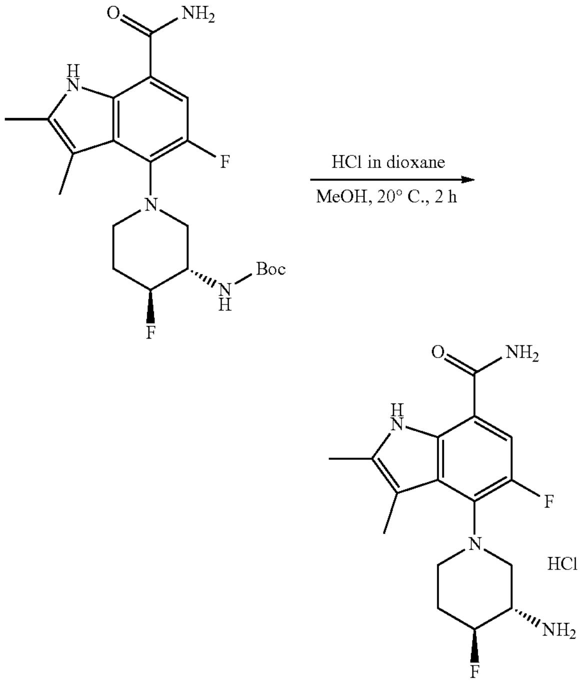

To a solution of tert-butyl ((3S,4S)-1-(7-carbamoyl-5-fluoro-2,3-dimethyl-1H-indol-4-yl)-4-fluoropiperidin-3-yl) carbamate (300 mg, 0.71 mmol) in methanol (5 mL) was added hydrogen chloride (10 mL, 4 M in 1,4-dioxane). The reaction mixture was stirred for 2 hours at 20° C. The resulting mixture was concentrated under vacuum to give 4-((3S,4S)-3-amino-4-fluoropiperidin-1-yl)-5-fluoro-2,3-dimethyl-1H-indole-7-carboxamide hydrochloride (320 mg, crude) as a yellow solid.

ESI-MS [M+H]+ calcd for ($C_{16}H_{20}F_2N_4O$) 323.16, found: 323.25.

Step 4: 4-((3S,4S)-3-acrylamido-4-fluoropiperidin-1-yl)-5-fluoro-2,3-dimethyl-1H-indole-7-carboxamide

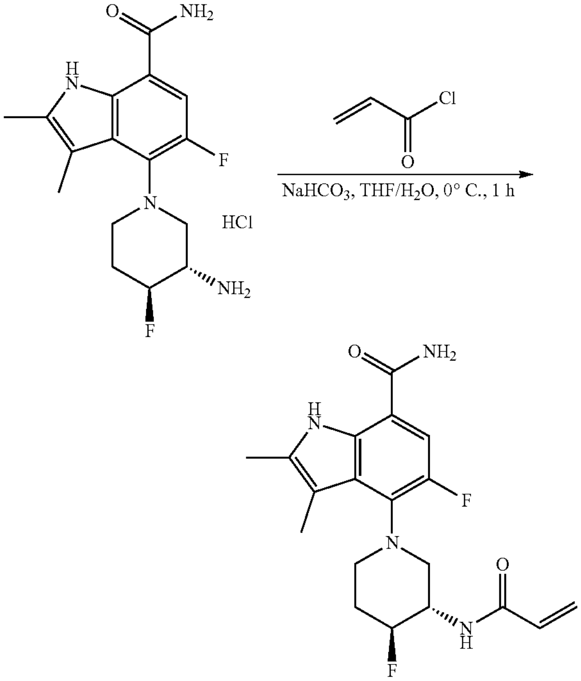

To a mixture of 4-((3S,4S)-3-amino-4-fluoropiperidin-1-yl)-5-fluoro-2,3-dimethyl-1H-indole-7-carboxamide hydrochloride (320 mg, 0.89 mmol) and sodium bicarbonate (749 mg, 8.92 mmol) in water (3.0 mL) and THE (12 mL) was added acryloyl chloride (81 mg, 0.89 mmol) at 0° C. The reaction mixture was stirred for 1 h and the resulting mixture was diluted with water (30 mL) and extracted with ethyl acetate (2×30 mL). The combined extracts were washed with water and brine and then dried over anhydrous sodium sulfate, filtered and concentrated under reduced vacuum. The residue was purified by Prep-HPLC (column: YMC-Actus Triart C18, 30×250 mm, 5 um; mobile phase A: water (10 mmol/L $NH_4HCO_3$+0.1% $NH_3 \cdot H_2O$), mobile phase B: acetonitrile; flow rate: 45 mL/min; Gradient: 35% B to 45% B in 7 min; 254, 220 nm, retention time=6.48 min to give 4-((3S,4S)-3-acrylamido-4-fluoropiperidin-1-yl)-5-fluoro-2,3-dimethyl-1H-indole-7-carboxamide (50.2 mg, 15%) as an off-white solid.

$^1$H NMR (300 MHz, DMSO-$d_6$) δ (ppm): 10.65 (s, 1H), 8.31 (s, 1H), 7.92 (s, 1H), 7.41 (d, J=14.1 Hz, 1H), 7.34 (s, 1H), 6.32-6.00 (m, 2H), 5.61 (dd, J=9.8, 2.5 Hz, 1H), 4.79-4.45 (m, 1H), 4.30-4.06 (m, 1H), 3.26-3.05 (m, 3H), 3.01-2.85 (m, 1H), 2.42 (s, 3H), 2.33 (s, 3H), 2.28-2.15 (m, 1H), 2.03-1.82 (m, 1H).

ESI-MS [M+H]+ calcd for ($C_{19}H_{22}F_2N_4O_2$) 377.17, found: 377.25.

Example 31

Synthesis of 4-((3S,4R)-3-acrylamido-4-fluoropiperidin-1-yl)-5-fluoro-2,3-dimethyl-1H-indole-7-carboxamide (Compound 31)

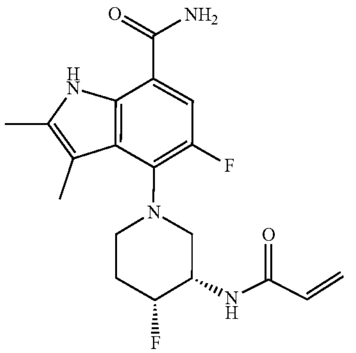 [SMILES: C=CC(=O)N[C@H]1CN(c2c(F)cc(C(N)=O)c3[nH]c(C)c(C)c23)CC[C@H]1F]

Step 1: Tert-butyl ((3S,4R)-1-(7-cyano-5-fluoro-2,3-dimethyl-1H-indol-4-yl)-4-fluoropiperidin-3-yl)carbamate

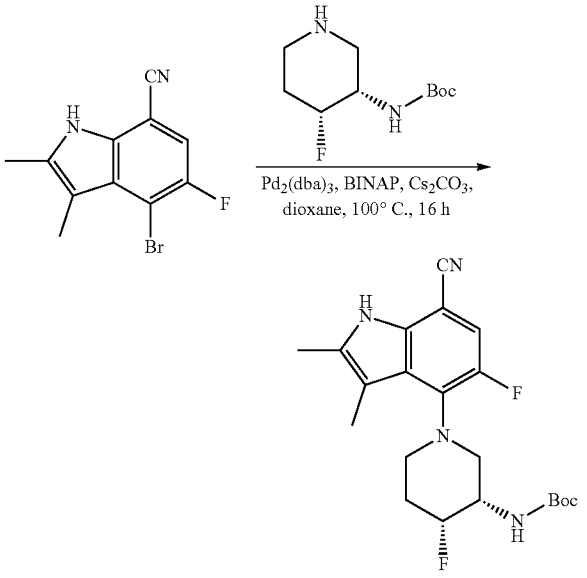

To a mixture of 4-bromo-5-fluoro-2,3-dimethyl-1H-indole-7-carbonitrile (250 mg, 0.94 mmol) and tert-butyl ((3S,4R)-4-fluoropiperidin-3-yl)carbamate (225 mg, 1.03 mmol) in 1,4-dioxane (10 mL) were added 1.1'-binaphthyl-2.2'-diphenyl phosphine (61 mg, 0.09 mmol), tris(dibenzylidene-acetone)dipalladium (86 mg, 0.09 mmol) and cesium carbonate (610 mg, 1.87 mmol). The reaction mixture was degassed and backfilled with nitrogen and then stirred for 16 hours at 100° C. The cooled mixture was diluted with water (50 mL) and extracted with ethyl acetate (3×50 mL). The combined extracts were washed with water (2×50 mL) and brine (50 mL), dried over anhydrous sodium sulfate, filtered and concentrated under vacuum. The residue was purified by column chromatography on silica gel (0 to 25% ethyl acetate in petroleum ether) to give tert-butyl ((3S,4R)-1-(7-cyano-5-fluoro-2,3-dimethyl-1H-indol-4-yl)-4-fluoropiperidin-3-yl)carbamate (238 mg, 63%) as a light yellow solid.

$^1$H NMR (400 MHz, DMSO-$d_6$) δ 11.58 (s, 1H), 7.37 (d, J=12.8 Hz, 1H), 7.01 (s, 1H), 4.97-4.78 (m, 1H), 3.91-3.72 (m, 1H), 3.25-3.14 (m, 2H), 3.00-2.79 (m, 2H), 2.34 (s, 3H), 2.29 (s, 3H), 2.09-1.87 (m, 2H), 1.35 (s, 9H).

ESI-MS [M+H]+ calcd for ($C_{21}H_{26}F_2N_4O_2$) 405.20, found: 405.25.

Step 2: Tert-butyl ((3S,4R)-1-(7-carbamoyl-5-fluoro-2,3-dimethyl-1H-indol-4-yl)-4-fluoropiperidin-3-yl)carbamate

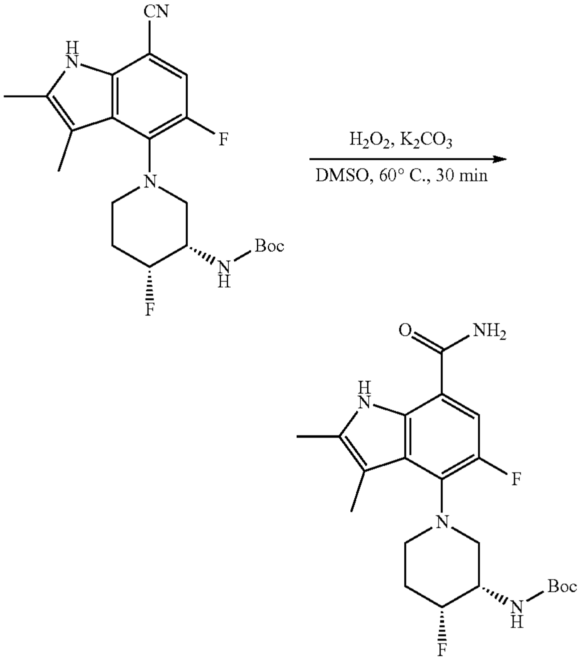

To a mixture of tert-butyl ((3S,4R)-1-(7-cyano-5-fluoro-2,3-dimethyl-1H-indol-4-yl)-4-fluoropiperidin-3-yl)carbamate (238 mg, 0.59 mmol) and potassium carbonate (244 mg, 1.77 mmol) in DMSO (5 mL) was added hydrogen peroxide (30%, 667 mg, 5.88 mmol). The reaction mixture was stirred for 30 min at 60° C. The cooled mixture was diluted with water (30 mL) and extracted with ethyl acetate (3×30 mL). The combined extracts were washed with water (3×30 mL) and brine (30 mL), dried over anhydrous sodium sulfate, filtered and concentrated under vacuum to give tert-butyl ((3S,4R)-1-(7-carbamoyl-5-fluoro-2,3-dimethyl-1H-indol-4-yl)-4-fluoropiperidin-3-yl)carbamate (240 mg, 97%) as a light yellow solid.

$^1$H NMR (400 MHz, DMSO-d6) δ 10.64 (s, 1H), 7.91 (s, 1H), 7.40 (d, J=14.0 Hz, 1H), 7.33 (s, 1H), 6.99 (s, 1H), 4.97-4.77 (m, 1H), 3.91-3.74 (m, 1H), 3.28-3.14 (m, 2H), 2.94-2.79 (m, 2H), 2.34 (s, 3H), 2.30 (s, 3H), 2.06-1.95 (m, 2H), 1.36 (s, 9H).

ESI-MS [M+H]+ calcd for ($C_{21}H_{28}F_2N_4O_3$) 423.21, found: 423.15.

Step 3: 4-((3S,4R)-3-amino-4-fluoropiperidin-1-yl)-5-fluoro-2,3-dimethyl-1H-indole-7-carboxamide hydrochloride

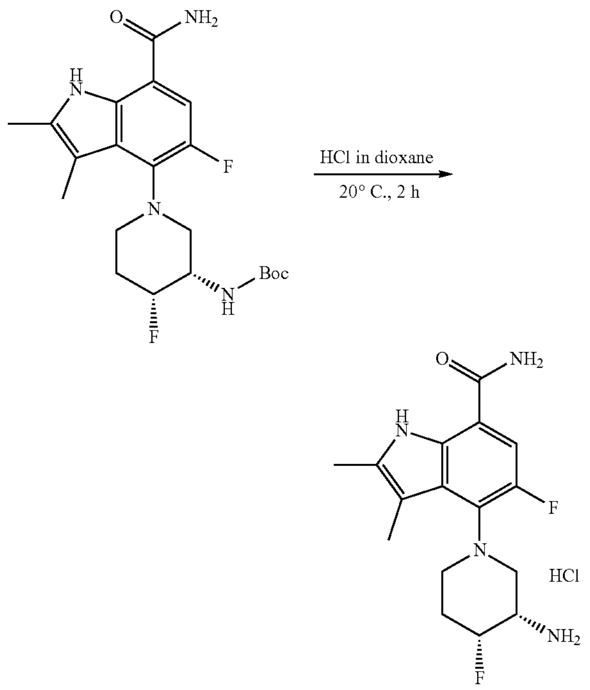

To a solution of tert-butyl ((3S,4R)-1-(7-carbamoyl-5-fluoro-2,3-dimethyl-1H-indol-4-yl)-4-fluoropiperidin-3-yl) carbamate (240 mg, 0.57 mmol) in methanol (5 mL) was added hydrogen chloride (10 mL, 4 M in 1,4-dioxane). The reaction mixture was stirred for 2 hours at 20° C. The resulting mixture was concentrated under vacuum to give 4-((3S,4R)-3-amino-4-fluoropiperidin-1-yl)-5-fluoro-2,3-dimethyl-1H-indole-7-carboxamide hydrochloride (260 mg, crude) as a light yellow solid.

ESI-MS [M+H]+ calcd for ($C_{16}H_{20}F_2N_4O$) 323.16, found: 323.25.

Step 4: 4-((3S,4R)-3-acrylamido-4-fluoropiperidin-1-yl)-5-fluoro-2,3-dimethyl-1H-indole-7-carboxamide

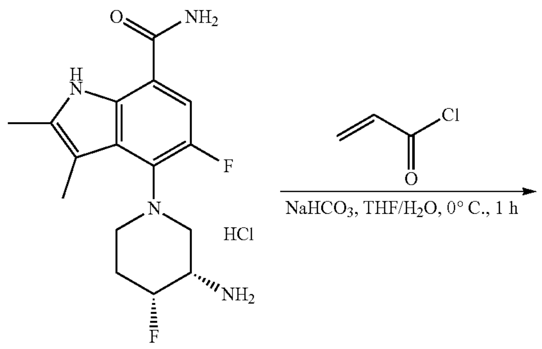

-continued

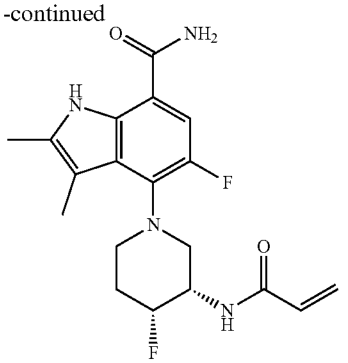

To a mixture of 4-((3S,4R)-3-amino-4-fluoropiperidin-1-yl)-5-fluoro-2,3-dimethyl-1H-indole-7-carboxamide hydrochloride (260 mg, 0.72 mmol) and sodium bicarbonate (609 mg, 7.25 mmol) in mixed solvents of water (3 mL) and THE (12 mL) was added acryloyl chloride (66 mg, 0.72 mmol) at 0° C. The reaction mixture was stirred for 1 hour at 0° C. The resulting mixture was diluted with water (30 mL) and extracted with ethyl acetate (2×30 mL). The combined extracts were washed with water (3×30 mL) and brine (30 mL), dried over anhydrous sodium sulfate, filtered and concentrated under reduced pressure. The residue was purified by Prep-IPLC (column: YMC-Actus Triart C18, 30×250 mm, 5 um; mobile phase A: water (10 mmol/L $NH_4HCO_3$), mobile phase B: acetonitrile; flow rate: 50 mL/min; gradient: 40% B to 70% B in 7 min; 220 nm; retention time=6.08 minutes to give 4-((3S,4R)-3-acrylamido-4-fluoropiperidin-1-yl)-5-fluoro-2,3-dimethyl-1H-indole-7-carboxamide (5.0 mg, 1.8%) as an off-white solid.

$^1$H NMR (300 MHz, DMSO-$d_6$) δ (ppm): 10.64 (s, 1H), 8.29 (s, 1H), 7.93 (s, 1H), 7.42 (d, J=14.1 Hz, 1H), 7.34 (s, 1H), 6.42-6.31 (m, 1H), 6.14-6.07 (m, 1H), 5.62-5.56 (m, 1H), 5.03-4.84 (m, 1H), 4.30-4.19 (m, 1H), 3.05-2.86 (m, 2H), 2.44-2.28 (m, 8H), 2.20-1.96 (m, 2H).

ESI-MS [M+H]+ calcd for ($C_{19}H_{22}F_2N_4O_2$) 377.17, found: 377.25.

Example 32

Synthesis of 4-(1-acryloyloctahydro-6H-pyrrolo[2,3-c]pyridin-6-yl)-5-fluoro-2,3-dimethyl-1H-indole-7-carboxamide (Compound 32)

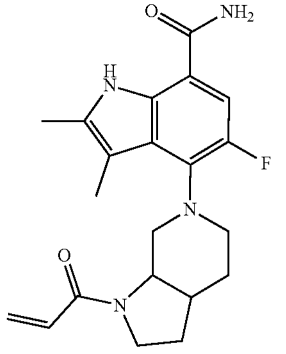 [SMILES: C=CC(=O)N1CCC2CCN(c3c(F)cc(C(N)=O)c4[nH]c(C)c(C)c34)CC21]

Step 1: Tert-butyl 6-(7-cyano-5-fluoro-2,3-dimethyl-1H-indol-4-yl)octahydro-1H-pyrrolo[2,3-c]pyridine-1-carboxylate

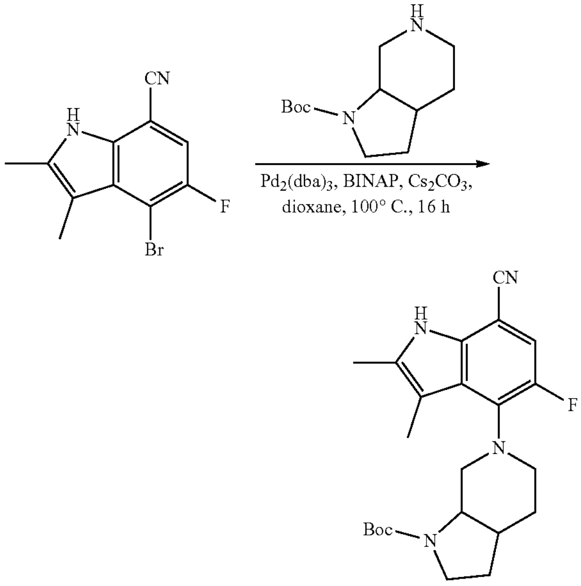

To a mixture of 4-bromo-5-fluoro-2,3-dimethyl-1H-indole-7-carbonitrile (650 mg, 2.43 mmol) and racemic cis-tert-butyl octahydropyrrolo[2,3-c]pyridine-1-carboxylate (606 mg, 2.68 mmol) in 1,4-dioxane (20 mL) were added 1.1'-binaphthyl-2.2'-diphenyl phosphine (152 mg, 0.24 mmol), tris(dibenzylideneacetone)dipalladium (223 mg, 0.24 mmol) and cesium carbonate (1.59 g, 4.86 mmol). The reaction mixture was degassed and backfilled with nitrogen three times and stirred under nitrogen atmosphere for 16 hours at 100° C. The cooled mixture was diluted with water (150 mL) and extracted with ethyl acetate (3×100 mL). The combined extracts were washed with water (2×100 mL) and brine (150 mL), dried over anhydrous sodium sulfate, filtered and concentrated under vacuum. The residue was purified by column chromatography on silica gel eluting (0 to 20% ethyl acetate in petroleum ether) to give tert-butyl 6-(7-cyano-5-fluoro-2,3-dimethyl-1H-indol-4-yl)octahydro-1H-pyrrolo[2,3-c]pyridine-1-carboxylate (410 mg, 41%) as a light yellow solid.

ESI-MS [M+H]+ calcd for ($C_{23}H_{29}FN_4O_2$) 413.23, found: 413.20.

Step 2: Tert-butyl 6-(7-carbamoyl-5-fluoro-2,3-dimethyl-1H-indol-4-yl)octahydro-1H-pyrrolo[2,3-c]pyridine-1-carboxylate

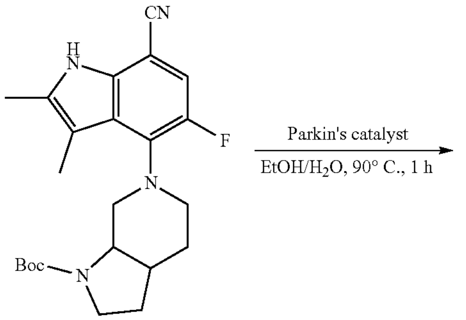

-continued

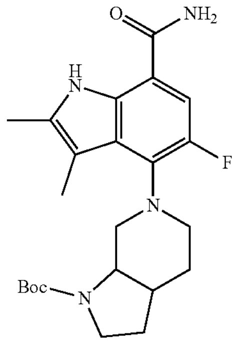

To a mixture of tert-butyl 6-(7-cyano-5-fluoro-2,3-dimethyl-1H-indol-4-yl)octahydro-1H-pyrrolo[2,3-c]pyridine-1-carboxylate (410 mg, 0.99 mmol) in ethanol (16 mL) and water (4.0 mL) was added Parkin's catalyst (22 mg, 0.05 mmol). The reaction mixture was stirred for 1 hour at 90° C. The cooled mixture was poured into water (50 mL). The precipitate was collected by filtration, washed with water (20 mL), and dried under reduced pressure to give tert-butyl 6-(7-carbamoyl-5-fluoro-2,3-dimethyl-1H-indol-4-yl)octahydro-1H-pyrrolo[2,3-c]pyridine-1-carboxylate (330 mg, 77%) as a light yellow solid.

ESI-MS [M+H]+ calcd for ($C_{23}H_{31}FN_4O_3$) 431.24, found: 431.15.

Step 3: 5-fluoro-2,3-dimethyl-4-(octahydro-6H-pyrrolo[2,3-c]pyridin-6-yl)-1H-indole-7-carboxamide 2,2,2-trifluoroacetate

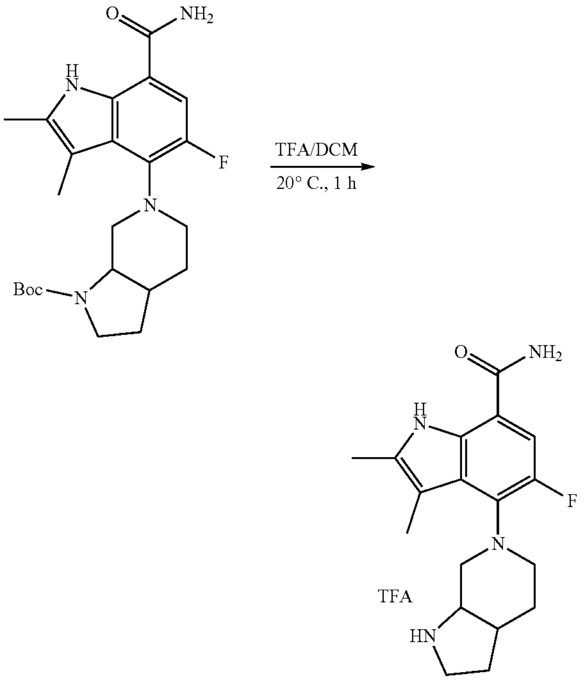

To a solution of tert-butyl 6-(7-carbamoyl-5-fluoro-2,3-dimethyl-1H-indol-4-yl)octahydro-1H-pyrrolo[2,3-c]pyridine-1-carboxylate (330 mg, 0.77 mmol) in dichloromethane (8 mL) was added trifluoroacetic acid (2.0 mL). The reaction mixture was stirred for 1 hour at 20° C. The reaction mixture was concentrated under vacuum to give 5-fluoro-2,3-dimethyl-4-(octahydro-6H-pyrrolo[2,3-c]pyridin-6-yl)-1H-indole-7-carboxamide 2,2,2-trifluoroacetate (400 mg) as a brown solid.

ESI-MS [M+H]+ calcd for ($C_{18}H_{23}FN_4O$) 331.19, found: 331.15.

Step 4: 4-(1-acryloyloctahydro-6H-pyrrolo[2,3-c]pyridin-6-yl)-5-fluoro-2,3-dimethyl-1H-indole-7-carboxamide

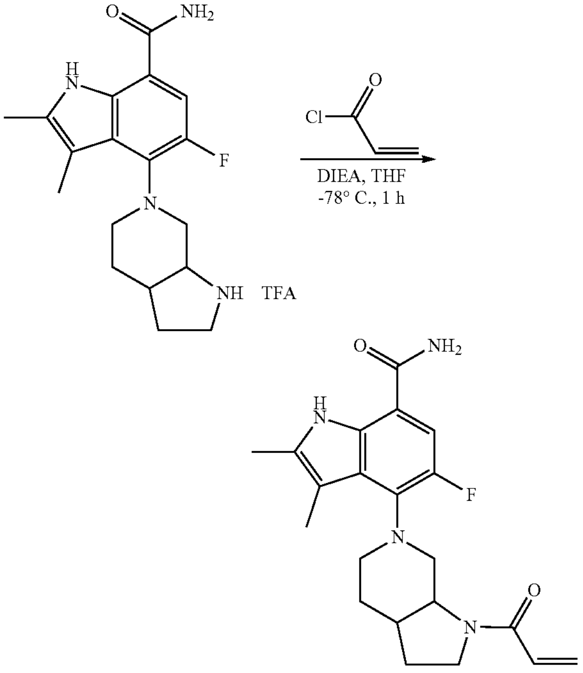

To a solution of 5-fluoro-2,3-dimethyl-4-(octahydro-6H-pyrrolo[2,3-c]pyridin-6-yl)-1H-indole-7-carboxamide 2,2,2-trifluoroacetate (400 mg, crude) and N,N-diisopropylethylamine (995 mg, 7.70 mmol) in tetrahydrofuran (15 mL) was added acryloyl chloride (70 mg, 0.77 mmol) at −78° C. The reaction mixture was stirred for 1 hour at −78° C. The reaction mixture was quenched with water (50 mL) and extracted with ethyl acetate (3x30 mL). The combined extracts were washed with water (2x30 mL) and brine (30 mL), dried over anhydrous sodium sulfate, filtered and concentrated under vacuum. The residue was purified by Prep-TLC (silica gel, eluent: dichloromethane/methanol=20:1) to give 4-(1-acryloyloctahydro-6H-pyrrolo[2,3-c]pyridin-6-yl)-5-fluoro-2,3-dimethyl-1H-indole-7-carboxamide (130 mg, 44% over two steps) as an off-white solid.

$^1$H NMR (300 MHz, DMSO-$d_6$) δ (ppm): 10.67-10.59 (m, 1H), 7.91 (s, 1H), 7.47-7.32 (m, 2H), 6.60-6.46 (m, 1H), 6.14-6.04 (m, 1H), 5.69-5.55 (m, 1H), 4.42-4.13 (m, 1H), 3.78-3.64 (m, 1H), 3.61-3.48 (m, 1H), 3.46-3.35 (m, 2H), 3.25-3.12 (m, 1H), 3.11-2.84 (m, 2H), 2.41 (s, 3H), 2.33 (s, 3H), 2.22-2.02 (m, 2H), 1.97-1.81 (m, 1H), 1.78-1.66 (m, 1H).

ESI-MS [M+H]$^+$ calcd for ($C_{21}H_{25}FN_4O_2$) 385.20, found: 385.30.

Step 5: Separation of Isomers

The isomers of 4-(1-acryloyloctahydro-6H-pyrrolo[2,3-c]pyridin-6-yl)-5-fluoro-2,3-dimethyl-1H-indole-7-carboxamide were separated by Prep-Chiral-HPLC (sample=130 mg, column: CHIRALPAK IA, 2x25 cm, 5 um; mobile phase A: MTBE (0.5% 2 M $NH_3$-MeOH), mobile phase B: IPA-HPLC; flow rate: 18 mL/min; gradient: 45% B, isocratic; 220/254 nm.

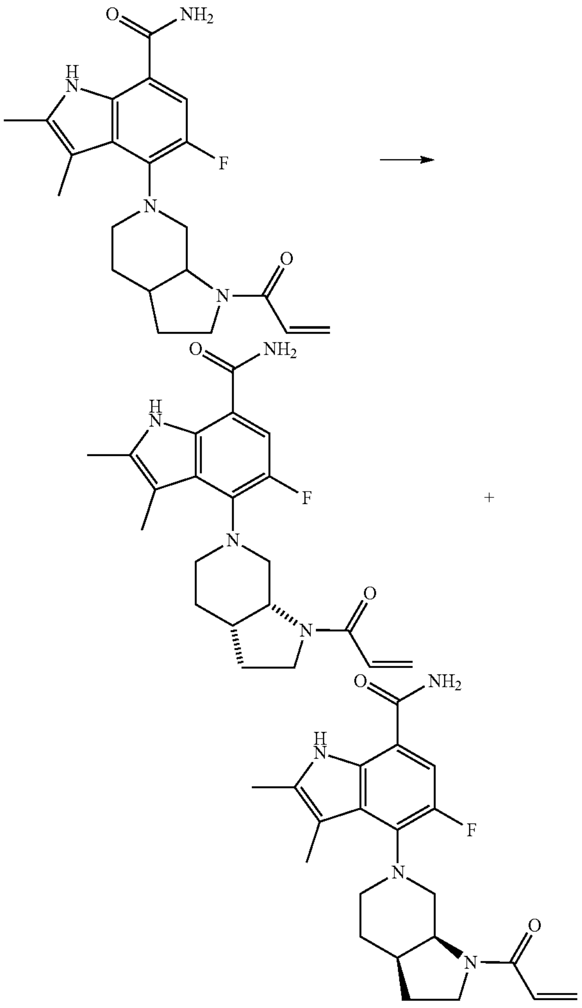

Compound 32a: Retention Time=4.826 Minutes (55 mg). Isolated as an Off-White Solid $^1$H NMR (300 MHz, DMSO-d6) δ (ppm): 10.65 (d, J=6.1 Hz, 1H), 7.93 (s, 1H), 7.42 (dd, J=14.2, 4.0 Hz, 1H), 7.35 (s, 1H), 6.54 (dd, J=16.9, 10.5 Hz, 1H), 6.10 (dd, J=16.7, 2.5 Hz, 1H), 5.63 (dd, J=10.3, 2.5 Hz, 1H), 4.42-4.16 (m, 1H), 3.81-3.67 (m, 1H), 3.61-3.47 (m, 1H), 3.46-3.37 (m, 2H), 3.27-3.14 (m, 1H), 3.10-2.74 (m, 2H), 2.42 (s, 3H), 2.33 (s, 3H), 2.25-2.01 (m, 2H), 1.95-1.79 (m, 1H), 1.78-1.68 (m, 1H).

ESI-MS [M+H]$^+$ calcd for ($C_{21}H_{25}FN_4O_2$) 385.20, found: 385.15.

Compound 32b: Retention Time=6.483 Minutes (52 mg). Isolated as an Off-White Solid $^1$H NMR (300 MHz, DMSO-d6) δ (ppm): 10.65 (d, J=6.1 Hz, 1H), 7.93 (s, 1H), 7.42 (dd, J=14.2, 4.0 Hz, 1H), 7.35 (s, 1H), 6.54 (dd, J=16.8, 10.2 Hz, 1H), 6.10 (dd, J=16.7, 2.5

Hz, 1H), 5.63 (dd, J=10.3, 2.5 Hz, 1H), 4.42-4.17 (m, 1H), 3.79-3.67 (m, 1H), 3.61-3.48 (m, 1H), 3.46-3.37 (m, 2H), 3.28-3.13 (m, 1H), 3.10-2.72 (m, 2H), 2.42 (s, 3H), 2.33 (s, 3H), 2.26-2.02 (m, 2H), 1.96-1.79 (m, 1H), 1.78-1.66 (m, 1H).

ESI-MS $[M+H]^+$ calcd for $(C_{21}H_{25}FN_4O_2)$ 385.20, found: 385.15.

Example 33

Synthesis of 4-((3S,5R)-3-(but-2-ynamido)-5-fluoropiperidin-1-yl)-5-fluoro-2,3-dimethyl-1H-indole-7-carboxamide (Compound 7)

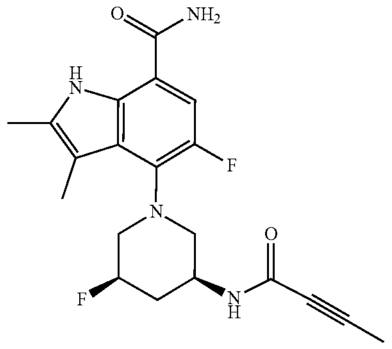 [SMILES: CC#CC(=O)N[C@H]1C[C@@H](F)CN(c2c(F)cc(C(N)=O)c3[nH]c(C)c(C)c23)C1]

Step 1: 4-bromo-5-fluoro-2,3-dimethyl-1H-indole-7-carbonitrile

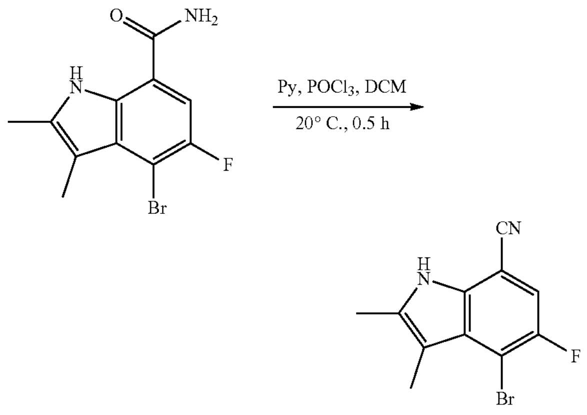

To a solution of 4-bromo-5-fluoro-2,3-dimethyl-1H-indole-7-carboxamide (600 mg, 2.10 mmol) in dichloromethane (12 mL) were added pyridine (416 mg, 5.26 mmol) and phosphorus oxychloride (484 mg, 3.16 mmol). The reaction mixture was stirred at 20° C. for 0.5 hour. After completed, the reaction mixture was concentrated under vacuum. The residue was washed with water, filtered and dried under reduced pressure to give 4-bromo-5-fluoro-2,3-dimethyl-1H-indole-7-carbonitrile (520 mg, 92%) as a red solid.

$^1$H NMR (300 MHz, DMSO-$d_6$) δ 11.96 (s, 1H), 7.58 (d, J=9.3 Hz, 1H), 2.38 (s, 3H), 2.33 (s, 3H).

Step 2: tert-butyl ((3S,5R)-1-(7-cyano-5-fluoro-2,3-dimethyl-1H-indol-4-yl)-5-fluoropiperidin-3-yl) carbamate

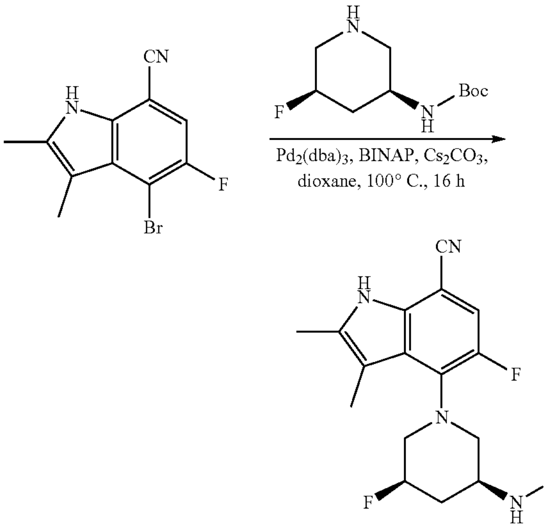

To a mixture of 4-bromo-5-fluoro-2,3-dimethyl-1H-indole-7-carbonitrile (400 mg, 1.50 mmol) and tert-butyl ((3S,5R)-5-fluoropiperidin-3-yl) carbamate (360 mg, 1.65 mmol) in dioxane (8 mL) were added tris(dibenzylideneacetone)dipalladium (137 mg, 0.15 mmol), 1.1'-binaphthyl-2.2'-diphenyl phosphine (93 mg, 0.15 mmol) and cesium carbonate (732 mg, 2.25 mmol). The reaction mixture was evacuated and flushed three times with nitrogen atmosphere and stirred under nitrogen at 100° C. for 16 hours. The cooled reaction mixture was quenched with water (20 ml) and was extracted with ethyl acetate (3×20 ml). The combined extracts were washed with brine (30 ml), dried over anhydrous sodium sulfate, filtered, and concentrated under vacuum. The residue was purified by column chromatography on silica gel (0 to 20% ethyl acetate in petroleum ether) to give tert-butyl ((3S,5R)-1-(7-cyano-5-fluoro-2,3-dimethyl-1H-indol-4-yl)-5-fluoropiperidin-3-yl) carbamate (350 mg, 58%) as a white solid.

$^1$H NMR (300 MHz, DMSO-$d_6$) δ 11.60 (s, 1H), 7.39 (d, J=12.6 Hz, 1H), 6.94 (d, J=8.1 Hz, 1H), 5.11-4.88 (m, 1H), 4.05-3.96 (m, 1H), 3.29-3.15 (m, 3H), 2.76-2.66 (m, 1H), 2.41 (s, 3H), 2.32 (s, 3H), 2.19-2.07 (m, 1H), 1.77-1.52 (m, 1H), 1.36 (s, 9H).

ESI-MS $[M+H]^+$ calcd for $(C_{21}H_{26}F_2N_4O_2)$ 405.20 found: 405.10.

Step 3: tert-butyl ((3S,5R)-1-(7-carbamoyl-5-fluoro-2,3-dimethyl-1H-indol-4-yl)-5-fluoropiperidin-3-yl) carbamate

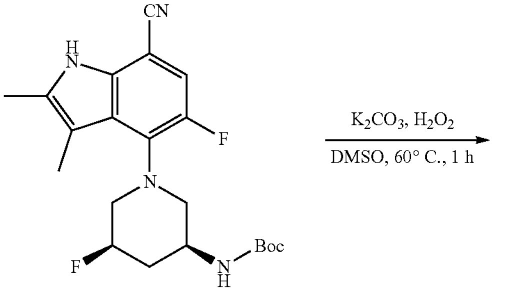

-continued

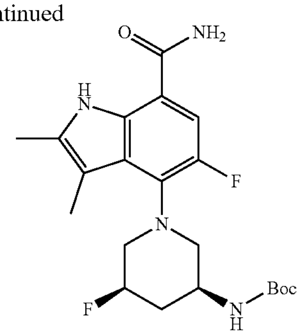

To a solution of tert-butyl ((3S,5R)-1-(7-cyano-5-fluoro-2,3-dimethyl-1H-indol-4-yl)-5-fluoropiperidin-3-yl) carbamate (320 mg, 0.79 mmol) in dimethyl sulfoxide (6.0 mL) were added potassium carbonate (328 mg, 2.37 mmol) and hydrogen peroxide (30%, 1.34 g, 11.87 mmol). The reaction mixture was stirred at 60° C. for 2 hours and then cooled to rt. The reaction mixture was diluted with water (15 ml) and extracted with ethyl acetate (3×20 mL). The combined extracts were washed with brine (30 ml), dried over anhydrous sodium sulfate, filtered, and concentrated under vacuum. The residue was purified by column chromatography on silica gel (0 to 80% ethyl acetate in petroleum ether) to give tert-butyl ((3S,5R)-1-(7-carbamoyl-5-fluoro-2,3-dimethyl-1H-indol-4-yl)-5-fluoropiperidin-3-yl) carbamate (250 mg, 75%) as a yellow solid.

$^1$H NMR (300 MHz, DMSO-$d_6$) δ 10.62 (s, 1H), 7.92 (s, 1H), 7.40 (d, J=14.1 Hz, 1H), 7.34 (s, 1H), 6.88 (d, J=8.1 Hz, 1H), 5.10-4.85 (m, 1H), 4.00-3.93 (m, 1H), 3.24-3.13 (m, 3H), 2.74-2.65 (m, 1H), 2.38 (s, 3H), 2.30 (s, 3H), 2.19-2.05 (m, 1H), 1.72-1.48 (m, 1H), 1.34 (s, 9H).

ESI-MS $[M+H]^+$ calcd for ($C_{21}H_{28}F_2N_4O_3$) 423.21, found: 423.30.

Step 4: 4-((3 S,5R)-3-amino-5-fluoropiperidin-1-yl)-5-fluoro-2,3-dimethyl-1H-indole-7-carboxamide hydrochloride

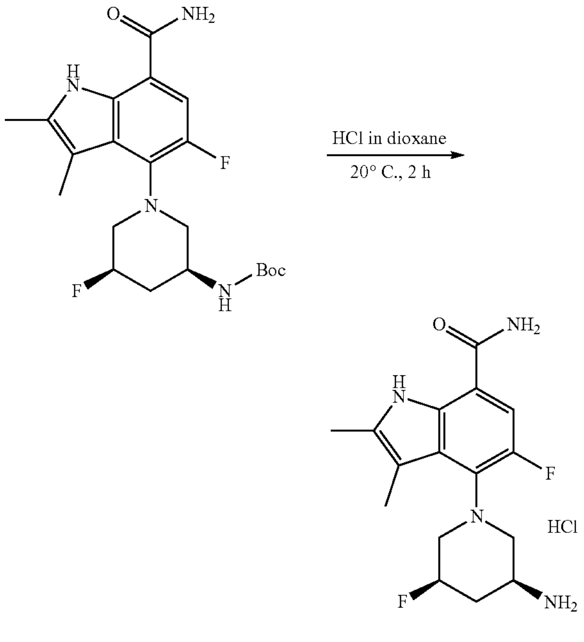

A mixture of tert-butyl ((3S,5R)-1-(7-carbamoyl-5-fluoro-2,3-dimethyl-1H-indol-4-yl)-5-fluoropiperidin-3-yl) carbamate (250 mg, 0.59 mmol) and hydrogen chloride (4 M in dioxane, 5.0 mL) was stirred at 20° C. for 2 hours. The reaction mixture was concentrated under vacuum to give 4-((3S,5R)-3-amino-5-fluoropiperidin-1-yl)-5-fluoro-2,3-dimethyl-1H-indole-7-carboxamide hydrochloride (240 mg) as a yellow solid.

ESI-MS $[M+H]^+$ calcd for ($C_{16}H_{20}F_2N_4O$) 323.16, found: 323.15.

Step 5: 4-((3 S,5R)-3-amino-5-fluoropiperidin-1-yl)-5-fluoro-2,3-dimethyl-1H-indole-7-carboxamide hydrochloride

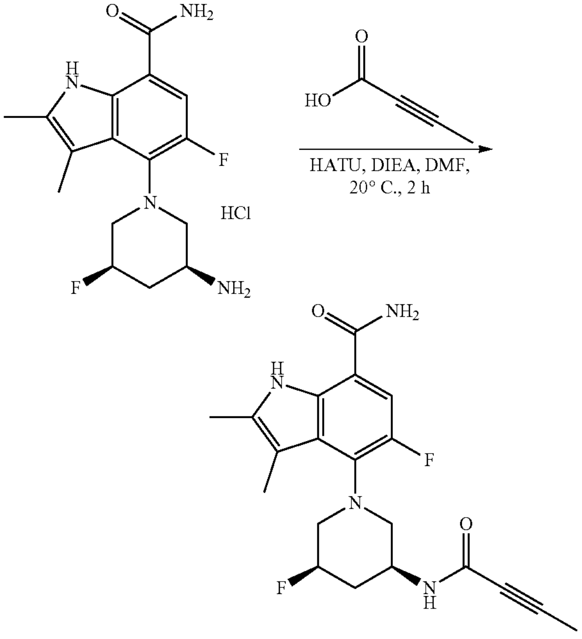

To a solution of but-2-ynoic acid (28 mg, 0.33 mmol) in N,N-dimethylformamide (3 mL) were added HATU (148 mg, 0.39 mmol), 4-((3S,5R)-3-amino-5-fluoropiperidin-1-yl)-5-fluoro-2,3-dimethyl-1H-indole-7-carboxamide hydrochloride (100 mg, 0.28 mmol), and N,N-diisopropylethylamine (108 mg, 0.84 mmol). The reaction mixture was stirred at 20° C. for 2 hours. The reaction mixture was quenched with water (15 ml) and extracted with ethyl acetate (3×10 mL). The combined extracts were washed with brine (30 ml), dried over anhydrous sodium sulfate, filtered, and concentrated under vacuum. The residue was purified by Prep-HPLC (column: X Bridge Shield RP18 OBD Column, 19×250 mm, 10 um; mobile phase A: water (10 mmoL/L $NH_4HCO_3$), mobile phase B: acetonitrile; flow rate: 25 mL/min; gradient: 35% B to 46% B, 9 min; 254 nm; retention time=8.03 minutes) to give 4-((3S,5R)-3-(but-2-ynamido)-5-fluoropiperidin-1-yl)-5-fluoro-2,3-dimethyl-1H-indole-7-carboxamide (46 mg, 42%) as an off-white solid.

$^1$H NMR (400 MHz, DMSO-$d_6$) δ 10.63 (s, 1H), 8.51 (d, J=8.4 Hz, 1H), 7.93 (s, 1H), 7.41 (d, J=14.0 Hz, 1H), 7.35 (s, 1H), 5.05-4.93 (m, 1H), 4.39-4.23 (m, 1H), 3.27-3.13 (m, 3H), 2.82-2.77 (m, 1H), 2.38 (s, 3H), 2.31 (s, 3H), 2.25-2.14 (m, 1H), 1.94 (s, 3H), 1.76-1.56 (m, 1H).

ESI-MS $[M+H]^+$ calcd for ($C_{20}H_{22}F_2N_4O_2$) 389.17, found: 389.05.

Example 34

Synthesis of 4-((3S,5R)-3-acrylamido-5-fluoropiperidin-1-yl)-5-fluoro-2,3-dimethyl-1H-indole-7-carboxamide (Compound 34)

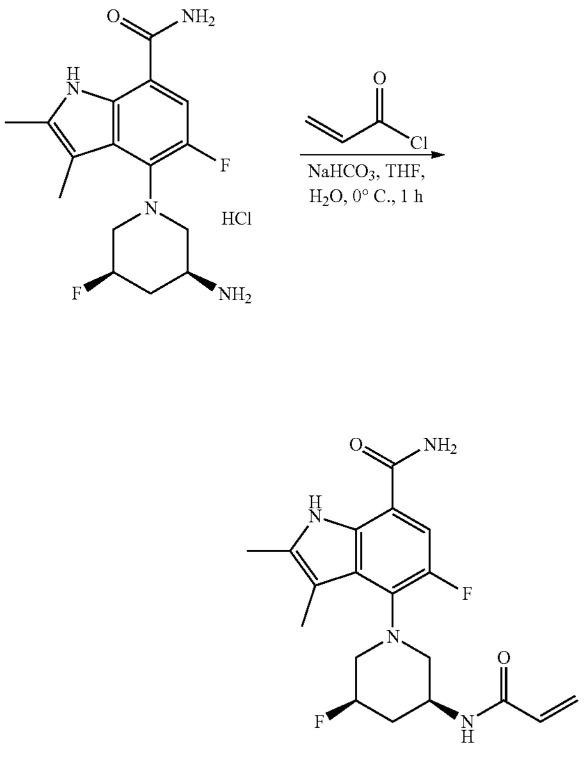

4-((3S,5R)-3-acrylamido-5-fluoropiperidin-1-yl)-5-fluoro-2,3-dimethyl-1H-indole-7-carboxamide: To a mixture of 4-[(3S,5R)-3-amino-5-fluoropiperidin-1-yl]-5-fluoro-2,3-dimethyl-1H-indole-7-carboxamide hydrochloride (100 mg, 0.28 mmol) in tetrahydrofuran (2.0 mL) and water (0.5 mL) were added sodium bicarbonate (70 mg, 0.84 mmol) and acryloyl chloride (30 mg, 0.33 mmol) at 0° C. The reaction mixture was stirred at 0° C. for 1 hour. The reaction mixture was diluted with water (20 ml) and extracted with ethyl acetate (3×20 mL). The combined extracts were washed with brine (30 ml), dried over sodium sulfate, filtered, and concentrated under vacuum. The residue was purified by Prep-HPLC (column: X Bridge Shield RP18 OBD Column, 19×250 mm, 10 um; mobile phase A: water (10 mmoL/L $NH_4HCO_3$), mobile phase B: acetonitrile; flow rate: 25 mL/min; gradient: 30% B to 50% B, 8 minutes; 254 nm; retention time=7.77 minutes) to give 4-((3S,5R)-3-acrylamido-5-fluoropiperidin-1-yl)-5-fluoro-2,3-dimethyl-1H-indole-7-carboxamide (42.7 mg, 41%) as a white solid.

$^1$H NMR (400 MHz, DMSO-$d_6$) δ 10.63 (s, 1H), 8.07 (d, J=8.0 Hz, 1H), 7.93 (s, 1H), 7.42 (d, J=14.0 Hz, 1H), 7.35 (s, 1H), 6.25-6.03 (m, 2H), 5.58 (dd, J=9.6, 2.4 Hz, 1H), 5.08-4.95 (m, 1H), 4.45-4.32 (m, 1H), 3.40-3.36 (m, 1H), 3.27-3.20 (m, 2H), 2.79 (t, J=9.6 Hz, 1H), 2.42 (s, 3H), 2.32 (s, 3H), 2.25-2.15 (m, 1H), 1.75-1.56 (m, 1H).

ESI-MS $[M+H]^+$ calcd for ($C_{19}H_{22}F_2N_4O_2$) 377.17, found: 377.10.

Example 35

Synthesis of 4-((3S,5S)-3-(but-2-ynamido)-5-fluoropiperidin-1-yl)-5-fluoro-2,3-dimethyl-1H-indole-7-carboxamide (Compound 35)

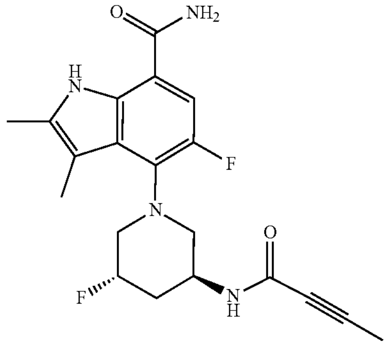 [SMILES: CC#CC(=O)N[C@H]1C[C@H](F)CN(c2c(F)cc(C(N)=O)c3[nH]c(C)c(C)c23)C1]

Step 1: tert-butyl ((3S,5S)-1-(7-cyano-5-fluoro-2,3-dimethyl-1H-indol-4-yl)-5-fluoropiperidin-3-yl) carbamate

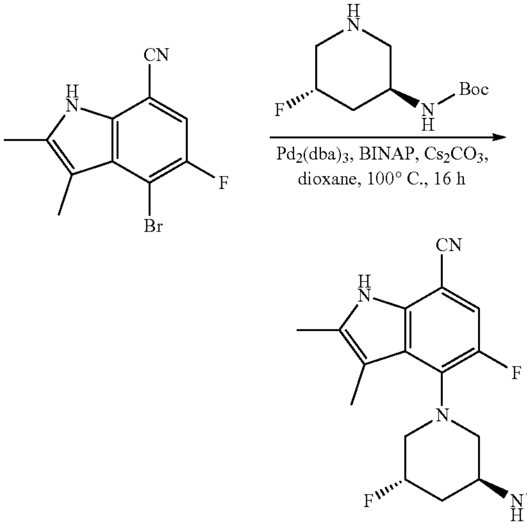

To a mixture of 4-bromo-5-fluoro-2,3-dimethyl-1H-indole-7-carbonitrile (600 mg, 2.25 mmol) and tert-butyl ((3S,5S)-5-fluoropiperidin-3-yl) carbamate (539 mg, 2.47 mmol) in 1,4-dioxane (10 mL) were added tris(dibenzylideneacetone)-dipalladium (206 mg, 0.22 mmol), 1.1'-Binaphthyl-2.2'-diphenyl phosphine (140 mg, 0.22 mmol) and cesium carbonate (1.10 g, 3.37 mmol). The reaction mixture was evacuated and flushed three times with nitrogen and stirred at 100° C. for 16 hours. The cooled reaction mixture was quenched with water (30 ml), extracted with ethyl acetate (3×30 mL). The combined extracts were then washed with brine (30 ml), dried over sodium sulfate, filtered, and concentrated under vacuum. The residue was purified by column chromatography on silica gel (0 to 20% ethyl acetate in petroleum ether) to give tert-butyl ((3S,5S)-1-(7-cyano-5-fluoro-2,3-dimethyl-1H-indol-4-yl)-5-fluoropiperidin-3-yl) carbamate (450 mg, 50%) as a white solid.

$^1H$ NMR (400 MHz, DMSO-$d_6$) δ 11.58 (s, 1H), 7.39 (d, J=12.4 Hz, 1H), 6.92 (d, J=8.0 Hz, 1H), 5.08-4.91 (m, 1H), 4.04-3.97 (m, 1H), 3.27-3.16 (m, 3H), 2.77-2.69 (m, 1H), 2.41 (s, 3H), 2.32 (s, 3H), 2.18-2.08 (m, 1H), 1.74-1.54 (m, 1H), 1.36 (s, 9H).

ESI-MS $[M+H]^+$ calcd for ($C_{21}H_{26}F_2N_4O_2$) 405.20, found: 405.25.

Step 2: tert-butyl ((3S,5S)-1-(7-carbamoyl-5-fluoro-2,3-dimethyl-1H-indol-4-yl)-5-fluoropiperidin-3-yl) carbamate

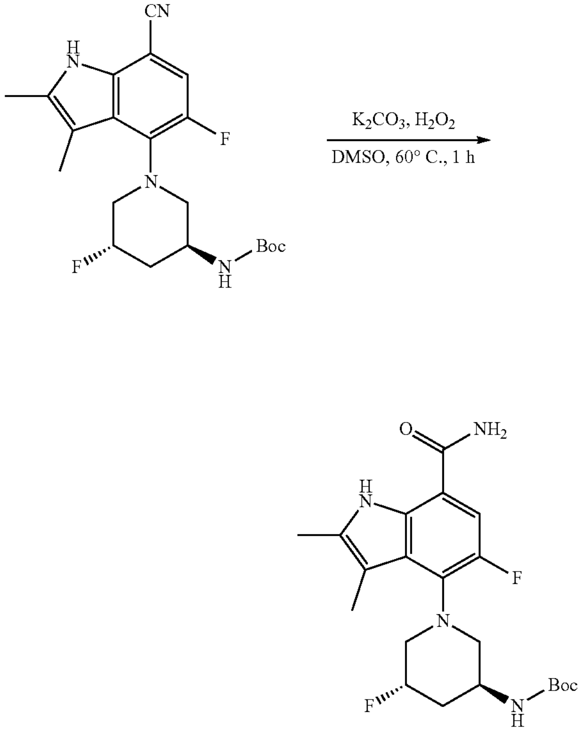

To a solution of tert-butyl ((3S,5S)-1-(7-cyano-5-fluoro-2,3-dimethyl-1H-indol-4-yl)-5-fluoropiperidin-3-yl) carbamate (450 mg, 1.11 mmol) in dimethyl sulfoxide (6.0 mL) were added potassium carbonate (461 mg, 3.34 mmol) and hydrogen peroxide (30%, 1.89 g, 16.69 mmol). The reaction mixture was stirred at 60° C. for 2 hours. The reaction mixture was diluted with water (25 ml), extracted with ethyl acetate (3×20 ml). The combined organic layers was washed with brine (30 ml), dried over sodium sulfate, filtered, and concentrated under vacuum. The residue was purified by column chromatography on silica gel (0 to 80% ethyl acetate in petroleum ether) to give tert-butyl ((3S,5S)-1-(7-carbamoyl-5-fluoro-2,3-dimethyl-1H-indol-4-yl)-5-fluoropiperidin-3-yl) carbamate (420 mg, 89%) as a yellow solid.

$^1H$ NMR (300 MHz, DMSO-$d_6$) δ 10.64 (s, 1H), 7.94 (s, 1H), 7.42 (d, J=13.8 Hz, 1H), 7.36 (s, 1H), 6.90 (d, J=7.8 Hz, 1H), 5.12-4.86 (m, 1H), 4.03-3.95 (m, 1H), 3.26-3.15 (m, 3H), 2.77-2.68 (m, 1H), 2.40 (s, 3H), 2.32 (s, 3H), 2.21-2.07 (m, 1H), 1.75-1.48 (m, 1H), 1.36 (s, 9H).

ESI-MS $[M+H]^+$ calcd for ($C_{21}H_{28}F_2N_4O_3$) 423.21, found: 423.25.

Step 3: 4-((3 S,5S)-3-amino-5-fluoropiperidin-1-yl)-5-fluoro-2,3-dimethyl-1H-indole-7-carboxamide hydrochloride

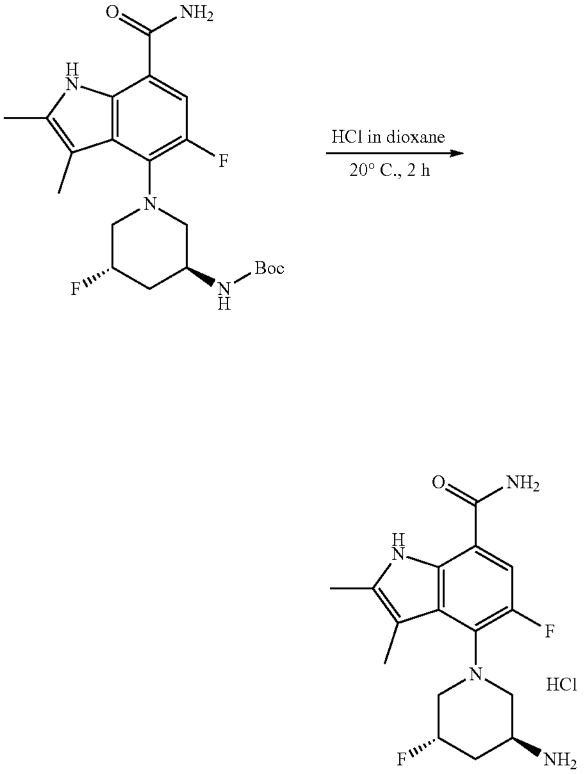

A mixture of tert-butyl ((3S,5S)-1-(7-carbamoyl-5-fluoro-2,3-dimethyl-1H-indol-4-yl)-5-fluoropiperidin-3-yl) carbamate (420 mg, 0.99 mmol) and hydrogen chloride (4 M in dioxane, 8 mL) was stirred at 20° C. for 2 hours. The reaction mixture was concentrated under vacuum to give 4-((3S,5S)-3-amino-5-fluoropiperidin-1-yl)-5-fluoro-2,3-dimethyl-1H-indole-7-carboxamide hydrochloride (350 mg) as a yellow solid.

ESI-MS $[M+H]^+$ calcd for ($C_{16}H_{20}F_2N_4O$) 323.16, found: 323.15.

Step 4: 4-((3S,5S)-3-(but-2-ynamido)-5-fluoropiperidin-1-yl)-5-fluoro-2,3-dimethyl-1H-indole-7-carboxamide

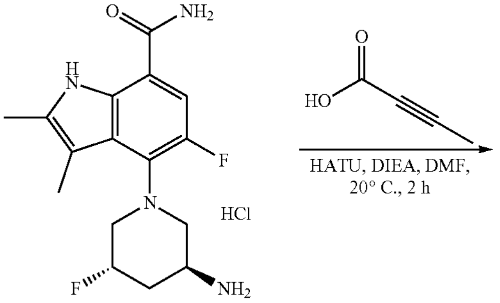

-continued

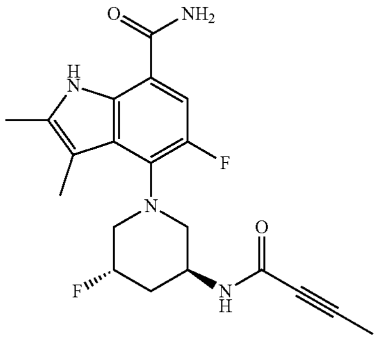

To a solution of but-2-ynoic acid (47 mg, 0.56 mmol) in N,N-dimethylformamide (5 mL) were added HATU (248 mg, 0.65 mmol), 4-((3S,5S)-3-amino-5-fluoropiperidin-1-yl)-5-fluoro-2,3-dimethyl-1H-indole-7-carboxamide hydrochloride (165 mg, 0.46 mmol), and N,N-diisopropylethylamine (180 mg, 1.40 mmol). The reaction mixture was stirred at 20° C. for 2 hours. The reaction mixture was quenched with water (30 ml) and extracted with ethyl acetate (3×20 mL). The combined extracts were washed with brine (30 ml), dried over sodium sulfate, filtered, and concentrated under vacuum. The residue was purified by Prep-HPLC (column: Xselect CSH OBD Column 30×150 mm, 5 um, mobile phase A: water (10 mmol/L $NH_4HCO_3$+0.1% $NH_3 \cdot H_2O$), mobile phase B: acetonitrile; flow rate: 60 mL/min; gradient: 25% B to 52% B in 7 min; 220 nm; retention time=6.17 minutes) to give 4-[(3S,5S)-3-(but-2-ynoylamino)-5-fluoropiperidin-1-yl]-5-fluoro-2,3-dimethyl-1H-indole-7-carboxamide (57.2 mg, 32%) as an off-white solid.

$^1$H NMR (300 MHz, DMSO-$d_6$) δ 10.63 (s, 1H), 8.51 (d, J=8.1 Hz, 1H), 7.93 (s, 1H), 7.45-7.35 (m, 2H), 5.07-4.91 (m, 1H), 4.42-4.24 (m, 1H), 3.28-3.13 (m, 3H), 2.82-2.75 (m, 1H), 2.38 (s, 3H), 2.31 (s, 3H), 2.20-2.09 (m, 1H), 1.94 (s, 3H), 1.78-1.53 (m, 1H).

ESI-MS $[M+H]^+$ calcd for ($C_{20}H_{22}F_2N_4O_2$) 389.17, found: 389.25.

Example 36

Synthesis of 4-((3S,5R)-3-acrylamido-5-fluoropiperidin-1-yl)-5-fluoro-2,3-dimethyl-1H-indole-7-carboxamide (Compound 36)

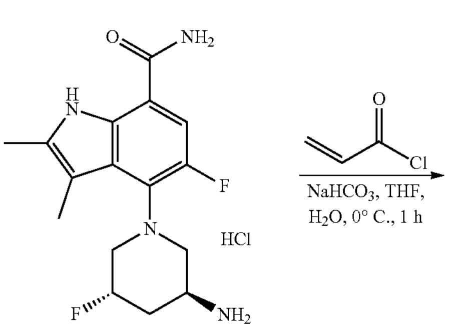

-continued

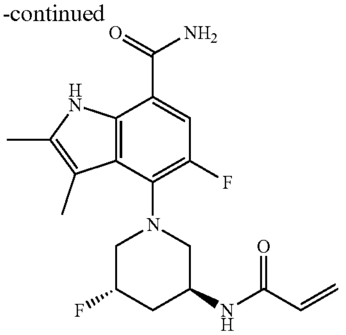

4-((3S,5S)-3-acrylamido-5-fluoropiperidin-1-yl)-5-fluoro-2,3-dimethyl-1H-indole-7-carboxamide: To a mixture of 4-[(3S,5S)-3-amino-5-fluoropiperidin-1-yl]-5-fluoro-2,3-dimethyl-1H-indole-7-carboxamide hydrochloride (220 mg, 0.62 mmol) in tetrahydrofuran (4.0 mL) and water (1.0 mL) were added sodium bicarbonate (156 mg, 1.86 mmol) and acryloyl chloride (67 mg, 0.74 mmol) at 0° C. The reaction mixture was stirred at 0° C. for 1 hour. The reaction mixture was diluted with water (30 mL) and extracted with ethyl acetate (3×25 mL). The combined extracts were washed with brine (30 mL), dried over sodium sulfate, filtered, and concentrated under vacuum. The residue was purified by Prep-HPLC (column: X select CSH OBD Column 30×150 mm, 5 um; Mobile phase A: water (10 mmol/L $NH_4HCO_3$+0.1% $NH_3 \cdot H_2O$), mobile phase B: acetonitrile; flow rate: 60 mL/min; gradient: 28% B to 48% B, 7 min; 220 nm; retention time=5.33 minutes) to give 4-((3S,5S)-3-acrylamido-5-fluoropiperidin-1-yl)-5-fluoro-2,3-dimethyl-1H-indole-7-carboxamide (82.4 mg, 35%) as a white solid.

$^1$H NMR (300 MHz, DMSO-$d_6$) δ 10.64 (s, 1H), 8.09 (d, J=7.8 Hz, 1H), 7.94 (s, 1H), 7.42 (d, J=14.1 Hz, 1H), 7.36 (s, 1H), 6.28-6.02 (m, 2H), 5.58 (dd, J=9.6, 2.7 Hz, 1H), 5.10-4.93 (m, 1H), 4.48-4.34 (m, 1H), 3.43-3.38 (m, 1H), 3.26-3.21 (m, 2H), 2.82-2.75 (m, 1H), 2.43 (s, 3H), 2.32 (s, 3H), 2.28-2.21 (m, 1H), 1.78-1.53 (m, 1H).

ESI-MS $[M+H]^+$ calcd for ($C_{19}H_{22}F_2N_4O_2$) 377.17, found: 377.30.

Example 37

Synthesis of 4-((3S,5R)-3-acrylamido-5-hydroxypiperidin-1-yl)-5-fluoro-2,3-dimethyl-1H-indole-7-carboxamide (Compound 37)

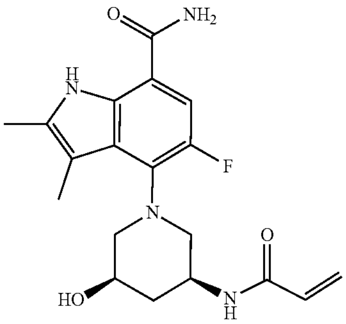 [SMILES: C=CC(=O)N[C@H]1C[C@@H](O)CN(c2c(F)cc(C(N)=O)c3[nH]c(C)c(C)c23)C1]

Step 1: tert-butyl ((3S,5R)-1-(7-carbamoyl-5-fluoro-2,3-dimethyl-1H-indol-4-yl)-5-hydroxypiperidin-3-yl) carbamate

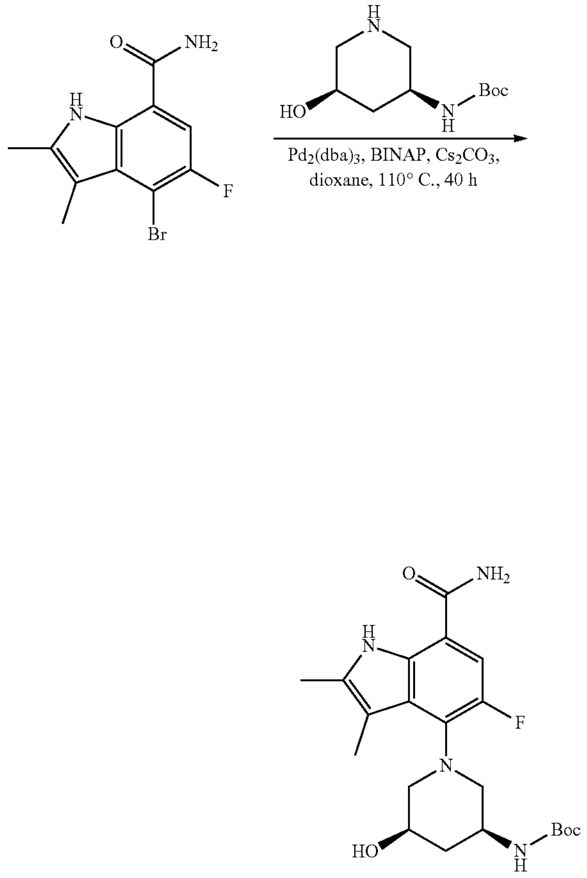

To a mixture of 4-bromo-5-fluoro-2,3-dimethyl-1H-indole-7-carboxamide (250 mg, 0.88 mmol) and tert-butyl ((3S,5R)-5-hydroxypiperidin-3-yl) carbamate (228 mg, 1.05 mmol) in 1,4-dioxane (5.0 mL) were added tris(dibenzylideneacetone)dipalladium (80 mg, 0.088 mmol), 1.1'-binaphthyl-2.2'-diphenyl phosphine (109 mg, 0.17 mmol), and cesium carbonate (429 mg, 1.32 mmol). The reaction mixture was evacuated and flushed three times with nitrogen and stirred under nitrogen at 110° C. for 40 hours. The cooled reaction mixture was quenched with water (30 ml) and extracted with ethyl acetate (3×20 ml). The combined extracts were washed with brine (30 ml), dried over anhydrous sodium sulfate, filtered, and concentrated under vacuum. The residue was purified by column chromatography on silica gel (0 to 60% ethyl acetate in petroleum ether) to give tert-butyl ((3S,5R)-1-(7-carbamoyl-5-fluoro-2,3-dimethyl-1H-indol-4-yl)-5-hydroxypiperidin-3-yl) carbamate (150 mg, 41%) as a yellow solid.

$^1$H NMR (400 MHz, DMSO-$d_6$) δ 10.65 (s, 1H), 7.94 (s, 1H), 7.41 (d, J=14.0 Hz, 1H), 7.36 (s, 1H), 6.93 (d, J=8.0 Hz, 1H), 4.91 (s, 1H), 3.72-3.63 (m, 2H), 3.13-3.07 (m, 2H), 2.77-2.58 (m, 2H), 2.34 (s, 3H), 2.32 (s, 3H), 2.07-2.04 (m, 1H), 1.35 (s, 9H), 1.26-1.23 (m, 1H).

ESI-MS $[M+H]^+$ calcd for ($C_{21}H_{29}F\ N_4O_4$) 421.22, found: 421.25.

Step 2: 4-((3S,5R)-3-amino-5-hydroxypiperidin-1-yl)-5-fluoro-2,3-dimethyl-1H-indole-7-carboxamide hydrochloride

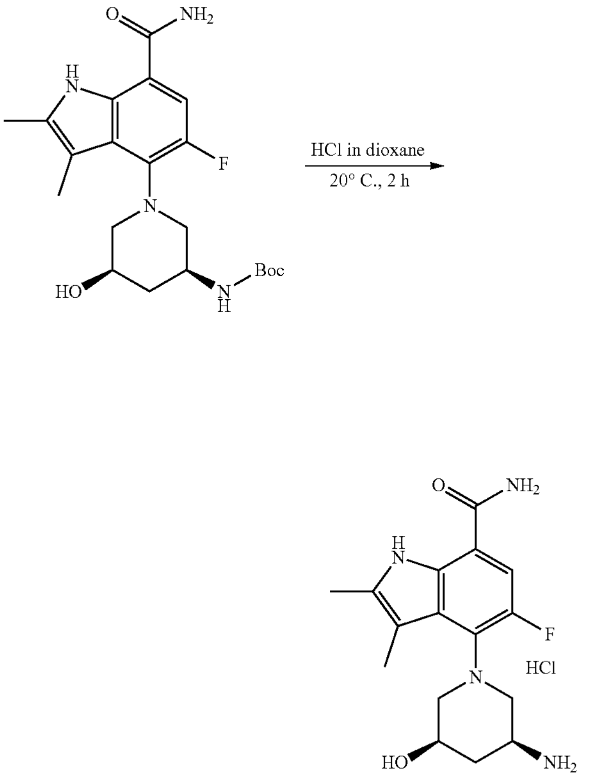 [SMILES: Cc1[nH]c2c(C(N)=O)cc(F)c(N3C[C@H](O)C[C@H](NC(=O)OC(C)(C)C)C3)c2c1C ; Cc1[nH]c2c(C(N)=O)cc(F)c(N3C[C@@H](N)C[C@@H](O)C3)c2c1C ; Cl]

A mixture of tert-butyl ((3S,5R)-1-(7-carbamoyl-5-fluoro-2,3-dimethyl-1H-indol-4-yl)-5-hydroxypiperidin-3-yl) carbamate (140 mg, 0.33 mmol) and hydrogen chloride (4 M in dioxane, 5.0 mL) was stirred at 20° C. for 2 hours. After completion, the reaction mixture was concentrated under vacuum to give 4-((3S,5R)-3-amino-5-hydroxypiperidin-1-yl)-5-fluoro-2,3-dimethyl-1H-indole-7-carboxamide hydrochloride (130 mg) as a yellow solid.

ESI-MS $[M+H]^+$ calcd for ($C_{16}H_{21}N_4O_2F$) 321.16, found: 321.25.

Step 3: 4-((3S,5R)-3-acrylamido-5-hydroxypiperidin-1-yl)-5-fluoro-2,3-dimethyl-1H-indole-7-carboxamide

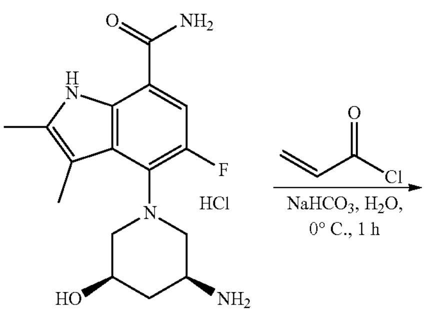

-continued

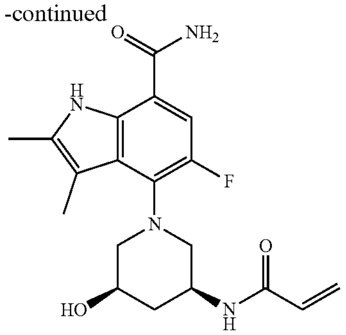

To a mixture of 4-((3S,5R)-3-amino-5-hydroxypiperidin-1-yl)-5-fluoro-2,3-dimethyl-1H-indole-7-carboxamide hydrochloride (130 mg, 0.37 mmol) in tetrahydrofuran (2.0 mL) and water (0.5 mL) were added sodium bicarbonate (95 mg, 1.13 mmol) and acryloyl chloride (41 mg, 451 umol) at 0° C. The reaction mixture was stirred at 0° C. for 1 hour. After completion, the reaction mixture was diluted with water (25 mL) and extracted with ethyl acetate (3×20 mL). The combined extracts were washed with brine (30 ml), dried over anhydrous sodium sulfate, filtered, and concentrated under vacuum. The residue was purified by Prep-HPLC (column: XBridge Prep OBD C18 Column, 30×150 mm, 5 um; mobile phase A: water (10 mmol/L $NH_4HCO_3$+0.1% $NH_3 \cdot H_2O$), mobile phase B: acetonitrile; flow rate: 60 mL/min; gradient: 5% B to 35% B in 7 min; 220 nm; retention time=5.48 minutes) to give 4-((3S,5R)-3-acrylamido-5-hydroxypiperidin-1-yl)-5-fluoro-2,3-dimethyl-1H-indole-7-carboxamide (32.3 mg, 23%) as an off-white solid.

$^1$H NMR (300 MHz, DMSO-$d_6$) δ 10.64 (s, 1H), 8.10 (d, J=7.8 Hz, 1H), 7.92 (s, 1H), 7.41 (d, J=14.1 Hz, 1H), 7.34 (s, 1H), 6.28-6.01 (m, 2H), 5.57 (dd, J=9.6, 2.7 Hz, 1H), 4.97 (d, J=4.8 Hz, 1H), 4.12-4.03 (m, 1H), 3.79-3.75 (m, 1H), 3.19-3.15 (m, 2H), 2.81-2.68 (m, 2H), 2.36 (s, 3H), 2.32 (s, 3H) 2.16-2.11 (m, 1H), 1.30-1.23 (m, 1H).

ESI-MS $[M+H]^+$ calcd for ($C_{19}H_{23}F\ N_4O_3$) 375.18, found: 375.25.

Example 38

Synthesis of 4-((3S,5S)-3-acrylamido-5-hydroxypiperidin-1-yl)-5-fluoro-2,3-dimethyl-1H-indole-7-carboxamide (Compound 38)

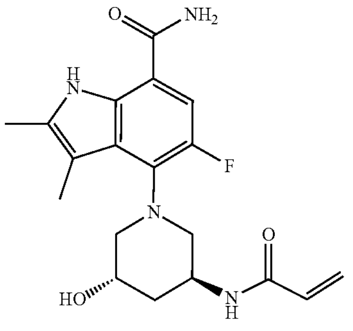 [SMILES: C=CC(=O)N[C@H]1C[C@H](O)CN(c2c(F)cc(C(N)=O)c3[nH]c(C)c(C)c23)C1]

Step 1: tert-butyl ((3S,5S)-1-(7-carbamoyl-5-fluoro-2,3-dimethyl-1H-indol-4-yl)-5-hydroxypiperidin-3-yl) carbamate

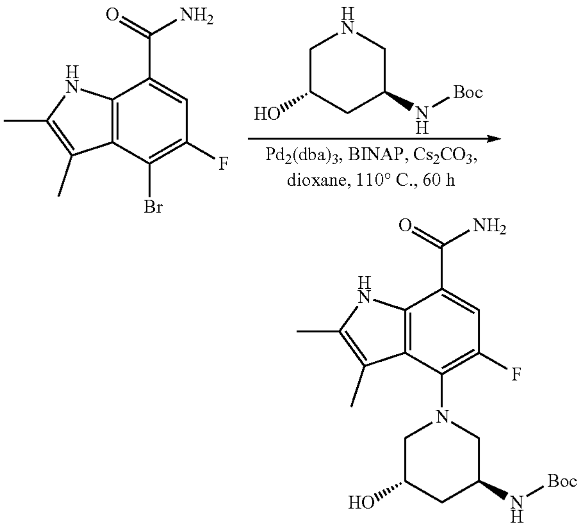

To a mixture of 4-bromo-5-fluoro-2,3-dimethyl-1H-indole-7-carboxamide (380 mg, 1.33 mmol) and tert-butyl ((3S,5S)-5-hydroxypiperidin-3-yl) carbamate (240 mg, 1.11 mmol) in 1,4-dioxane (7.0 mL) were added tris(dibenzylideneacetone)dipalladium (102 mg, 0.11 mmol), 1.1'-binaphthyl-2.2'-diphenyl phosphine (138 mg, 0.22 mmol), and cesium carbonate (542 mg, 1.66 mmol). The reaction mixture was evacuated and flushed three times with nitrogen and stirred under nitrogen at 110° C. for 60 hours. After completion, the cooled reaction mixture was quenched with water (30 mL) and extracted with dichloromethane (3×30 mL). The combined extracts were washed with brine (30 mL), dried over anhydrous sodium sulfate, filtered, and concentrated under vacuum. The residue was purified by Prep-TLC (100% ethyl acetate, Rf=0.6) to give tert-butyl ((3S,5S)-1-(7-carbamoyl-5-fluoro-2,3-dimethyl-1H-indol-4-yl)-5-hydroxypiperidin-3-yl) carbamate (110 mg) as a yellow solid.

ESI-MS $[M+H]^+$ calcd for ($C_{21}H_{29}F\ N_4O_4$) 421.22, found: 421.35.

Step 2: 4-((3S,5S)-3-amino-5-hydroxypiperidin-1-yl)-5-fluoro-2,3-dimethyl-1H-indole-7-carboxamide hydrochloride

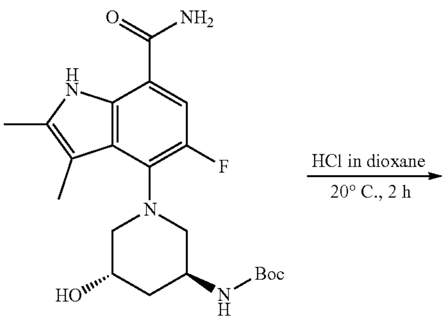

-continued

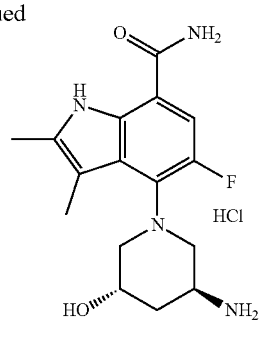

A mixture of tert-butyl ((3S,5S)-1-(7-carbamoyl-5-fluoro-2,3-dimethyl-1H-indol-4-yl)-5-hydroxypiperidin-3-yl) carbamate (110 mg, 0.33 mmol) and hydrogen chloride (4 M in dioxane, 5.0 mL) was stirred at 20° C. for 2 hours. After completion, the reaction mixture was concentrated under vacuum to give 4-((3S,5S)-3-amino-5-hydroxypiperidin-1-yl)-5-fluoro-2,3-dimethyl-1H-indole-7-carboxamide hydrochloride (80 mg) as a yellow solid.

ESI-MS [M+H]+ calcd for ($C_{16}H_{21}F$ $N_4O_2$) 321.16, found: 321.15.

Step 3: 4-((3S,5S)-3-acrylamido-5-hydroxypiperidin-1-yl)-5-fluoro-2,3-dimethyl-1H-indole-7-carboxamide

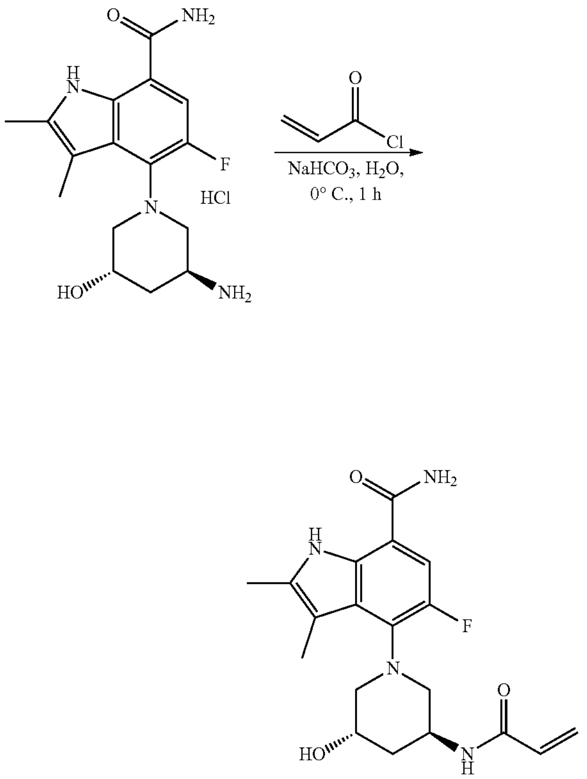

To a solution of 4-((3S,5S)-3-amino-5-hydroxypiperidin-1-yl)-5-fluoro-2,3-dimethyl-1H-indole-7-carboxamide hydrochloride (68 mg, 0.19 mmol) in tetrahydrofuran (2.0 mL) and water (0.5 mL) were added sodium bicarbonate (47 mg, 0.56 mmol) and acryloyl chloride (20 mg, 0.22 mmol) at 0° C. The reaction mixture was stirred at 0° C. for 1 hour. After completion, the reaction mixture was diluted with water (20 mL), extracted with ethyl acetate (3×15 mL). The combined extracts were washed with brine (20 mL), dried over anhydrous sodium sulfate, filtered, and concentrated under vacuum. The residue was purified by Prep-HPLC (column: XBridge Prep OBD C18 Column, 30×150 mm, 5 um; mobile phase A: water (10 mmol/L $NH_4HCO_3$+0.1% $NH_3 \cdot H_2O$), mobile phase B: acetonitrile; flow rate: 60 mL/min; gradient: 15% B to 30% B, 7 minutes; 220 nm; retention time=6.02 minutes) to give 4-((3S,5S)-3-acrylamido-5-hydroxypiperidin-1-yl)-5-fluoro-2,3-dimethyl-1H-indole-7-carboxamide (13.1 mg, 19%) as a white solid.

$^1$H NMR (400 MHz, DMSO-$d_6$) δ 10.60 (s, 1H), 7.98-7.92 (m, 2H), 7.43-7.33 (m, 2H), 6.40-6.14 (m, 1H), 6.04 (dd, J=17.2, 2.0 Hz, 1H), 5.55 (dd, J=10.0, 2.0 Hz, 1H), 4.90-3.95 (m, 3H), 3.21-2.95 (m, 3H), 2.68-2.63 (m, 1H), 2.49-2.30 (m, 6H), 2.08-1.91 (m, 1H), 1.60-1.40 (m, 1H).

ESI-MS [M+H]$^+$ calcd for ($C_{19}H_{23}F$ $N_4O_3$) 375.18, found: 375.15.

Example 39

Synthesis of 4-(trans-2-acryloyloctahydro-5H-pyrrolo[3,4-c]pyridin-5-yl)-3-chloro-5-fluoro-2-methyl-1H-indole-7-carboxamide (Compound 39)

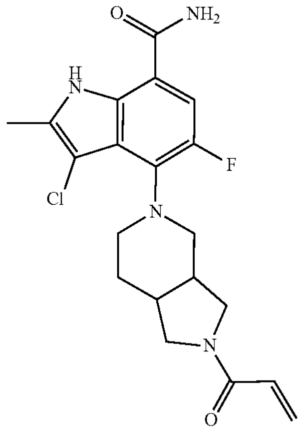 [SMILES: C=CC(=O)N1CC2CCN(c3c(F)cc(C(N)=O)c4[nH]c(C)c(Cl)c34)CC2C1]

Step 1: tert-Butyl trans-5-(7-cyano-5-fluoro-2-methyl-1H-indol-4-yl)octahydro-2H-pyrrolo[3,4-c]pyridine-2-carboxylate

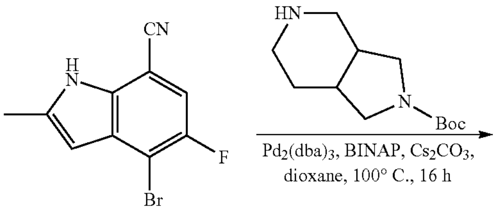

-continued

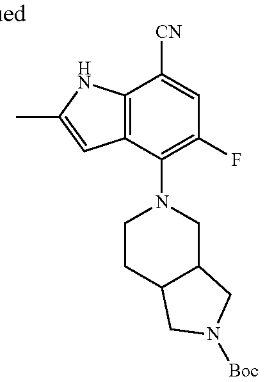

To a mixture of 4-bromo-5-fluoro-2-methyl-1H-indole-7-carbonitrile (600 mg, 2.37 mmol) and tert-butyl trans-octahydro-2H-pyrrolo[3,4-c]pyridine-2-carboxylate (536 mg, 2.37 mmol) in 1,4-dioxane (10 mL) were added tris (dibenzylideneacetone)dipalladium (217 mg, 0.24 mmol), 1.1'-Binaphthyl-2.2'-diphenyl phosphine (295 mg, 0.47 mmol) and cesium carbonate (2.32 g, 7.11 mmol). The reaction mixture was evacuated and flushed three times with nitrogen and stirred under nitrogen at 100° C. for 16 hours. After completion, the cooled reaction mixture was quenched with water (40 ml) and extracted with ethyl acetate (3×30 mL). The combined extracts were washed with brine (30 mL), dried over anhydrous sodium sulfate, filtered, and concentrated under vacuum. The residue was purified by column chromatography (silica gel, 0-30% ethyl acetate in petroleum ether) to give tert-butyl trans-5-(7-cyano-5-fluoro-2-methyl-1H-indol-4-yl)octahydro-2H-pyrrolo[3,4-c]-pyridine-2-carboxylate (500 mg, 53%) as a yellow solid.

$^1$H NMR (300 MHz, DMSO-d6) δ 7.36 (d, J=12.9 Hz, 1H), 6.35 (s, 1H), 3.77-3.66 (m, 2H), 3.57-3.43 (m, 2H), 3.15-3.03 (m, 2H), 2.91-2.79 (m, 2H), 2.37 (s, 3H), 1.92-1.85 (m, 2H), 1.75-1.63 (m, 1H), 1.58-1.49 (m, 1H), 1.41 (s, 9H).

ESI-MS [M+H]+ calcd for ($C_{22}H_{27}FN_4O_2$) 399.21, found: 399.15.

Step 2: tert-butyl trans-5-(7-carbamoyl-5-fluoro-2-methyl-1H-indol-4-yl)octahydro-2H-pyrrolo[3,4-c] pyridine-2-carboxylate

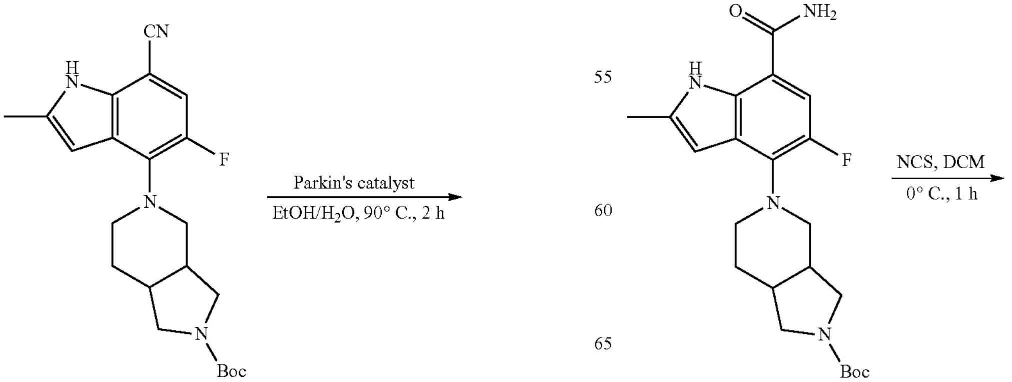

-continued

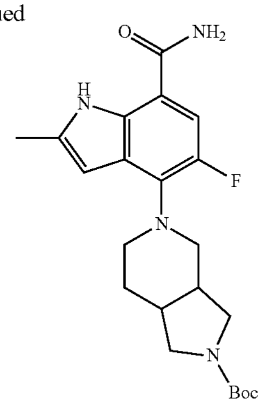

To a mixture of tert-butyl trans-5-(7-cyano-5-fluoro-2-methyl-1H-indol-4-yl)octahydro-2H-pyrrolo[3,4-c]pyridine-2-carboxylate (500 mg, 1.11 mmol) in ethanol (12 mL) and water (3.0 mL) was added Parkin's catalyst (47 mg, 0.11 mmol). The reaction mixture was stirred at 90° C. for 2 hours. After completion, the cooled reaction mixture was diluted with water (30 mL) and extracted with ethyl acetate (3×30 mL). The combined extracts were washed with brine (50 mL), dried over anhydrous sodium sulfate, filtered, and concentrated under vacuum. The residue was purified by column chromatography (silica gel, 0-60% ethyl acetate in petroleum ether) to give tert-butyl trans-5-(7-carbamoyl-5-fluoro-2-methyl-1H-indol-4-yl)octahydro-2H-pyrrolo[3,4-c]pyridine-2-carboxylate (420 mg, 80%) as a yellow solid.

$^1$H NMR (300 MHz, DMSO-$d_6$) δ 10.83 (s, 1H), 7.89 (s, 1H), 7.46 (d, J=14.4 Hz, 1H), 7.27 (s, 1H), 6.22 (s, 1H), 3.72-3.43 (m, 4H), 3.18-3.00 (m, 2H), 2.94-2.77 (m, 2H), 2.39 (s, 3H), 1.95-1.79 (m, 2H), 1.75-1.50 (m, 2H), 1.41 (s, 9H).

ESI-MS $[M+H]^+$ calcd for ($C_{22}H_{29}FN_4O_3$) 417.22, found: 417.15.

Step 3: tert-butyl trans-5-(7-carbamoyl-3-chloro-5-fluoro-2-methyl-1H-indol-4-yl)octahydro-2H-pyrrolo[3,4-c]pyridine-2-carboxylate -continued

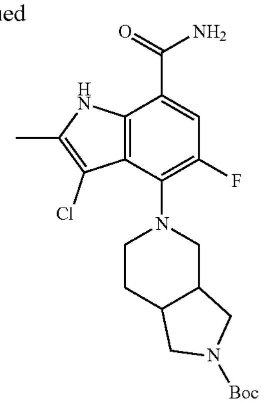

To a mixture of tert-butyl trans-5-(7-carbamoyl-5-fluoro-2-methyl-1H-indol-4-yl)octahydro-2H-pyrrolo[3,4-c]pyridine-2-carboxylate (400 mg, 0.96 mmol) in dichloromethane (10 mL) was added N-chlorosuccinimide (128 mg, 0.96 mmol) at 0° C. The reaction mixture was stirred at 0° C. for 1 hour. After completion, the reaction mixture was quenched with water (30 mL) and extracted with ethyl acetate (3×20 mL). The combined extracts were washed with brine (30 mL), dried over anhydrous sodium sulfate, filtered, and concentrated under vacuum. The residue was purified by column chromatography (silica gel, 0-60% ethyl acetate in petroleum ether) to give tert-butyl trans-5-(7-carbamoyl-3-chloro-5-fluoro-2-methyl-1H-indol-4-yl)octahydro-2H-pyrrolo-[3,4-c]pyridine-2-carboxylate (400 mg, 92%) as a yellow solid.

ESI-MS $[M+H]^+$ calcd for ($C_{22}H_{28}ClFN_4O_3$) 451.18, 453.18; found: 451.10, 453.10.

Step 4: 3-chloro-5-fluoro-2-methyl-4-(trans-octahydro-5H-pyrrolo[3,4-c]pyridin-5-yl)-1H-indole-7-carboxamide hydrochloride

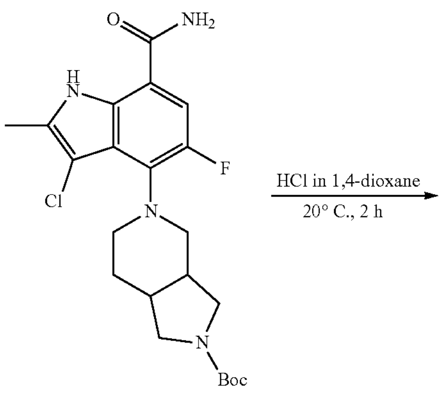

-continued

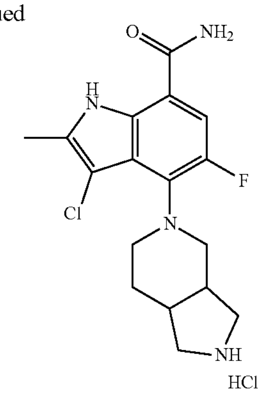

A mixture of tert-butyl trans-5-(7-carbamoyl-3-chloro-5-fluoro-2-methyl-1H-indol-4-yl)octahydro-2H-pyrrolo[3,4-c]pyridine-2-carboxylate (400 mg, 0.89 mmol) and hydrogen chloride (4M in dioxane, 8.0 mL) was stirred at 20° C. for 2 h. After completion, the reaction mixture was concentrated under vacuum to give 3-chloro-5-fluoro-2-methyl-4-(trans-octahydro-5H-pyrrolo[3,4-c]pyridin-5-yl)-1H-indole-7-carboxamide hydrochloride (420 mg) as a yellow solid.

ESI-MS $[M+H]^+$ calcd for ($C_{17}H_{20}ClFN_4O$) 351.13, 353.13; found: 351.05, 353.05.

Step 5: 4-(trans-2-acryloyloctahydro-5H-pyrrolo[3,4-c]pyridin-5-yl)-3-chloro-5-fluoro-2-methyl-1H-indole-7-carboxamide

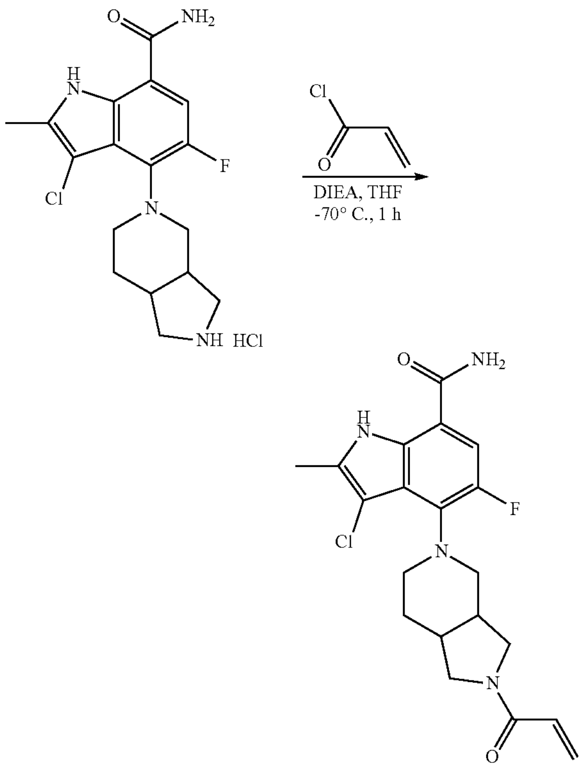

To a mixture of 3-chloro-5-fluoro-2-methyl-4-(trans-octahydro-5H-pyrrolo[3,4-c]pyridin-5-yl)-1H-indole-7-carboxamide hydrochloride (300 mg, 0.77 mmol) in tetrahydrofuran (5.0 mL) was added N,N-diisopropylethylamine (500 mg, 3.87 mmol). After 10 min, acryloyl chloride (84 mg, 0.93 mmol) was added to the stirred solution at −70° C. The reaction mixture was stirred at −70° C. for 1 h. After completion, the reaction mixture was quenched with water (20 mL) and extracted with ethyl acetate (3×20 mL). The combined extracts were washed with brine (40 mL), dried over anhydrous sodium sulfate, filtered, and concentrated under vacuum. The residue was purified by Prep-HPLC (column: Xselect CSH OBD Column 30×150 mm 5 um, mobile phase A: water (10 mmol/L $NH_4HCO_3$+0.1% $NH_3 \cdot H_2O$), mobile phase B: acetonitrile, flow rate: 60 mL/min, gradient: 35% B to 55% B in 7 min, 220 nm, retention time=5.27 minutes) to afford 4-(trans-2-acryloyloctahydro-5H-pyrrolo[3,4-c]pyridin-5-yl)-3-chloro-5-fluoro-2-methyl-1H-indole-7-carboxamide (78.6 mg, 25%, mixture of trans enantiomers) as a white solid.

$^1$H NMR (400 MHz, DMSO-$d_6$) δ 11.24 (s, 1H), 8.00 (s, 1H), 7.54 (d, J=14.0 Hz, 1H), 7.43 (s, 1H), 6.62-6.51 (m, 1H), 6.14 (dd, J=16.8, 2.4 Hz, 1H), 5.69-5.64 (m, 1H), 3.86-3.65 (m, 2H), 3.41-3.38 (m, 1H), 3.30-3.20 (m, 1H), 3.19-3.08 (m, 3H), 2.93-2.90 (m, 1H), 2.38 (s, 3H), 2.10-1.68 (m, 4H).

ESI-MS [M+H]+ calcd for ($C_{20}H_{22}ClFN_4O_2$) 405.14, 407.14; found: 405.10, 407.10.

Example 40

Synthesis of 4-(1-(but-2-ynoyl)octahydro-6H-pyrrolo[3,4-b]pyridin-6-yl)-3-chloro-5-fluoro-2-methyl-1H-indole-7-carboxamide (Compound 40)

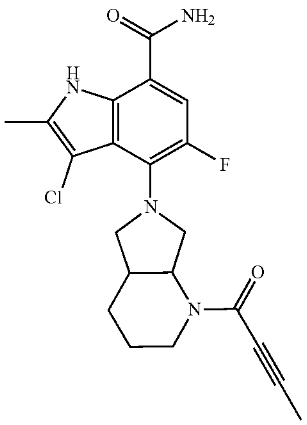 [SMILES: CC#CC(=O)N1CCCC2CN(c3c(F)cc(C(N)=O)c4[nH]c(C)c(Cl)c34)CC21]

Step 1: tert-butyl 6-(7-cyano-5-fluoro-2-methyl-1H-indol-4-yl)octahydro-1H-pyrrolo[3,4-b]pyridine-1-carboxylate

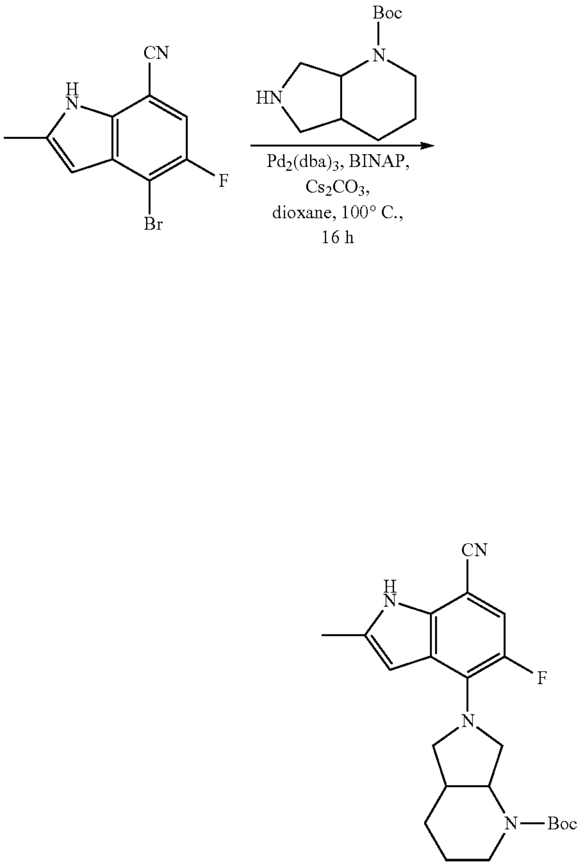

To a mixture of 4-bromo-5-fluoro-2-methyl-1H-indole-7-carbonitrile (600 mg, 2.37 mmol) and tert-butyl octahydro-1H-pyrrolo[3,4-b]pyridine-1-carboxylate (643 mg, 2.85 mmol) in 1,4-dioxane (10 mL) were added 1.1'-binaphthyl-2.2'-diphenyl phosphine (295 mg, 0.47 mmol), tris(dibenzylideneacetone)dipalladium (217 mg, 0.23 mmol) and cesium carbonate (2.32 g, 7.11 mmol). The reaction mixture was degassed and backfilled with nitrogen for five times and stirred at 100° C. for 16 h. The cooled mixture was diluted with water (30 mL) and extracted with ethyl acetate (3×30 mL). The combined extracts were washed with water (2×30 mL) and brine (30 mL), dried over anhydrous sodium sulfate, filtered, and concentrated under vacuum. The residue was purified by column chromatography (silica gel, 25% ethyl acetate in petroleum ether) to give tert-butyl 6-(7-cyano-5-fluoro-2-methyl-1H-indol-4-yl)octahydro-1H-pyrrolo[3,4-b]pyridine-1-carboxylate (720 mg, 76%) as a yellow solid.

1H NMR (300 MHz, DMSO-$d_6$) δ 11.49 (s, 1H), 7.26 (d, J=14.7 Hz, 1H), 6.62 (s, 1H), 4.73-4.54 (m, 1H), 4.17-4.07 (m, 1H), 3.98-3.82 (m, 2H), 3.67-3.56 (m, 1H), 3.54-3.46 (m, 1H), 2.95-2.81 (m, 1H), 2.33 (s, 3H), 2.26-2.10 (m, 1H), 1.79-1.61 (m, 2H), 1.42 (s, 9H), 1.40-1.30 (m, 2H).

ESI-MS [M+H]+ calcd for ($C_{22}H_{27}FN_4O_2$) 399.21, found: 399.30.

Step 2: tert-butyl 6-(7-carbamoyl-5-fluoro-2-methyl-1H-indol-4-yl)octahydro-1H-pyrrolo[3,4-b]pyridine-1-carboxylate

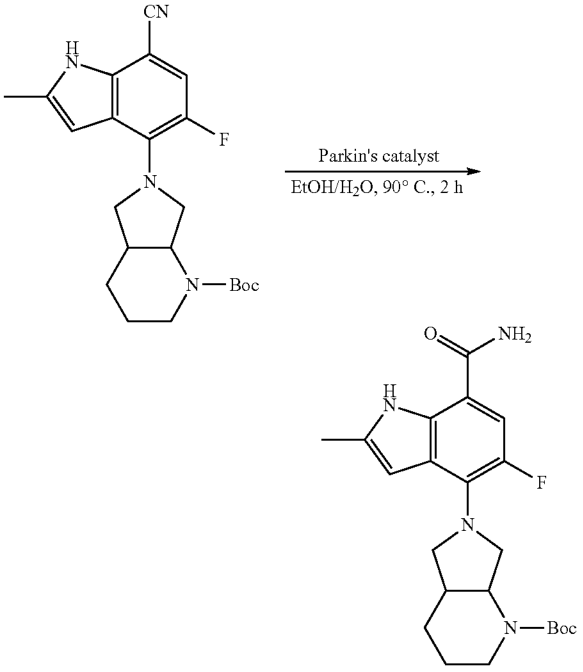

To a mixture of tert-butyl 6-(7-cyano-5-fluoro-2-methyl-1H-indol-4-yl)octahydro-1H-pyrrolo[3,4-b]pyridine-1-carboxylate (720 mg, 1.81 mmol) in ethanol (8 mL) and water (2.0 mL) was added Parkin's catalyst (38 mg, 0.09 mmol). The reaction mixture was stirred at 90° C. for 2 h. The cooled mixture was diluted with water (40 mL) and extracted with ethyl acetate (3x40 mL). The combined extracts were washed water (2x30 mL) and brine (50 mL), dried over anhydrous sodium sulfate, filtered, and concentrated under vacuum. The residue was purified by column chromatography (silica gel, 50% ethyl acetate in petroleum ether) to give tert-butyl 6-(7-carbamoyl-5-fluoro-2-methyl-1H-indol-4-yl)octahydro-1H-pyrrolo[3,4-b]pyridine-1-carboxylate (600 mg, 79%) as a yellow solid.

ESI-MS [M+H]+ calcd for ($C_{22}H_{29}FN_4O_3$) 417.22, found: 417.20.

Step 3: tert-butyl 6-(7-carbamoyl-3-chloro-5-fluoro-2-methyl-1H-indol-4-yl)octahydro-1H-pyrrolo[3,4-b]pyridine-1-carboxylate

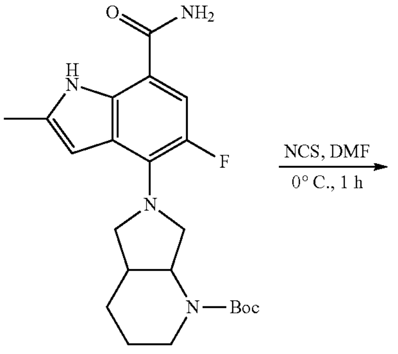

-continued

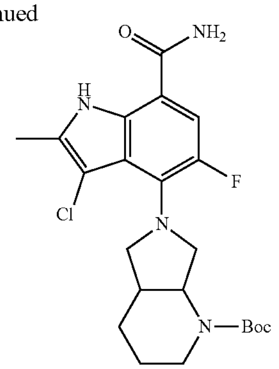

To a solution of tert-butyl 6-(7-carbamoyl-5-fluoro-2-methyl-1H-indol-4-yl)octahydro-1H-pyrrolo[3,4-b]pyridine-1-carboxylate (600 mg, 1.44 mmol) in DMF (10 mL) was added 1-chloropyrrolidine-2,5-dione (192 mg, 1.44 mmol) at 0° C. The reaction mixture was stirred at 0° C. for 1 h. The mixture was diluted with water (30 mL) and extracted with ethyl acetate (3x30 mL). The combined extracts were washed water (2x30 mL) and brine (40 mL), dried over anhydrous sodium sulfate, filtered, and concentrated under vacuum. The residue was purified by column chromatography (silica gel, 40% ethyl acetate in petroleum ether) to give tert-butyl 6-(7-carbamoyl-3-chloro-5-fluoro-2-methyl-1H-indol-4-yl)octahydro-1H-pyrrolo[3,4-b]pyridine-1-carboxylate (600 mg, 92%) as a yellow solid.

ESI-MS [M+H]+ calcd for ($C_{22}H_{28}ClFN_4O_3$) 451.18, 453.18; found: 451.20, 453.20.

Step 4: 3-chloro-5-fluoro-2-methyl-4-(octahydro-6H-pyrrolo[3,4-b]pyridin-6-yl)-1H-indole-7-carboxamide 2,2,2-trifluoroacetate

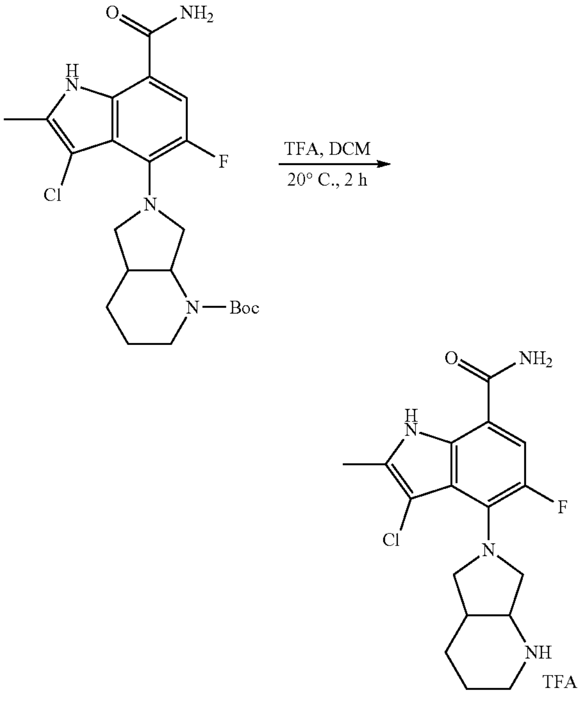

To a solution of tert-butyl 6-(7-carbamoyl-3-chloro-5-fluoro-2-methyl-1H-indol-4-yl)octahydro-1H-pyrrolo[3,4-b]pyridine-1-carboxylate (600 mg, 1.33 mmol) in dichloromethane (5.0 mL) was added trifluoroacetic acid (5.0 mL). The reaction mixture was stirred for 2 h at 20° C. The resulting mixture was concentrated under vacuum to give 3-chloro-5-fluoro-2-methyl-4-(octahydro-6H-pyrrolo[3,4-b]pyridin-6-yl)-1H-indole-7-carboxamide 2,2,2-trifluoroacetate (600 mg) as a yellow solid.

ESI-MS [M+H]+ calc'd for ($C_{17}H_{20}ClFN_4O$) 351.13, 353.13; found: 351.10, 353.10.

Step 5: 4-(1-(but-2-ynoyl)octahydro-6H-pyrrolo[3,4-b]pyridin-6-yl)-3-chloro-5-fluoro-2-methyl-1H-indole-7-carboxamide

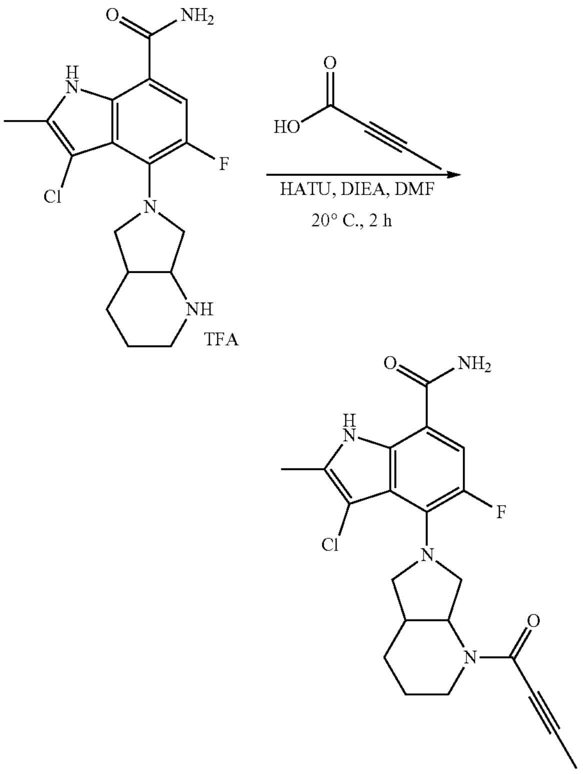

To a mixture of 3-chloro-5-fluoro-2-methyl-4-(octahydro-6H-pyrrolo[3,4-b]pyridin-6-yl)-1H-indole-7-carboxamide 2,2,2-trifluoroacetate (600 mg, 1.33 mmol) in DMF (10 mL) was added O-(7-Azabenzotriazol-1-yl)-N,N,N',N'-tetramethyluronium hexafluorophosphate (757 mg, 1.99 mmol), but-2-ynoic acid (134 mg, 1.60 mmol) and N,N-diisopropylethylamine (663 mg, 5.13 mmol). The reaction mixture was stirred at 20° C. for 2 h. The resulting mixture was diluted with water (30 mL) and extracted with ethyl acetate (2×30 mL). The combined extracts were washed with water (2×30 mL) and brine (30 mL), dried over anhydrous sodium sulfate, filtered, and concentrated under vacuum. The residue was purified by Prep-HPLC (column: Xselect CSH OBD Column 30×150 mm 5 um, mobile phase A: water (10 M $NH_4HCO_3$+0.1% $NH_3 \cdot H_2O$); mobile phase B: acetonitrile; flow rate: 60 mL/min; gradient: 40% B to 60% B, 7 min; 220 nm; retention time=6.02 minutes) to give 4-(1-(but-2-ynoyl)octahydro-6H-pyrrolo[3,4-b]pyridin-6-yl)-3-chloro-5-fluoro-2-methyl-1H-indole-7-carboxamide (28.6 mg, 5%) as an off-white solid.

$^1$H NMR (300 MHz, DMSO-$d_6$) δ 11.26 (d, J=4.8 Hz, 1H), 8.03 (s, 1H), 7.65-7.40 (m, 2H), 5.19-5.03 (m, 1H), 4.32-4.17 (m, 1H), 3.65-3.40 (m, 2H), 3.31-3.02 (m, 2.4H), 2.78-2.65 (m, 0.6H), 2.43-2.16 (m, 4H), 2.05 (d, J=5.7 Hz, 3H), 1.91-1.70 (m, 3H), 1.52-1.24 (m, 1H).

ESI-MS [M+H]+ calcd for ($C_{21}H_{22}ClFN_4O_2$) 417.14, 419.14; found: 417.10, 419.10.

Example 41

Compounds 41a-41t, as shown in Table 7, are prepared according to similar methods as described in the preceding schemes and examples by employing correspondingly appropriate starting materials.

TABLE 7

| COMPOUNDS 41A-41T | | |
|---|---|---|
| Cmpd. No. | Structure | Name |
| 41a | 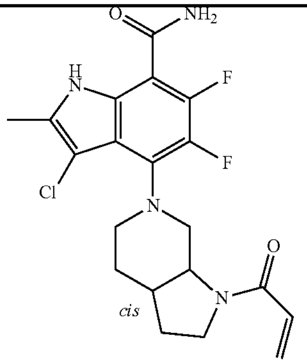 | 4-(1-acryloyloctahydro-6H-pyrrolo[2,3-c]pyridin-6-yl)-3-chloro-5,6-difluoro-2-methyl-1H-indole-7-carboxamide |

TABLE 7-continued

COMPOUNDS 41A-41T

| Cmpd. No. | Structure | Name |
|---|---|---|
| 41b | 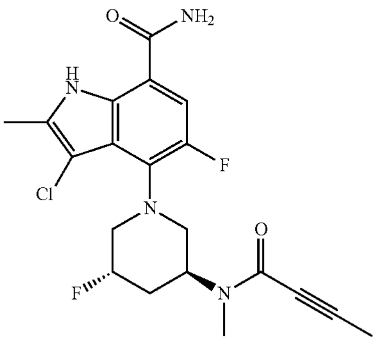 [SMILES: CC#CC(=O)N(C)[C@H]1C[C@H](F)CN(c2c(F)cc(C(N)=O)c3[nH]c(C)c(Cl)c23)C1] | 3-chloro-5-fluoro-4-((3S,5S)-3-fluoro-5-(N-methylbut-2-ynamido)piperidin-1-yl)-2-methyl-1H-indole-7-carboxamide |
| 41c | 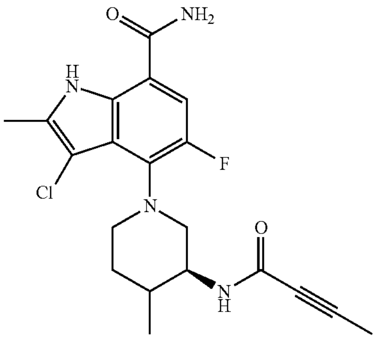 [SMILES: CC#CC(=O)N[C@@H]1CN(c2c(F)cc(C(N)=O)c3[nH]c(C)c(Cl)c23)CCC1C] | 4-((3S)-3-(but-2-ynamido)-4-methylpiperidin-1-yl)-3-chloro-5-fluoro-2-methyl-1H-indole-7-carboxamide |
| 41d | 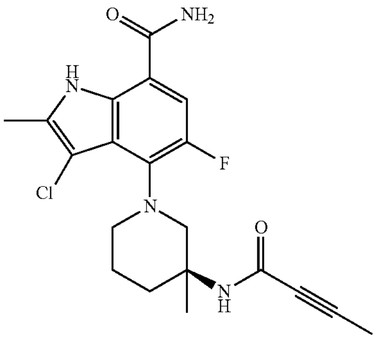 [SMILES: CC#CC(=O)N[C@@]1(C)CCCN(c2c(F)cc(C(N)=O)c3[nH]c(C)c(Cl)c23)C1] | (S)-4-(3-(but-2-ynamido)-3-methylpiperidin-1-yl)-3-chloro-5-fluoro-2-methyl-1H-indole-7-carboxamide |
| 41e | 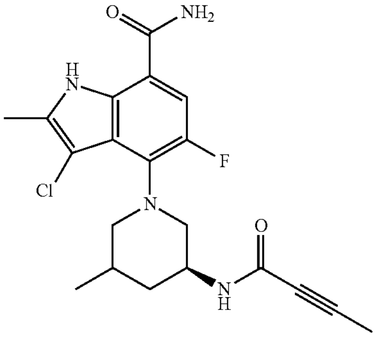 [SMILES: CC#CC(=O)N[C@H]1CC(C)CN(c2c(F)cc(C(N)=O)c3[nH]c(C)c(Cl)c23)C1] | 4-((3S)-3-(but-2-ynamido)-5-methylpiperidin-1-yl)-3-chloro-5-fluoro-2-methyl-1H-indole-7-carboxamide |

TABLE 7-continued

| COMPOUNDS 41A-41T | | |
|---|---|---|
| Cmpd. No. | Structure | Name |
| 41f | 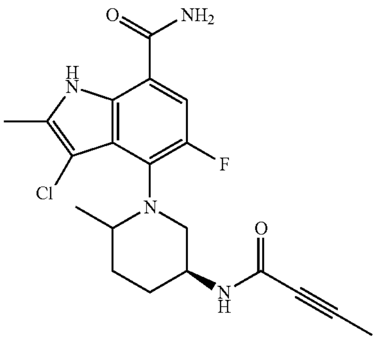 [SMILES: CC#CC(=O)N[C@H]1CCC(C)N(c2c(F)cc(C(N)=O)c3[nH]c(C)c(Cl)c23)C1] | 4-((5S)-5-(but-2-ynamido)-2-methylpiperidin-1-yl)-3-chloro-5-fluoro-2-methyl-1H-indole-7-carboxamide |
| 41g | 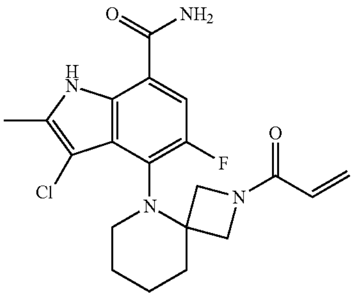 [SMILES: C=CC(=O)N1CC2(CCCCN2c2c(F)cc(C(N)=O)c3[nH]c(C)c(Cl)c23)C1] | 4-(2-acryloyl-2,5-diazaspiro[3.5]nonan-5-yl)-3-chloro-5-fluoro-2-methyl-1H-indole-7-carboxamide |
| 41h | 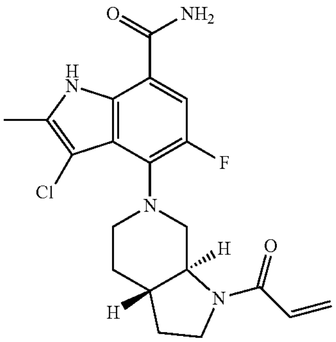 [SMILES: C=CC(=O)N1CC[C@@H]2CCN(c3c(F)cc(C(N)=O)c4[nH]c(C)c(Cl)c34)C[C@H]21] | 4-((3aS,7aS)-1-acryloyloctahydro-6H-pyrrolo[2,3-c]pyridin-6-yl)-3-chloro-5-fluoro-2-methyl-1H-indole-7-carboxamide |
| 41i | 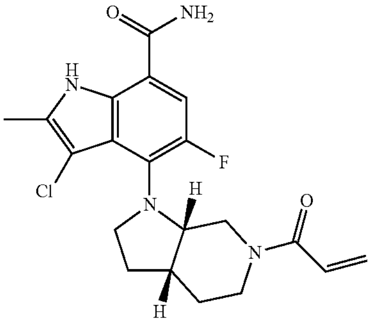 [SMILES: C=CC(=O)N1CC[C@@H]2CCN(c3c(F)cc(C(N)=O)c4[nH]c(C)c(Cl)c34)[C@@H]2C1] | 4-((3aS,7aS)-6-acryloyloctahydro-1H-pyrrolo[2,3-c]pyridin-1-yl)-3-chloro-5-fluoro-2-methyl-1H-indole-7-carboxamide |

TABLE 7-continued

| COMPOUNDS 41A-41T | | |
|---|---|---|
| Cmpd. No. | Structure | Name |
| 41j | 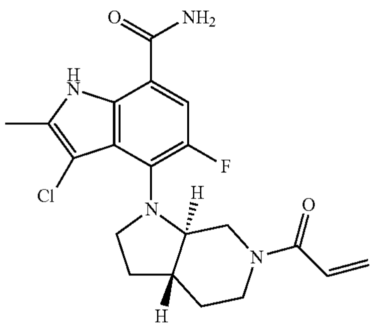 [SMILES: C=CC(=O)N1CC[C@@H]2CCN(c3c(F)cc(C(N)=O)c4[nH]c(C)c(Cl)c34)[C@H]2C1] | 4-((3aS,7aR)-6-acryloyloctahydro-1H-pyrrolo[2,3-c]pyridin-1-yl)-3-chloro-5-fluoro-2-methyl-1H-indole-7-carboxamide |
| 41k | 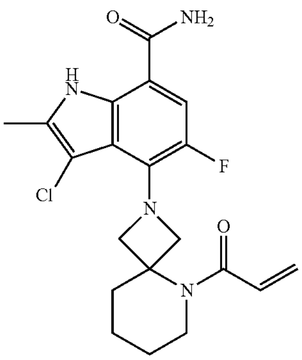 [SMILES: C=CC(=O)N1CCCCC12CN(c1c(F)cc(C(N)=O)c3[nH]c(C)c(Cl)c13)C2] | 4-(5-acryloyl-2,5-diazaspiro[3.5]nonan-2-yl)-3-chloro-5-fluoro-2-methyl-1H-indole-7-carboxamide |
| 41l | 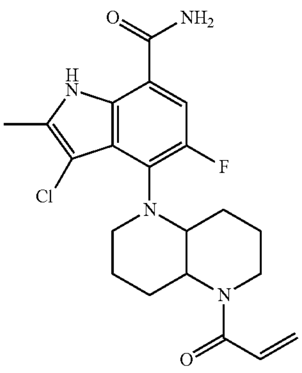 [SMILES: C=CC(=O)N1CCCC2C1CCCN2c1c(F)cc(C(N)=O)c2[nH]c(C)c(Cl)c12] | 4-(5-acryloyloctahydro-1,5-naphthyridin-1(2H)-yl)-3-chloro-5-fluoro-2-methyl-1H-indole-7-carboxamide |
| 41m | 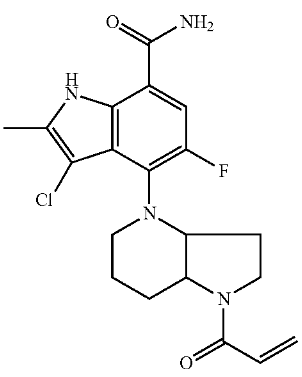 [SMILES: C=CC(=O)N1CCC2C1CCCN2c1c(F)cc(C(N)=O)c2[nH]c(C)c(Cl)c12] | 4-(1-acryloyloctahydro-4H-pyrrolo[3,2-b]pyridin-4-yl)-3-chloro-5-fluoro-2-methyl-1H-indole-7-carboxamide |

TABLE 7-continued
| COMPOUNDS 41A-41T | | |
|---|---|---|
| Cmpd. No. | Structure | Name |
| 41n | 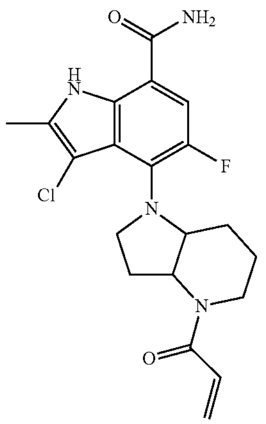 [SMILES: C=CC(=O)N1CCCC2C1CCN2c1c(F)cc(C(N)=O)c2[nH]c(C)c(Cl)c12] | 4-(4-acryloyloctahydro-1H-pyrrolo[3,2-b]pyridin-1-yl)-3-chloro-5-fluoro-2-methyl-1H-indole-7-carboxamide |
| 41o | 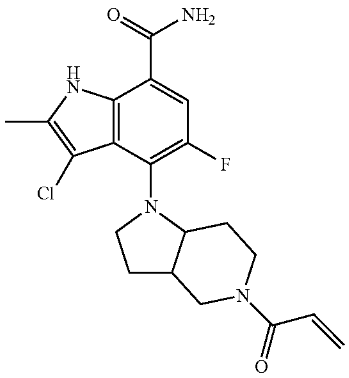 [SMILES: C=CC(=O)N1CCC2C(CCN2c2c(F)cc(C(N)=O)c3[nH]c(C)c(Cl)c23)C1] | 4-(5-acryloyloctahydro-1H-pyrrolo[3,2-c]pyridin-1-yl)-3-chloro-5-fluoro-2-methyl-1H-indole-7-carboxamide |
| 41p | 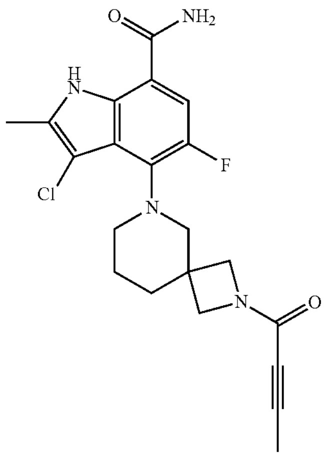 [SMILES: CC#CC(=O)N1CC2(CCCN(c3c(F)cc(C(N)=O)c4[nH]c(C)c(Cl)c34)C2)C1] | 4-(2-(but-2-ynoyl)-2,6-diazaspiro[3.5]nonan-6-yl)-3-chloro-5-fluoro-2-methyl-1H-indole-7-carboxamide |

TABLE 7-continued

| COMPOUNDS 41A-41T | | |
|---|---|---|
| Cmpd. No. | Structure | Name |
| 41q | 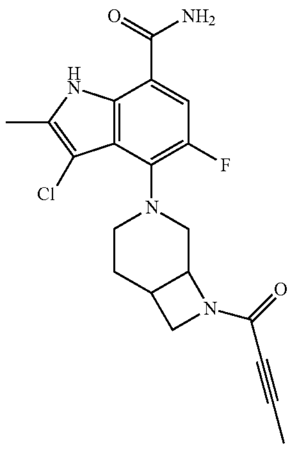 [SMILES: CC#CC(=O)N1CC2CCN(c3c(F)cc(C(N)=O)c4[nH]c(C)c(Cl)c34)CC21] | 4-(8-(but-2-ynoyl)-3,8-diazabicyclo[4.2.0]octan-3-yl)-3-chloro-5-fluoro-2-methyl-1H-indole-7-carboxamide |
| 41r | 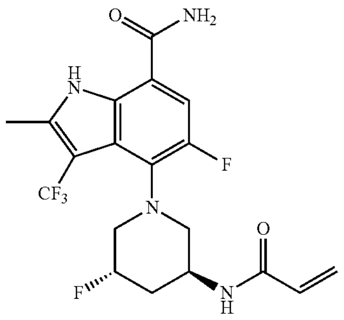 [SMILES: C=CC(=O)N[C@H]1C[C@H](F)CN(c2c(F)cc(C(N)=O)c3[nH]c(C)c(C(F)(F)F)c23)C1] | 4-((3S,5S)-3-acrylamido-5-fluoropiperidin-1-yl)-5-fluoro-2-methyl-3-(trifluoromethyl)-1H-indole-7-carboxamide |
| 41s | 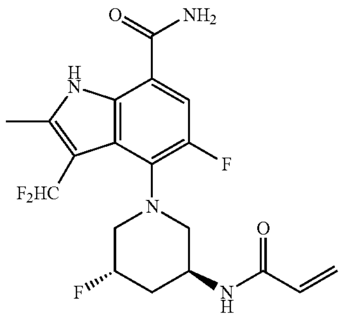 [SMILES: C=CC(=O)N[C@H]1C[C@H](F)CN(c2c(F)cc(C(N)=O)c3[nH]c(C)c(C(F)F)c23)C1] | 4-((3S,5S)-3-acrylamido-5-fluoropiperidin-1-yl)-3-(difluoromethyl)-5-fluoro-2-methyl-1H-indole-7-carboxamide |
| 41t | 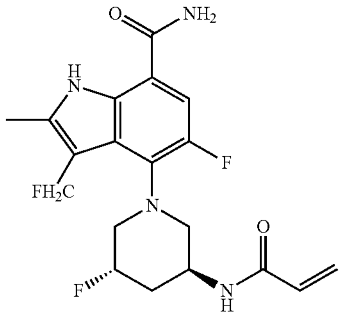 | 4-((3S,5S)-3-acrylamido-5-fluoropiperidin-1-yl)-5-fluoro-3-(fluoromethyl)-2-methyl-1H-indole-7-carboxamide |

Example 42

Synthesis of Compounds 42a-42x

Compounds 42a-42x, as shown in Table 8, were prepared according to similar methods as described in the preceding schemes and examples by employing correspondingly appropriate starting materials.

TABLE 8

| COMPOUNDS 42A-42X | | | |
|---|---|---|---|
| Cmpd. No. | Structure | NMR | MS |
| 42a | 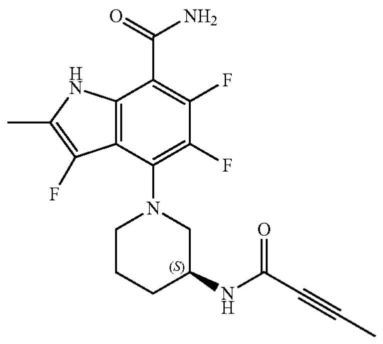 | (300 MHz, DMSO-$d_6$) δ 10.79 (s, 1H), 8.57-8.40 (m, 1H), 7.76 (s, 1H), 7.58 (s, 1H), 3.95-3.66 (m, 1H), 3.48-3.35 (m, 1H), 3.32-3.22 (m, 1H), 3.09-2.84 (m, 2H), 2.30 (s, 3H), 1.95 (s, 3H), 1.93-1.81 (m, 1H), 1.80-1.51 (m, 2H), 1.50-1.25 (m, 1H). | 393.15 |
| 42b | 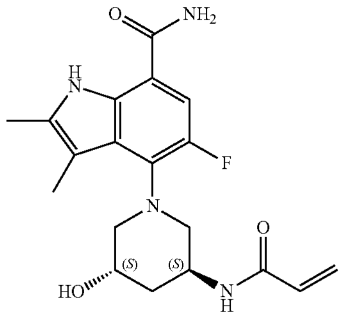 | (400 MHz, DMSO-$d_6$) δ 10.60 (s, 1H), 7.98-7.92 (m, 2H), 7.43-7.33 (m, 2H), 6.40-6.14 (m, 1H), 6.04 (dd, J = 17.2, 2.0 Hz, 1H), 5.55 (dd, J = 10.0, 2.0 Hz, 1H), 4.90-3.95 (m, 3H), 3.21-2.95 (m, 3H), 2.68-2.63 (m, 1H), 2.49-2.30 (m, 6H), 2.08-1.91 (m, 1H), 1.60-1.40 (m, 1H). | 375.15 |
| 42c | 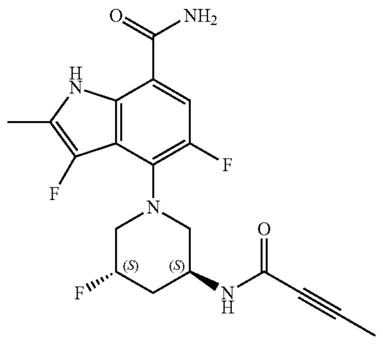 | (300 MHz, DMSO-$d_6$) δ 10.76 (s, 1H), 8.62-8.36 (m, 1H), 8.13-7.73 (m, 1H), 7.63-7.24 (m, 2H), 5.14-4.76 (m, 1H), 4.26 (s, 1H), 3.45-3.37 (m, 2H), 3.33-3.19 (m, 1H), 2.93 (t, J = 10.5 Hz, 1H), 2.34 (s, 3H), 2.24-2.04 (m, 1H), 1.95 (s, 3H), 1.86-1.52 (m, 1H). | 393.15 |

TABLE 8-continued
| COMPOUNDS 42A-42X | | | |
|---|---|---|---|
| Cmpd. No. | Structure | NMR | MS |
| 42d | 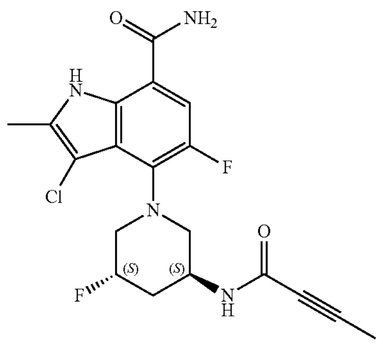 | (400 MHz, DMSO-$d_6$) δ 11.28 (s, 1H), 8.45 (s, 1H), 8.03 (s, 1H), 7.62-7.44 (m, 2H), 5.12-4.88 (m, 1H), 4.62-4.40 (m, 1H), 3.51-3.35 (m, 1H), 3.32-3.15 (m, 2H), 2.90-2.70 (m, 1H), 2.37 (s, 3H), 2.21-2.03 (m, 1H), 1.94 (s, 3H), 1.78-1.44 (m, 1H). | 409.10, 411.10 |
| 42e | 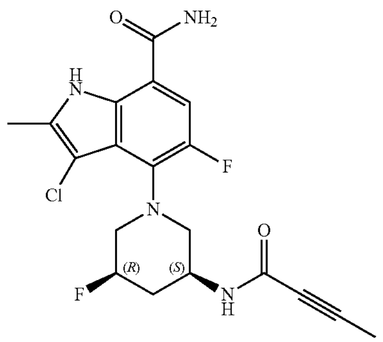 | (400 MHz, DMSO-$d_6$) δ 11.27 (s, 1H), 8.43 (s, 1H), 8.03 (s, 1H), 7.61-7.42 (m, 2H), 5.15-4.85 (m, 1H), 4.49 (s, 1H), 3.32-3.15 (m, 2H), 2.90-2.70 (m, 1H), 2.45-2.35 (m, 4H), 2.20-2.08 (m, 1H), 1.94 (s, 3H), 1.75-1.50 (m, 1H). | 409.05, 411.05 |
| 42f | 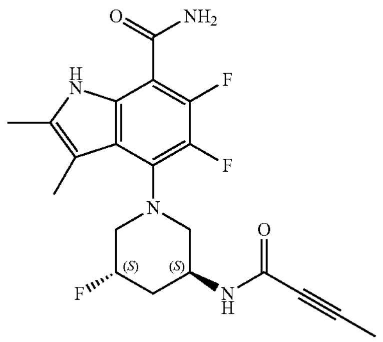 | (400 MHz, DMSO-$d_6$) δ 10.71 (s, 1H), 8.64-8.45 (m, 1H), 7.78 (s, 1H), 7.64 (s, 1H), 5.13-4.85 (m, 1H), 4.32 (s, 1H), 3.32-3.05 (m, 3H), 2.78 (t, J = 10.8 Hz, 1H), 2.36 (s, 3H), 2.28 (s, 3H), 2.23-2.05 (m, 1H), 2.01-1.90 (m, 3H), 1.83-1.54 (m, 1H). | 407.20 |
| 42g | 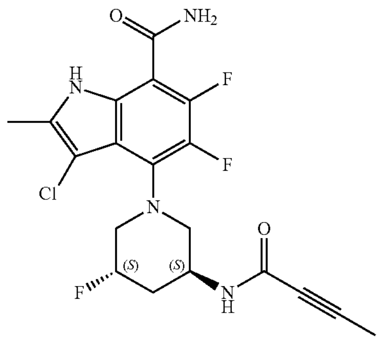 | (400 MHz, DMSO-$d_6$) δ 11.33 (s, 1H), 8.43 (brs, 1H), 8.07-7.56 (m, 2H), 5.25-4.83 (m, 1H), 4.60-4.41 (m, 1H), 3.33-3.12 (m, 3H), 2.88-2.72 (m, 1H), 2.34 (s, 3H), 2.21-2.01 (m, 1H), 1.94 (s, 3H), 1.84-1.44 (m, 1H). | 427.25, 429.25 |

TABLE 8-continued
| COMPOUNDS 42A-42X | | | |
|---|---|---|---|
| Cmpd. No. | Structure | NMR | MS |
| 42h | 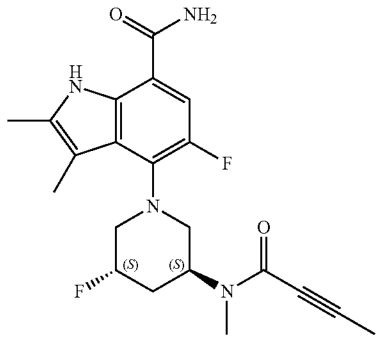 | (400 MHz, DMSO-$d_6$) δ 10.71-10.59 (m, 1H), 7.95 (s, 1H), 7.43 (dd, J = 13.9, 5.2 Hz, 1H), 7.38 (s, 1H), 5.21-4.87 (m, 2H), 3.53-3.39 (m, 0.5H), 3.32-3.13 (m, 2.5H), 3.10-2.90 (m, 2H), 2.78 (s, 2H), 2.46-2.36 (m, 3H), 2.35-2.29 (m, 3H), 2.22-1.94 (m, 5H). | 403.20 |
| 42i | 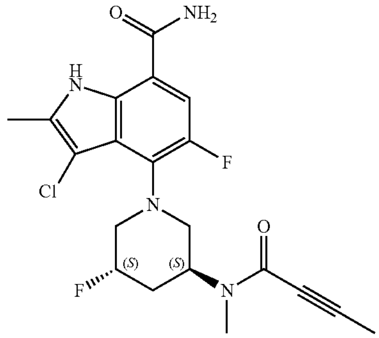 | (300 MHz, DMSO-$d_6$) δ 11.28-11.25 (m, 1H), 8.03 (s, 1H), 7.57-7.47 (m, 2H), 5.26-4.95 (m, 2H), 3.60-3.36 (m, 2H), 3.28-3.14 (m, 2H), 3.06 (s, 1H), 2.76 (s, 2H), 2.38 (d, J = 4.5 Hz, 3H), 2.28-1.94 (m, 5H). | 423.10, 425.10 |
| 42j | 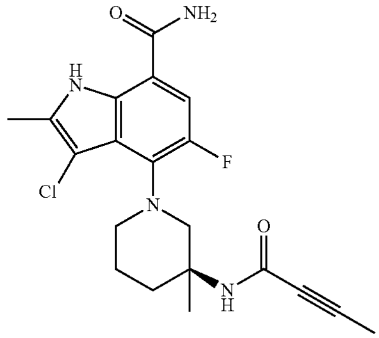 [SMILES: CC#CC(=O)N[C@@]1(C)CCCN(c2c(F)cc(C(N)=O)c3[nH]c(C)c(Cl)c23)C1] | (400 MHz, DMSO-$d_6$) δ 11.28 (s, 1H), 8.22-7.89 (m, 1H), 7.62-7.30 (m, 2H), 3.30-3.01 (m, 3H), 2.89-3.70 (m, 1H), 2.37 (s, 3H), 2.36-2.20 (m, 1H), 2.12-1.97 (m, 1H), 1.92 (s, 3H), 1.87-1.36 (m, 3H), 1.31 (s, 3H). | 405.05, 407.05 |
| 42k | 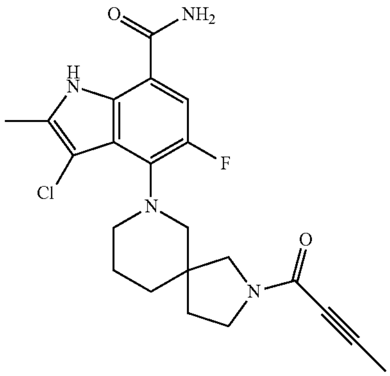 [SMILES: CC#CC(=O)N1CCC2(CCCN(c3c(F)cc(C(N)=O)c4[nH]c(C)c(Cl)c34)C2)C1] | (300 MHz, DMSO-$d_6$) δ 11.26 (s, 1H), 8.01 (s, 1H), 7.53 (d, J = 14.1, 1H), 7.45 (s, 1H), 4.39-3.70 (m, 1H), 3.70-3.59 (m, 1H), 3.59-3.45 (m, 1H), 3.18 (s, 3H), 3.05-2.72 (m, 2H), 2.39 (s, 3H), 2.09-1.82 (m, 4H), 1.81-1.37 (m, 5H). | LC-MS 431.10, 433.10 |

TABLE 8-continued
COMPOUNDS 42A-42X
| Cmpd. No. | Structure | NMR | MS |
| --- | --- | --- | --- |
| 42l | 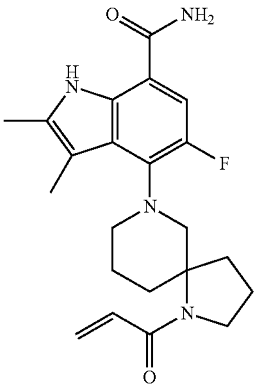 [SMILES: C=CC(=O)N1CCCC12CCCN(c1c(F)cc(C(N)=O)c3[nH]c(C)c(C)c13)C2] | (300 MHz, DMSO-$d_6$) δ 10.65 (s, 1H), 7.93 (s, 1H), 7.62-7.11 (m, 2H), 6.73-6.37 (m, 1H), 6.10 (d, J = 16.2 Hz, 1H), 5.62 (d, J = 9.9 Hz, 1H), 4.65-4.22 (m, 1H), 3.68-3.48 (m, 2H), 3.09-2.87 (m, 3H), 2.70-2.59 (m, 1H), 2.42-2.35 (m, 4H), 2.35-2.28 (m, 3H), 1.95-1.69 (m, 5H), 1.50-1.40 (m, 1H). | 399.35 |
| 42m1 | 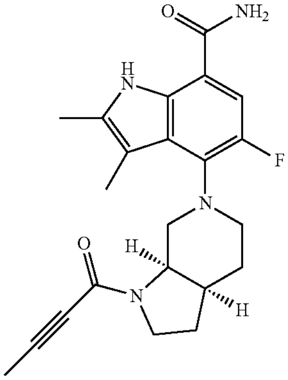 | (400 MHz, DMSO-$d_6$) δ 10.72-10.61 (m, 1H), 7.94 (s, 1H), 7.46-7.30 (m, 2H), 4.42-4.16 (m, 1H), 4.00-3.51 (m, 1H), 3.50-3.39 (m, 1H), 3.36-3.32 (m, 2H), 3.00-2.72 (m, 2H), 2.47-2.40 (m, 3H), 2.35-2.30 (m, 3H), 2.23-2.04 (m, 1H), 2.00 (s, 3H), 1.99-1.80 (m, 3H), 1.80-1.60 (m, 1H). | 397.15 |
| 42m2 | 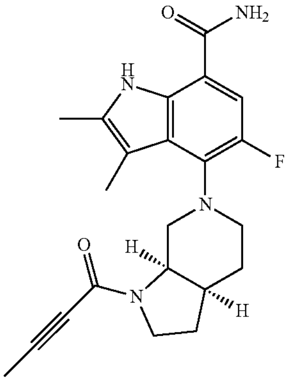 [SMILES: CC#CC(=O)N1CC[C@@H]2CCN(c3c(F)cc(C(N)=O)c4[nH]c(C)c(C)c34)C[C@@H]21] Assumed | (300 MHz, DMSO-$d_6$) δ 10.87-10.47 (m, 1H), 7.93 (s, 1H), 7.54-7.24 (m, 2H), 4.46-4.09 (m, 1H), 3.89-3.37 (m, 2H), 3.31-2.52 (m, 5H), 2.46-2.28 (m, 6H), 2.25-1.96 (m, 3H), 1.95-1.80 (m, 3H), 1.79-1.65 (m, 1H). | 397.10 |

TABLE 8-continued
COMPOUNDS 42A-42X
| Cmpd. No. | Structure | NMR | MS |
|---|---|---|---|
| 42n | 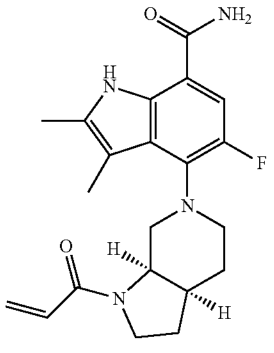 assumed | (300 MHz, DMSO-$d_6$) δ 10.65 (d, J = 6.1 Hz, 1H), 7.93 (s, 1H), 7.42 (dd, J = 14.2, 4.0 Hz, 1H), 7.35 (s, 1H), 6.54 (dd, J = 16.9, 10.5 Hz, 1H), 6.10 (dd, J = 16.7, 2.5 Hz, 1H), 5.63 (dd, J = 10.3, 2.5 Hz, 1H), 4.42-4.16 (m, 1H), 3.81-3.67 (m, 1H), 3.61-3.47 (m, 1H), 3.46-3.37 (m, 2H), 3.27-3.14 (m, 1H), 3.10-2.74 (m, 2H), 2.42 (s, 3H), 2.33 (s, 3H), 2.25-2.01 (m, 2H), 1.95-1.79 (m, 1H), 1.78-1.68 (m, 1H). | 385.15 |
| 42o | 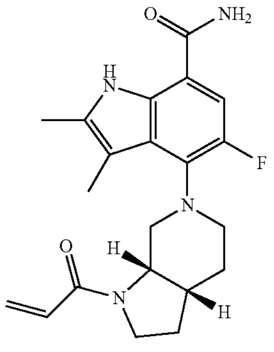 assumed | (300 MHz, DMSO-$d_6$) δ 10.65 (d, J = 6.1 Hz, 1H), 7.93 (s, 1H), 7.42 (dd, J = 14.2, 4.0 Hz, 1H), 7.35 (s, 1H), 6.54 (dd, J = 16.8, 10.2 Hz, 1H), 6.10 (dd, J = 16.7, 2.5 Hz, 1H), 5.63 (dd, J = 10.3, 2.5 Hz, 1H), 4.42-4.17 (m, 1H), 3.79-3.67 (m, 1H), 3.61-3.48 (m, 1H), 3.46-3.37 (m, 2H), 3.28-3.13 (m, 1H), 3.10-2.72 (m, 2H), 2.42 (s, 3H), 2.33 (s, 3H), 2.26-2.02 (m, 2H), 1.96-1.79 (m, 1H), 1.78-1.66 (m, 1H). | 385.15 |
| 42p | 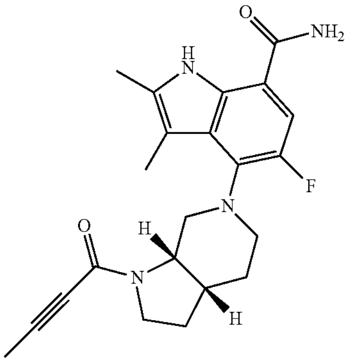 Assumed | (300 MHz, DMSO-$d_6$) δ 10.84-10.53 (m, 1H), 7.94 (s, 1H), 7.60-7.17 (m, 2H), 4.46-4.11 (m, 1H), 3.87-3.38 (m, 2H), 3.32-3.09 (m, 2H), 3.06-2.72 (m, 2H), 2.48-2.32 (m, 7H), 2.30-2.08 (m, 2H), 2.07-2.02 (m, 1H), 1.98-1.68 (m, 4H). | 397.10 |

TABLE 8-continued
| COMPOUNDS 42A-42X | | | |
|---|---|---|---|
| Cmpd. No. | Structure | NMR | MS |
| 42q | 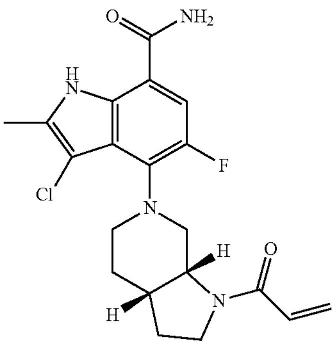 assumed | (400 MHz, DMSO-$d_6$) δ 11.27 (d, J = 12.0 Hz, 1H), 8.02 (s, 1H), 7.61-7.31 (m, 2H), 6.64-6.48 (m, 1H), 6.15-6.07 (m, 1H), 5.69-5.57 (m, 1H), 4.41-4.24 (m, 1H), 3.77-3.69 (m, 0.5H), 3.61-3.49 (m, 1H), 3.48-3.37 (m, 1H), 3.31-3.11 (m, 2H), 3.06-2.85 (m, 2H), 2.60-2.51 (m, 0.5H), 2.39 (d, J = 5.2 Hz, 3H), 2.28-2.06 (m, 2H), 1.93-1.65 (m, 2H). | 405.10, 407.10 |
| 42r | 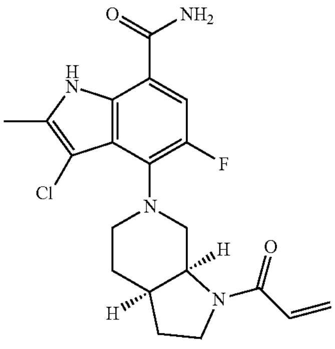 assumed | (400 MHz, DMSO-$d_6$) δ 11.27 (d, J = 12.0 Hz, 1H), 8.02 (s, 1H), 7.58-7.39 (m, 2H), 6.65-6.48 (m, 1H), 6.16-6.06 (m, 1H), 5.69-5.59 (m, 1H), 4.39-4.23 (m, 1H), 3.77-3.69 (m, 0.5H), 3.58-3.48 (m, 1H), 3.49-3.35 (m, 1H), 3.32-3.10 (m, 2H), 3.06-2.88 (m, 2H), 2.58-2.54 (m, 05.H), 2.39 (d, J = 5.2 Hz, 3H), 2.27-2.06 (m, 2H), 1.95-1.76 (m, 1H), 1.75-1.61 (m, 1H). | 405.10, 407.10 |
| 42s | 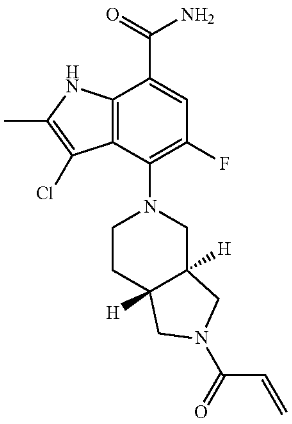 [SMILES: C=CC(=O)N1C[C@@H]2CN(c3c(F)cc(C(N)=O)c4[nH]c(C)c(Cl)c34)CC[C@H]2C1] | (400 MHz, DMSO-$d_6$) δ 11.24 (s, 1 H), 8.00 (s, 1H), 7.54 (d, J = 14.0 Hz, 1H), 7.43 (s, 1H), 6.62-6.51 (m, 1H), 6.14 (dd, J = 16.8, 2.4 Hz, 1H), 5.69-5.64 (m, 1H), 3.86-3.65 (m, 2H), 3.41-3.38 (m, 1H), 3.30-3.20 (m, 1H), 3.19-3.08 (m, 3H), 2.93-2.90 (m, 1H), 2.38 (s, 3H), 2.10-1.68 (m, 4H). | 405.10, 407.10 |

TABLE 8-continued
COMPOUNDS 42A-42X
| Cmpd. No. | Structure | NMR | MS |
| --- | --- | --- | --- |
| 42t | 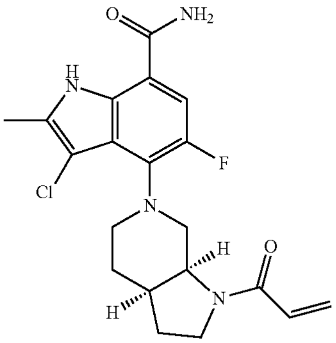 [SMILES: C=CC(=O)N1CC[C@H]2CCN(c3c(F)cc(C(N)=O)c4[nH]c(C)c(Cl)c34)C[C@H]21] | (400 MHz, DMSO-$d_6$) δ 11.26 (d, J = 12.0 Hz, 1H), 8.01 (s, 1H), 7.60-7.35 (m, 2H), 6.63-6.48 (m, 1H), 6.15-6.05 (m, 1H), 5.69-5.58 (m, 1H), 4.38-4.27 (m, 1H), 3.77-3.69 (m, 0.5H), 3.58-3.49 (m, 1H), 3.49-3.36 (m, 1H), 3.32-3.10 (m, 2H), 3.05-2.87 (m, 2H), 2.58-2.52 (m, 0.5H), 2.39 (d, J = 5.2 Hz, 3H), 2.28-2.06 (m, 2H), 1.95-1.63 (m, 2H). | 405.10, 407.10 |
| 42u | 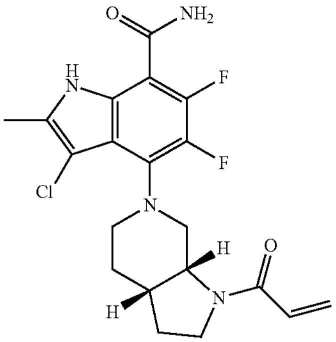 Assumed | (300 MHz, DMSO-$d_6$) δ 11.31 (d, J = 8.7 Hz, 1H), 7.82 (s, 1H), 7.68 (s, 1H), 6.61-6.48 (m, 1H), 6.14-6.03 (m, 1H), 5.66-5.57 (m, 1H), 4.36-4.24 (m, 1H), 3.74 (t, J = 10.2 Hz, 0.5H), 3.57-3.33 (m, 2H), 3.28-3.12 (m, 2H), 3.09-2.87 (m, 2H), 2.45-2.35 (m, 0.5H), 2.33 (d, J = 3.6 Hz, 3H), 2.25-2.03 (m, 2H), 1.93-1.65 (m, 2H). | 423.25, 425.25 |
| 42v1 | 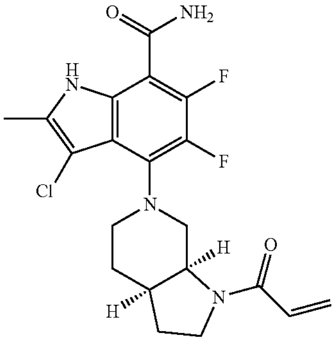 Assumed | (300 MHz, DMSO-$d_6$) δ 11.31 (d, J = 8.7 Hz, 1H), 7.82 (s, 1H), 7.68 (s, 1H), 6.61-6.48 (m, 1H), 6.14-6.03 (m, 1H), 5.66-5.57 (m, 1H), 4.36-4.24 (m, 1H), 3.74 (t, J = 10.5 Hz, 0.5H), 3.57-3.33 (m, 2H), 3.28-3.12 (m, 2H), 3.12-2.87 (m, 2H), 2.45-2.35 (m, 0.5H), 2.33 (d, J = 3.6 Hz, 3H), 2.25-2.03 (m, 2H), 1.93-1.63 (m, 2H). | 423.25, 425.25 |
| 42v2 | 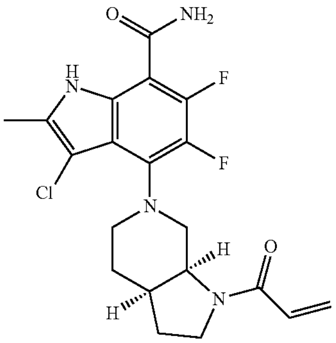 [SMILES: C=CC(=O)N1CC[C@H]2CCN(c3c(F)c(F)c(C(N)=O)c4[nH]c(C)c(Cl)c34)C[C@H]21] | (300 MHz, DMSO-$d_6$) δ 11.31 (d, J = 8.4 Hz, 1H), 7.85 (s, 1H), 7.72 (s, 1H), 6.65-6.49 (m, 1H), 6.17-6.05 (m, 1H), 5.69-5.60 (m, 1H), 4.45-4.04 (m, 1H), 3.74 (t, J = 10.2 Hz, 0.5H), 3.59-3.36 (m, 2H), 3.32-3.12 (m, 2H), 3.12-2.85 (m, 2H), 2.46-2.39 (m, 0.5H), 2.36 (d, J = 3.9 Hz, 3H), 2.29-2.03 (m, 2H), 1.98-1.63 (m, 2H). | 423.05, 425.05 |

TABLE 8-continued
COMPOUNDS 42A-42X
| Cmpd. No. | Structure | NMR | MS |
|---|---|---|---|
| 42w | 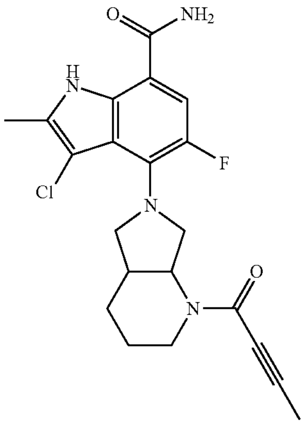 [SMILES: CC#CC(=O)N1CCCC2CN(c3c(F)cc(C(N)=O)c4[nH]c(C)c(Cl)c34)CC21] | (300 MHz, DMSO-$d_6$) δ 11.26 (d, J = 4.8 Hz, 1H), 8.03 (s, 1H), 7.65-7.40 (m, 2H), 5.19-5.03 (m, 1H), 4.32-4.17 (m, 1H), 3.65-3.40 (m, 2H), 3.31-3.02 (m, 2.4H), 2.78-2.65 (m, 0.6H), 2.43-2.16 (m, 4H), 2.05 (d, J = 5.7 Hz, 3H), 1.91-1.70 (m, 3H), 1.52-1.24 (m, 1H). | 417.10, 419.10 |
| 42x | 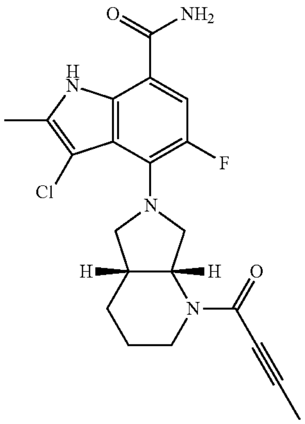 Assumed | (300 MHz, DMSO-$d_6$) δ 11.26 (d, J = 5.1 Hz, 1H), 8.02 (s, 1H), 7.65-7.40 (m, 2H), 5.19-5.03 (m, 1H), 4.35-4.16 (m, 1H), 3.65-3.40 (m, 2H), 3.31-3.02 (m, 2H), 2.80-2.65 (m, 1H), 2.41-2.35 (m, 3H), 2.17-2.30 (m, 1H), 2.05 (d, J = 5.4 Hz, 3H), 1.93-1.70 (m, 3H), 1.52-1.30 (m, 1H). | 417.10, 419.10 |
| 42y | 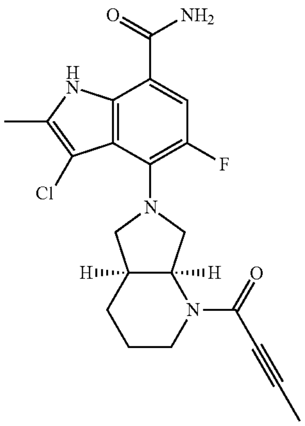 Assumed | (300 MHz, DMSO-$d_6$) δ 11.26 (d, J = 4.5 Hz, 1H), 8.02 (s, 1H), 7.65-7.40 (m, 2H), 5.19-5.03 (m, 1H), 4.33-4.17 (m, 1H), 3.65-3.40 (m, 2H), 3.31-3.02 (m, 2H), 2.80-2.65 (m, 1H), 2.41-2.35 (m, 3H), 2.17-2.30 (m, 1H), 2.05 (d, J = 5.4 Hz, 3H), 1.93-1.70 (m, 3H), 1.52-1.28 (m, 1H). | 417.10, 419.10 |

Example 43

Assay to Determine Activity Against BTK

Solutions of compounds (test or control) in DMSO were prepared at the desired concentrations, and serially diluted to 11 concentrations by 3-fold dilution in 384pp-plate using TECAN EVO200. 20 nL of stock were transferred to 384 plate using Echo550. DMSO was used as vehicle control.

Two separate solutions were prepared—an ATP solution containing MgCl2 (10 mM), Brij-35 (0.01%), DTT (2 mM), BSA (0.05%), EGTA (1 mM), HEPE (pH7.5) (50 mM), FLPeptide (6 uM) and ATP (4 mM); and a BTK solution containing MgCl2 (10 mM), Brij-35 (0.01%), DTT (2 mM), BSA (0.05%), EGTA (1 mM), HEPE (pH7.5) (50 mM) and BTK (2.67 nM). (BTK was obtained from Carna; FLPeptide2 was obtained from PerkinElmer and Ibrutinib was obtained from Selleck.) 5 uL of ATP solution were added to each well, followed by addition of 15 uL of BTK solution to initiate the reaction. (Note the final volume of each well was 20 uL containing MgCl2 (10 mM), Brij-35 (0.01%), DTT (2 mM), BSA (0.05%), EGTA (1 mM), HEPE (pH7.5) (50 mM), FLPeptide (1.5 uM), ATP (1 mM) and BTK (2 nM).

The plates were incubated at room temperature for 90 minutes and then stopping buffer added (75 uL, containing 0.5 M EDTA) to terminate the reaction. Samples from each well were analyzed using EZ reader. The % remaining activity was calculated using read conversion ratio (CR) according to the equation:

$$\text{Remaining Activity (\%)} = 100 \times \frac{CR_{Compound}}{CR_{Vehicle}}$$

XLFit (equation 201) was used to calculate $IC_{50}$s by floating both bottom and top.

BTK $IC_{50}$ values are provided for representative compounds of the present invention in Table 9 below. With respect to BTK activity, Table 4 lists activity as follows:

"A" denotes an $IC_{50}$ of less than 10 nM,

"B" denotes an $IC_{50}$ of from 10 nM to less than 100 nM; and

"C" denotes and $IC_{50}$ of 100 nM or more.

Example 44

Assay to Determine BTK Activity in RAMOS B Cells

On the day before assay, Ramos B cells were plated in plating medium (RPMI1640 medium containing 1% FBS and 1× pencillin-streptomycin). On the day of the assay, 2× dye solution was prepared following the manual of the FLIRP Calcium 6 Assay Kit: Dilute the dye with assay buffer (20 mM HEPES in 1×HBSS, pH7.4); Add probenecid to the final concentration of 5 mM; vortex vigorously for 1-2 minutes. Cells were collected by centrifuging, and the pellet was resuspended in plating medium. After counting, cells were resuspended at a density of 3x106/ml in plating medium. Equal volume of 2× dye solution was added to the cell suspension. Cells were then plated at 20 µl/well into a 384-well poly-D-lysine coated plate. Plate was centrifuged at 1000 rpm for 3 minutes and then incubated at 37° C. for 2 hours followed by an additional 15-minute incubation at 25° C. Compounds were prepared at 3× concentration in dilution buffer (20 mM HEPES and 0.1% BSA in 1×HBSS, pH 7.4). Serially diluted compound was transferred from source plate to a 384-well compound plate by using an Echo 550 (Labcyte). 20 µl/well compound dilution buffer was added to the compound plate and mixed on plate shaker for 2 mins. 4×$EC_{80}$ of Anti-IgM (Jackson ImmunoResearch) was prepared in dilution buffer and 20 µl/well was added to a new 384-well compound plate. After 60 mins of incubation at 25° C. in the dark; cell plate, compound plate containing 4×$EC_{80}$ of anti-IgM and FLIPR tips were placed into FLIPR (Molecular Devices). 10 ul/well of 4×$EC_{80}$ anti-IgM was transferred to the cell plate by FLIPR. Plates were read for 160 sec with 1 sec interval.

$IC_{50}$ values are provided for representative compounds of the present invention in Table 9, below. With respect to Ramos activity, Table 9 lists activity as follows:

"A" denotes an $IC_{50}$ of less than 10 nM;

"B" denotes an $IC_{50}$ of from 10 nM to less than 100 nM; and

"C" denotes and $IC_{50}$ of 100 nM or more.

TABLE 9

ACTIVITY OF REPRESENTATIVE COMPOUNDS

| Compound No. | BTK ($IC_{50}$) | Ramos ($IC_{50}$) |
|---|---|---|
| 1 | A | A |
| 2 | A | A |
| 2a | A | A |
| 2b | B | B |
| 3 | A | A |
| 4 | A | A |
| 5 | A | B |
| 6a | A | A |
| 6b | A | A |
| 7 | A | A |
| 8 | A | A |
| 9 | A | A |
| 10 | B | B |
| 11 | C | C |
| 12 | C | C |
| 13 | A | A |
| 14 | C | C |
| 15 | B | B |
| 16 | A | A |
| 17 | C | C |
| 18 | C | C |
| 19 | C | C |
| 20a | A | A |
| 20b | A | A |
| 20c | C | C |
| 20d | — | — |
| 20e | A | A |
| 20f | C | C |
| 20g | A | B |
| 20h | C | C |
| 20i | A | B |
| 20j | A | B |
| 21a | A | B |
| 21b | A | A |
| 21c | C | C |
| 21d | B | B |
| 21e | B | B |
| 22a | A | B |
| 22b | C | C |
| 22c | C | C |
| 22d | C | C |
| 22e | A | A |
| 22f | — | — |
| 23 | B | B |
| 24a | B | C |
| 24b | C | C |
| 24c | B | C |
| 24d | C | C |
| 25a | B | B |
| 25b | B | C |
| 25c | C | C |

TABLE 9-continued

| ACTIVITY OF REPRESENTATIVE COMPOUNDS | | |
|---|---|---|
| Compound No. | BTK ($IC_{50}$) | Ramos ($IC_{50}$) |
| 25d | B | C |
| 25e | B | C |
| 26 | C | C |
| 27 | A | A |
| 28 | A | A |
| 29 | B | B |
| 29a | B | B |
| 29b | A | B |
| 30 | B | B |
| 31 | B | B |
| 32 | B | B |
| 32a | B | B |
| 32b | B | B |
| 33 | A | A |
| 34 | B | C |
| 35 | A | A |
| 36 | A | A |
| 37 | B | C |
| 38 | B | B |
| 39 | C | C |
| 40 | A | B |

Example 45

Assay to Determine BTK Inactivation Rate in Human Whole Blood

Human Whole Blood Compound Treatment and Lysis

Human whole blood is obtained from StemExpress and kept at ambient temperature until the time of the experiment. A 1× lysis buffer is prepared by using 10× lysis buffer (Cell Signaling Technology, #9083S), distilled water, 100× protease and phosphatase inhibitor cocktail (ThermoFisher, #78440), and GBD-1066 probe (final: 0.4 μM). This is prepared fresh each experimental day. Lysis buffer is added in the volume of 30 μL to all wells in a v-bottom plate (GreinerBio, #651261) in preparation for timepoint collections. Compounds are reconstituted to stocks of 10 mM and are diluted in two-fold serial dilutions to generate an 8-point curve in DMSO, with the last point being DMSO only, creating a 100× dilution series. A working 10× dilution series is created using 1.0 μL of the prepared DMSO titration, 100×, into 300 μL 1×PBS in order to keep the DMSO constant. The human whole blood is added in the volume of 225 μL per well in a new 96w v-bottom plate, where one column of eight wells is sufficient for testing one compound. For compound treatment, 25 μL of 10× dilution series in PBS is added to the 225 μL whole blood, followed by briefly pipetting up and down twice. The plates are covered with lids and incubated at 37° C. for 5, 15, 30, 60 minutes. At each timepoint, 30 μL of treated blood is pulled from each column and added to preloaded collection plates that contain 30 μL of supplemented lysis buffer and mixed briefly. The collected and lysed samples shake on rotator for 60 minutes at room temperature. These samples are used fresh for detection via ELISA, and remaining sample is frozen at −80° C. if a repeat is necessary.

ELISA: Determining Amount of Unoccupied BTK

All streptavidin pre-coated plates (R&D Systems, #CP004) are brought to room temperature while samples are lysing. Assay Buffer 1, 1×PBS+0.05% Tween 20+1% BSA is prepared and stored at 4° C. when not in use. Using this Assay Buffer, assay buffer+1× protease/phosphatase inhibitor cocktail (PICs) is prepared in the amount needed for all samples. Assay Buffer+PICs in the volume of 90 μL/well is added to the ELISA plate. Lysed blood sample (10 μL) is added to the ELISA plate. BTK recombinant protein dilutions are prepared in assay buffer+PICS for use as a μM). The standard is loaded into the ELISA plate at 100 μL/well, in duplicate. These samples and standards remain in the plate, sealed, overnight at 4° C. The following day, the plate is washed four times with 1× Wash Buffer (1×PBS+0.05% Tween 20) using a plate washer. The plate is inverted to expel all fluid each time and blotted on clean paper towels to remove remaining liquid. Assay Buffer 2 is prepared (1×PBS+0.05% Tween 20+0.05% BSA) and kept at 4° C. when not in use. The antibody α-BTK (clone D3H5, Cell Signaling Technology #8547S) is diluted 1:500 in Assay Buffer 2. Diluted a-BTK antibody is added at 100 μl/well. The plate is covered with adhesive film and incubated for 90 minutes at room temperature. The plate is washed four times with 1× Wash Buffer (1×PBS+0.05% Tween 20) using a plate washer. The plate is inverted to expel all fluid each time and blotted on clean paper towels to remove remaining liquid. The tertiary antibody (Jackson Immuno Research, #711-005-152) is diluted 1:2,500 with Assay Buffer 2. The diluted antibody is added at 100 μl/well. The plate is covered with adhesive film and incubated for one hour at room temperature. The plate is washed four times with 1× Wash Buffer using a plate washer. The plate is inverted to expel all fluid each time and blotted on clean paper towels to remove remaining liquid. Prewarmed TMB substrate (ThermoFisher, #34029) is added to the plate at 100 μl/well. The plate is incubated at room temperature in the dark for −5-10 minutes. The reaction is stopped by adding 50 μl/well 2N sulfuric acid ($H_2SO_4$) (R&D Systems, #DY994). The plate is read in a plate reader at the wavelengths 460 nm and 570 nm (correction wavelength). Using Graphpad Prism, an XY table+graph is created, listing 0-60 minutes as X axis and concentration as Y axis. A One Phase Decay model fit is applied to the data. Checking Results table, the K values are obtained and new XY table+graph are created. Concentration is assigned to the X axis and K values from first analysis are entered. The Michaelis-Menten equation is applied to the data. From the results table, the Vmax (Kinact) and Km (KI) values are used to calculate the Kinact/Ki 10-4 nM-1 min-1 by dividing Vmax, Km*10000.

With respect to the inactivation rate, Kinact/Ki values are provided for representative compounds of the present disclosure in Table 10 below. With respect to the same, Table 10 lists activity as follows:

- "A" denotes a Kinact/Ki $>10\times10^{-4}$ $nM^{-1}$ $min^{-1}$,
- "B" denotes a Kinact/Ki of from $10\times10^{-4}$ $nM^{-1}$ $min^{-1}$ to $1\times10^{-4}$ $nM^{-1}$ $min^{-1}$, and
- "C" denotes a Kinact/Ki$<1\times10^{-4}$ $nM^{-1}$ $min^{-1}$.

TABLE 10

| BTK INACTIVATION ACTIVITY OF REPRESENTATIVE COMPOUNDS | |
|---|---|
| Compound No. | BTK hWB Kinact/Ki |
| Ibrutinib | C |
| Acalabrutinib | C |
| Branebrutinib | A |
| 1 | A |
| 2a | A |
| 2b | B |
| 4 | A |

TABLE 10-continued

| BTK INACTIVATION ACTIVITY OF REPRESENTATIVE COMPOUNDS | |
|---|---|
| Compound No. | BTK hWB Kinact/Ki |
| 6a | A |
| 6b | A |
| 15 | A |
| 16 | A |
| 20a | C |
| 20b | B |
| 22a | B |
| 27 | B |
| 28 | B |
| 29 | B |
| 29a | C |
| 32 | C |
| 32a | A |
| 32b | C |
| 33 | A |
| 35 | A |
| 36 | A |
| 40 | C |

Example 46

Determination of Plasma and Total Brain Concentrations at 1 h Post a Single Oral Administration of Test Compound to Female C57BL/6 Mice Test Articles Acalabrutinib, Ibrutinib and Branebrutinib were used as comparative control compounds.

Acalabrutinib (CALQUENCE®) is a BTK inhibitor, approved for the treatment of non-Hodgkin lymphoma known as mantle cell lymphoma (MCL), chronic lymphocytic leukemia (CLL) or small lymphocytic leukemia (SLL).

Ibrutinib (IMBRUVICA®) is a BTK inhibitor approved for the treatment of mantle cell lymphoma (MCL), Chronic lymphocytic leukemia (CLL)/Small lymphocytic lymphoma (SLL), Waldenström's macroglobulinemia (WM), marginal zone lymphoma (MZL) and chronic graft versus host disease (cGVHD).

Branebrutinib is a BTK inhibitor approved for the treatment of mantle cell lymphoma (MCL) and is in clinical trials for the treatment of Rheumatoid Arthritis, Systemic Lupus Erythematosus and Primary Sjögren's Syndrome Test Article Preparation The appropriate amount of test article was dissolved 10% dimethylacetamide (DMA)/90% (20% hydroxypropyl-b-cyclodextrin (HP-β-CD) w/v in water to obtain a final concentration of 1 mg/mL for oral dosing. Sonication, vortex, and homogenization was used as needed. Three female C57BL/6 mice aged 7-9 weeks (20-30 grams) were dosed by oral gavage 10 mg/kg solution of the test article.

Sample Collection and Processing

| | |
|---|---|
| Collection Site: | Cardiac puncture vein |
| Volume Collected: | ~0.10 mL |
| Anticoagulant: | EDTA-$K_2$ |
| Blood Samples Processing and Storage: | 1) Approximately 0.10 mL blood is collected at each time point. Blood of each sample is transferred to plastic micro centrifuge tubes containing anticoagulant of EDTA-$K_2$. Collection tubes with blood samples and anticoagulant are inverted several times for proper mixing of the tube contents and then placed on wet ice prior to centrifugation for plasma.<br>2) Blood samples centrifuged at 4,000 g, 5 mins, 4° C. to obtain plasma.<br>3) Samples stored at −75 ± 15° C. prior to analysis. |
| Brain Sample Processing and Storage: | 1) The animals are fully exsanguinated with a rising concentration of $CO_2$ gas prior to tissue collection. Procedure: open chest cavity, cut ventricle and perform a gentle iv saline flush (saline flush volume ~20 mL) with the animal placed head down at a 45 degree angle to facilitate blood removal.<br>2) For brain collection. Tissue samples are collected at adopted time point, then dried with clean gauze and put into the weighed tube. Brain samples are weighed and frozen in liquid nitrogen and kept at −75 ± 15° C. before analysis. |

Sample Analysis

Concentrations of representative test compounds in the plasma and brain samples (using plasma and brain homogenate standard curve for all samples appropriately) were analyzed using LC-MS/MS. With respect to the brain: plasma ratio, Table 11 lists the results as follows:

"A" denotes a ratio >0.5;

"B" denotes a ratio between 0.1 and 0.5; and

"C" denotes a ratio <0.1.

TABLE 11

BRAIN AND PLASMA DRUG LEVELS

| Compound | Brain:plasma ratio |
|---|---|
| Acalabrutinib | C |
| Branebrutinib | C |
| Ibrutinib | C |
| 1 | C |
| 2a | B |
| 6a | B |
| 6b | B |
| 16 | B |
| 20b | B |
| 22a | B |
| 27 | B |
| 29 | B |
| 29a | B |
| 32b | C |
| 33 | C |
| 35 | C |
| 40 | A |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

All publications, patents, and patent applications mentioned in this specification are herein incorporated by reference to the same extent as if each individual publication, patent, or patent application was specifically and individually indicated to be incorporated by reference.

The invention claimed is:

1. A compound having the structure of formula (I):

Formula (I)

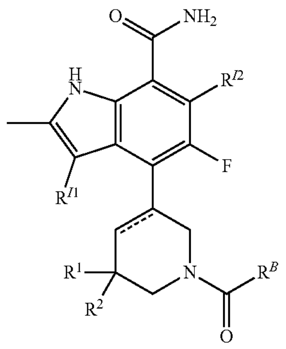

or a pharmaceutically acceptable salt, solvate, hydrate, isomer, tautomer, racemate, or isotope thereof, wherein:

--- represents a single bond or a double bond;

$R^1$ is $-H$, $-CH_3$ or $-F$;

$R^2$ is $-H$, $-CH_3$ or $-F$;

or $R^1$ and $R^2$ together with the C atom to which they are attached form a $C_{3-6}$-membered carbocyclic ring;

$R^{I1}$ is $-Cl$, $-F$, $-CN$, $-CH_3$, $-CH_2F$, $-CHF_2$ or $-CF_3$;

$R^{I2}$ is $-H$ or $-F$; and $R^B$ is $-CH{=}CH_2$, $-C{\equiv}CH$ or $-C{\equiv}C-CH_3$;

and wherein when $R^{I1}$ is $-CH_3$, at least one of $R^1$ and $R^2$ is $-CH_3$ or $-F$.

2. The compound of claim 1, wherein --- represents a single bond.

3. The compound of claim 1, wherein $R^1$ is $-H$ and $R^2$ is $-H$.

4. The compound of claim 1, wherein $R^1$ is $-H$ and $R^2$ is $-F$.

5. The compound of claim 1, wherein $R^{I2}$ is $-H$.

6. The compound of claim 1, wherein $R^{I2}$ is $-F$.

7. The compound of claim 1, wherein $R^B$ is $-CH{\equiv}CH_2$.

8. The compound of claim 1, wherein $R^B$ is $-C{\equiv}CH$.

9. The compound of claim 1, wherein $R^B$ is $-C{\equiv}C-CH_3$.

10. The compound of claim 1, wherein:

--- represents a single bond;

$R^{I2}$ is $-H$;

$R^1$ is $-H$; and $R^2$ is $-H$.

11. The compound of claim 1, wherein:

--- represents a single bond;

$R^{I2}$ is $-F$;

$R^1$ is $-H$; and $R^2$ is $-H$.

12. The compound of claim 1, having the structure of formula (I-S) or (I-R):

(I-S)

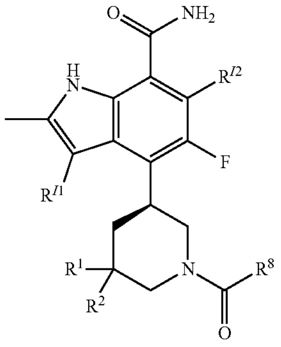

(I-R)

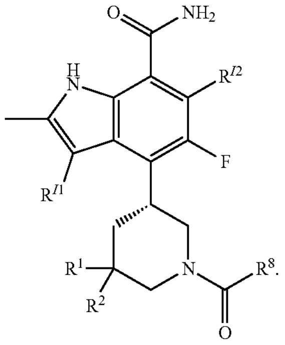

13. A compound having any one of the following structures, or a pharmaceutically acceptable salt, solvate, hydrate, isomer, tautomer, racemate, or isotope thereof:

| Cmpd. No. | Structure | Name |
|---|---|---|
| 1 | 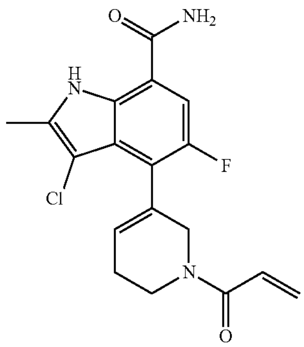 [SMILES: C=CC(=O)N1CCC=C(c2c(F)cc(C(N)=O)c3[nH]c(C)c(Cl)c23)C1] | 4-(1-acryloyl-1,2,5,6-tetrahydropyridin-3-yl)-3-chloro-5-fluoro-2-methyl-1H-indole-7-carboxamide |

-continued

| Cmpd. No. | Structure | Name |
|---|---|---|
| 2 | 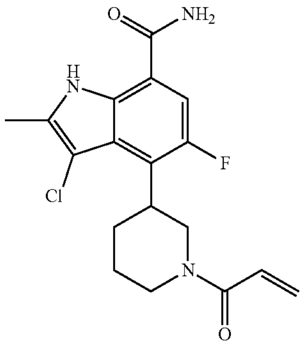 [SMILES: C=CC(=O)N1CCCC(c2c(F)cc(C(N)=O)c3[nH]c(C)c(Cl)c23)C1] | 4-(1-acryloylpiperidin-3-yl)-3-chloro-5-fluoro-2-methyl-1H-indole-7-carboxamide |
| 2a | 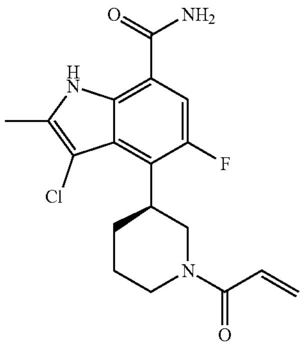 [SMILES: C=CC(=O)N1CCC[C@@H](c2c(F)cc(C(N)=O)c3[nH]c(C)c(Cl)c23)C1] | (S)-4-(1-acryloylpiperidin-3-yl)-3-chloro-5-fluoro-2-methyl-1H-indole-7-carboxamide |
| and | | |
| 2b | 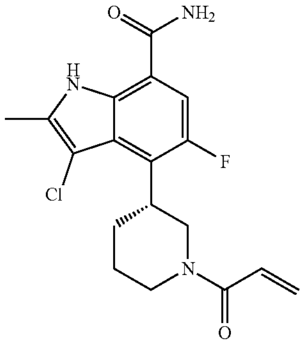 [SMILES: C=CC(=O)N1CCC[C@H](c2c(F)cc(C(N)=O)c3[nH]c(C)c(Cl)c23)C1] | (R)-4-(1-acryloylpiperidin-3-yl)-3-chloro-5-fluoro-2-methyl-1H-indole-7-carboxamide |
| 3 | 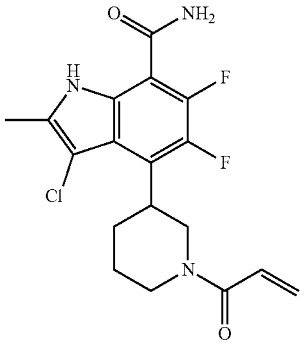 [SMILES: C=CC(=O)N1CCCC(c2c(F)c(F)c(C(N)=O)c3[nH]c(C)c(Cl)c23)C1] | 4-(1-acryloylpiperidin-3-yl)-3-chloro-5,6-difluoro-2-methyl-1H-indole-7-carboxamide |

| Cmpd. No. | Structure | Name |
|---|---|---|
| 4 | 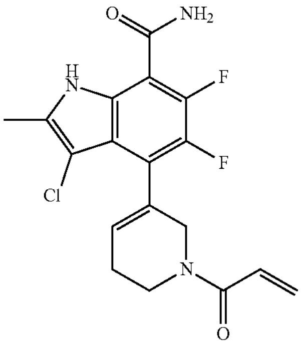 [SMILES: C=CC(=O)N1CCC=C(c2c(F)c(F)c(C(N)=O)c3[nH]c(C)c(Cl)c23)C1] | 4-(1-acryloyl-1,2,5,6-tetrahydropyridin-3-yl)-3-chloro-5,6-difluoro-2-methyl-1H-indole-7-carboxamide |
| 5 | 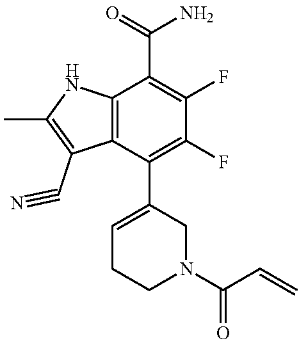 [SMILES: C=CC(=O)N1CCC=C(c2c(F)c(F)c(C(N)=O)c3[nH]c(C)c(C#N)c23)C1] | 4-(1-acryloyl-1,2,5,6-tetrahydropyridin-3-yl)-3-cyano-5,6-difluoro-2-methyl-1H-indole-7-carboxamide |
| 6a | 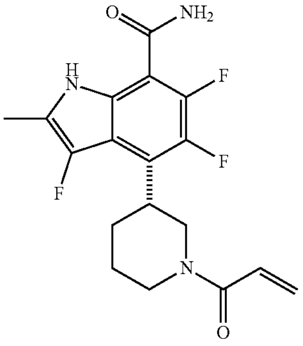 | (R)-4-(1-acryloylpiperidin-3-yl)-3,5,6-trifluoro-2-methyl-1H-indole-7-carboxamide |
| 6b | 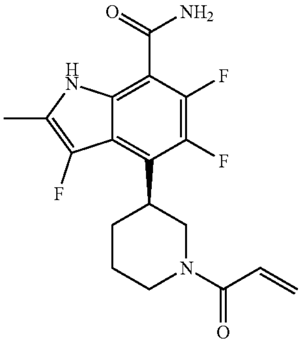 [SMILES: C=CC(=O)N1CCC[C@@H](c2c(F)c(F)c(C(N)=O)c3[nH]c(C)c(F)c23)C1] | (S)-4-(1-acryloylpiperidin-3-yl)-3,5,6-trifluoro-2-methyl-1H-indole-7-carboxamide |

| Cmpd. No. | Structure | Name |
|---|---|---|
| 7 | 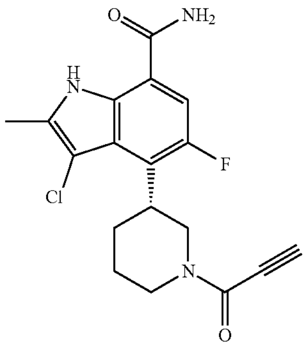 Assumed | (R)-3-chloro-5-fluoro-2-methyl-4-(1-propioloylpiperidin-3-yl)-1H-indole-7-carboxamide |
| 8 | 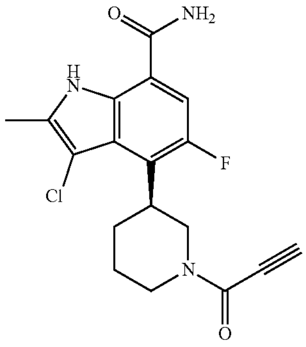 Assumed | (S)-3-chloro-5-fluoro-2-methyl-4-(1-propioloylpiperidin-3-yl)-1H-indole-7-carboxamide |
| 9 | 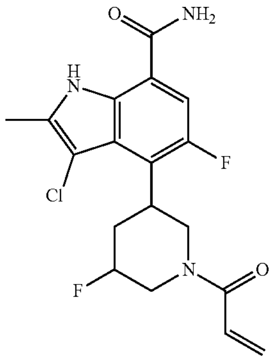 [SMILES: C=CC(=O)N1CC(F)CC(c2c(F)cc(C(N)=O)c3[nH]c(C)c(Cl)c23)C1] | 4-(1-acryloyl-5-fluoropiperidin-3-yl)-3-chloro-5-fluoro-2-methyl-1H-indole-7-carboxamide |
| 10 | 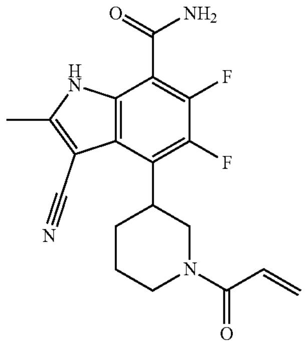 [SMILES: C=CC(=O)N1CCCC(c2c(F)c(F)c(C(N)=O)c3[nH]c(C)c(C#N)c23)C1] | 4-(1-acryloylpiperidin-3-yl)-3-cyano-5,6-difluoro-2-methyl-1H-indole-7-carboxamide |

-continued

| Cmpd. No. | Structure | Name |
|---|---|---|
| 11 | 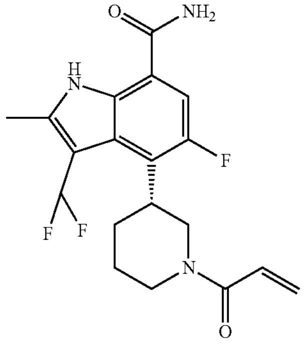 Assumed | (R)-4-(1-acryloylpiperidin-3-yl)-3-(difluoromethyl)-5-fluoro-2-methyl-1H-indole-7-carboxamide |
| 12 | 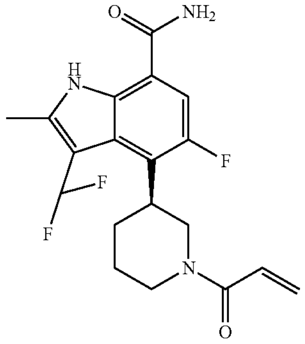 Assumed | (S)-4-(1-acryloylpiperidin-3-yl)-3-(difluoromethyl)-5-fluoro-2-methyl-1H-indole-7-carboxamide |
| 13 | 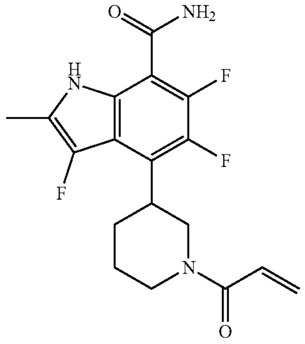 [SMILES: C=CC(=O)N1CCCC(c2c(F)c(F)c(C(N)=O)c3[nH]c(C)c(F)c23)C1] | 4-(1-acryloylpiperidin-3-yl)-3,5,6-trifluoro-2-methyl-1H-indole-7-carboxamide |
| 14 | 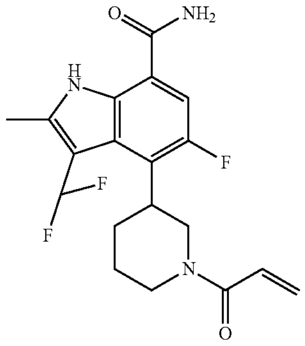 [SMILES: C=CC(=O)N1CCCC(c2c(F)cc(C(N)=O)c3[nH]c(C)c(C(F)F)c23)C1] | 4-(1-acryloylpiperidin-3-yl)-3-(difluoromethyl)-5-fluoro-2-methyl-1H-indole-7-carboxamide |
| 15 | 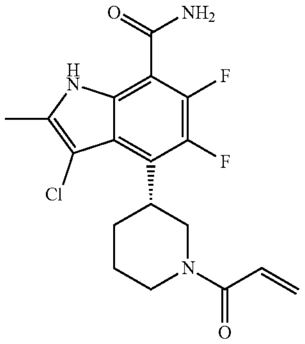 assumed | (R)-4-(1-acryloylpiperidin-3-yl)-3-chloro-5,6-difluoro-2-methyl-1H-indole-7-carboxamide |
| 16 | 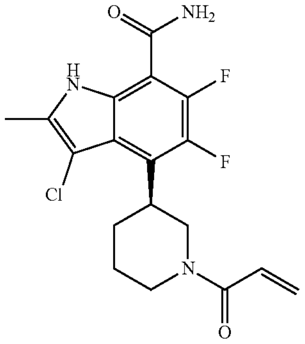 assumed | (S)-4-(1-acryloylpiperidin-3-yl)-3-chloro-5,6-difluoro-2-methyl-1H-indole-7-carboxamide |
| 17 | 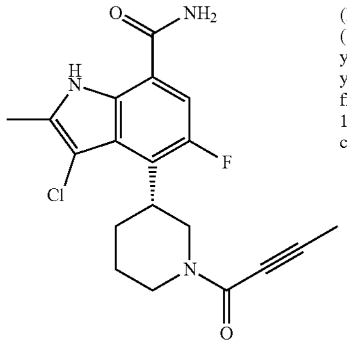 Assumed | (R)-4-(1-(but-2-ynoyl)piperidin-3-yl)-3-chloro-5-fluoro-2-methyl-1H-indole-7-carboxamide |
| 18 | 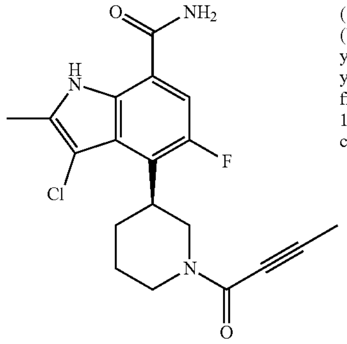 Assumed | (S)-4-(1-(but-2-ynoyl)piperidin-3-yl)-3-chloro-5-fluoro-2-methyl-1H-indole-7-carboxamide |

-continued

| Cmpd. No. | Structure | Name |
|---|---|---|
| 19 | 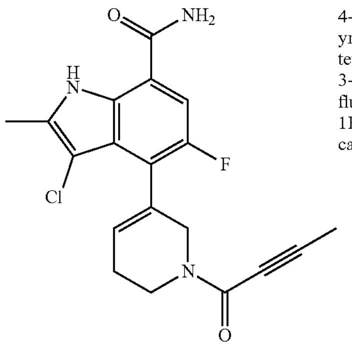 | 4-(1-(but-2-ynoyl)-1,2,5,6-tetrahydropyridin-3-yl)-3-chloro-5-fluoro-2-methyl-1H-indole-7-carboxamide |

14. A pharmaceutically acceptable salt of a compound of claim 1.

15. A pharmaceutical composition comprising a compound of claim 1, or a pharmaceutically acceptable salt, solvate, hydrate, isomer, tautomer, racemate or isotope thereof.

16. The pharmaceutical composition of claim 15, further comprising a pharmaceutically acceptable carrier, adjuvant or vehicle.

17. A method of inhibiting a protein kinase comprising contacting the protein kinase with an effective amount of a compound of claim 1, or a pharmaceutically acceptable salt, solvate, hydrate, isomer, tautomer, racemate, isotope, or pharmaceutical composition thereof.

18. The method of claim 17, wherein the protein kinase is BTK.

19. A method for treating a BTK dependent condition, comprising administering to a subject in need thereof, an effective amount of a compound of claim 1, or a pharmaceutically acceptable salt, solvate, hydrate, isomer, tautomer, racemate, isotope, or pharmaceutical composition thereof.

20. The method of claim 19, wherein, wherein the BTK dependent condition is primary CNS lymphoma.

21. The method of claim 19, wherein, wherein the BTK dependent condition is cancer, an autoimmune disease, an inflammatory disease, or a theromboembolic disease.

22. The method of claim 21, wherein the autoimmune disease is multiple sclerosis, rheumatoid arthritis, psoriasis, Sjogren's syndrome, or systemic lupus erythematosus.

23. The method of claim 21, wherein the inflammatory disease is urticaria.

24. A compound having the structure of formula (II):

Formula (II)

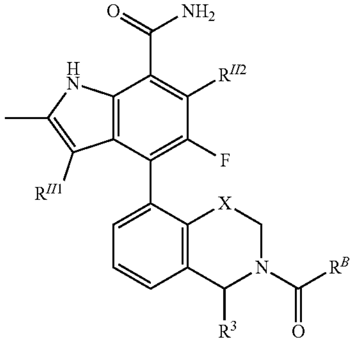

or a pharmaceutically acceptable salt, solvate, hydrate, isomer, tautomer, racemate or isotope thereof, wherein:

$R^{II1}$ is Cl, F, $—CH_2F$, $—CHF_2$, $—CF_3$ or —CN;

$R^{II2}$ is H or F;

$R^3$ is H, Me or cyclopropyl;

X is $—CH^2CH^2—$ or $—CR^{x1}R^{x2}—$;

$R^{x1}$ is H, F or Me;

$R^{x2}$ is H, F or Me;

or $R^{x1}$ and $R^{x2}$ together with the C atom to which there are attached form a $C_{3-6}$-membered carbocyclic ring;

or $R^{x1}$ is H and $R^{x2}$ and $R^3$ together form an alkylene bridge; and $R^B$ is $—CH{=}CH_2$, —C≡CH or $—C≡C—CH_3$.

25. A compound having the structure of Formula (III):

Formula (III)

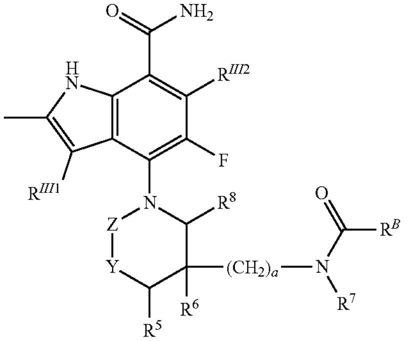

or a pharmaceutically acceptable salt, solvate, hydrate, isomer, tautomer, racemate or isotope thereof, wherein:

Z is $—CH_2—$, —CHMe- or a bond;

Y is $—CHR^4—$ or a bond;

$R^4$ is H, F, or OH;

$R^5$ is H, F, or Me;

$R^6$ is H or Me;

$R^7$ is H or Me;

$R^8$ is H;

or $R^5$ and $R^7$, taken together, form a 5- or 6-membered heterocycle;

or $R^6$ and $R^7$, taken together, form a 4-, 5- or 6-membered heterocycle;

or $R^8$ and $R^7$, taken together, form a 5- or 6-membered heterocycle;

a is 0, 1 or 2;

$R^{III1}$ is Cl, F, $—CH_2F$, $CHF_2$, $—CF_3$ or —CN; or $R^{III1}$ is $—CH_3$ when $R^4$ is F or OH, or when $R^5$ is F, or when $R^5$ and $R^7$ or $R^8$ and $R^7$, taken together, form a 5- or 6-membered heterocycle, or when $R^6$ and $R^7$, taken together, form a 4-, 5- or 6-membered heterocycle;

$R^{III2}$ is H or F; and $R^B$ is $—CH{=}CH_2$, —C≡CH or $—C≡C—CH_3$.

* * * * *